(12) United States Patent
Heinrich et al.

(10) Patent No.: US 7,595,154 B2
(45) Date of Patent: Sep. 29, 2009

(54) METHOD OF DETECTING A NEOPLASIA ASSOCIATED WITH AN ACTIVATING PLATELET DERIVED GROWTH FACTOR RECEPTOR ALPHA (PDGFRA) MUTATION

(75) Inventors: Michael C. Heinrich, Lake Oswego, OR (US); Christopher C. Corless, Portland, OR (US); Jonathan A. Fletcher, Brookline, MA (US); George D. Demetri, Brookline, MA (US)

(73) Assignees: Oregon Health and Science University, Portland, OR (US); Dana-Farber Cancer Institute, Boston, MA (US); Brigham and Women's Hospital, Boston, MA (US)

( * ) Notice: Subject to any disclaimer, the term of this patent is extended or adjusted under 35 U.S.C. 154(b) by 535 days.

(21) Appl. No.: 10/517,905

(22) PCT Filed: Jun. 13, 2003

(86) PCT No.: PCT/US03/18901

§ 371 (c)(1),
(2), (4) Date: Dec. 10, 2004

(87) PCT Pub. No.: WO03/105773

PCT Pub. Date: Dec. 24, 2003

(65) Prior Publication Data

US 2006/0084142 A1     Apr. 20, 2006

Related U.S. Application Data

(60) Provisional application No. 60/389,107, filed on Jun. 13, 2002, provisional application No. 60/438,899, filed on Jan. 8, 2003.

(51) Int. Cl.
  *C12Q 1/68*   (2006.01)
  *G01N 33/53*   (2006.01)
  *G01N 33/574*   (2006.01)
(52) U.S. Cl. ............................ 435/6; 435/7.2; 435/7.23
(58) Field of Classification Search .................... None
  See application file for complete search history.

(56) References Cited

U.S. PATENT DOCUMENTS

| 5,795,975 | A | | 8/1991 | Oefner et al. |
| 5,686,572 | A | * | 11/1997 | Wolf et al. .................. 530/350 |
| 5,795,976 | A | | 8/1998 | Oefner et al. |
| 5,833,986 | A | | 11/1998 | LaRochelle et al. |

(Continued)

OTHER PUBLICATIONS

Abu-Duhier et al., "FLT3 internal tandem duplication mutations in adult acute myeloid leukaemia define a high-risk group," *J. Haematol* 111(1): 190 (Oct. 2000).

(Continued)

*Primary Examiner*—Elizabeth C. Kemmerer
*Assistant Examiner*—Zachary C Howard
(74) *Attorney, Agent, or Firm*—Klarquist Sparkman LLP

(57) ABSTRACT

This disclosure provides tyrosine kinase protein and nucleic acid variants, particularly PDGFRA variants, which are activating forms of these molecules and are linked to neoplasms and/or the development or progression of cancer. The disclosure further provides methods of diagnosis and prognosis, and development of new therapeutic agents using these molecules and fragments thereof, and kits for employing these methods and compositions.

44 Claims, 7 Drawing Sheets

U.S. PATENT DOCUMENTS

| | | |
|---|---|---|
| 6,187,536 B1 | 2/2001 | Weinberg et al. |
| 6,194,158 B1 | 2/2001 | Kroes et al. |
| 6,291,661 B1 | 9/2001 | Graddis et al. |

OTHER PUBLICATIONS

Abu-Duhier et al., "Identification of novel FLT-3 Asp835 mutations in adult acute myeloid leukaemia," *J. Haematol* 113(4):983-988 (Jun. 2001).

Al-Ali et al., "High incidence of BCR-ABL kinase domain mutations and absence of mutations of the PDGFR and KIT activation loops in CML patients with secondary resistance to imatinib," *Hematol J.* 5(1):55-60 (2004).

Blanke et al., "Evaluation of the Safety and Efficacy of an Oral Molecularly-Targeted Therapy, STI571, in Patients (Pts) with Unresectable or Metastatic Gastrointestinal Stromal Tumors (GISTS) Expressing C-KIT (CD117)," *ASCO*, May 12-15, 2001 (*Meeting Abstract*).

Borg et al., "Novel mode of action of c-kit tyrosine kinase inhibitors leading to NK cell-dependent antitumor effects," *J. Clinical. Investigation* 114(3):379-388 (Aug. 2004).

Chen et al., "Imatinib inhibits various types of activating mutant kit found in gastrointestinal stromal tumors," *J. Cancer* 105(1):130-135 (May 20, 2003).

Corless et al., "Biology of gastrointestinal stromal tumors," *J. Clin. Oncol.* 22(18):3813-3825 (Sep. 15, 2004).

Debiec-Rychter et al., "Use of c-KIT/PDGFRA mutational analysis to predict the clinical response to imatinib in patients with advanced gastrointestinal stromal tumours entered in phase I and II stidies of the EORTC Soft Tissue and Bone Sarcoma Group," *Eur J Cancer*, 40(5):689-95 (Mar. 2004).

Demetri, "Targeting *c-kit* Mutations in Solid Tumors: Scientific Rationale and Novel Therapeutic Options," *Semin Oncol.* 5 Suppl 17:19-26 (Oct. 2001).

Demetri et al., "Phase III dose-randomized study of imatinib mesylate (Gleevec, STI571) for GIST: intergroup S0033 early results," *ASCO* May 18-21, 2002 (*Meeting Abstract*).

Duensing et al., "Protein Kinase C theta (PKCtheta) expression and constitutive activation in gastrointestinal stromal tumors (GISTs)," *Cancer Res.* 64(15):5127-5131 (Aug. 1, 2004).

Fenski et al., "Constitutive activation of FLT3 in acute myeloid leukaemia and its consequences for growth of 32D cells," *J. Haematol* 108(2):322-330 (Feb. 2000).

Gari et al., "c-kit proto-ocogene exon 8 in-frame deletion plus insertion mutations in acute myeloid leukaemia," *J. Haematol* 105(4):894-900 (Jun. 1999).

Griswold et al., "Effects of MLN518, a dual FLT3 and KIT inhibitor, on normal and malignant hematopoiesis," *Blood* 104(9):2912-2918 (Jul. 8, 2004).

Heinrich et al., "Biology and genetic aspects of gastrointestinal stromal tumors: KIT activation and cytogenetic alternations," *Hum. Pathol.* 33(5):484-95 (May 2002).

Heinrich et al., "Inhibition of c-kit receptor tyrosine kinase activity by STI 571, a selective tyrosine kinase inhibitor," *Blood* 96(3):925-932 (Aug. 1, 2000).

Heinrich et al., "Inhibition of KIT Tyrosine Kinase Activity: A Novel Molecular Approach to the Treatment of KIT-Positive Malignancies," *J. Clinical Oncology* 20(6):1692-1703 (Mar. 15, 2002).

Heinrich et al., "Kinase mutations and imatinib response in patients with metastatic gastrointestinal stromal tumor," *J. Clin Oncol.* 21(23):4342-4349 (Dec. 1, 2003).

Heinrich et al., "KIT mutational status predicts clinical response to STI571 in patients with metastatic gastrointestinal stromal tumors (GISTs)," *ASCO* May 18-21, 2002 (*Meeting Abstract*).

Heinrich et al., "Targeting mutant kinases in gastrointestinal stromal tumors: a paradigm for molecular therapy of other sarcomas," *Cancer Treatment Res.* 120:129-150 (2004).

Heinrich et al., "*PDGFRA* Activating Mutations in Gastrointestinal Stromal Tumors," *Science* 299:708-710 (Jan. 31, 2003).

Hirota et al., "Gain-of-function mutation at the extracellular domain of KIT in gastrointestinal stromal tumours," *J Pathol.* 193(4):505-510 (Apr. 2001).

Hochhaus et al., "Interim analysis of imatinib treatment in 300 patients with chronic myelogenous leukemia (CML): evaluation of response and resistance," *ASCO* May 18-21, 2002 (*Meeting Abstract*).

Joensuu et al., "Effect of the tyrosine kinase inhibitor STI571 in a patient with a metastatic gastrointestinal stromal tumor," *N Engl J Med* 344(14):1052-1056 (Apr. 5, 2001).

Joensuu et al., "Gastrointestinal stromal tumor (GIST) patients who respond to imatinib (STI571, Gleevec) show marked decline of circulating levels of VEGF, KIT, and bFGF in serum, but not stem cell factor (SCF) levels," *ASCO*, May 18-21, 2002 (*Meeting Abstract*).

Johnson et al., "Phase II study of STI571 (Gleevec™) for patients with small cell lung cancer," *ASCO* May 18-21, 2002 (*Meeting Abstract*).

Kubota et al., "Chemosensitivity of gastric cancer detected by cDNA microarray," *ASCO* May 18-21, 2002 (*Meeting Abstract*).

Madani et al., "Expression of KIT and epidermal growth factor receptor (EGFR) in chemotherapy refractory non-seminomatous germ cell tumors (GCT)," *ASCO* May 28-21, 2002 (*Meeting Abstract*).

Medeiros et al., "KIT-negative gastrointestinal stromal tumors: proof of concept and therapeutic implications," *Am J. Surg Pathol.* 28(7):889-894 (Jul. 2004).

Nakamura et al., "Abnormalities of the p53, N-ras, DCC and FLT-3 genes in myelodysplastic syndromes," *J. Nippon Med Sch* 68(2):143-148 (Apr. 2001) (*English Abstract Only*).

O'Farrell et al., "Analysis of mechanism of action and biomarkers for kinase inhibitor SU5416 in AML patients," *ASCO* May 18-21, 2002 (*Meeting Abstract*).

O'Farrell et al., "SU11248 is a novel FLT3 tyrosine kinase inhibitor with potent activity in vitro and in vivo," *Blood* 101(9):3597-3605 (May 1, 2003).

Rubin et al., "KIT Activation is Ubiquitous Feature of Gastrointestinal Stromal Tumors," *Cancer Research* 61:8118-8121 (Nov. 15, 2001).

Singer et al., "Prognostic Value of *KIT* Mutation Type, Mitotic Activity, and Histologic Subtype in Gastrointestinal Stromal Tumors," *J. Clinical Oncology* 20(18):3898-3905 (Sep. 15, 2002).

Subramanian et al., "Gastrointestinal stromal tumors (GISTs) with KIT and PDGFRA mutations have distinct gene expression profiles," *Oncogene* 23(47):7780-7790 (Oct. 14, 2004).

van Oosterom et al., "Safety and efficacy of imatinib (STI571) in metastatic gastrointestinal stromal tumours: a phase I study," *Lancet* 358(9291):1421-1423 (Oct. 27, 2001).

van Oosterom et al., "STI571, an Active Drug in Metastatic Gastro Intestinal Stromal Tumors (GIST), and EORTC Phase I Study," *ASCO* May 12-15, 2001 (*Meeting Abstract*).

von Mehren et al., "High incidence of durable responses induced by imatinib mesylate (Gleevec) in patients with unresectable and metastatic gastrointestinal stromal tumors (GISTs)," *ASCO* May 18-21, 2002 (*Meeting Abstract*).

"Gleevec™ Shows Promise for Type of Gastrointestinal Tumor," *National Cancer Institute—Clinical Trial Results* http://www.cancer.gove/clinicaltrials/results/gleevec-shows-promise0202, posted Jul. 20, 2001; printed Feb. 26, 2005.

*Homo sapiens* platelet-derived growth factor receptor, alpha polypeptide (PDGFRA), mRNA, Locus ID: XM_011186, PRI Feb. 7, 2002, *NCBI*, printed Apr. 18, 2002.

Human DNA for alpha-platelet-derived growth factor receptor, exon 1, Locus ID: D50001S01, PRI Apr. 14, 2000, *NCBI*, printed Jun. 5, 2002.

PDGFRA: platelet-derived growth factor receptor, alpha polypeptide, Locus ID: 5156, *NCBI*, printed Jun. 5, 2002.

Omura et al., "Immunoglobulin-like Domain 4-mediated Receptor-Receptor Interactions contribute to Platelet-derived Growth Factor-induced Receptor Dimerization" *JBC* 272(19):12676-12682, 1997.

Bai et al., "The SH2-containing Adapter Protein GRB10 interacts with BCR-ABL" *Oncogene* 17:941-948, 1998.

Baxter et al., "The t(4:22)(q12;q11) in Atypical Chronic Myeloid Leukaemia fuses BCR to PDGFRA" *Human Molecular Genetics* 11(12):1391-1397, 2002.

Hirota et al., "Gain-of-Function Mutations of Platelet-Derived Growth Factor Receptor α Gene in Gastrointestinal Stromal Tumors," *Gastroenterology* 125:660-667 (2003).

* cited by examiner

FIGURE 7A

```
181551  GCTTTCTCTC TGTTGGGAGT GGGTGGAGTG AGAACCTGGG AGAAGGCCAG
        CGAAAGAGAG ACAACCCTCA CCCACCTCAC TCTTGGACCC TCTTCCGGTC
         A  F  S  L   L  G  V   G  G  V   R  T  W   E  K  A  S     Frame 3

PDGFrA 181634F
181601  CCCTTTATAT CCAGGCAGAC AGCTCCAAGT GCCACCATGG ATCAGCCAGT
        GGGAAATATA GGTCCGTCTG TCGAGGTTCA CGGTGGTACC TAGTCGGTCA
         P  L  Y   P  G  R  Q   L  Q  V   P  P  W   I  S  Q  S     Frame 3

PDGFrA 181640F          PDGFrA 181671F
181651  CTTGCAGGGG TGATGCTATT CAGCTACAGA TGGCTTGATC CTGAGTCATT
        GAACGTCCCC ACTACGATAA GTCGATGTCT ACCGAACTAG GACTCAGTAA
         C  R  G   D  A  I   Q  L  Q  M   A  *  S    *  V  I       Frame 3

181701  TCTTCCTTTT CCATGCAGTG TGTCCACCGT GATCTGGCTG CTCGCAACGT    Exon 18
        AGAAGGAAAA GGTACGTCAC ACAGGTGGCA CTAGACCGAC GAGCGTTGCA
         S  S  F  S   M  Q  C   V  H  R   D  L  A   A  R  N  V     Frame 3

PDGFrA 181752F (SNP Exclusion)
181751  CCTCCTGGCA CAAGGAAAAA TTGTGAAGAT CTGTGACTTT GGCCTGGCCA
        GGAGGACCGT GTTCCTTTTT AACACTTCTA GACACTGAAA CCGGACCGGT
         L  L  A   Q  G  K  I   V  K  I   C  D  F   G  L  A  R     Frame 3

181801  GAGACATCAT GCATGATTCG AACTATGTGT CGAAAGGCAG TGTACGTCCT
        CTCTGTAGTA CGTACTAAGC TTGATACACA GCTTTCCGTC ACATGCAGGA
         D  I  M   H  D  S   N  Y  V  S   K  G  S   V  R  P        Frame 3

PDGFrA 181862R          PDGFrA 181874R
181851  CACTTCCCTC ACTGGTCAGG CTCATCCTCC TTCACTTTAA TCTCTAAAGT
        GTGAAGGGAG TGACCAGTCC GAGTAGGAGG AAGTGAAATT AGAGATTTCA
         H  F  P   H  W  S  G   S  S  S   F  T  L   I  S  K  V     Frame 3

181901  CAGGTGTTGC TTCTAGAGAT TCGGTGCCTG TTTTTTAAAA CATCAATAGA
        GTCCACAACG AAGATCTCTA AGCCACGGAC AAAAAATTTT GTAGTTATCT
         R  C  C   F  *  R  F   G  A  C   F  L  K   H  Q  *  I     Frame 3
```

FIGURE 7B

```
170551 AAGCATAGCA ACCTAGTTCA GTGCTTGGCA CAGAGAAGGA GCTCAGCAAT
       TTCGTATCGT TGGATCAAGT CACGAACCGT GTCTCTTCCT CGAGTCGTTA
        K  H  S  N   L  V  Q    C  L  A    Q  R  R  S    S  A  I      Frame 1

PDGFrA 170636F
170601 TACATGTGGA GTGAACGTTG TTGGACTCTA CTGTGTCCAG TCACTGTGCT
       ATGTACACCT CACTTGCAAC AACCTGAGAT GACACAGGTC AGTGACACGA
        T  C  G   V  N  V  V   G  L  Y    C  V  Q    S  L  C  C      Frame 1

PDGFrA 170658F
170651 GCTTCAGTGA AGCTCTGGTG CACTGGGACT TTGGTAATTC ACCAGTTACC
       CGAAGTCACT TCGAGACCAC GTGACCCTGA AACCATTAAG TGGTCAATGG
         F  S  E   A  L  V   H  W  D  F   G  N  S    P  V  T        Frame 1

170701 TGTCCTGGTC ATTTATAGAA ACCGAGGTAT GAAATTCGCT GGAGGGTCAT         Exon 12
       ACAGGACCAG TAAATATCTT TGGCTCCATA CTTTAAGCGA CCTCCCAGTA
        C  P  G  H   L  *  K    P  R  Y    E  I  R    W  R  V  I     Frame 1

170751 TGAATCAATC AGCCCAGATG GACATGAATA TATTTATGTG GACCCGATGC
       ACTTAGTTAG TCGGGTCTAC CTGTACTTAT ATAAATACAC CTGGGCTACG
         E  S  I   S  P  D   H  E  Y    I  Y  V    D  P  M  Q        Frame 1

170801 AGCTGCCTTA TGACTCAAGA TGGGAGTTTC CAAGAGATGG ACTAGTGCTT
       TCGACGGAAT ACTGAGTTCT ACCCTCAAAG GTTCTCTACC TGATCACGAA
        L  P  Y   D  S  R   W  E  F  P    R  D  G    L  V  L        Frame 1

PDGFrA 170866R              PDGFrA 170894R
170851 GGTAAGTTCC ATGGGGTAAC CTCCCAAGAC TCCCTTTTCC CTTGCACACA
       CCATTCAAGG TACCCCATTG GAGGGTTCTG AGGGAAAAGG GAACGTGTGT
        G  K  F  H   G  V  T    S  Q  D    S  L  F  P    C  T  Q     Frame 1

170901 ACTTTACAAT TTATAGGCCT TGGCAGAATA GAGATCTGAG CTTGTGCTTA
       TGAAATGTTA AATATCCGGA ACCGTCTTAT CTCTAGACTC GAACACGAAT
        L  Y  N   L  *  A  L    A  E  *    R  S  E    L  V  L  S     Frame 1
```

FIGURE 8
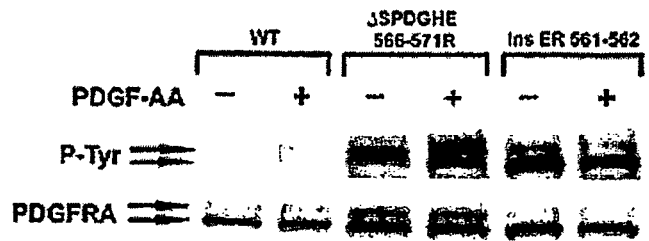
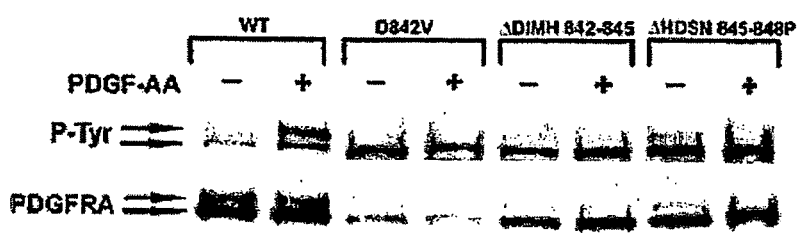
FIGURE 9
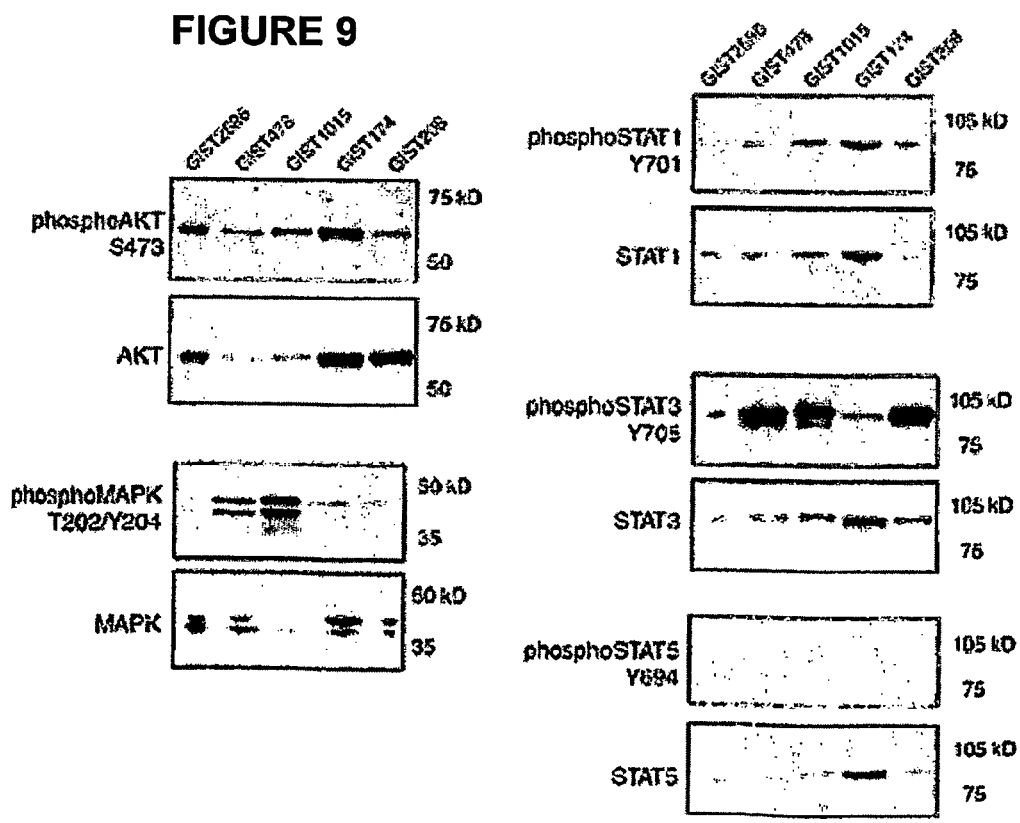

METHOD OF DETECTING A NEOPLASIA ASSOCIATED WITH AN ACTIVATING PLATELET DERIVED GROWTH FACTOR RECEPTOR ALPHA (PDGFRA) MUTATION

CROSS REFERENCE TO RELATED APPLICATIONS

This is a U.S. National Stage of International Application No. PCT/US03/18901, filed Jun. 13, 2003, which was published in English under PCT Article 21(2), which in turn claims the benefit of U.S. Provisional Applications No. 60/389,107, filed Jun. 13, 2002, and No. 60/438,899, filed Jan. 8, 2003. These provisional applications are incorporated herein in their entirety.

STATEMENT OF GOVERNMENT SUPPORT

This invention was made with United States government support pursuant to employment of one of the inventors as a Federal employee, as well as grant funding from a Veterans Affairs Merit Review Grant; the United States government has certain rights in the invention.

FIELD

This disclosure relates to tyrosine kinases, particularly receptor tyrosine kinases with one or more activation mutations. Further, it relates to methods of using these molecules in screens and analyses, including diagnoses, prognoses, and systems for identification and/or selection of pharmaceutical compounds.

BACKGROUND OF THE DISCLOSURE

Tyrosine kinases are expressed by many human cancers. These enzymes are attractive targets for the development of anticancer drugs, as it has been possible to optimize compounds with excellent inhibitory potency and selectivity to individual target tyrosine kinases. The utility of this approach has been highlighted by the success of imatinib mesylate (Gleevec™) in the treatment of chronic myelogenous leukemia (CML) and gastrointestinal stromal tumors (GISTs).

Expression of tyrosine kinases is ubiquitous in both cancers and normal tissues. Therefore, the efficacy of a kinase inhibitor is dependent on two factors: 1) the degree to which the target kinase is activated in a particular cancer, and 2) the degree to which the growth and survival of the cancer cells is dependent on the activated target kinase.

Gastrointestinal stromal tumors provide an excellent example of this principle. KIT tyrosine kinase is detectable by immunohistochemistry in a wide variety of cancers and normal tissues, but mutations of the KIT gene that yield constitutively active KIT kinase are found in only a small subset of tumors (Heinrich et al., *J. Clin. Oncol.*, 20: 1692-1703, 2002). More than 85% of GISTs harbor such activating mutations (Blanke et al., *Proceedings of ASCO* 20, 1a-1a. 2001; Heinrich et al., *J. Clin. Oncol.*, 20: 1692-1703, 2002; Hirota et al., *J. Pathol.*, 193: 505-510, 2001; Rubin et al., *Cancer Res*, 61: 8118-8121, 2001) and, correspondingly, phosphorylation of KIT kinase (a marker of activation) was recently demonstrated in most fresh-frozen GIST specimens (Rubin et al., *Cancer Res*, 61: 8118-8121, 2001). Such phosphorylation of KIT is rarely observed in other cancer specimens. Recent success in the treatment of advanced malignant GISTs with imatinib mesylate is thought to reflect an important role of KIT activation in the growth and/or survival of GIST tumor cells (Blanke et al., *Proceedings of ASCO* 20, 1a-1a. 2001; Joensuu et al., *N Engl J Med*, 1052: 1052-1056, 2001; Van Oosterom et al., *Lancet*, 358:1421-1423, 2001). The observation that treatment results with imatinib mesylate are significantly better for tumors with evidence of mutational activation of KIT than for tumors with no KIT mutation further supports this view (Heinrich et al., *J. Clin. Oncol.*, 20: 1692-1703, 2002). Thus, in the case of GISTs, testing of clinical specimens for genomic mutations resulting in tyrosine kinase activation will be useful in determining which patients are most likely to respond to a tyrosine kinase inhibitor.

The PDGFRA (or PDGFR-α) protein is a type III receptor tyrosine kinase with homology to KIT, FLT3, CSF1-R and PDGFRβ (PDGFRB). Although PDGFRA activation has been hypothesized to be involved in certain cancers, most notably gliomas, evidence of genomic activation in human cancer has only recently been reported in two cases of myeloproliferative disease associated with translocation of the BCR and PDGFRA genes.

SUMMARY OF THE DISCLOSURE

Disclosed herein are novel mutations of PDGFRA that result in constitutive activation of this tyrosine kinase. These mutations were initially discovered in GISTs. Also disclosed are consensus PDGFRA nucleic acid and amino acid sequences, which summarize certain groups of activating mutations and regions of relatively active mutation.

Thus, this disclosure provides several novel PDGFRA variant proteins, and nucleic acids encoding these variants. Also disclosed are methods of using these molecules in detecting biological conditions associated with an activating PDGFRA mutation in a subject, methods of treating such conditions, methods of selecting treatments (e.g., specific tyrosine kinase inhibitors), and methods of screening for inhibitors of PDGFRA activity, particularly activated PDGFRA variant activity. Oligonucleotides for use in examples of such methods are also provided.

Also disclosed herein are protein specific binding agents, such as antibodies, that bind specifically to at least one epitope of a PDGFRA variant protein preferentially compared to wildtype PDGFRA, and methods of using such antibodies in diagnosis, treatment, and screening.

Kits are also provided for carrying out the methods described herein.

The foregoing and other features and advantages will become more apparent from the following detailed description of several embodiments, which proceeds with reference to the accompanying figures.

BRIEF DESCRIPTION OF THE FIGURES

FIG. 7: Differential sensitivity of various KIT activation loop mutants to imatinib mesylate. FIG. 7 shows the genomic sequences of PDGFRA around exon 18 (FIG. 7A) and exon 12 (FIG. 7B). PDGFRA primers are indicated; PDGFRA exon sequences and amino acid translations are also shown.

FIG. 8: DGFRA mutations in GISTs result in constitutive activation of PDGFRA kinase. FIG. 8 shows a series of immunoblots, probed with antibodies to phosphor-tyrosine and PDGFRA. CHO cells were transiently transfected with expression vectors encoding cDNAs for wild-type or mutant PDGFRA. Transfected cells were serum starved overnight and treated with vehicle or ligand (recombinant human PDGF-AA) for 10 minutes. Whole cell lysates were immunostained sequentially for phospho-tyrosine and PDGFRA. Wild type PDGFRA displays low-level phosphorylation that is upregulated by ligand stimulation with PDGF-AA. In contrast, the mutant PDGFRA proteins display ligand-independent phosphorylation.

FIG. 9: Cell signaling profiles in PDGFRA-mutant (2686, 478, and 1015) and KIT-mutant GISTs (174 and 208). FIG. 9 shows a series of immunoblots, illustrating the cell signaling profiles of the indicated mutants. Whole cell lysates were prepared from snap-frozen GISTs, and immunoblots were detected with antibodies to phosphorylated and total forms of AKT, MAPK, and STATs. All GISTs express phosphorylated AKT, MAPK, STAT1, and STAT3, whereas STAT5 is not tyrosine phosphorylated.

SEQUENCE LISTING

Figure 1:
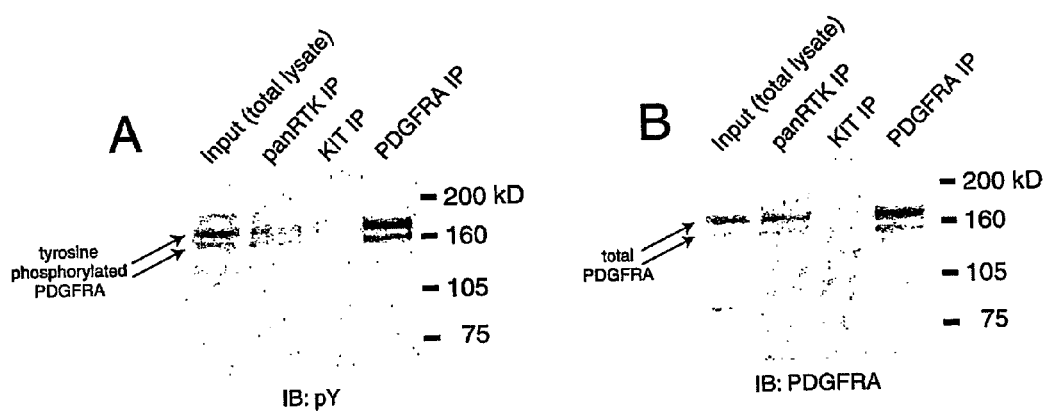
FIG. 1: Immunostaining for phosphotyrosine (A) and PDGFRA (B) in GIST478. A) A strongly tyrosine phosphorylated doublet at 150/170 kD is seen in the RTK immunoprecipitate (lane 2). This phosphorylated doublet corresponds to two of the stronger phosphoproteins in the total cell lysate (lane 1), and comigrates with the strongly phosphorylated PDGFRA doublet (lane 4). KIT is not demonstrably phosphorylated (lane 3). B) The strongly phosphorylated RTK (lane 2) was confirmed as PDGFRA, by stripping and restaining the blot with a specific antibody to PDGFRA.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. Unless specifically noted otherwise herein, the position numbering associated with the name of a variant PDGFRA molecule is based on numbering in the corresponding wildtype molecule. Where a reference is made to positions in a variant, the numbering is based on the actual position in the specified variant. In the accompanying sequence listing:

SEQ ID NO: 1 shows the nucleic acid sequence of the human PDGFRA cDNA (GenBank Accession No. XM_011186); the sequence list also shows the encoded protein.

SEQ ID NO: 2 shows the amino acid sequence of human PDGFRA protein.

SEQ ID NO: 3 shows the nucleic acid sequence of the human PDGFRA D842V variant cDNA; the sequence list also shows the encoded protein.

SEQ ID NO: 4 shows the amino acid sequence of human PDGFRA D842V variant protein.

SEQ ID NO: 5 shows the nucleic acid sequence of the human PDGFRA DIMH842-845 variant cDNA; the sequence list also shows the encoded protein.

SEQ ID NO: 6 shows the amino acid sequence of human PDGFRA DIMH842-845 variant protein.

SEQ ID NO: 7 shows the nucleic acid sequence of the human PDGFRA HSDN845-848P variant cDNA; the sequence list also shows the encoded protein.

SEQ ID NO: 8 shows the amino acid sequence of human PDGFRA HSDN845-848P variant protein.

SEQ ID NO: 9 shows the nucleic acid sequence of the human PDGFRA ER561-562 variant cDNA; the sequence list also shows the encoded protein.

SEQ ID NO: 10 shows the amino acid sequence of human PDGFRA ER561-562 variant protein.

SEQ ID NO: 11 shows the nucleic acid sequence of the human PDGFRA SPDGHE566-571R variant cDNA; the sequence list also shows the encoded protein.

SEQ ID NO: 12 shows the amino acid sequence of human PDGFRA SPDGHE566-571R variant protein.

SEQ ID NOs: 13-18 are amino acid sequences of the RTK catalytic domain sequences of different families of human RTK proteins.

SEQ ID NO: 19 is the genomic sequence of PDGFRA, with introns and exons indicated. Regions where the sequence is unknown or unconfirmed have been indicated with "n" designations using standard conventions. This sequence is available in the April 2002 release of the human genome project, as provided by University of California, Santa Cruz, on their Internet website.

SEQ ID NO: 20 shows the nucleic acid sequence of the human PDGFRA V561D variant cDNA; the sequence list also shows the encoded protein.

SEQ ID NO: 21 shows the amino acid sequence of human PDGFRA V561D variant protein.

SEQ ID NO: 22 shows the nucleic acid sequence of the human PDGFRA RVIES560-564 variant cDNA; the sequence list also shows the encoded protein.

SEQ ID NO: 23 shows the amino acid sequence of human PDGFRA RVIES560-564 variant protein.

SEQ ID NO: 24 shows the nucleic acid sequence of the human PDGFRA Deletion RD841-842KI variant cDNA; the sequence list also shows the encoded protein SEQ ID NO: 25 shows the amino acid sequence of human PDGFRA Deletion RD841-842KI variant protein.

SEQ ID NO: 26 shows the consensus sequence produced by aligning the nucleic acid sequences of each of the identified activating PDGFRA mutants (SEQ ID NOs: 3, 5, 7, 9, 11, 20, 22, and 24), and the consensus protein encoded thereby.

SEQ ID NO: 27 shows a PDGFRA consensus sequence.

DETAILED DESCRIPTION

I. Abbreviations

2D-PAGE two-dimensional polyacrylamide gel electrophoresis
ASO allele-specific oligonucleotide
ASOH allele-specific oligonucleotide hybridization
DASH dynamic allele-specific hybridization
ELISA enzyme-linked immunosorbant assay
HPLC high pressure liquid chromatography
MALDI-TOF matrix-assisted laser desorption/ionization time-of-flight
PCR polymerase chain reaction
PDGFRA platelet derived growth factor receptor alpha
PDGFRB platelet derived growth factor receptor beta
RT-PCR reverse-transcription polymerase chain reaction
SSCP single-strand conformation polymorphism
TKI tyrosine kinase inhibitor II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Antisense, Sense, and Antigene: Double-stranded DNA (dsDNA) has two strands, a 5'->3' strand, referred to as the plus strand, and a 3'->5' strand (the reverse complement), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though waste times also influence stringency. Calculations regarding hybridization conditions required for attaining particular degrees of stringency are discussed by Sambrook et al. (ed), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

For present purposes, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Injectable composition: A pharmaceutically acceptable fluid composition including at least one active ingredient The active ingredient is usually dissolved or suspended in a physiologically acceptable carrier, and the composition can additionally include amounts of one or more non-toxic auxiliary substances, such as emulsifying agents, preservatives, and pH buffering agents and the like. Such injectable compositions that are useful for use with the provided nucleotides and proteins are conventional; appropriate formulations are well known in the art.

In vitro amplification: Techniques that increase the number of copies of a nucleic acid molecule in a sample or specimen. An example of in vitro amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification may be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as defined below, but generally refers to the subset of constitutional alterations that have arisen within the past few generations in a kindred and that are not widely disseminated in a population group. In particular embodiments, the term is directed to those constitutional alterations that have major impact on the health of affected individuals.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 500 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include PNA molecules.

Particular oligonucleotides and oligonucleotide analogs can include linear sequences up to about 300 nucleotides in length, for example a sequence (such as DNA or RNA) that is at least 6 bases, for example at least 8, 10, 15, 20, 25, 30, 35, 40, 45, 50, 100 or even 200 or more bases long, or from about 6 to about 50 bases, for example about 10-25 bases, such as 12, 15, 20, or 25 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame (ORF): A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Parenteral: Administered outside of the intestine, e.g., not via the alimentary tract Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful with the compositions provided herein are conventional. By way of example, Martin, in *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: Variant in a sequence of a gene, usually carried from one generation to another in a population. Polymorphisms can be those variations (nucleotide sequence differences) that, while having a different nucleotide sequence, produce functionally equivalent gene products, such as those variations generally found between individuals, different ethnic groups, geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased or increased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNases, and so forth).

Probes and primers: Nucleic acid probes and primers can be readily prepared based on the nucleic acid molecules provided as indicators of disease or disease progression. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as the PDGFRA or other tyrosine kinase sequences described herein, for example, by using computer programs intended for that purpose such as Primer (Version 0.5, ©1991, Whitehead Institute for Biomedical Research, Cambridge, Mass.).

One of ordinary skill in the art will appreciate that the specificity of a particular probe or primer increases with its length. Thus, for example, a primer comprising 30 consecutive nucleotides of a tyrosine kinase protein encoding nucleotide will anneal to a target sequence, such as another homolog of the designated tyrosine kinase protein, with a higher specificity than a corresponding primer of only 15 nucleotides. Thus, in order to obtain greater specificity, probes and primers can be selected that comprise at least 20, 23, 25, 30, 35, 40, 45, 50 or more consecutive nucleotides of a tyrosine kinase-encoding nucleotide sequences.

Also provided are isolated nucleic acid molecules that comprise specified lengths of tyrosine kinase-encoding nucleotide sequences. Such molecules may comprise at least 10, 15, 20, 23, 25, 30, 35, 40, 45 or 50 or more (e.g., at least 100, 150, 200, 250, 300 and so forth) consecutive nucleotides of these sequences or more. These molecules may be obtained from any region of the disclosed sequences (e.g., a PDGFRA nucleic acid may be apportioned into halves or quarters based on sequence length, and isolated nucleic acid molecules may be derived from the first or second halves of the molecules, or any of the four quarters, etc.). A cDNA or other encoding sequence also can be divided into smaller regions, e.g. about eighths, sixteenths, twentieths, fiftieths, and so forth, with similar effect.

Another mode of division, provided by way of example, is to divide a tyrosine kinase-encoding sequence based on the regions of the sequence that are relatively more or less homologous to other tyrosine kinase sequences.

Another mode of division is to select the 5' (upstream) and/or 3' (downstream) region associated with a tyrosine kinase gene (e.g., PDGFRA).

Nucleic acid molecules may be selected that comprise at least 10, 15, 20, 25, 30, 35, 40, 50, 100, 150, 200, 250, 300 or more consecutive nucleotides of any of these or other portions of a PDGFRA nucleic acid molecule, such as those disclosed herein, and associated flanking regions. Thus, representative nucleic acid molecules might comprise at least 10 consecutive nucleotides of the PDGFRA cDNA shown in SEQ ID NO: 1.

Protein: A biological molecule expressed by a gene or recombinant or synthetic coding sequence and comprised of amino acids.

Purified: The term "purified" does not require absolute purity; rather, it is intended as a relative term Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g. by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of human PDGFRA protein, and the corresponding cDNA or gene sequence(s), will possess a relatively high degree of sequence identity when aligned using standard methods. This homology will be more significant when the orthologous proteins or genes or cDNAs are derived from species that are more closely related (e.g., human and chimpanzee sequences), compared to species more distantly related (e.g., human and *C. elegans* sequences).

Methods of alignment of sequences for comparison are well known in the art Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual,* CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to a human tyrosine kinase protein-encoding sequence will typically hybridize to a probe based on either an entire human tyrosine kinase protein-encoding sequence or selected portions of the encoding sequence under wash conditions of 2×SSC at 50° C.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target. Thus a protein-specific binding agent binds substantially only the specified protein. By way of example, as used herein, the term "PDGFRA-protein specific binding agent" includes anti-PDGFRA protein antibodies (and functional fragments thereof) and other agents (such as soluble receptors) that bind substantially only to the PDGFRA protein.

Anti-PDGFRA protein antibodies (or antibodies to another tyrosine kinase) may be produced using standard procedures described in a number of texts, including Harlow and Lane (*Antibodies, A Laboratory Manual,* CSHL, New York, 1988). The determination that a particular agent binds substantially only to the specified protein may readily be made by using or adapting routine procedures. One suitable in vitro assay makes use of the Western blotting procedure (described in many standard texts, including Harlow and Lane (*Antibodies, A Laboratory Manual,* CSHL, New York, 1988)). Western blotting may be used to determine that a given protein binding agent, such as an anti-PDGFRA protein monoclonal antibody, binds substantially only to the PDGFRA protein.

Shorter fragments of antibodies can also serve as specific binding agents. For instance, Fabs, Fvs, and single-chain Fvs (SCFvs) that bind to a specified protein would be specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals.

Target sequence: "Target sequence" is a portion of ssDNA, dsDNA or RNA that, upon hybridization to a therapeutically effective oligonucleotide or oligonucleotide analog, results in the inhibition of expression. For example, hybridization of therapeutically effectively oligonucleotide to a PDGFRA target sequence results in inhibition of PDGFRA expression. Either an antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

One embodiment is an isolated variant PDGFRA polypeptide. Specific examples of such polypeptides comprise an amino acid sequence as set forth in SEQ ID NO: 4, 6, 8, 10, 12, 21, 23, or 25 or a fragment thereof comprising at least 10 contiguous amino acids including the variant site as set forth in position(s) 842 of SEQ ID NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25. Also encompassed herein are the PDGFRA polypeptides defined by the consensus sequence shown in SEQ ID NO: 27, and fragments thereof, particularly fragments that overlap one or more of the noted variable regions.

Also provided are isolated nucleic acid molecules encoding such polypeptides, recombinant nucleic acid molecules comprising a promoter sequence operably linked to these nucleic acid molecules, and cells transformed with such recombinant nucleic acid molecules. Specific examples of nucleic acid molecules comprise a nucleotide sequence as set forth in SEQ ID NO: 3, 5, 7, 9, 11, 20, 22, or 24; or a fragment thereof comprising including the variant nucleic sequence shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2017 and 2072 of SEQ ID NO: 22, or 2916 to 2919 of SEQ ID NO: 24. Also encompassed herein are the PDGFRA nucleic acid molecules defined by the consensus sequence shown in SEQ ID NO: 26, and fragments thereof particularly fragments that overlap one or more of the noted variable regions.

A further embodiment is a method of detecting a biological condition (e.g., neoplasia) associated with an activating PDGFRA mutation in a subject, comprising determining whether the subject has an activating mutation in PDGFRA, and wherein the activating mutation comprises the variant nucleic sequence shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2017 and 2072 of SEQ ID NO: 22, or 2916 to 2919 of SEQ ID NO: 24, or in any one or more of the variable positions indicated in SEQ ID NO: 26. Specific examples of biological conditions contemplated herein are neoplasias that comprise a GIST.

In specific examples of these methods, the method involves reacting at least one PDGFRA molecule contained in a clinical sample from the subject with a reagent comprising a PDGFRA-specific binding agent to form a PDGFRA:agent complex. For instance, the PDGFRA molecule in some instances is a PDGFRA encoding nucleic acid or a PDGFRA protein, and the PDGFRA specific binding agent is a PDGFRA oligonucleotide or a PDGFRA protein specific binding agent In some embodiments, the sample from the subject includes a neoplastic cell, or is prepared from a neoplastic cell or a sample comprising a neoplastic cell.

In some of the provided methods of detecting a biological condition, the PDGFRA molecule is a PDGFRA encoding nucleic acid sequence. Specific examples of such methods involve using an agent that comprises a labeled nucleotide probe. For instance, the nucleotide probe will in some instances have a sequence as shown in SEQ ID NO: 3, 5, 7, 9, 11, 20, 22, or 24, or a fragments of one of these sequences that is at least 15 nucleotides in length, and that includes the sequence shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2017 and 2072 of SEQ ID NO: 22, or 2916 to 2919 of SEQ ID NO: 24.

Specific method embodiments involve in vitro amplifying a PDGFRA nucleic acid prior to detecting the activating PDGFRA mutation. By way of example, the PDGFRA nucleic acid is in some cases in vitro amplified using at least one oligonucleotide primer derived from a PDGFRA-protein encoding sequence, such as the specific oligonucleotide primers listed herein. Other specific oligonucleotide primers comprise at least 15 contiguous nucleotides from SEQ ID NO: 3, 5, 7, 9, 11, 20, 22, or 24. For instance, representative examples of such primers include a sequence as represented by at least 15 contiguous nucleotides shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2017 and 2072 of SEQ ID NO: 22, or 2916 to 2919 of SEQ ID NO: 24. Also included are primers that would be situated across a region including one or more of these variant positions, or any variant position indicated in SEQ ID NO: 26, so that the primers could be used to prime the amplification of a nucleic acid sequence encompassing one or more of the variants.

In other method of detection embodiments, the PDGFRA molecule is a PDGFRA protein, for instance a variant PDGFRA protein comprising a sequence as shown in SEQ ID NO: 4, 6, 8, 10, 12, 21, 23, or 25. In examples of such methods, the complexes are detected by western blot assay, or by ELISA.

Specific examples of PDGFRA-specific binding agents are PDGFRA-specific antibody or a functional fragment thereof, for instance monoclonal antibodies or fragments of monoclonal antibodies. Optionally, such monoclonal antibodies recognize an epitope of a variant PDGFRA (such as an epitope of a variant PDGFRA having an amino acid sequence as shown in SEQ ID NO: 4, 6, 8, 10, 12, 21, 23, or 25) and not (or to a lesser extent) an epitope of wildtype PDGFRA. In particular methods, the antibody is reactive to an epitope including the amino acid sequence shown in position(s) 842 of SEQ ID NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25.

Also provided in the disclosure are kits for detecting an activating PDGFRA mutation in a subject using methods described herein. Examples of such kits are used with protein-detection methods, and include at least one PDGFRA protein specific binding agent. For instance, in specific kits the agent (e.g., an antibody) is capable of specifically binding to an epitope within a PDGFRA variant protein but not to an epitope of wildtype PDGFRA. Thus, some such agents are capable of specifically binding to an epitope within the amino acid sequence shown in SEQ ID NO: 4, 6, 8, 10, 12, 21, 23, or 25, or more particularly antigenic fragments of (a) that comprise the sequence shown in position(s) 842 of SEQ ID NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25. Examples of the protein-detection kits further include a means for detecting binding of the PDGFRA protein binding agent to a PDGFRA polypeptide.

A further embodiment is a kit for determining whether or not a subject (e.g. an animal, or more particularly a mammal) has a biological condition (e.g., neoplasia, such as that comprising a GIST) associated with an activating PDGFRA mutation by detecting a mutant PDGFRA sequence in the subject, which kit includes a container comprising at least one oligonucleotide specific for a PDGFRA mutation sequence; and instructions for using the kit, the instructions indicating steps for performing a method to detect the presence of mutant PDGFRA nucleic acid in the sample; and analyzing data generated by the method, wherein the instructions indicate that presence of the mutant nucleic acid in the sample indicates that the individual has or is predisposed to the biological condition. Optionally, such kits further include at least one container that comprises a detectable oligonucleotide. Specific examples of oligonucleotides (labeled or not) that may be included in these kits will be specific for a PDGFRA mutation sequence. For instance, particular example oligonucleotides comprise a sequence specific for a PDGFRA encoding sequence and containing the specific sequence shown in shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2017 and 2072 of SEQ ID NO: 22, or 2916 to 2919 of SEQ ID NO: 24.

Another specific embodiment is a kit for determining whether or not a subject (e.g. an animal, or more particularly a mammal) has a biological condition (e.g., neoplasia, such as that comprising a GIST) associated with an activating PDGFRA mutation, the kit including a container comprising a PDGFRA mutant specific antibody; a container comprising a negative control sample; and instructions for using the kit, the instructions indicating steps for: performing a test assay to detect a quantity of PDGFRA mutant protein in a test sample of tissue and/or bodily fluid from the subject, performing a negative control assay to detect a quantity of PDGFRA mutant protein in the negative control sample; and comparing data generated by the test assay and negative control assay, wherein the instructions indicate that a quantity of PDGFRA mutant protein in the test sample more than the quantity of PDGFRA mutant protein in the negative control sample indicates that the subject has the biological condition. Specific examples of such kits further include one or more detectable antibodies that bind to the antibody specific for PDGFRA mutant protein (e.g., to be used in detection of the primary antibody).

Yet another embodiment is a method of screening for a compound useful in influencing (for instance, inhibiting or treating) PDGFRA-mediated neoplasia in a mammal, comprising determining if a test compound binds to or interacts with the polypeptide or fragment according to claim 1, and selecting a compound that so binds. In specific examples of this method, binding of the compound inhibits a PDGFRA protein biological activity (e.g., kinase activity). In certain examples, the test compound is applied to a test cell. Compounds identified or selected by such methods, whether or not formulated for use as therapeutic agents, are also contemplated.

Also provided are compositions that include at least one antigenic fragment of a provided PDGFRA variant protein, where the antigenic fragment includes the variant sequence as shown at position(s) 842 of SEQ ID. NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25.

IV. Identification of Activating Mutations of PDGFRA

The inventors have determined that mutations in the platelet derived growth factor receptor alpha (PDGFRA) gene, particularly mutations that produce activated PDGFRA protein, are linked to neoplastic disease such as cancer, and thereby can be used to assess whether a subject suffers from or is susceptible to such a condition. The following examples illustrate this by showing particular examples of mutations that are associated with specific cancers in human subjects. Moreover, guidance is provided about finding other mutations associated with other specific cancers, both in PDGFRA and in other tyrosine kinases. Hence, in its broadest aspect, the disclosure is not limited to particular mutations, but is instead premised on the finding that activating PDGFRA mutations are associated with neoplastic disease.

The PDGFRA protein is a type III receptor tyrosine kinase with homology to KIT, FLT3, CSF1-R, and PDGFR beta (PDGFRB). Although PDGFRA activation has been hypothesized to be involved in certain cancers, most notably gliomas, evidence of genomic activation in human cancer has only recently been reported in two cases of myeloproliferative disease associated with translocation of the BCR and PDGFRA genes. We report herein several novel mutations of PDGFRA resulting in constitutive activation. These mutations were initially discovered in GISTs. Based on experience with KIT and FLT3, it is likely that mutations in other regions of the PDGFRA gene may result in constitutive activation of tyrosine kinase activity. At least in the case of KIT, the site of mutation varies between different diseases (e.g., mastocytosis vs. GIST). Finally, findings reported herein strongly suggest that similar mutations can activate related family members PDGFRB and CSF-1R, and that these mutant proteins are likely to be therapeutic targets in human cancer.

The discovery that mutations in the sequence of PDGFRA predisposes a subject to developing neoplasms also enables a variety of diagnostic, prognostic, and therapeutic methods that are further embodiments. The new appreciation of the role of activated PDGFRA in neoplastic diseases, such as cancers, enables detection of predisposition to or diagnosis of these conditions in a subject. This disclosure also enables early detection of subjects at high risk of these conditions, identification of subjects with particularly severe disease and/or tendency to progress, and in some embodiments detection of resistance or susceptibility of a subject to drug(s). Identification of the activating mutations described herein provides opportunities for prevention and/or early treatment as well as particular treatment selection.

V. Diagnostic and Therapeutic Applications

The presence of PDGFRA gene mutations in GIST strongly suggests that other human cancers will have similar mutations. When present in a cancer, mutant isoforms of PDGFRA represent a therapeutic target for tyrosine kinase inhibitors (TKIs), immunotherapy and other novel targeted approaches. Because PDGFRA gene mutations are not found in all tumors, the selection of patients for therapy targeting mutant PDGFRA isoforms would be optimized by pre-therapy analysis of cancer cells for the presence of PDGFRA gene mutations.

Such analysis can be based on PCR-based assays for these mutations, using for instance one or more of the following approaches: size fractionation by gel electrophoresis, direct sequencing, single-strand conformation polymorphism (SSCP), high pressure liquid chromatography (including partially denaturing HPLC), allele-specific hybridization, amplification refractory mutation screening, PDGFRA mutation screening by oligonucleotide microarray, restriction fragment polymorphism, MALDI-TOF mass spectrometry, or various related technologies (Abu-Duhier et al., *Br. J Haematol.*, 113: 983-988, 2001; Kottaridis et al., *Blood*, 98: 1752-1759, 2001; Choy et al, *Ann. Hum. Gen.*, 63: 383-391, 1999; Grompe, *Nature Genetics*, 5: 111-117, 1993; Perlin & Szabady, *Hum. Mutat.*, 19: 361-373, 2002; Amos & and Patnaik, *Hum. Mutat.*, 19: 324-333, 2002; Cotton, *Hum. Mutat.*, 19: 313-314, 2002; Stirewalt et al., *Blood*, 97: 3589-3595, 2001; Hung et al., *Blood Coagul. Fibrinolysis*, 13: 117-122, 2002; Larsen et al., *Pharmacogenomics*, 2: 387-399, 2001; Shchepinov et al., *Nucleic Acids Res.*, 29: 3864-3872, 2001).

In addition, mutant PDGFRA proteins may be detected through novel epitopes recognized by polyclonal and/or monoclonal antibodies used in ELISA, immunoblotting, flow cytometric, immunohistochemical and other mutant protein detection strategies (Wong et al., *Cancer Res.*, 46: 6029-6033, 1986; Luwor et al., *Cancer Res.*, 61: 5355-5361, 2001; Mishima et al., *Cancer Res.*, 61: 5349-5354, 2001; Ijaz et al., *J. Med. Virol.*, 63: 210-216, 2001). Additionally mutant PDGFRA proteins could be detected by mass spectrometry assays coupled to immunaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of tumor derived proteins separated by two-dimensional polyacrylamide gel electrophoresis (2D-PAGE) (Kiernan et al., *Anal. Biochem.*, 301: 49-56, 2002; Poutanen et al., *Mass Spectrom.*, 15: 1685-1692, 2001). All of these approaches may be used to detect a sequence anomaly or variant of the PDGFRA protein, a relative increase in the phosphorylation of the protein, or an increase in the inherent kinase activity of the protein.

In addition to direct detection of mutant PDGFRA proteins, it is expected that various PDGFRA mutants will result in distinctive signal transduction profiles that could be detected by global gene expression profile or analysis of the activation of various signaling intermediates (e.g., STAT5) (Hofmann et al., *Lancet*, 359: 481-486, 2002).

Utility of this disclosure is highlighted by the correlative studies of response to imatimb mesylate and tumor KIT genotype in patients treated in a phase II trial of imatinib mesylate. In this trial, response to treatment was vastly superior in patients with an imatinib mesylate-sensitive KIT mutation compared with patients with no detectable KIT mutation (Heinrich et al., *Proc. of ASCO*, 21:2A, 2002).

It is believed that the nature and location of PDGFRA mutations affects the sensitivity of the resultant mutant protein to various TKIs. For example, imatinib mesylate is highly active against the kinase activity of wild-type KIT and against activating mutations involving the extracellular, juxtamembrane and TK1 domain (Tuveson et al., *Oncogene*, 20: 5054-5058, 2001; Heinrich et al., *Blood*, 96: 925-932, 2000). In contrast, imatinib mesylate has no clinically useful activity against mutations of the aspartic acid residue at position 816 (e.g. D816V, D816Y, D816F, or D816H) (Ma et al., *Blood*, 99: 1741-1744, 2002). The KIT D816V mutation is homologous to the D842V PDGFRA mutation described in this application. In addition, indolinone and tyrphostin compounds have little or no activity against KIT D816 mutations (or the equivalent D814 residue in murine KIT) but are potent inhibitors of the kinase activity of wild-type and juxtamembrane mutant KIT polypeptides (Ma et al., *Blood*, 99: 1741-1744, 2002; Ikeda et al., *Blood* 96, 99a-99a. Nov. 16, 2000; Ma et al., *J. Invest. Derma.*, 114: 392-394, 2000). However, imatinib mesylate has some activity against other KIT activation loop mutations that involve residues other than aspartic acid 816.

Based on homology to KIT, it is predicted that imatinib mesylate and indolinone compounds would have minimal activity against the D842V PDGFRA mutation but might have clinically useful activity against PDGFRA deletion and/or insertion mutations. In the absence of structural biology information concerning the structure of both wild type and mutant PDGFRA proteins and the site of binding of imatinib mesylate or other TKIs to these proteins, it will be necessary to empirically determine the activity of TKIs against the kinase activity of various mutant PDGFRA proteins. This could be accomplished by cloning cDNAs of the various PDGFRA mutant isoforms and the recombinant protein in prokaryotic or eukaryotic cells (Ma et al., *Blood*, 99: 1741-

1744, 2002; Wood et al., *Cancer Res*, 60: 2178-2189, 2000). Protein expressed in such a manner could be used to determine biochemical activity of existing TKIs and could also be used in high throughput screening of chemical libraries to help identify and optimize pre-clinical development of new compounds against these or other PDGFRA mutant isoforms (Chroeder et al., *J. Med. Chem.*, 44: 1915-1926, 2001; Hamby et al., *J. Med. Chem.*, 40: 2296-2303, 1997; Druker et al., *Nature Medicine*, 2: 561-566, 1996). Prior determination of biochemical potency of specific compounds to different PDGFRA mutations would allow clinical testing of patient specimens for PDGFRA mutations and selection of the appropriate TKI based on the specific mutation and sensitivity associated with that patient's tumor.

Since the novel PDGFRA activating protein variants are only expressed by neoplastic cells, they have the potential to serve as tumor-specific antigens for cytotoxic T-lymphocytes (CTL). Indeed, it has been shown that the unique peptide sequence generated by the BCR-ABL fusion protein characteristic of chronic myelogenous leukemia can serve as the basis of an in vivo immune therapy that utilizes BCR-ABL peptide loaded dendritic cells to generate CTL with BCR-ABL specificity (He et al., *Cancer Immunol. Immunother.*, 50: 3140, 2001).

VI. Prediction of Additional Types of PDGFRA Mutations

Based on experience with KIT and FLT3, it is likely that mutations in other regions of the PDGFRA gene may result in constitutive activation of tyrosine kinase activity. Other likely sites of PDGFRA activating mutations include the proximal extra-cellular, juxtamembrane, and TK1 domains of PDG-FRA (Rubin et al., *Cancer Res*, 61: 8118-8121, 2001; Lux et al., *Am. J. Pathol.*, 156: 791-795, 2000; Abu-Duhier et al., *Br. J. Haematol.*, 111: 190-195, 2000). Indeed, it should be noted that there is one solitary case report of an astrocytoma with a large in-frame deletion of 81 amino acids involving portions of the fourth and fifth immunoglobulin domains of PDGFRA. The tumor in that report had genomic amplification of this PDGFRA mutant allele. The activity of PDGFRA kinase of this mutant isoform was not reported (Kumabe et al., *Oncogene*, 7: 627-633, 1992). Recently Baxter et al. reported a translocation having the structure t(4; 22)(q12;q11) in two cases of atypical chronic myeloid leukemia. Molecular cloning of the translocation revealed fusion of a portion of the BCR gene with part of exon 12 of PDGFRA (Baxter et al., *Hum. Mol. Genet.* 11:1391-1397, 2002). The fusion gene from these translocations is predicted to encode a constitutively activated tyrosine kinase, however no formal biochemical characterization of these proteins was performed (Baxter et al., 2002). Without meaning to be limited to a single interpretation, it is believed that fusion mechanisms of oncogenesis involving PDGFRA (e.g., the BCR-PDGFRA fusions reported by Baxter et al.) likely are a rare occurrence, while point mutation and deletion activations are expected to be more common, and that these two mechanisms are independent of each other.

In KIT, FLT3, and CSF-1R, kinase activation results from a variety of amino acid substitutions at the conserved aspartic acid in the activation loop (D816 KIT, D835 FLT3, and D802 of CSF-1R) (Morley et al., *Oncogene*, 18: 3076-3084, 1999; Moriyama et al., *J. Biol. Chem.*, 271: 3347-3350, 1996). In the case of KIT and FLT3, a number of these substitutions have been found in association with certain malignancies (Ma et al., *Blood*, 99: 1741-1744, 2002; Abu-Duhier et al., *Br. J Haematol.*, 113: 983-988, 2001; Yamamoto et al., *Blood*, 97: 2434-2439, 2001; Longley et al., *Leuk. Res.*, 25: 571-576, 2001; Ning et al., *Leuk. Lymphoma*, 41: 513-522, 2001). To date, no mutations of D802 of CSF-LR have been found in any human cancer. Thus far, we have found only a valine substitution at D842 of PDGFRA, but it can be predicted that a variety of amino acid substitutions at this position of PDG-FRA would be activating. Assuming a single nucleotide change in codon 842, the most likely possible mutations of PDGFRA would be substitution of Asparagine, Tyrosine, Histidine, Valine, Alanine, Glycine, or Glutamic acid for the normal Aspartic acid. We predict that these additional PDG-FRA mutations would also be oncogenic and will be found in one or more human neoplasms.

VII. Prediction of Similar Activating Mutations in PDGFRB

The amino acid sequence of the members of the Type III receptor tyrosine kinase family are highly conserved in the activation loop:

| | |
|---|---|
| DFGLARDIMHDSN | Human PDGFRA |
| DFGLARDIMRDSN | Human PDGFRB |
| DFGLARDIKNDSN | Human KIT |
| DFGLARDIMNDSN | Human CSF-1R |
| DFGLARDIMSDSN | Human FLT3 |

As noted above, amino acid substitutions at the conserved aspartic acid (shown in bold) result in constitutive activation of the tyrosine kinase activity of KIT, PDGFRA or FLT3 in different human malignancies (Rosnet et al., *Blood*, 82: 1110-1119, 1993; Claesson-Welsh et al., *Proc. Natl. Acad. Sci. U.S.A*, 86: 4917-4921, 1989; Gronwald et al., *Proc. Natl. Acad. Sci. U.S.A*, 85: 3435-3439, 1988; Yarden et al., *Nature*, 323: 226-232, 1986). Amino acid substitution at the same aspartic acid of CSF-1R is also activating, but has not yet been found in association with human disease. Based on our findings, we predict that amino acid substitution at the same aspartic acid of PDGFRB would also be activating and that this mutation will be found in some human malignancies.

VIII. Identification of Compounds that Inhibit PDGFRA Variants

This disclosure further relates in some embodiments to novel methods for screening test compounds for their ability to treat, detect, analyze, ameliorate, reverse, and/or prevent neoplasia, especially pre-cancerous lesions. In particular, the present disclosure provides methods for identifying test compounds that can be used to treat, ameliorate, reverse, and/or prevent neoplasia, including precancerous lesions. The compounds of interest can be tested by exposing the novel activating PDGFRA variants described herein to the compounds, and if a compound inhibits one of the PDGFRA variants, the compound is then further evaluated for its anti-neoplastic properties.

One aspect involves a screening method to identify a compound effective for treating, preventing, or ameliorating neoplasia, which method includes ascertaining the compound's inhibition of a provided novel activating PDGFRA variant or another activating PDGFRA variant. In some embodiments, the screening method further includes determining whether the compound inhibits the growth of tumor cells in a cell culture.

By screening compounds in this fashion, potentially beneficial and improved compounds for treating neoplasia can be identified more rapidly and with greater precision than possible in the past.

A. In General

Activating tyrosine kinase mutants, for instance the novel activating PDGFRA variants described herein, are useful to identify compounds that can be used to treat, ameliorate, or prevent neoplasms.

The screening or creation, identification and selection of appropriate high affinity inhibitors of activating PDGFRA mutants can be accomplished by a variety of methods. Broadly speaking these may include, but are not limited to, two general approaches. One approach is to use structural knowledge about the target enzyme to design a candidate molecule with which it will precisely interact. An example would be computer assisted molecular design. A second approach is to use combinatorial or other libraries of molecules, whereby a large library of molecules is screened for affinity with regard to the target enzyme.

Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences tumor growth kinetics. Resolving which of the many aspects of cell growth a test compound affects can be important to the discovery of a relevant target for pharmaceutical therapy. Screening assays based on this technology can be combined with other tests to determine which compounds have growth inhibiting and pro-apoptotic activity.

B. Inhibitor Screening

Some embodiments provided herein involve determining the ability of a given compound to inhibit activating PDGFRA mutants, for instance the ability to specifically inhibit constitutive kinase and/or transforming activities in the PDGFRA D842V, PDGFRA V561D, PDGFRA DIMH842-845, PDGFRA HSDN845-848P, insertion ER561-562, or SPDGHE566-571R, RD841-842KI, or RVIES560-564 deletion mutants described herein. Test compounds can be assessed for their probable ability to treat neoplastic lesions either directly, or indirectly by comparing their activities against compounds known to be useful for treating neoplasia In particular, the compounds are tested for their ability to inhibit a neoplasia that is found to contain an activating PDGFRA mutation.

C. Determining Tyrosine Kinase Influencing Activity

Compounds can be screened for inhibitory or other effects on the activity of the novel activating PDGFRA mutants described herein using an expressed recombinant version of the enzyme, or a homolog or ortholog isolated from another species. Alternatively, cells expressing one of these tyrosine kinases can be treated with a test compound and the effect of the test compound on phosphorylation of a specific target can be determined, for instance using one of the techniques described herein. Additional detail regarding methods for determining tyrosine kinase phosphorylation influencing activity (e.g., inhibition) is provided herein.

D. Determining Whether a Compound Reduces the Number of Tumor Cells

In an alternate embodiment, provided screening methods involve further determining whether the compound reduces the growth of tumor cells, for instance tumor cells known to express an activated tyrosine kinase mutation such as a mutation in PDGFRA.

Various cell lines can be used, which may be selected based on the tissue to be tested. For example, these cell lines include: SW-480—colonic adenocarcinoma; HT-29—colonic adenocarcinoma, A427—lung adenocarcinoma carcinoma; MCF-7—breast adenocarcinoma; and UACC-375—melanoma line; and DU145—prostate carcinoma. Cell lines can also be used that are known to express activated, mutant, tyrosine kinase proteins, for example: GIST882—gastrointestinal stromal tumor cell line expressing KIT tyrosine kinase point mutant; SKBR3—breast carcinoma cell line expressing ERBB2 amplification mutant; and K562—leukemia cell line expressing BCR-ABL tyrosine kinase fusion mutant. Cytotoxicity data obtained using these cell lines are indicative of an inhibitory effect on neoplastic lesions. Certain cell lines are well characterized, and are used for instance by the United States National Cancer Institute (NCI) in their screening program for new anti-cancer drugs. Though a compound may be identified by its ability to inhibit a specific tyrosine kinase activating mutant, its activity likely will not be limited to inhibition of only that mutant protein, thus testing in different cell lines and samples is beneficial to determine the scope of its activity.

By way of example, a test compound's ability to inhibit tumor cell growth in vitro can be measured using the HT-29 human colon carcinoma cell line obtained from ATCC (Bethesda, Md.). HT-29 cells have previously been characterized as a relevant colon tumor cell culture model (Fogh & Trempe, In: *Human Tumor Cells in Vitro*, Fogh (ed.), Plenum Press, N.Y., pp. 115-159, 1975). HT-29 cells are maintained in RPMI media supplemented with 5% fetal bovine calf serum (Gemini Bioproducts, Inc., Carlsbad, Calif.) and 2 mM glutamine, and 1% antibiotic-antimycotic, in a humidified atmosphere of 95% air and 5% $CO_2$ at 37° C. Briefly, HT-29 cells are plated at a density of 500 cells/well in 96 well microtiter plates and incubated for 24 hours at 37° C. prior to the addition of test compound. Each determination of cell number involved six replicates. After six days in culture, the cells are fixed by the addition of cold trichloroacetic acid (TCA) to a final concentration of 10% and protein levels are measured, for instance using the sulforhodamine B (SRB) colorimetric protein stain assay as previously described by Skehan et al. (*J. Natl. Cancer Inst.* 82: 1107-112, 1990). In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

Significant tumor cell growth inhibition greater than about 30% at a dose of 100 μM or below is further indicative that the compound is useful for treating neoplastic lesions. An $IC_{50}$ value may be determined and used for comparative purposes. This value is the concentration of drug needed to inhibit tumor cell growth by 50% relative to the control. In some embodiments, the $IC_{50}$ value is less than 100 μM in order for the compound to be considered further for potential use for treating, ameliorating, or preventing neoplastic lesions.

E. Determining Whether a Test Compound Induces Apoptosis

In other embodiments, screening methods provided herein further involve determining whether the test compound induces apoptosis in cultures of tumor cells.

Two distinct forms of cell death may be described by morphological and biochemical criteria: necrosis and apoptosis. Necrosis is accompanied by increased permeability of the plasma membrane, whereby the cells swell and the plasma membrane ruptures within minutes. Apoptosis is characterized by membrane blebbing, condensation of cytoplasm, and the activation of endogenous endonucleases.

Apoptosis occurs naturally during normal tissue turnover and during embryonic development of organs and limbs. Apoptosis also can be induced by various stimuli, including cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc.

Test compounds can be screened for induction of apoptosis using cultures of tumor cells maintained under conditions as described above. In some examples of such screening methods, treatment of cells with test compounds involves either pre- or post-confluent cultures and treatment for two to seven days at various concentrations of the test compounds. Apoptotic cells can be measured in both the attached and "floating" portions of the cultures. Both are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature (e.g., Piazza et al., *Cancer Res.*, 55:3110-16, 1995). Particular features include collecting both floating and attached cells, identification of the optimal treatment times and dose range for observing apoptosis, and identification of optimal cell culture conditions.

Following treatment with a test compound, cultures can be assayed for apoptosis and necrosis, for instance by fluorescent microscopy following labeling with acridine orange and ethidium bromide. Many methods for measuring apoptotic cells are known to those of ordinary skill in the art; for instance, one method for measuring apoptotic cell number has been described by Duke & Cohen (*Curr. Prot. Immuno.*, Coligan et al., eds., 3.17.1-3.17.1, 1992).

For example, floating and attached cells are collected by trypsinization and washed three times in PBS. Aliquots of cells are then centrifuged. The pellet is resuspended in media and a dye mixture containing acridine orange and ethidium bromide prepared in PBS and mixed gently. The mixture then can be placed on a microscope slide and examined for morphological features of apoptosis.

Apoptosis also can be quantified by measuring an increase in DNA fragmentation in cells that have been treated with test compounds. Commercial photometric EIA for the quantitative in vitro determination of cytoplasmic histone-associated-DNA-fragments (mono- and oligo-nucleosomes) are available (e.g., Cell Death Detection ELISA, Boehringer Mannheim). The Boehringer Mannheim assay is based on a sandwich-enzyme-immunoassay principle, using mouse monoclonal antibodies directed against DNA and histones, respectively. This allows the specific determination of mono- and oligo-nucleosomes in the cytoplasmic fraction of cell lysates. According to the vendor, apoptosis is measured as follows: The sample (cell-lysate) is placed into a streptavidin-coated microtiter plate ("MTP"). Subsequently, a mixture of anti-histone-biotin and anti-DNA peroxidase conjugates is added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

By way of example, SW480 colon adenocarcinoma cells are plated in a 96-well MTP at a density of 10,000 cells per well. Cells are then treated with test compound, and allowed to incubate for 48 hours at 37° C. After the incubation, the MTP is centrifuged and the supernatant is removed. The cell pellet in each well is then resuspended in lysis buffer for 30 minutes. The lysates are then centrifuged and aliquots of the supernatant (i.e., cytoplasmic fraction) are transferred into a streptavidin-coated MTP. Care is taken not to shake the lysed pellets (i.e., cell nuclei containing high molecular weight, un-fragmented DNA) in the MTP. Samples are then analyzed. Fold stimulation (FS=$OD_{max}/OD_{veh}$), an indicator of apoptotic response, is determined for each compound tested at a given concentration. $EC_{50}$ values may also be determined by evaluating a series of concentrations of the test compound.

Statistically significant increases of apoptosis (i.e., greater than 2 fold stimulation at a test compound concentration of 100 µM) are further indicative that the compound is useful for treating neoplastic lesions. Preferably, the $EC_{50}$ value for apoptotic activity should be less than 100 µM for the compound to be further considered for potential use for treating neoplastic lesions. $EC_{50}$ is understood herein to be the concentration that causes 50% induction of apoptosis relative to vehicle treatment.

F. Organ Culture Model Tests

Test compounds identified by the methods described herein can be tested for antineoplastic activity by their ability to inhibit the incidence of preneoplastic lesions in an organ culture system, such as a mammary gland organ culture system. The mouse mammary gland organ culture technique has been successfully used by other investigators to study the effects of known antineoplastic agents such as NSAIDs, retinoids, tamoxifen, selenium, and certain natural products, and is useful for validation of the screening methods provided herein.

By way of example, female BALB/c mice can be treated with a combination of estradiol and progesterone daily, in order to prime the glands to be responsive to hormones in vitro. The animals are sacrificed, and thoracic mammary glands are excised aseptically and incubated for ten days in growth media supplemented with insulin, prolactin, hydrocortisone, and aldosterone. DMBA (7,12-dimethylbenz(a)anthracene) is added to medium to induce the formation of premalignant lesions. Fully developed glands are then deprived of prolactin, hydrocortisone, and aldosterone, resulting in the regression of the glands but not the premalignant lesions.

The test compound is dissolved in, for instance, DMSO and added to the culture media for the duration of the culture period. At the end of the culture period, the glands are fixed in 10% formalin, stained with alum carmine, and mounted on glass slides. The incidence of forming mammary lesions is the ratio of the glands with mammary lesions to glands without lesions. The incidence of mammary lesions in test compound treated glands is compared with that of the untreated glands.

The extent of the area occupied by the mammary lesions can be quantitated by projecting an image of the gland onto a digitation pad. The area covered by the gland is traced on the pad and considered as 100% of the area. The space covered by each of the unregressed structures is also outlined on the digitization pad and quantitated by the computer.

The following examples are provided to illustrate certain particular features and/or embodiments. These examples should not be construed to limit the invention to the particular features or embodiments described.

EXAMPLES

The PDGFRA protein is a type III receptor tyrosine kinase with homology to KIT, FLT3, CSF1-R and PDGFR beta (PDGFRB). Although PDGFRA activation has been suspected to be involved in certain cancers, most notably gliomas, evidence of genomic activation in human cancer has not been previously reported. Provided herein are novel mutations of PDGFRA resulting in constitutive activation. These mutations were initially discovered in GISTs. It is expected that other human cancers will have identical or similar mutations. Based on experience with KIT and FLT3, it is likely that mutations in other regions of the PDGFRA gene may result in constitutive activation of tyrosine kinase activity. At least in the case of KIT, the site of mutation varies between different diseases (e.g., mastocytosis vs. GIST). Finally, these findings strongly suggest that similar mutations can activate related family members PDGFRB and CSF-1R, and that these mutant proteins are likely to be therapeutic targets in human cancer.

Example 1

Activating Mutations in PDGFRA in GISTs

Methods

Three to five mm$^3$ pieces of frozen gastrointestinal stromal tumors were homogenized by 5 to 10 strokes of a Tissue Tearor™ homogenizer in ice-cold lysis buffer (1% Nonidet P-40, 50 mmol/L Tris, pH 8.0, 100 mmol/L sodium fluoride, 30 mmol/L sodium pyrophosphate, 2 mmol/L sodium molybdate, 5 mmol/L ethylenediaminetetraacetic acid, 2 mmol/L sodium vanadate, 10 µg/ml aprotinin 10 µg/ml leupeptin, and 100 µg/ml phenylmethylsulfonyl fluoride) and rocked overnight at 4° C. Residual cell debris was removed by centrifugation (14,000 g) for 20 minutes at 4° C., and the supernatant protein concentrations were determined using the BioRad™ MMT assay. Five hundred microliters (µl) of protein cell lysates (2 mg/ml) were pre-cleared with 20 µl of normal rabbit serum (Zymed Laboratories) and 20 µl of protein A sepharose 4B (Zymed Laboratories) for one hour at 4° C., followed by sequential additions of 20 µl of panRTK antibodies and 20 µl of protein A sepharose 4B with end-to-end rotation for two hours after each addition.

Antibodies used for immunoprecipitation were to KIT (Santa Cruz sc-168), PDGFRA (Santa Cruz sc-338), and panRTK. The panRTK antibodies were raised against combinations of epitopes, each epitope representing one variation of the conserved RTK catalytic domain sequence (#1 YVHRDLAARNIL (SEQ ID NO: 13); #2 CIHRDLAARNVL (SEQ ID NO: 14); #3 FVHRDLAARNCM (SEQ ID NO: 15); #4 LVHRDLAARNVL (SEQ ID NO: 16); #5 FIHRDIAARNCL (SEQ ID NO: 17); and #6 FVHRDLATRNCL (SEQ ID NO: 18)). Each rabbit was injected with three panRTK epitopes, either combination #1 (YVHRDLAARNIL, CIHRDLAARNVL and FVHRDLAARNCM) or combination #2 (LVHRDLAARNVL, FIHRDIAARNCL, and FVHRDLATRNCL). The panRTK antisera were then affinity purified using the same combinations of epitopes against which they had been raised. These panRTK antisera are expected to react with all human and murine RTKs, and with a subset of nonreceptor tyrosine kinase proteins (e.g., JAK family members, SRC family members, FAK/PTK2, ABL, and ARG) that contain the conserved epitope. The panRTK antisera immunoprecipitate individual RTK proteins with lower efficiency than specific kinase antibodies, inasmuch as they react with the entire class of RTK proteins, rather than targeting a specific kinase protein. Typically, 10-20 µg of panRTK antisera are required per immunoprecipitation, in order to purify the same amount of each RTK protein that would typically be immunoprecipitated with 2-4 µg of an optimized, specific antibody.

The immunoprecipitates were then washed three times in lysis buffer, 10 minutes each wash, and once in 10 mM Tris for one hour. After discharging the supernatant, 20 µl of sodium dodecyl sulfate (SDS)-polyacrylamide gel electrophoresis loading buffer was added to the immunoprecipitates, and heated for six minutes at 95° C. The supernatants were then collected and loaded into 4-12% sodium dodecyl sulfate-polyacrylamide gel gradient gels (NuPAGE™, Invitrogen, Carlsbad, Calif.), followed by electrophoretic transfer to nitrocellulose membranes (PROTRAN™, Schleicher & Schuell, Keene, N.H.). Ponceau S solution was used to confirm adequate protein transfer (Sigma Chemical Co., St Louis, Mo.).

The membranes were then blocked overnight using a 1% solution of bovine serum albumin (BSA; Sigma Chemical Co., St Louis, Mo.) in 0.01% phosphate-buffered saline (PBS)-Tris at pH 7.4. Protein tyrosine phosphorylation was detected by staining the membranes with anti-phosphotyrosine monoclonal mouse antibody (PY99; Santa Cruz Biotechnology, Santa Cruz, Calif.; 1: 4000) in 1% BSA/0.01% PBS-Tris solution for 2 hours at room temperature (RT) and with anti-mouse immunoglobulin-horseradish peroxidase goat polyclonal antibody (Amersham Pharmacia Biotech, Piscataway, N.J.; 1:5000). The membranes were then stripped, blocked with 5% non-fat milk/0.01% PBS-Tris solution for one hour at room temperature, and restained with specific antibodies to PDGFRA (Santa Cruz) or KIT (Dako). All antibody reactions were detected by chemiluminescence (ECL; Pierce, Rockford, Ill.).

Tumor tissue was identified on unstained, 5 µm sections by comparison with H&E (Hematoxylin and Eosin) stained slides and was carefully collected using a clean, sterile scalpel blade into a microfuge tube. Dissection by this approach was straightforward and there was minimal contamination from adjacent normal tissue. Dissected tissue was deparaffinized by serial extraction with xylene and ethanol and allowed to air-dry. DNA was extracted using the Qiagen mini-kit (Qiagen, 51304) in accordance with the manufacturer's recommendations.

0.5 µg of purified tumor DNA was subjected to 45 cycles of in vitro amplification by polymerase chain reaction (PCR) using the High Fidelity PCR System (Roche #1732078). Primer pairs for each exon analyzed are listed in Table 1. Negative controls were included in every set of amplifications. In a minority of cases there was insufficient amplified DNA for screening by HPLC after single step amplification and therefore a second round of amplification was performed using nested primers (Table 1).

For the analysis of mutations in PDGFRA exon 18, the following primer pairs used were 1) PDGFRA 181634F (residues 181634 through 181653 of SEQ ID NO: 19) and PDGFRA 181874R (residues 181844 through 181874 of SEQ ID NO: 19) or 2) PDGFRA 181752F (SNP exclusion) (residues 181752 through 181772 of SEQ ID NO: 19) and PDGFRA 181874R The locations of these primers are indicated in FIG. 7A, along with PDGFRA 181671F (residues 181671 through 181690 of SEQ ID NO: 19) and PDGFRA 181862R (residues 181842 through 181862 of SEQ ID NO: 19).

For the analysis of mutations in PDGFRA exon 12, the following primer pairs were used: 1) PDGFRA 170636F (residues 170636 through 170655 of SEQ ID NO: 19) and PDGFRA 170894R (residues 170876 through 170894 of SEQ ID NO: 19), and 2) PDGFRA 170658F (residues 170658 through 170677 of SEQ ID NO: 19) and PDGFRA 170866R (residues 170847 through 170866 of SEQ ID NO: 19).

Five to 20 µl aliquots of the final PCR reaction were screened for mutations on a Transgenomic WAVE HPLC system (D-HPLC; Transgenomic, Inc., Omaha, Nebr.) by running at non-denaturing (50° C.) or partially denaturing temperature (61° C.). D-HPLC-detected mutations were confirmed by two methods: 1) re-amplification of the exon and repeat D-HPLC analysis on a different day; 2) bi-directional sequence analysis on an ABI 377 sequencer using the BigDye terminator kit (Applied Biosciences, Inc.). D-HPLC-detected mutations were confirmed by two methods: 1) re-amplification of the exon and repeat D-HPLC analysis on a different day; 2) bi-directional sequence analysis on an ABI 377 sequencer using the BigDye terminator kit (Applied Biosciences, Inc) (Corless et al., *Am. J. Pathol.* 160, 1567, 2002).

Figure 3:
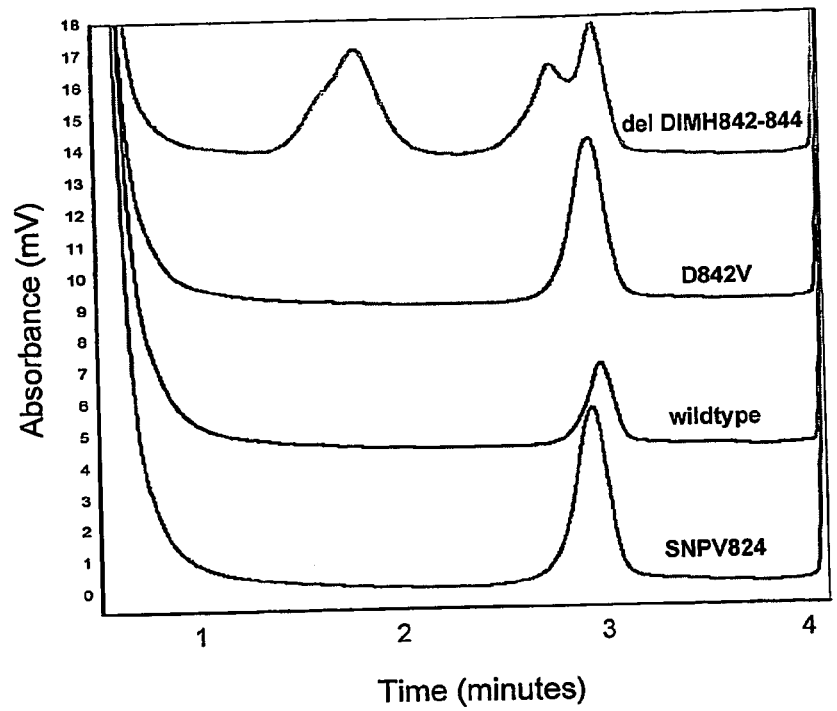
FIG. 3: Detection of PDGFRA activation loop deletion mutations by D-HPLC. DNA was isolated from GISTs and amplified using primer pair PDGFRA 181634F and PDGFRA 181874R as described herein. Amplicons were analyzed at 50° C. using a Transgenomics WAVE™ D-HPLC system Sample 1 has the DIMH deletion described herein. The deletion mutant is readily detected due to the appearance of novel peaks representing species homozygous for the deletion and heteroduplexes of wild-type and deletion mutation.
Figure 4:
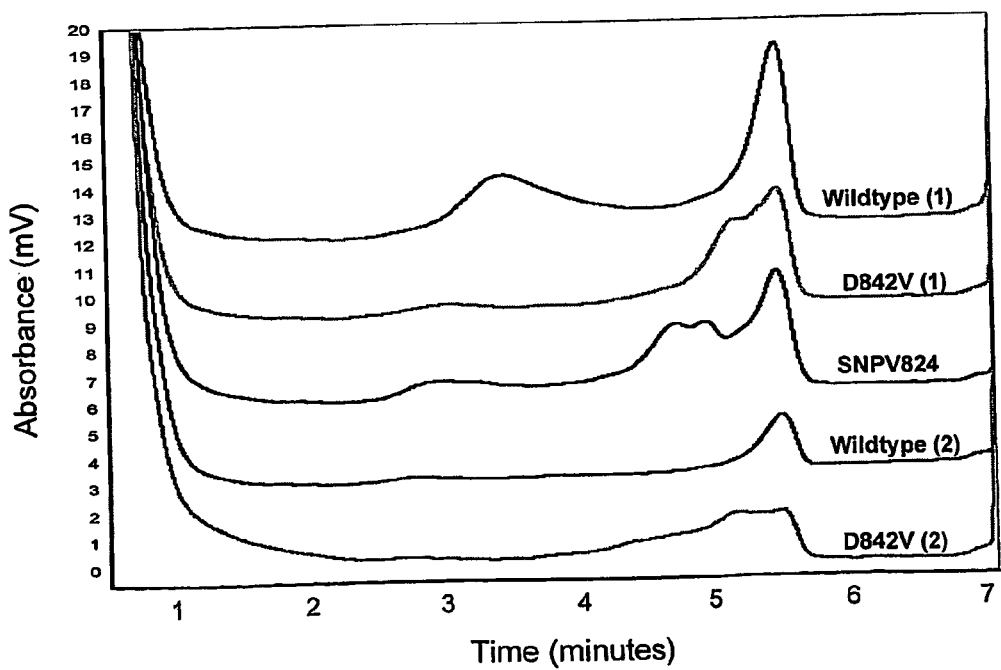
FIG. 4: Detection of PDGFRA activation loop V824V SNP and D842V point mutation by D-HPLC. Amplicons were prepared from GISTs using the PDGFRA 181634F and PDGFRA 18174R primer pair as described above and analyzed at 61° C. using a Transgenomics WAVE™ D-HPLC system. Under partially denaturing conditions, amplicons with the V824V SNP and the D842V point mutation (two examples) elute in a complex pattern. The V824V and D842V amplicons have unique elution profiles. Direct DNA sequencing was performed to confirm that the V824V and D842V amplicons contained the equivalent stretch of PDGFRA nucleotide sequence.
Figure 5:
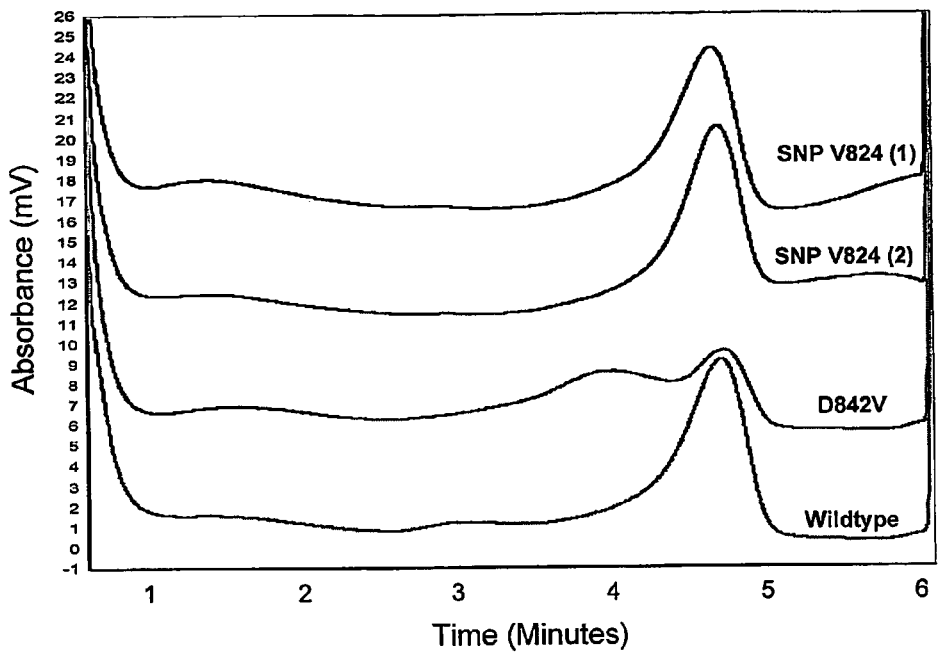
FIG. 5: Detection of D842V point mutation using a primer pair that excludes the V824V SNP. Amplicons were prepared from GISTs using the PDGFRA 181752F (SNP exclusion) and PDGFRA 181874R primer pair as described above and analyzed at 61° C. using a Transgenomics WAVE™ D-HPLC system. Under partially denaturing conditions, amplicons with the D842V point mutation elute in a complex pattern. Note that this amplicon does not contain the V824V SNP and therefore these amplicons have the same elution profile as for wild-type PDGFRA. Direct DNA sequencing was performed to confirm that the amplicons from GISTs with V824V (two examples) versus D842V contained the equivalent stretch of PDGFRA nucleotide sequence.
Figure 6:
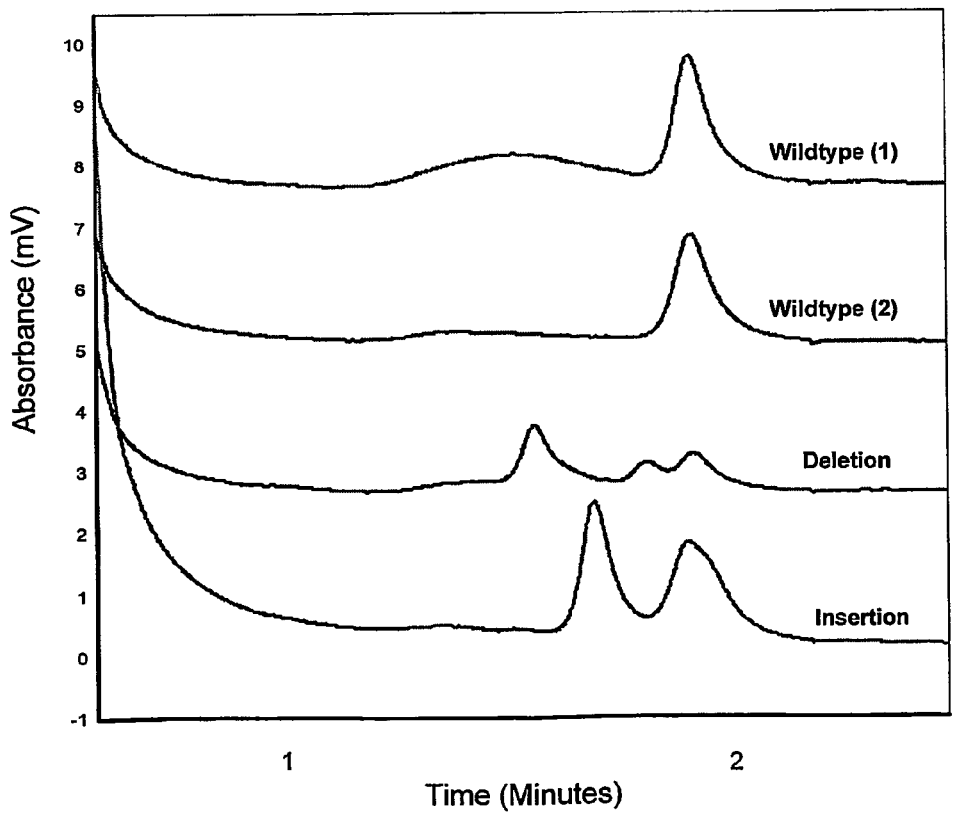
FIG. 6: Detection of PDGFRA Exon 12 Deletion and Insertion Variants. Amplicons were prepared from GISTs using the PDGFRA 170636F and PDGFRA 170894R primer pair as described above and analyzed at 50° C. using a Transgenomics WAVE™ D-HPLC system. The amplicons prepared from the two samples with wild-type PDGFRA exon 12 elute as a single peak. In contrast, amplicons from tumors with either a deletion mutation or an insertion are easily detected due to the appearance of novel peaks representing species homozygous for the deletion and heteroduplexes of wild-type and deletion mutation. In tumors homozygous for these mutations, only a single unique elution peak would be detected. These mutations would identifiable based on the unique peak elution profile compared with wild type amplicons.

Using primer pair 1, it was possible to reliably detect the D842V point mutation as well as the deletion and insertion mutations (FIGS. 3 and 4). However, there is a fairly common single nucleotide polymorphism (SNP) in the PDGFRA gene that is detected using these primer pairs and D-HPLC analysis. This SNP is C2472T (V824V) in PDGFRA cDNA (using numbering system of Genbank Accession No. XM_011186). To exclude this SNP, the mutation detection assay was further optimized by using primer pair 2. The forward primer of this set begins immediately 3' of the SNP and thus the resultant amplicon from this primer set does not contain the SNP. Using this primer pair, the D842V activating mutation can be reliably detected and differentiated from the C2472T (V824V) SNP (FIG. 5).

To further verify the sequence of the PDGFRA exon 18 deletion mutations we cloned the amplification products into pCR®4-TOPO using the TOPO TA cloning kit (Invitrogen, version H) and the ligated plasmids were used to transform competent *E. coli* (OneShot TOP10, Invitrogen). Isolated plasmids were screened for the mutant exon insert by PCR and D-HPLC. Direct sequence analysis of cloned mutant DNA confirmed the presence of an in-frame exon 18 deletion in these cases.

Results

Activation of PDGFRA in GISTs

Using methods described above, RTK activation was assessed in three GISTs lacking apparent KIT oncoproteins. This was accomplished by immunoprecipitating with pan-RTK antibodies, and then immunoblotting with an antibody against phosphotyrosine (FIG. 1). Normally, KIT is heavy phosphorylated in GISTs and is one of the dominant tyrosine phosphorylated protein (FIG. 1).

By sequentially stripping and reprobing the membrane with additional antibodies, the predominant RTK phosphoprotein appeared to be PDGFRA. The possibility of a highly activated PDGFRA protein was then confirmed by immunoprecipitating PDGFRA, using a specific antibody to this protein. These studies revealed that the highly activated phosphoRTK comigrated with equally strongly phosphorylated PDGFRA (FIG. 1). Further, these studies showed that KIT was inactive (nonphosphorylated) in the GISTs with strongly phosphorylated PDGFRA. Therefore, the studies revealed that PDGFRA is highly activated in a subset of GISTs that lack KIT activation, and—furthermore—PDGFRA is the predominant activated RTK, and indeed one of the predominant tyrosine phosphorylated proteins (FIG. 1) in those GISTs.

Figure 2A:
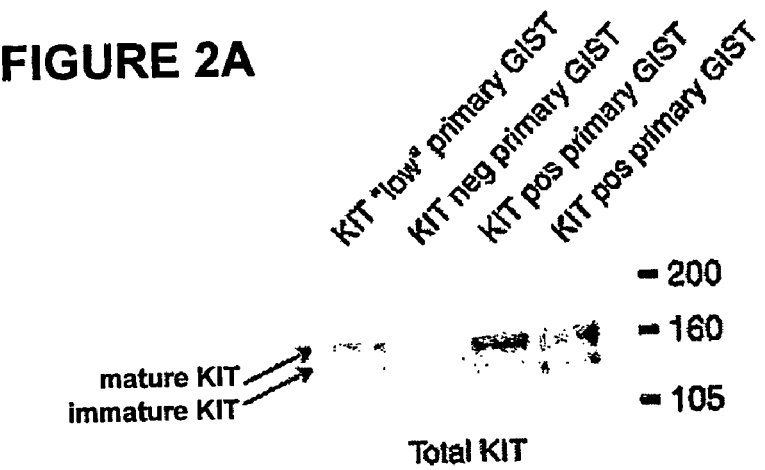
FIG. 2: Sequential staining of GIST immunoblot for KIT (A), phosphoPDGFRA Y754 (B), and total PDGFRA (C). A) The four GISTs analyzed here include two cases with a low (lane 1) or absent (lane 2) level of KIT expression and two cases with strong KIT expression (lanes 3 and 4). B) Strongly phosphorylated PDGFRA (doublet at 150/170 kD) is seen in the GISTs with low-to-absent KIT expression. C) Total PDGFRA is also expressed strongly in the two GISTs with low-to-absent KIT expression. The two GISTs with phosphoPDGFRA have D842V oncogenic mutations.
Figure 2B:
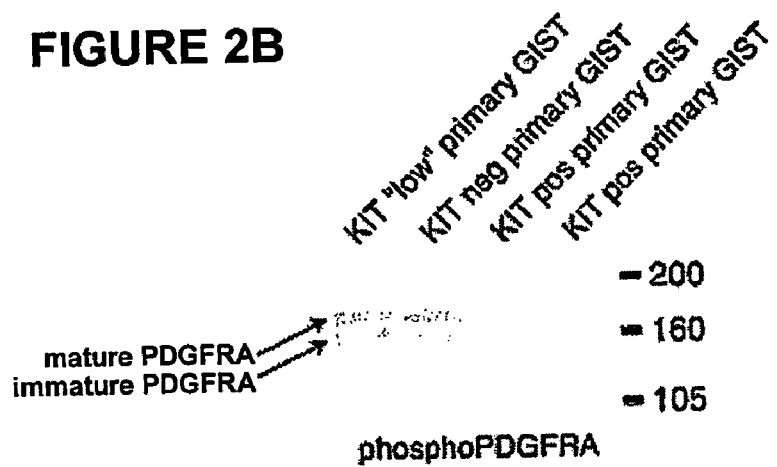
Figure 2C:
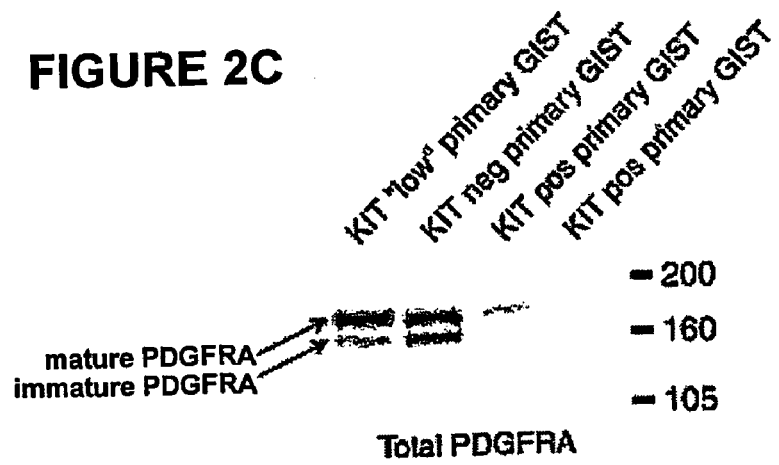

Additional studies indicated that KIT and PDGFRA oncoproteins are typically alternative, rather than synergistic, mechanisms of transformation in GISTs. Therefore, PDGFRA activation and high-level PDGFRA expression can be found in GISTs that have reduced levels of KIT expression (FIG. 2) and that lack KIT genomic oncogenic mutations.

Analysis of Genomic Mechanisms of PDGFRA Activation in GISTs

The large amount of phosphorylated PDGFRA in these GISTs suggested the possibility of activating mutations in the PDGFRA gene. Clues to a possible location for such mutations came from comparisons with other related kinases. As mentioned above, mutation of KIT is common in GISTs (approximately 80-90% of cases); mutations also occur in seminoma (25% of cases), mastocytosis (95%+) and rarely in cases of Acute myeloid leukemia (AML) (Heinrich et al., *J. Clin. Oncol.*, 20: 1692-1703, 2002; Rubin et al., *Cancer Res*, 61: 8118-8121, 2001; Lux et al., *Am. J. Pathol.*, 156: 791-795, 2000). KIT mutations in GIST are found most commonly in the juxtamembrane and extracellular domains, as well as the first portion of the tyrosine kinase domain, whereas mutations in mastocytosis and seminoma are found in the activation loop located in the second portion of the tyrosine kinase domain (Hirota et al., *J. Pathol.*, 193: 505-510, 2001; Lasota et al., *Am. J Pathol.*, 157: 1091-1095, 2000; Lux et al., *Am. J. Pathol.*, 156: 791-795, 2000; Ma et al., *Blood*, 99: 1741-1744, 2002; Beghini et al., *Blood*, 95: 726-727, 2000; Tian et al., *Am. J. Pathol.*, 154: 1643-1647, 1999; Longley et al., *Nature Genetics*, 12: 312-314, 1996). Somatic mutation of FLT3 has also been associated with certain human malignancies. Mutation of FLT3 has been reported in approximately 20-40% of cases of AML and rarely in Acute Lymphoblastic Leukemia. In AML, mutations of FLT3 are most commonly found in the juxtamembrane domain and less commonly in the activation loop (Abu-Duhier et al., *Br. J Haematol.*, 113: 983-988, 2001; Kottaridis et al., *Blood*, 98: 1752-1759, 2001; Meshinchi et al., *Blood*, 97: 89-94, 2001; Yamamoto et al., *Blood*, 97: 2434-2439, 2001).

Based on the homology of PDGFRA to KIT and FLT3, we hypothesized that mutation of the PDGFRA activation loop in a subset of GISTs might result in activation of tyrosine kinase activity. Thus, we developed a polymerase chain reaction (PCR) based assay to test for mutations of the PDGFRA activation loop (exon 18) (see FIG. 7). Genomic DNA was purified from formalin fixed, paraffin embedded archival pathology specimens or fresh frozen tumor specimens that were obtained in accordance with the rules and regulations of both OHSU and the Portland VA Medical Center. Amplification of PDGFRA exon 18 was performed using primer sets described in the methods section below. Amplicons were analyzed using a Transgenomic WAVE HPLC instrument using both non-denaturing (50° C.) and partially denaturing temperatures (58° C.). Amplicons with abnormal HPLC elution profiles were directly sequenced.

Two different classes of PDGFRA activation loop mutations were identified in GISTs using this technique—point mutation and small in-frame deletions (FIG. 3). These amplicons have been directly sequenced and/or cloned into plasmids and the resultant clones sequenced. The most common mutation is a change of the conserved aspartic acid at position 842 of PDGFRA to valine (D842V). This aspartic acid is highly conserved in kinases related to PDGFRA. The homologous mutation D816V of KIT is observed in mastocytosis and seminoma, while the homologous D835V mutation of FLT3 is found in some cases of AML.

Two different in-frame deletions of PDGFRA exon 18 were identified in GISTs. The first is deletion of genomic nucleotides 53264-53275, which encode PDGRA amino residues 842-845 (DIMH). In this mutation the conserved aspartic residue at position 842 is substituted by the aspartic acid at position 846 that is immediately 3' of the deletion. The second deletion found to date is a deletion with insertion of a single cytosine at the 3' end of the deletion—the result is deletion of residues 845-848 (HDSN) with generation of a novel proline residue that follows the normal methionine residue at position 844. Thus, these two deletions are partially overlapping. These deletions are novel; it is believed that they result in constitutive activation of the tyrosine kinase activity of PDGFRA. This is based on prior observations that in-frame deletions or insertion in the activation loop of the related FLT3 RTK are known to result in constitutive activation of tyrosine kinase activity (Abu-Duhier et al., *Br. J Haematol.*, 113: 983-988, 2001); and our observations that PDGFRA is strongly activated in protein lysates from GIST tumors that harbor these PDGFRA mutations, but not in GISTs expressing wild-type PDGFRA (see FIGS. 1 and 2).

We have also found one GIST with an acquired mutation of exon 12 of PDGFRA, specifically insertion of GAGAGG at nucleotide position 1681 of PDGFRA. This mutation results in insertion of novel amino acid residues ER between amino acids 560 and 561. Based on analogy with similar length mutations in FLT3 and KIT, this inframe insertion would be predicted to result in constitutive activation of PDGFRA kinase activity. We have also found a second example of an insertion/deletion mutation in exon 12 in a GIST: SPDGHE566-571R.

TABLE 2

| Mutation | Cases (% total) |
|---|---|
| D842V | 10 (24.4%) |
| Exon 18 Deletion | 2 (4.9%) |
| Exon 12 Insertion/Deletion | 2 (4.9%) |
| No mutation | 27 (65.9%) |
| Total | 41 (100.0%) |

In our analysis of GISTs to date, we have found KIT mutation and PDGFRA mutation to be mutually exclusive. That is, PDGFRA mutations have only been found in GISTs without any detectable KIT mutation. Based on our studies to date, we believe that mutations of PDGFRA are found in approximately 34-35% of KIT wild-type GISTs or 3-6% of all GISTs.

Example 2

Other Activating PDGFRA Mutations

With the provision herein of the correlation between activating PDGFRA mutations and neoplastic disease, the isolation and identification of additional activating PDGFRA mutations is enabled. Any conventional method for the identification of genetic mutations in a population can be used to identify such additional mutations.

For instance, existing populations (e.g., human populations) are assessed for the presence of neoplastic or tumorous cells, and individuals within the population are genotyped as relates to a PDGFRA sequence. These PDGFRA sequences are then compared to a reference PDGFRA sequence, such as the alleles described herein, to determine the presence of one or more variant nucleotide positions. Once variant nucle-

TABLE 1

| Genotype | DNA sequence (top line)<br>Translation (bottom line) |
|---|---|
| *PDGFRA* Wild type<br>(Ac. No. XM_011186;<br>SEQ ID NOs: 1 and 2) | 2906\* GGCCTGGCCAGAGACATCATGCATGATTCGAACTATGTG<br>838  G  L  A  R  D  I  M  H  D  S  N  Y  V |
| D842V<br>(SEQ ID NOs: 3 and 4) | 2906  GGCCTGGCCAGAGTCATCATGCATGATTCGAACTATGTG<br>838  G  L  A  R  V  I  M  H  D  S  N  Y  V |
| Deletion of DIMH842-845<br>(SEQ ID NOs: 5 and 6) | 2906  GGCCTGGCCAGA------------GATTCGAACTATGTG<br>838  G  L  A  R  -  -  -  -  D  S  N  Y  V |
| Deletion of HSDN845-848P<br>(SEQ ID NOs: 7 and 8) | 2906  GGCCTGGCCAGAGACATCATGC---------CCTATGTG<br>838  G  L  A  R  D  I  M  P          Y  V |
| *PDGFRA* Wild type | 2060  GAAATTCGCTGGAGGGTCATTGAATCA<br>556  E  I  R  W  R  V  I  E  S |
| PDGFRA Insertion ER561-562<br>(SEQ ID NOs: 9 and 10) | 2060  GAAATTCGCTGGAGGGAGAGGGTCATTGAATCA<br>556  E  I  R  W  R  E  R  V  I  E  S |
| *PDGFRA* Wild type | 2081  GAATCAATCAGCCCGGATGGACATGAATATATT<br>563  E  S  I  S  P  D  G  H  E  Y  I |
| PDGFRA Deletion SPDGHE566-571R<br>(SEQ ID NOs: 11 and 12) | 2081  GAATCAATC---------------CCGTATATT<br>563  E  S  I  -  -  -  -  -  -  R  Y  I |

\*Numbering as in SEQ ID NO: 1 and SEQ ID NO: 2.

otides are identified, statistical analysis of the population is used to determine whether these variants are correlated with neoplasm or tumorous growth or development.

By way of example, it is predicted that additional mutations will be identified at least in positions similar to those identified herein. SEQ ID NO: 26 shows a nucleic acid consensus sequence for the PDGFRA activating mutations discussed herein; the consensus polypeptide encoded by SEQ ID NO: 26 is shown in SEQ ID NO: 27. Explicitly contemplated herein are additional PDGFRA mutations and variant molecules that occur in the variable positions indicated in these consensus sequences, alone or in combination with one or more of the mutations described herein. Included are insertion and deletion mutations, such as examples provided herein, as well as point mutations.

Example 3

Clinical Uses of PDGFRA Variants

To perform a diagnostic test for the presence or absence of a mutation in a PDGFRA sequence of an individual, a suitable genomic DNA-containing sample from a subject is obtained and the DNA extracted using conventional techniques. For instance, a blood sample, a buccal swab, a hair follicle preparation, or a nasal aspirate is used as a source of cells to provide the DNA sample; similarly, a surgical specimen, biopsy, or other biological sample containing genomic DNA could be used. It is particularly contemplated that tumor biopsies or tumor DNA found in plasma or other blood products can serve as a source. The extracted DNA is then subjected to amplification, for example according to standard procedures. The allele of the single base-pair mutation is determined by conventional methods including manual and automated fluorescent DNA sequencing, primer extension methods (Nildforov, et al., *Nucl Acids Res.* 22:4167-4175, 1994), oligonucleotide ligation assay (OLA) (Nickerson et al., *Proc. Natl. Acad. Sci. USA* 87:8923-8927, 1990), allele-specific PCR methods (Rust et al., *Nucl. Acids Res.* 6:3623-3629, 1993), RNase mismatch cleavage, single strand conformation polymorphism (SSCP), denaturing gradient gel electrophoresis (DGGE), Taq-Man™, oligonucleotide hybridization, and the like. Also, see the following U.S. Patents for descriptions of methods or applications of polymorphism analysis to disease prediction and/or diagnosis: U.S. Pat. No. 4,666,828 (RFLP for Huntington's); U.S. Pat. No. 4,801,531 (prediction of atherosclerosis); U.S. Pat. No. 5,110,920 (HLA typing); U.S. Pat. No. 5,268,267 (prediction of small cell carcinoma); and U.S. Pat. No. 5,387,506 (prediction of dysautonomia).

Examples of activating tyrosine kinase mutations are the PDGFRA D842V and V561D point mutations, the ER561-562 in frame insertion, and the DIMH842-845, HDSN845-848P, RD841-842KI, RVIES560-564, and SPDGHE566-571R in-frame deletions. In addition to these particular mutations, other mutations can be detected that may be associated with variable predisposition to development of a neoplastic disease or likelihood of having a tumor, and used in combination with the disclosed PDGFRA mutations, to predict the probability that a subject will develop neoplasia, or have a tumor with drug responsive tyrosine kinase activity.

The activating mutations of the present disclosure can be utilized for the detection of and differentiation of, individuals who are homozygous and heterozygous for activating and/or drug responsive variants. The value of identifying individuals who carry an activating allele of PDGFRA (i.e., individuals who are heterozygous or homozygous for an allele that contains the D842V or V561D point mutation, the ER561-562 in frame insertion, or one of the DIMH842-845, HDSN845-848P, RD841-842KI, RVIES560-564, or SPDGHE566-571R in-frame deletions, or any combination thereof, or another mutation in one or proximal to one of the variable regions indicated in SEQ ID NOs: 26 or 27) is that these individuals could then initiate customized therapies (such as specific drug therapies that inhibit the mutant, activated, PDGFRA), or undergo more aggressive treatment of the condition, and thereby beneficially alter its course.

Example 4

Mutation Gene Probes and Markers

Sequences surrounding and overlapping single base-pair mutations and deletions and insertions in the PDGFRA gene can be useful for a number of gene mapping, targeting, and detection procedures. For example, genetic probes can be readily prepared for hybridization and detection of the D842V or the V561D point mutation, the ER561-562 in frame insertion, or one of the DIMH842-845, HDSN845-848P, RD841-842KI, RVIES560-564, or SPDGHE566-571R in-frame deletion mutations. As will be appreciated, probe sequences may be greater than about 12 or more oligonucleotides in length and possess sufficient complementarity to distinguish between the variant sequence and the wildtype, for instance, between the Valine (at amino acid residue 842 in the D842V activating allele) and Aspartic acid (in the wildtype allele). Similarly, sequences surrounding and overlapping any of the specifically disclosed mutations (or other mutations found in accordance with the present teachings, including those encompassed in or proximal to the variable regions indicated in SEQ ID NOs: 26 or 27), or longer sequences encompassing for instance the entire length of exon 18 of PDGFRA, or portions thereof, can be utilized in allele specific hybridization procedures. A similar approach can be adopted to detect other PDGFRA mutations.

Sequences surrounding and overlapping a PDGFRA mutation, or any portion or subset thereof that allows one to identify the mutations, are highly useful. Thus, another embodiment provides a genetic marker predictive of the one or more of the D842V or the V561D point mutation, the ER561-562 in frame insertion, or the DIMH842-845, HDSN845-848P, RD841-842KI, RVIES560-564, or SPDGHE566-571R in-frame deletions of PDGFRA, comprising a partial sequence of the human genome including at least about 10 contiguous nucleotide residues such as those shown in Table 1 or Table 3, and sequences complementary therewith.

Example 5

Detecting Single Nucleotide Alterations

PDGFRA single nucleotide alterations, whether categorized as SNPs or new mutations (such as that giving rise to the D842V variant) can be detected by a variety of techniques. Clinically relevant PDGFRA single nucleotide alterations include those arising as somatic mutations—i.e., restricted to the neoplastic cells—as well as those that are present constitutionally in both normal and neoplastic cells in a given individual. The constitutional single nucleotide alterations can arise either from new germline mutations, or can be inherited from a parent who possesses a SNP or mutation in their own germline DNA. The techniques used in evaluating either somatic or germline single nucleotide alterations include allele-specific oligonucleotide hybridization (ASOH) (Stoneking et al., *Am. J. Hum. Genet.* 48:370-382, 1991) which involves hybridization of probes to the sequence, stringent washing, and signal detection. Other new methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*BioTechniques* 19:442-447, 1995). Alternatively, ASOH with single- or dual-labeled probes can be merged with PCR, as in the 5'-exonuclease assay (Heid et al., *Genome Res.* 6:986-994, 1996), or with molecular beacons (as in Tyagi and Kramer, *Nat. Biotechnol.* 14:303-308, 1996).

Another technique is dynamic allele-specific hybridization (DASH), which involves dynamic heating and coincident monitoring of DNA denaturation, as disclosed by Howell et al. (*Nat. Biotech.* 17:87-88, 1999). A target sequence is amplified by PCR in which one primer is biotinylated. The biotinylated product strand is bound to a streptavidin-coated microtiter plate well, and the non-biotinylated strand is rinsed away with alkali wash solution. An oligonucleotide probe, specific for one allele, is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

A variety of other techniques can be used to detect the mutations in DNA. Merely by way of example, see U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods.

Example 6

Detection of PDGFRA Nucleic Acid Level(s)

Individuals carrying activating mutations in the PDGFRA gene, or having amplifications or heterozygous or homozygous deletions of the PDGFRA gene, may be detected at the DNA or RNA level with the use of a variety of techniques. The detection of point mutations, or SNPs, was discussed above; in the following example, techniques are provided for detecting the level of PDGFRA nucleic acid molecules in a sample.

For such diagnostic procedures, a biological sample of the subject (an animal, such as a mouse or a human), which biological sample contains either DNA or RNA derived from the subject, is assayed for a mutated, amplified or deleted PDGFRA encoding sequence, such as a genomic amplification of the PDGFRA gene or an over- or under-abundance of a PDGFRA mRNA. Suitable biological samples include samples containing genomic DNA or mRNA obtained from subject body cells, such as those present in peripheral blood, urine, saliva, tissue biopsy, surgical specimen, amniocentesis samples and autopsy material. The detection in the biological sample of a mutant PDGFRA gene, a mutant PDGFRA RNA, or an amplified or homozygously or heterozygously deleted PDGFRA gene, may be performed by a number of methodologies.

Gene dosage (copy number) can be important in disease states, and can influence mRNA and thereby protein level; it is therefore advantageous to determine the number of copies of PDGFRA nucleic acids in samples of tissue. Probes generated from the encoding sequence of PDGFRA (PDGFRA probes or primers) can be used to investigate and measure genomic dosage of the PDGFRA gene.

Appropriate techniques for measuring gene dosage are known in the art; see for instance, U.S. Pat. No. 5,569,753 ("Cancer Detection Probes") and Pinkel et al. (*Nat. Genet.* 20:207-211, 1998) ("High Resolution Analysis of DNA Copy Number Variation using Comparative Genomic Hybridization to Microarrays").

Determination of gene copy number in cells of a patient-derived sample using other techniques is known in the art. For example, PDGFRA amplification in immortalized cell lines as well as uncultured cells taken from a subject can be carried out using bicolor FISH or chromogenic in situ hybridization (CISH) analysis. FISH or CISH evaluations of PDGFRA amplification can be performed in various cell and tissue preparations that include, but are not limited to, venipuncture, biopsy, fine needle aspiration, and cell scraping. Such clinical materials can be analyzed in various forms, which include, but are not limited to, cytogenetic preparations; touch preparations from fresh or frozen biopsies; disaggregated cells from fresh, frozen or paraffin-embedded materials; histological sections from frozen or paraffin-embedded materials; and cytological preparations including cytospins and cell smears (Xiao et al., *Am J Pathol*; Hsi et al. *Pathol.* 147:896-904; 1995; Davison et al., *Am. J. Pathol.* 153:1401-1409; 1998. By way of example, interphase FISH analysis of immortalized cell lines can be carried out as previously described (Barlund et al., *Genes Chromo. Cancer* 20:372-376, 1997). The hybridizations can be evaluated using a Zeiss fluorescence microscope. By way of example, approximately 20 non-overlapping nuclei with intact morphology based on DAPI counterstain are scored to determine the mean number of hybridization signals for each test and reference probe.

Likewise, FISH can be performed on tissue microarrays, as described in Kononen et al., *Nat. Med.* 4:844-847, 1998. Briefly, consecutive sections of the array are deparaffinized, dehydrated in ethanol, denatured at 74° C. for 5 minutes in 70% formamide/2×SSC, and hybridized with test and reference probes. The specimens containing tight clusters of signals or >3-fold increase in the number of test probe as compared to chromosome 17 centromere in at least 1.0% of the tumor cells may be considered as amplified. Microarrays using various tissues can be constructed as described in WO 99/44063 and WO 99/44062.

Overexpression of the PDGFRA gene can also be detected by measuring the cellular level of PDGFRA-specific mRNA. mRNA can be measured using techniques well known in the art, including for instance Northern analysis, RT-PCR and mRNA in situ hybridization.

Example 7

Expression of PDGFRA Polypeptides

The expression and purification of proteins, such as the PDGFRA protein, can be performed using standard laboratory techniques. After expression, purified PDGFRA protein may be used for functional analyses, antibody production, diagnostics, and patient therapy. Furthermore, the DNA sequence of the PDGFRA cDNA can be manipulated in studies to understand the expression of the gene and the function of its product. Mutant forms of the human PDGFRA gene may be isolated based upon information contained herein, and may be studied in order to detect alteration in expression patterns in terms of relative quantities, tissue specificity and functional properties of the encoded mutant PDGFRA protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to PDGFRA proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coli* in large amounts for functional studies. Methods and plasmid vectors for producing fusion proteins and intact native proteins in bacteria are described in Sambrook et al. (In *Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). Fusion proteins may be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and animals (Pursel et al., *Science* 244:1281-1288, 1989), which cell or organisms are rendered transgenic by the introduction of the heterologous PDGFRA cDNA.

For expression in mammalian cells, the cDNA sequence may be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J.* 1:841, 1982), lipofection (Felgner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Tyrosine kinase encoding sequences can also be delivered to target cells in vitro via non-infectious systems, for instance liposomes.

These eukaryotic expression systems can be used for studies of PDGFRA encoding nucleic acids and mutant forms of these molecules, the PDGFRA protein and mutant forms of this protein. Such uses include, for example, the identification of regulatory elements located in the 5' region of the PDGFRA gene on genomic clones that can be isolated from human genomic DNA libraries using the information contained in the present disclosure. The eukaryotic expression systems may also be used to study the function of the normal complete protein, specific portions of the protein, or of naturally occurring or artificially produced mutant proteins.

Using the above techniques, the expression vectors containing the PDGFRA gene sequence or cDNA, or fragments or variants or mutants thereof, can be introduced into human cells, mammalian cells from other species or non-mammalian cells as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

The present disclosure thus encompasses recombinant vectors that comprise all or part of the PDGFRA gene or cDNA sequences, for expression in a suitable host. The PDGFRA DNA is operatively linked in the vector to an expression control sequence in the recombinant DNA molecule so that the PDGFRA polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this disclosure, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant PDGFRA DNA sequences, similar systems are employed to express and produce the mutant product. In addition, fragments of the PDGFRA protein can be expressed essentially as detailed above. Such fragments include individual PDGFRA protein domains or sub-domains, as well as shorter fragments such as peptides. PDGFRA protein fragments having therapeutic properties may be expressed in this manner also.

Example 8

Production of PDGFRA Protein Specific Binding Agents

Monoclonal or polyclonal antibodies may be produced to either the normal PDGFRA protein or mutant forms of this protein, for instance particular portions that contain a mutation and therefore may provide a distinguishing epitope. Optimally, antibodies raised against these proteins or peptides would specifically detect the protein or peptide with which the antibodies are generated. That is, an antibody generated to the PDGFRA protein or a fragment thereof would recognize and bind the PDGFRA protein and would not substantially recognize or bind to other proteins found in human cells. In some embodiments, an antibody is specific for (or measurably preferentially binds to) an epitope in a variant protein versus the wildtype protein, or vice versa, as discussed more fully herein.

The determination that an antibody specifically detects the PDGFRA protein is made by any one of a number of standard immunoassay methods; for instance, the western blotting technique (Sambrook et al., In *Molecular Cloning: A Laboratory Manual*, CSHL, New York, 1989). To determine that a given antibody preparation (such as one produced in a mouse) specifically detects the PDGFRA protein by western blotting, total cellular protein is extracted from human cells (for example, lymphocytes) and electrophoresed on a sodium dodecyl sulfate-polyacrylamide gel. The proteins are then transferred to a membrane (for example, nitrocellulose) by western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the PDGFRA protein will, by this technique, be shown to bind to the PDGFRA protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-PDGFRA protein binding.

Substantially pure PDGFRA protein or protein fragment (peptide) suitable for use as an immunogen may be isolated from the transfected or transformed cells as described above. Concentration of protein or peptide in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the PDGFRA protein identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein (Example 7), which can be unmodified or modified to enhance immunogenicity. Effective polyclonal antibody production is affected by many factors related both to the antigen and the host species. For example, small molecules tend to be less immunogenic than others and may require the use of carriers and adjuvant Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against the PDGFRA protein or peptides is to use one or more synthetic peptides synthesized on a commercially available peptide synthesizer based upon the predicted amino acid sequence of the PDGFRA protein or peptide. Polyclonal antibodies can be generated by injecting these peptides into, for instance, rabbits or mice.

D. Antibodies Raised by Injection of PDGFRA Encoding Sequence

Antibodies may be raised against PDGFRA proteins and peptides by subcutaneous injection of a DNA vector that expresses the desired protein or peptide, or a fragment thereof, into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the PDGFRA encoding sequence under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample; or for immunolocalization of the PDGFRA protein.

In addition, antibodies to PDGFRA are commercially available. See, for instance, rabbit anti-PDGFRA, catalog no. sc-338, from Santa Cruz Biotechnology Inc. (Santa Cruz, Calif.) and rabbit ant-PDGFR, catalog no. 6495, from Upstate Biotechnology (Waltham, Mass.).

For administration to human patients, antibodies, e.g. PDGFRA-specific monoclonal antibodies, can be humanized by methods known in the art. Antibodies with a desired binding specificity can be commercially humanized (Scotgene, Scotland, UK; Oxford Molecular, Palo Alto, Calif.).

E. Antibodies Specific for Mutant PDGFRA

With the provision of several activating variant PDGFRA proteins, the production of antibodies that specifically recognize these proteins (and peptides derived therefrom) is enabled. In particular, production of antibodies (and fragments and engineered versions thereof) that recognize at least one PDGFRA variant with a higher affinity than they recognize wild type PDGFRA is beneficial, as the resultant antibodies can be used in diagnosis and treatment, as well as in study and examination of the PDGFRA proteins themselves.

In particular embodiments, it is beneficial to generate antibodies from a peptide taken from a mutation or variation-specific region of the PDGFRA protein. By way of example, such regions include a portion or all of exon 18 of PDGFRA, or a portion or all of exon 12. More particularly, it is beneficial to raise antibodies against peptides of four or more contiguous amino acids that overlap the mutations identified in SEQ ID NO: 4, 6, 8, or 25, and particularly which comprise at least four contiguous amino acids including the residue(s) shown in position(s) 842 of SEQ ID NO: 4, positions 841 and 842 of SEQ ID NO: 6, positions 846 and 847 of SEQ ID NO: 8, or positions 841 and 842 of SEQ ID NO: 25.

Similarly, it is beneficial to raise antibodies against peptides of 4 or more contiguous amino acids that overlap the mutations identified in SEQ ID NO: 10, 12, 21, or 23, and particularly which comprise at least four contiguous amino acids including the residue(s) shown in position(s) 561 and 562 of SEQ ID NO: 10 positions 565 and 566 of SEQ ID NO: 12, position 561 of SEQ ID NO: 21, or positions 559 and 560 of SEQ ID NO: 23.

Longer peptides also can be used, and in some instances will produce a stronger or more reliable immunogenic response. Thus, it is contemplated in some embodiments that more than four amino acids are used to elicit the immune response, for instance, at least 5, at least 6, at least 8, at least 10, at least 12, at least 15, at least 18, at least 20, at least 25, or more, such as 30, 40, 50, or even longer peptides. Also, it will be understood by those of ordinary skill that it is beneficial in some instances to include adjuvants and other immune response enhancers, including passenger peptides or proteins, when using peptides to induce an immune response for production of antibodies.

Embodiments are not limited to antibodies that recognize epitopes containing the actual mutation identified in each variant. Instead, it is contemplated that variant-specific antibodies also may each recognize an epitope located anywhere throughout the PDGFRA variant molecule, which epitopes are changed in conformation and/or availability because of the activating mutation. Antibodies directed to any of these variant-specific epitopes are also encompassed herein.

By way of example, the following references provide descriptions of methods for making antibodies specific to mutant proteins: Hills et al., (*Int. J. Cancer,* 63: 537-543, 1995); Reiter & Maihle (*Nucleic Acids Res.,* 24: 4050-4056, 1996); Okamoto et al. (*Br. J. Cancer,* 73: 1366-1372, 1996); Nakayashiki et al., (*Jpn. J. Cancer Res.,* 91: 1035-1043, 2000); Gannon et al. (*EMBO J.,* 9: 1595-1602, 1990); Wong et al. (*Cancer Res.,* 46: 6029-6033, 1986); and Carney et al. (*J. Cell Biochem.,* 32: 207-214, 1986). Similar methods can be employed to generate antibodies specific to specific PDGFRA variants.

Example 9

Protein-Based Diagnosis

An alternative method of diagnosing PDGFRA mutation, gene amplification, or deletion as well as abnormal PDGFRA expression, is to quantitate the level of PDGFRA protein, and/or to evaluate activation (phosphorylation) of PDGFRA in the cells of an individual. The oncogenic, activating mutations disclosed herein result in constitutive PDGFRA activation as manifested by PDGFRA tyrosine phosphorylation. Therefore, antibodies specific for phosphotyrosine-containing PDGFRA epitopes can be used to routinely detect such mutant, activated, PDGFRA proteins in any mammalian cell type. Such evaluations can be performed, for example, in lysates prepared from cells, in fresh or frozen cells, in cells that have been smeared or touched on glass slides and then either fixed and/or dried, or in cells that have been fixed, embedded (e.g., in paraffin), and then prepared as histological sections on glass slides. This diagnostic tool would also be useful for detecting reduced levels of the PDGFRA protein that result from, for example, mutations in the promoter regions of the PDGFRA gene or mutations within the coding region of the gene that produced truncated, non-functional or unstable polypeptides, as well as from deletions of a portion of or the entire PDGFRA gene. Alternatively, amplification of a PDGFRA-encoding sequence may be detected as an increase in the expression level of PDGFRA protein. Such an increase in protein expression may also be a result of an up-regulating mutation in the promoter region or other regulatory or coding sequence within the PDGFRA gene, or by virtue of a point mutation within the PDGFRA coding sequence, which protects the PDGFRA protein from degradation.

Localization and/or coordination of PDGFRA expression (temporally or spatially) can also be examined using known techniques, such as isolation and comparison of PDGFRA from subcellular fractions, including specific organelles, or from specific cell or tissue types, or at specific time points after an experimental manipulation. Demonstration of reduced or increased PDGFRA protein levels, in comparison to such expression in a control cell (e.g., normal, as in taken from a subject not suffering from a neoplastic disease, such as cancer), would be an alternative or supplemental approach to the direct determination of PDGFRA gene deletion, amplification or mutation status by the methods outlined above and equivalents.

The availability of antibodies specific to the PDGFRA protein will facilitate the detection and quantitation of cellular PDGFRA by one of a number of immunoassay methods which are well known in the art and are presented in Harlow and Lane (*Antibodies, A Laboratory Manual,* CSHL, New York, 1988). Methods of constructing such antibodies are discussed above, in Example 8.

Any standard immunoassay format (e.g. ELISA, western blot, or RIA assay) can be used to measure PDGFRA polypeptide or protein levels, and to compare these with PDGFRA expression levels in control, reference, cell populations. Altered PDGFRA polypeptide expression may be indicative of an abnormal biological condition related to unregulated cell growth or proliferation, in particular a neoplasm, and/or a predilection to development of neoplastic disease. Immunohistochemical techniques may also be utilized for PDGFRA polypeptide or protein detection. For example, a tissue sample may be obtained from a subject, and a section stained for the presence of PDGFRA using a PDGFRA specific binding agent (e.g., anti-PDGFRA antibody) and any standard detection system (e.g., one which includes a secondary antibody conjugated to horseradish peroxidase). General guidance regarding such techniques can be found in, e.g., Bancroft and Stevens (*Theory and Practice of Histological Techniques,* Churchill Livingstone, 1982) and Ausubel et al. (*Current Protocols in Molecular Biology,* John Wiley & Sons, New York, 1998).

For the purposes of quantitating a PDGFRA protein, a biological sample of the subject (which can be any animal, for instance a mouse or a human), which sample includes cellular proteins, is required. Such a biological sample may be obtained from body cells, such as those present in a tissue biopsy, surgical specimens, or autopsy material. In particular embodiments biological samples may be obtained from peripheral blood sample, urine, saliva, amniocentesis samples, and so forth. Quantitation of PDGFRA protein can be achieved by immunoassay and compared to levels of the protein found in control cells (e.g., healthy, non-neoplastic cells of the same lineage or type as those under evaluation, or from a patient known not to have a neoplastic disease). Detection of tyrosine phosphorylated PDGFRA (using an antibody, i.e. a phospho-specific antibody, that detects such forms and does not detect non-phosphorylated PDGFRA) could be taken as an indication of a PDGFRA protein containing an activating mutation. Detection of phosphorylated PDGFRA could also indicate activation by other mechanisms, such as overexpression of PDGFRA by genomic amplification, or over-expression of PDGFRA ligands, e.g. PDGF-A. A significant (e.g., 10% or greater) reduction in the amount of PDGFRA protein in the cells of a subject compared to the amount of PDGFRA protein found in normal human cells could be taken as an indication that the subject may have deletions or mutations in the PDGFRA gene, whereas a significant (e.g., 10% or greater) increase would indicate that a duplication (amplification), or mutation that increases the stability of the PDGFRA protein or mRNA, may have occurred. Deletion, mutation, and/or amplification within the PDGFRA encoding sequence, and substantial under- or overexpression of PDGFRA protein, may be indicative of neoplastic disease (such as a tumor) and/or a predilection to develop neoplastic disease.

Example 10

Differentiation of Individuals Homozygous Versus Heterozygous for Activating Mutation(s)

Though it is believed that the activating variants described herein are the result of sporadic mutations rather than germline mutations, it may sometimes be beneficial to determine whether a subject is homozygous or heterozygous for the mutation.

By way of example, the oligonucleotide ligation assay (OLA), as described at Nickerson et al. (*Proc. Natl. Acad. Sci. USA* 87:8923-8927, 1990), allows the differentiation between individuals who are homozygous versus heterozygous for the D842V or the V561D point mutation, the ER561-562 in frame insertion, or the DIMH842-845, HDSN845-848P, RD841-842KI, RVIES560-564, or SPDGHE566-571R in-frame deletions. This feature allows one to rapidly and easily determine whether an individual is homozygous for at least one tyrosine kinase activating mutation, which condition is linked to a relatively high predisposition to developing neoplastic disease and/or an increased likelihood of having a tumor. Alternatively, OLA can be used to determine whether a subject is homozygous for either of these mutations.

As an example of the OLA assay, when carried out in microtiter plates, one well is used for the determination of the presence of the PDGFRA allele that contains a T at nucleotide position 2919 (numbering from SEQ ID NO: 1) and a second well is used for the determination of the presence of the PDGFRA allele that contains an A at that nucleotide position in the wildtype sequence. Thus, the results for an individual who is heterozygous for the mutation will show a signal in each of the A and T wells.

Example 11

Suppression of PDGFRA Expression

A reduction of PDGFRA protein expression in a transgenic cell may be obtained by introducing into cells an antisense construct based on the PDGFRA encoding sequence, including the human PDGFRA cDNA or genomic sequence (SEQ ID NOs: 1 and 19, respectively) or flanking regions thereof. For antisense suppression, a nucleotide sequence from a PDGFRA encoding sequence, e.g. all or a portion of the PDGFRA cDNA or gene, is arranged in reverse orientation relative to the promoter sequence in the transformation vector. Other aspects of the vector may be chosen as discussed above (Example 7).

The introduced sequence need not be the full-length human PDGFRA cDNA or gene or reverse complement thereof, and need not be exactly homologous to the equivalent sequence found in the cell type to be transformed. Generally, however, where the introduced sequence is of shorter length, a higher degree of homology to the native PDGFRA sequence will be needed for effective antisense suppression. The introduced antisense sequence in the vector may be at least 30 nucleotides in length, and improved antisense suppression will typically be observed as the length of the antisense sequence increases. The length of the antisense sequence in the vector advantageously may be greater than 100 nucleotides. For suppression of the PDGFRA gene itself, transcription of an antisense construct results in the production of RNA molecules that are the reverse complement of mRNA molecules transcribed from the endogenous PDGFRA gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous PDGFRA expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Expression of PDGFRA can also be reduced using small inhibitory RNAs, for instance using techniques similar to those described previously (see, e.g., Tuschl et al., *Genes Dev* 13, 3191-3197, 1999; Caplen et al., *Proc. Natl. Acad. Sci. U.S.A.* 98, 9742-9747, 2001; and Elbashir et al., *Nature* 411, 494-498, 2001).

Finally, dominant negative mutant forms of PDGFRA may be used to block endogenous PDGFRA activity.

Example 12

PDGFRA Gene Therapy

Gene therapy approaches for combating activating mutations in PDGFRA, or reducing the risk of developing neoplastic disease such as cancer, in subjects are now made possible by the present disclosure.

Retroviruses have been considered a preferred vector for experiments in gene therapy, with a high efficiency of infection and stable integration and expression (Orkin et al., *Prog. Med. Genet.* 7:130-142, 1988). The full-length PDGFRA gene or cDNA can be cloned into a retroviral vector and driven from either its endogenous promoter or from the retroviral LTR (long terminal repeat). Other viral transfection systems may also be utilized for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

Recent developments in gene therapy techniques include the use of RNA-DNA hybrid oligonucleotides, as described by Cole-Strauss et al. (*Science* 273:1386-1389, 1996). This technique may allow for site-specific integration of cloned sequences, thereby permitting accurately targeted gene replacement.

In addition to delivery of a PDGFRA encoding sequence to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol.* 23:172-187, 1996). For instance, cationic liposomes have been analyzed for their ability to transfect monocytic leukemia cells, and shown to be a viable alternative to using viral vectors (de Lima et al., *Mol. Membr. Biol.* 16:103-109, 1999). Such cationic liposomes can also be targeted to specific cells through the inclusion of, for instance, monoclonal antibodies or other appropriate targeting ligands (Kao et al., *Cancer Gene Ther.* 3:250-256, 1996).

To reduce the level of PDGFRA expression, gene therapy can be carried out using antisense or other suppressive constructs, the construction of which is discussed above (Example 11).

Example 13

Kits

Kits are provided which contain the necessary reagents for determining the presence or absence of mutation(s) in a PDG- FRA-encoding sequence, such as probes or primers specific for the PDGFRA gene or a highly variable region of this gene, such as those regions indicated in SEQ ID NO: 26. Such kits can be used with the methods described herein to determine whether a subject is predisposed to neoplastic disease or tumor development, or whether the subject is expected to respond to one or another therapy, such as a particular tyrosine kinase inhibitory compound.

The provided kits may also include written instructions. The instructions can provide calibration curves or charts to compare with the determined (e.g., experimentally measured) values. Kits are also provided to determine elevated or depressed expression of mRNA (i.e., containing probes) or PDGFRA protein (i.e., containing antibodies or other PDGFRA-protein specific binding agents).

A. Kits for Amplification of PDGFRA Sequences

Oligonucleotide probes and primers, including those disclosed herein, can be supplied in the form of a kit for use in detection of a predisposition to neoplastic disease or tumor formation in a subject. In such a kit, an appropriate amount of one or more of the oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of a PDGFRA mutation can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may for instance be found in Innis et al. (PCR Protocols, A Guide to Methods and Applications, Academic Press, Inc., San Diego, Calif., 1990), Sambrook et al. (In Molecular Cloning: A Laboratory Manual, Cold Spring Harbor, N.Y., 1989), and Ausubel et al. (In Current Protocols in Molecular Biology, Greene Publ. Assoc. and Wiley-Intersciences, 1992).

A kit may include more than two primers, in order to facilitate the in vitro amplification of PDGFRA sequences, for instance the PDGFRA gene or the 5' or 3' flanking region thereof.

In some embodiments, kits may also include the reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of PDGFRA mutation(s). In certain embodiments, these probes will be specific for a potential mutation that may be present in the target amplified sequences. The appropriate sequences for such a probe will be any sequence that includes one or more of the identified polymorphic sites, particularly nucleotide positions that overlap with the variants shown in Table 1 or Table 3, such that the sequence the probe is complementary to is a polymorphic site and the surrounding PDGFRA sequence.

It may also be advantageous to provide in the kit one or more control sequences for use in the amplification reactions. The design of appropriate positive control sequences is well known to one of ordinary skill in the appropriate art.

B. Kits for Detection of PDGFRA mRNA Expression

Kits similar to those disclosed above for the detection of PDGFRA mutations directly can be used to detect PDGFRA mRNA expression, such as over- or under-expression. Such kits include an appropriate amount of one or more oligonucleotide primers for use in, for instance, reverse transcription PCR reactions, similarly to those provided above with art-obvious modifications for use with RNA amplification.

In some embodiments, kits for detection of altered expression of PDGFRA mRNA may also include some or all of the reagents necessary to carry out RT-PCR in vitro amplification reactions, including, for instance, RNA sample preparation reagents (including e.g., an RNase inhibitor), appropriate buffers (e.g., polymerase buffer), salts (e.g., magnesium chloride), and deoxyribonucleotides (dNTPs). Written instructions may also be included.

Such kits may in addition include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction. In certain embodiments, these probes will be specific for a potential mutation that may be present in the target amplified sequences, for instance specific for the D842V or V561D point mutation, the ER561-562 in frame insertion, or the DIMH842-845, HDSN845-848P, RD841-842KI, RVIES560-564, or SPDGHE566-571R in-frame deletion, or another mutation identified in PDGFRA.

It may also be advantageous to provide in the kit one or more control sequences for use in the RT-PCR reactions. The design of appropriate positive control sequences is well known to one of ordinary skill in the appropriate art.

Alternatively, kits may be provided with the necessary reagents to carry out quantitative or semi-quantitative Northern analysis of PDGFRA mRNA. Such kits include, for instance, at least one PDGFRA-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme. In certain embodiments, such probes will be specific for a potential mutation that may be present in the target amplified sequence, such as the mutations disclosed herein.

C. Kits for Detection of PDGFRA Protein Expression

Kits for the detection of PDGFRA protein expression (such as over- or under-expression) are also encompassed. Such kits may include at least one target protein specific binding agent (e.g., a polyclonal or monoclonal antibody or antibody fragment that specifically recognizes the PDGFRA protein) and may include at least one control (such as a determined amount of PDGFRA protein, or a sample containing a determined amount of PDGFRA protein). The PDGFRA-protein specific binding agent and control may be contained in separate containers. Likewise, kits for detection of activated PDGFRA may include at least one target protein binding agent (e.g. a polyclonal or monoclonal antibody or antibody fragment) that specifically recognizes the PDGR-A protein only when PDGFRA is expressed in activated manner. These kits include, but are not limited to, those in which the PDGFRA binding agent recognizes, and binds specifically with, epitopes in which one or more tyrosine residues are phosphorylated. Kits for detection of activated/phosphorylated PDGFRA might include at least two controls, including a positive control with tyrosine phosphorylated PDGFRA and a negative control lacking tyrosine phosphorylated PDGFRA. The positive controls may include lysates or paraffin sections from cells and tissues expressing mutant (activated) PDGFRA, or expressing native PDGFRA that has been activated by exposure of the cells to PDGFA. The negative controls may include lysates or paraffin sections from cells and tissues expressing non-activated PDGFRA, e.g. tissues expressing non-mutant PDGFRA, and without exposure to PDGF-A.

The PDGFRA protein expression detection kits may also include a means for detecting PDGFRA:binding agent complexes, for instance the agent may be detectably labeled. If the detectable agent is not labeled, it may be detected by second antibodies or protein A for example, which may also be provided in some kits in one or more separate containers. Such techniques are well known.

Additional components in specific kits may include instructions for carrying out the assay. Instructions will allow the tester to determine whether PDGFRA expression levels are elevated. Reaction vessels and auxiliary reagents such as chromogens, buffers, enzymes, etc. may also be included in the kits.

D. Kits for Detection of Homozygous Versus Heterozygous Allelism

Also provided are kits that allow differentiation between individuals who are homozygous versus heterozygous for the D842V or V561D point mutations, the E1561-562 in frame insertion, or the DIMH842-845, HDSN845-848P, RD841-842KI, RVIES560-564, or SPDGHE566-571R in-frame deletion mutations of PDGFRA. Such kits provide the materials necessary to perform oligonucleotide ligation assays (OLA), as described at Nickerson et al. (*Proc. Natl. Acad. Sci. USA* 87:8923-8927, 1990). In specific embodiments, these kits contain one or more microtiter plate assays, designed to detect mutation(s) in the PDGFRA sequence of a subject, as described herein.

Additional components in some of these kits may include instructions for carrying out the assay. Instructions will allow the tester to determine whether a PDGFRA allele is homozygous or heterozygous. Reaction vessels and auxiliary reagents such as chromogens, buffers, enzymes, etc. may also be included in the kits.

It may also be advantageous to provide in the kit one or more control sequences for use in the OLA reactions. The design of appropriate positive control sequences is well known to one of ordinary skill in the appropriate art.

Example 14

PDGFRA Knockout and Overexpression Transgenic Animals

Mutant organisms that under-express or over-express PDGFRA protein are useful for research. Such mutants allow insight into the physiological and/or pathological role of PDGFRA in a healthy and/or pathological organism. These mutants are "genetically engineered," meaning that information in the form of nucleotides has been transferred into the mutant's genome at a location, or in a combination, in which it would not normally exist. Nucleotides transferred in this way are said to be "non-native." For example, a non-PDGFRA promoter inserted upstream of a native PDGFRA encoding sequence would be non-native. An extra copy of a PDGFRA gene on a plasmid, transformed into a cell, would be non-native.

Mutants may be, for example, produced from mammals, such as mice, that either over-express PDGFRA or under-express PDGFRA, or that do not express PDGFRA at all. Over-expression mutants are made by increasing the number of PDGFRA genes in the organism, or by introducing an PDGFRA gene into the organism under the control of a constitutive or inducible or viral promoter such as the mouse mammary tumor virus (MMTV) promoter or the whey acidic protein (WAP) promoter or the metallothionein promoter. Mutants that under-express PDGFRA may be made by using an inducible or repressible promoter, or by deleting the PDGFRA gene, or by destroying or limiting the function of the PDGFRA gene, for instance by disrupting the gene by transposon insertion.

Antisense genes may be engineered into the organism, under a constitutive or inducible promoter, to decrease or prevent PDGFRA expression, as discussed above in Example 11.

A gene is "functionally deleted" when genetic engineering has been used to negate or reduce gene expression to negligible levels. When a mutant is referred to in this application as having the PDGFRA gene altered or functionally deleted, this refers to the PDGFRA gene and to any ortholog of this gene. When a mutant is referred to as having "more than the normal copy number" of a gene, this means that it has more than the usual number of genes found in the wild-type organism, e.g. in the diploid mouse or human.

A mutant mouse over-expressing PDGFRA may be made by constructing a plasmid having a PDGFRA encoding sequence driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which the subject expression construct is driven by a promoter regulated by an agent that can be fed to the mouse, such as tetracycline. Such techniques are well known in the art.

A mutant knockout animal (e.g., mouse) from which a PDGFRA gene is deleted can be made by removing all or some of the coding regions of the PDGFRA gene from embryonic stem cells. The methods of creating deletion mutations by using a targeting vector have been described (Thomas and Capecch, *Cell* 51:503-512, 1987).

Engineered PDGFRA knockout animals are known. See, for instance, Bostrom et al., *Dev. Dyn.*, 223:155-162, 2002; Fruttiger et al., *Development*, 126:457-467, 1999; Hellstrom et al., *J. Cell Biol.*, 153:543-553, 2001; Kaminski et al., *Blood*, 97:1990-1998, 2001; Karlsson et al., *Development*, 127:3457-3466, 2000. In addition, Patch mutant mice have a congenital chromosomal deletion that includes the PDGFR-α gene locus.

Example 15

Knock-In Organisms

In addition to knock-out systems, it is also beneficial to generate "knock-ins" that have lost expression of the wild-type protein but have gained expression of a different, usually mutant form of the same protein. By way of example, the activating mutant PDGFRA mutant proteins provided herein (e.g., as shown in SEQ ID NO: 4, 6, 8, 10, 12, 21, 23, 25, and 27) can be expressed in a knockout background, such as the Patch mutant mice, in order to provide model systems for studying the effects of these mutants. In particular embodiments, the resultant knock-in organisms provide systems for studying neoplasia.

Those of ordinary skill in the relevant art know methods of producing knock-in organisms. See, for instance, Rane et al. (*Mol. Cell Biol.*, 22: 644-656, 2002); Sotillo et al. (*EMBO J.*, 20: 6637-6647, 2001); Luo et al. (*Oncogene*, 20: 320-328, 2001); Tomasson et al. (*Blood*, 93: 1707-1714, 1999); Voncken et al. (86: 4603-4611, 1995); Andrae et al. (*Mech. Dev.*, 107: 181-185, 2001); Reinertsen et al. (*Gene Expr.*, 6: 301-314, 1997); Huang et al. (*Mol. Med.*, 5: 129-137, 1999); Reichert et al. (*Blood*, 97: 1399-1403, 2001); and Huettner et al. (*Nat. Genet.*, 24: 57-60, 2000), by way of example.

Example 16

Demonstration of PDGFRA Fusion Oncoproteins in Human Leukemias

The PDGFRA activating genomic mutations disclosed herein involve intragenic point mutations or deletions. These models of genomic PDGFRA mutation can readily be extended to different mechanisms of activation, e.g. as might result from chromosomal rearrangement in which the promoter and 5' end of an ectopic gene are fused to the 3' end—including the kinase domain—of PDGFRA. The principle of receptor tyrosine kinase activation, in which cytogenetic rearrangement produces a gene fusion, has been established for several kinase proteins, including FGFR1, FGFR3, NTRK3, and ALK, and have been reported recently for PDGFRA, in two patients with chronic myelogenous leukemia, in which PDGFRA was fused with the BCR gene. In the PDGFRA context, the applicants have identified four leukemias in which cytogenetic banding analyses reveal translocation breakpoints in the PDGFRA gene (chromosome band 4q12) region, and in which—based on cytogenetic correlates—the putative PDGFRA fusion gene is not expected to be BCR. Therefore, these leukemias may contain novel forms of PDGFRA fusion oncogenes. FISH analyses will be performed to determine whether any of these translocations targets PDGFRA, in which case the translocation partner gene will be identified by rapid amplification of cDNA ends, and the activating nature of the PDGFRA fusion will be determine by expressing the PDGFRA fusion gene in cell types such as Ba/F3 and CHO.

Example 17

Additional PDGFRA Activating Mutations in Gastrointestinal Stromal Tumors

Using methods essentially as described in Example 1, three additional PDGFRA activating mutations were identified in GISTs. These mutations are as shown in Table 3.

TABLE 3

| Genotype | DNA sequence (top line) Translation (bottom line) |
|---|---|
| PDGFRA Wild type (SEQ ID NOs: 1 and 2) | 2906* GGCCTGGCCAGAGACATCATGCATGATTCGAACTATGTG<br>838 G L A R D I M H D S N Y V |
| PDGFRA Deletion RD841-842KI (SEQ ID NOs: 24 and 25) | 2906 GGCCTGGCCAAAATCATCATGCATGATTCGAACTATGTG<br>838 G L A K I I M H D S N Y V |
| PDGFRA Wild type | 2060 GAAATTCGCTGGAGGGTCATTGAATCAATCAGCCCGGAT<br>556 E I R W R V I E S I S P D |
| V561D (SEQ ID NOs: 20 and 21) | 2060 GAAATTCGCTGGAGGGACATTGAATCAATCAGCCCGGAT<br>556 E I R W R D I E S I S P D |
| PDGFRA Deletion RVIES560-564 (SEQ ID NOs: 22 and 23) | 2060 GAAATTCGCTGG---------------ATCAGCCCGGAT<br>556 E I R W - - - - - I S P D |

*Numbering as in SEQ ID NO: 1 and SEQ ID NO: 2.

After taking into account these three additional mutations, and additional instances of other identified mutations, the total number of each of the identified activating mutations was as shown in Table 4 and Table 5.

TABLE 4

Summary of PDGFRA mutations in KIT-WT GISTs.

| PDGFRA Region | Mutation | #GISTs |
|---|---|---|
| Activation Loop (exon 18) | D842V | 15 |
| | Del DIMH | 4 |
| | Del HDSN845-848P | 1 |
| | Del RD841-842KI | 1 |
| Juxtamembrane (exon 12) | V561D | 1 |
| | Ins ER561-562 | 1 |
| | Del RVIES560-564 | 1 |
| | Del SPDGHE566-571R | 1 |

TABLE 5

| Mutation | Cases (% total) |
|---|---|
| D842V | 15 (21.7%) |
| Exon 18 Deletion | 6 (8.7%) |
| Exon 12 Insertion/Deletion/PM | 4 (5.8%) |
| No mutation | 44 (63.7%) |
| Total | 69 (100.0%) |

The nucleic acid sequences of all of the identified activating PDGFRA mutations were aligned to produce the consensus sequence shown in SEQ ID NO: 26; the numbering in the consensus sequence aligns with that in the wildtype PDGFRA nucleic acid sequence (SEQ ID NO: 1). In the consensus sequence, the insertion identified in variant PDGFRA Insertion ER561-562 is indicated in a miscellaneous features field in the Sequence Listing. As emphasized and clearly illustrated in the consensus sequence, clusters of activating mutations in the PDGFRA nucleic acid sequence are found in positions 2072 to 2107 and 2916 to 2937, though it is noted that positions 2087, 2088, and 2089 appear to be invariable at least in the current studies.

Example 18

Additional Characterization of PDGFRA Activating Mutations in GISTs

Materials and Methods

Reagents

Antibodies used for immunoblotting were to phosphotyrosine (Santa Cruz PY99), actin (Sigma 1PKCA4), KIT (Dako A4502), PDGFRA (Santa Cruz sc-338), phosphoPDGFRA Y754 (Santa Cruz sc-12911), MAPK (Zymed 61-7400), phosphoMAPK Thr202Thr204 (Cell Signaling 9106), AKT (Cell Signaling 9272), phosphoAKT S473 (Cell Signaling 9271S), STAT1 (Zymed ST1-3D4), phosphoSTAT1 Y701, (Zymed ST1P-11A5), STAT3 (Zymed 13-7000), phosphoSTAT3 Y705 (Cell Signaling 9131), STAT5 (Zymed ST5-8F7), and phosphoSTAT5 Y694 (Zymed ST5P-4A9). Antibodies to phosphorylated kinases were validated as phosphospecific by evaluation of phosphatase treated cell lysates, and by evaluation of lysates from GIST cells treated with kinase inhibitors.

Cytogenetic Analyses

Tumor specimens were chopped with scalpel blades, disaggregated enzymatically, and seeded into T25 flasks. The monolayer cultures were expanded for two-to-five days prior to metaphase cell harvesting with Colcemid. Tissue culture, metaphase harvesting, metaphase slide making, and Giemsa-trypsin banding were performed as described previously (Fletcher et al., *N. Engl. J. Med.* 324, 436, 1991).

Cloning, Expression and Characterization of PDGFRA Mutant cDNAs

PDGFRA mutations were cloned by site-directed mutagenesis of the wild type PDGFRA cDNA. CHO cells were transiently transfected with expression vectors encoding for mutant or wild-type PDGFRA cDNA. Transfected cells were serum starved overnight and stimulated with vehicle or 100 ng/ml recombinant human PDGF-AA for 10 minutes before harvesting cells and preparing whole cell lysates for immunoblotting. The membranes were sequentially immunoblotted with antiserum against phosphorylated tyrosines (PY20 Transduction Laboratories) or total PDGFRA (Santa Cruz sc-338).

Results and Discussion

The biochemical consequences of somatic PDGFRA mutations were studied by transient expression of wild-type and mutant PDGFRA cDNA constructs in Chinese hamster ovary (CHO) cells. Baseline tyrosine phosphorylation was weak for non-mutant PDGFRA, and was substantially increased by ligand stimulation (FIG. 8). By contrast, baseline tyrosine phosphorylation was strong in all five of the tested PDGFRA mutants, and was not increased by ligand stimulation (FIG. 8).

Next the signal transduction pathways activated in PDGFRA-mutant versus KIT-mutant GISTs were compared. The PDGFRA-mutant GISTs showed uniform activation of signaling intermediates AKT, MAPK, STAT1, and STAT3, which are also activated in most KIT-mutant GISTs (FIG. 9). The PDGFRA-mutant GISTs lacked expression of phosphoSTAT5, despite strong expression of total STAT5, which is also typical of KIT-mutant GISTs. The cytogenetic profiles of four PDGFRA-mutant GISTs and 52 KIT-mutant GISTs were also compared. KIT mutations are early events in GIST tumorigenesis, whereas cytogenetic aberrations occur later in disease progression (Heinrich et al., *Hum. Pathol.* 33, 484, 2002). Most of these GISTs—irrespective of PDGFRA or KIT mutation—featured noncomplex karyotypes with deletions of chromosome 1p, and with monosomies of chromosomes 14 and 22. Hence, these results suggest that the mechanisms of cytogenetic progression and oncoprotein-driven signal transduction are similar in GISTs expressing oncogenic forms of PDGFRA and KIT.

Activating mutations of KIT or PDGFRA appear to be mutually exclusive oncogenic events in GISTs, and these mutations have similar biological consequences. The data presented also highlight a crucial role for PDGFRA in the pathogenesis of a solid tumor. Notably, a translocation involving the BCR and PDGFRA genes has been described in BCR-ABL negative chronic myelogenous leukemia, and is predicted to result in dimerization and kinase activation of the fusion protein (Baxter et al., *Hum. Mol. Genet.* 11, 1391, 2002). PDGFRA is widely expressed in human tissues, so it will be important to determine whether PDGFRA mutations play a role in other human malignancies. Such tumors could be sensitive to Gleevec and other small molecule drugs that inhibit PDGFRA kinase activity (Buchdunger et al., *J. Pharmacol. Exp. Ther.* 295, 139, 2000; Lokker et al., *Cancer Res.* 62, 3729, 2002; Sun et al., *J. Med. Chem.* 43, 2655, 2000).

This disclosure provides tyrosine kinase protein and nucleic acid variants, particularly PDGFRA variants, which are activating forms of these molecules and are linked to neoplasms and/or the development or progression of cancer. The disclosure further provides methods of diagnosis and prognosis, using these molecules and fragments thereof, and kits for employing these methods and compositions. It will be apparent that the precise details of the compositions and methods described may be varied or modified without departing from the spirit of the described invention. We claim all such modifications and variations that fall within the scope and spirit of the claims below.

We claim:

1. A method of detecting a neoplasia associated with an activating platelet derived growth factor receptor alpha (PDGFRA) mutation in a subject, comprising determining whether the subject has an activating mutation in PDGFRA, and wherein the activating mutation comprises a variant nucleic acid sequence shown in one or more of positions 2072 through 2107 or 2916 through 2937 of SEQ ID NO: 26.

2. The method of claim 1, wherein the activating mutation comprises a variant nucleic acid sequence that results in one or more of the following amino acid variants: substitution D842V (shown in SEQ ID NO: 4); deletion of DIMH842-845 (shown in SEQ ID NO: 6); deletion of HSDN845-858P (shown in SEQ ID NO: 8); insertion ER561-562 (shown in SEQ ID NO: 10); deletion of SPDGHE566-571R (shown in SEQ ID NO: 12); substitution V561D (shown in SEQ ID NO: 21); deletion of RVIES560-564 (shown in SEQ ID NO: 23); and deletion of RD841-842KI (shown in SEQ ID NO: 25).

3. The method of claim 1, wherein the neoplasia comprises a gastrointestinal stromal tumor (GIST).

4. The method of claim 1, comprising:
reacting at least one PDGFRA molecule contained in a clinical sample from the subject with a reagent comprising a PDGFRA-specific binding agent to form a PDGFRA:agent complex.

5. The method of claim 4, wherein the PDGFRA molecule is a PDGFRA encoding nucleic acid or a PDGFRA protein.

6. The method of claim 4, wherein the PDGFRA-specific binding agent is a PDGFRA oligonucleotide or a PDGFRA protein-specific binding agent.

7. The method of claim 4, wherein the sample comprises a neoplastic cell or is prepared from a neoplastic cell.

8. The method of claim 4 wherein the PDGFRA molecule is a PDGFRA encoding nucleic acid sequence.

9. The method of claim 8, wherein the method comprises HPLC denaturation analysis of a PDGFRA encoding nucleic acid molecule.

10. The method of claim 8, wherein the agent comprises a labeled nucleotide probe.

11. The method of claim 10, wherein the nucleotide probe has a sequence selected from the group consisting of:
(a) SEQ ID NO: 3, 5, 7, 9, 11, 20, 22, or 24; or
(b) fragments of (a) at least 15 nucleotides in length, and including the sequence encoding one or more of the following amino acid variants: substitution D842V (shown in SEQ ID NO: 4); deletion of DIMH842-845 (shown in SEQ ID NO: 6); deletion of HSDN845-858P (shown in SEQ ID NO: 8); insertion ER561-562 (shown in SEQ ID NO: 10); deletion of SPDGHE566-571R (shown in SEQ ID NO: 12); substitution V561D (shown in SEQ ID NO: 21); deletion of RVIES560-564 (shown in SEQ ID NO: 23); and deletion of RD841-842KI (shown in SEQ ID NO: 25).

12. The method of claim 1, further comprising in vitro amplifying a PDGFRA nucleic acid prior to detecting the activating PDGFRA mutation.

13. The method of claim 12, wherein the PDGFRA nucleic acid is in vitro amplified using at least one oligonucleotide primer derived from a PDGFRA-protein encoding sequence.

14. The method of claim 13, wherein at least one oligonucleotide primer comprises at least 15 contiguous nucleotides from SEQ ID NO: 3, 5, 7, 9, 11, 20, 22, or 24.

15. The method of claim 13, wherein at least one oligonucleotide primer is at least 15 nucleotides in length and overlaps the sequence encoding one or more of the following amino acid variants: substitution D842V (shown in SEQ ID NO: 4); deletion of DIMH842-845 (shown in SEQ ID NO: 6); deletion of HSDN845-858P (shown in SEQ ID NO: 8); insertion ER561-562 (shown in SEQ ID NO: 10); deletion of SPDGHE566-571R (shown in SEQ ID NO: 12); substitution V561D (shown in SEQ ID NO: 21); deletion of RVIES560-564 (shown in SEQ ID NO: 23); and/or deletion of RD841-842KI (shown in SEQ ID NO: 25).

16. The method of claim 5, wherein the PDGFRA molecule is a PDGFRA protein.

17. The method of claim 16, wherein the complexes are detected by western blot assay.

18. The method of claim 16, wherein the complexes are detected by ELISA.

19. The method of claim 16, wherein the PDGFRA protein comprises a sequence selected from the group consisting of SEQ ID NO: 4, 6, 8, 10, 12, 21, 23, and 25.

20. The method of claim 16, wherein the PDGFRA-specific binding agent is a PDGFRA-specific antibody or an antigen-binding fragment thereof.

21. The method of claim 20, wherein the agent is an antibody.

22. The method of claim 21, wherein the antibody is a monoclonal antibody.

23. The method of claim 22, wherein the monoclonal antibody recognizes an epitope of a variant PDGFRA and not an epitope of wildtype PDGFRA.

24. The method of claim 23, wherein the monoclonal antibody recognizes an epitope of a variant PDGFRA having the amino acid sequence as shown in SEQ ID NO: 4, 6, 8, 10, 12, 21, 23, or 25.

25. The method of claim 20, wherein the antibody is reactive to an epitope including one or more of the following amino acid variants: substitution D842V (shown in SEQ ID NO: 4); deletion of DIMH842-845 (shown in SEQ ID NO: 6); deletion of HSDN845-858P (shown in SEQ ID NO: 8); insertion ER561-562 (shown in SEQ ID NO: 10); deletion of SPDGHE566-571R (shown in SEQ ID NO: 12); substitution V561D (shown in SEQ ID NO: 21); deletion of RVIES560-564 (shown in SEQ ID NO: 23); and deletion of RD841-842KI (shown in SEQ ID NO: 25).

26. A method of detecting a gastrointestinal stromal tumor (GIST) associated with an activating PDGFRA mutation in a subject, comprising determining whether the subject has an activating mutation in PDGFRA, and wherein the activating mutation comprises a variant nucleic acid sequence shown in position 2919 of SEQ ID NO: 3.

27. The method of claim 26, comprising reacting at least one PDGFRA molecule contained in a clinical sample from the subject with a reagent comprising a PDGFRA-specific binding agent to form a PDGFRA:agent complex.

28. The method of claim 27, wherein the PDGFRA molecule is a PDGFRA encoding nucleic acid or a PDGFRA protein.

29. The method of claim 27, wherein the PDGFRA-specific binding agent is a PDGFRA oligonucleotide or a PDGFRA protein-specific binding agent.

30. The method of claim 27, wherein the sample comprises a neoplastic cell or is prepared from a neoplastic cell.

31. The method of claim 27 wherein the PDGFRA molecule is a PDGFRA encoding nucleic acid sequence.

32. The method of claim 31, wherein the method comprises HPLC denaturation analysis of a PDGFRA encoding nucleic acid molecule.

33. The method of claim 31, wherein the agent comprises a labeled nucleotide probe.

34. The method of claim 33, wherein the nucleotide probe has a sequence selected from the group consisting of:
   (a) SEQ ID NO: 3; or
   (b) fragments of SEQ ID NO: 3 at least 15 nucleotides in length, and including the sequence shown in position 2919 of SEQ ID NO: 3.

35. The method of claim 26, further comprising in vitro amplifying a PDGFRA nucleic acid prior to detecting the activating PDGFRA mutation.

36. The method of claim 35, wherein the PDGFRA nucleic acid is in vitro amplified using at least one oligonucleotide primer derived from a PDGFRA-protein encoding sequence.

37. The method of claim 36, wherein at least one oligonucleotide primer comprises at least 15 contiguous nucleotides from SEQ ID NO: 3.

38. The method of claim 28, wherein the PDGFRA molecule is a PDGFRA protein.

39. The method of claim 38, wherein the complexes are detected by western blot assay.

40. The method of claim 38, wherein the complexes are detected by ELISA.

41. The method of claim 38, wherein the PDGFRA-specific binding agent is a PDGFRA-specific antibody or an antigen-binding fragment thereof.

42. The method of claim 41, wherein the agent is an antibody.

43. The method of claim 42, wherein the antibody is a monoclonal antibody.

44. The method of claim 43, wherein the monoclonal antibody recognizes an epitope of a variant PDGFRA and not an epitope of wildtype PDGFRA.

* * * * *

UNITED STATES PATENT AND TRADEMARK OFFICE
CERTIFICATE OF CORRECTION

PATENT NO. : 7,595,154 B2
APPLICATION NO. : 10/517905
DATED : September 29, 2009
INVENTOR(S) : Heinrich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1127 days.

In Section 56 "Reference Cited", under "Other Publications":
Page 2, Column 1, Debiec-Rychter *et al.*, "stidies" should be --studies--.

Page 2, Column 1, Gari *et al.*, "proto-ocogene" should be --proto-oncogene--.

Page 2, Column 1, Heinrich *et al.* (first entry), "alternations" should be --alterations--.

Page 2, Column 2, Madani *et al.*, "28-21" should be --18-21--.

Page 2, Column 2, Gleevec™..., "gove/" should be --gov/--.

In the Specification:

Column 2, Line 2, "1052" should be --344--.

Column 3, Lines 10-11, "system Sample" should be --system. Sample--.

Column 3, Line 18, "18174R" should be --181874R--.

Column 3, Line 52, "would identifiable" should be --would be identifiable--.

Column 3, Line 58, "DGFRA" should be --PDGFRA--.

Column 3, Line 61, "phosphor-tyrosine" should be --phospho-tyrosine--.

Column 5, Line 16, "protein SEQ ID NO: 25" is missing a return, and should be
--protein.
SEQ ID NO: 25-- (new paragraph).

Signed and Sealed this

Twenty-third Day of November, 2010

David J. Kappos
*Director of the United States Patent and Trademark Office*

CERTIFICATE OF CORRECTION (continued)
U.S. Pat. No. 7,595,154 B2

Column 6, Line 48, "to" should be --two--.

Column 6, Line 54, "target The" should be --target. The--.

Column 7, Line 27, "ingredient The" should be --ingredient. The--.

Column 9, Line 11, "tract Generally" should be --tract. Generally--.

Column 9, Line 55, "or increased or increased" should be --or increased or decreased--.

Column 10, Line 53, "sequences." should be --sequence--.

Column 11, Line 20, "term Thus" should be --term. Thus--.

Column 11, Line 48, "art Various" should be --art. Various--.

Column 12, Line 12, "Tm" should be --$T_m$--.

Column 13, Line 2, "F(ab')2" should be -- $F(ab')_2$--.

Column 13, Line 18, "effectively oligonucleotide" should be --effective oligonucleotide(s)--.

Column 14, Line 15, "thereof comprising including" should --thereof including--.

Column 14, Line 46, "agent In" should be --agent. In--.

Column 14, Line 55, "fragments" should be --fragment--.

Column 16, Line 7, "shown in shown in" should be --shown in--.

Column 17, Line 60, "& and" should be --&--.

Column 18, Line 8, "immunaffinity" should be --immunoaffinity--.

Column 18, Line 27, "imatimb" should be --imatinib--.

Column 18, Line 38, "TK1" should be --TKI--.

Column 19, Line 24, "3140" should be --31-40--.

Column 19, Line 31, "TK1" should be --TKI--.

Column 20, Line 1, "CSF-LR" should be --CSF-1R--.

Column 21, Lines 41-42, "neoplasia In" should be --neoplasia. In--.

Column 25, Line 9, "CSF1-R" should be --CSF-1R--.

Column 25, Line 39, "aprotinin 10 μg" should be --aprotinin, 10 μg--.

Column 26, Line 66, "181874R The" should be --181874R. The--.

Column 29, Line 8, "PDGRA" should be --PDGFRA--.

Column 31, Lines 35-36, "Nildforov" should be --Nikiforov--.

Column 34, Line 30, "1998." should be --1998).--.

Column 39, Line 29, "adjuvant Also" should be --adjuvant. Also--.

Column 40, Line 13, "ant-PDGFR" should be --anti-PDGFRA--.

Column 40, Line 47, "SE ID NO: 10 positions" should be --SEQ ID NO: 10, positions--.

CERTIFICATE OF CORRECTION (continued)
U.S. Pat. No. 7,595,154 B2

Column 45, Line 66, "sequence the" should be --sequence of the --.

Column 46, Line 63, "PDGR-A" should be --PDGFRA--.

Column 47, Line 29, "E1561" should by --ER561--.

Column 49, Line 34, "(86:4603-4611" should be --(*Blood*, 86:4603-4611--.

Column 50, Line 1, "determine" should be --determined--.

Column 51, Line 21, "Thr202Thr204" should be --Thr202/Thr204--.

Column 51, Line 24, "Y701, (Zymed" should be --Y701 (Zymed--.

UNITED STATES PATENT AND TRADEMARK OFFICE
CERTIFICATE OF CORRECTION

| | | |
|---|---|---|
| PATENT NO. | : 7,595,154 B2 | Page 1 of 1 |
| APPLICATION NO. | : 10/517905 | |
| DATED | : September 29, 2009 | |
| INVENTOR(S) | : Heinrich et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1128 days.

Signed and Sealed this
First Day of February, 2011

David J. Kappos
*Director of the United States Patent and Trademark Office*

SEQUENCE LISTING

<160> NUMBER OF SEQ ID NOS: 27

<210> SEQ ID NO 1
<211> LENGTH: 6633
<212> TYPE: DNA

```
<213> ORGANISM: Homo sapiens
<220> FEATURE:
<221> NAME/KEY: CDS
<222> LOCATION: (395)..(3664)

<400> SEQUENCE: 1
ttctccccgc cccccagttg ttgtcgaagt ctggggttg ggactggacc ccctgattgc      60
gtaagagcaa aaagcgaagg cgcaatctgg acactgggag attcggagcg cagggagttt    120
gagagaaact tttattttga agagaccaag gttgagggg ggcttatttc ctgacagcta    180
tttacttaga gcaaatgatt agttttagaa ggatggacta taacattgaa tcaattacaa    240
aacgcggttt ttgagcccat tactgttgga gctacaggga gagaaacagg aggagactgc    300
aagagatcat ttgggaaggc cgtgggcacg ctctttactc catgtgtggg acattcattg    360
cggaataaca tcggaggaga agtttcccag agct atg ggg act tcc cat ccg gcg    415
                                     Met Gly Thr Ser His Pro Ala
                                      1               5 ttc ctg gtc tta ggc tgt ctt ctc aca ggg ctg agc cta atc ctc tgc      463
Phe Leu Val Leu Gly Cys Leu Leu Thr Gly Leu Ser Leu Ile Leu Cys
           10                  15                  20 cag ctt tca tta ccc tct atc ctt cca aat gaa aat gaa aag gtt gtg      511
Gln Leu Ser Leu Pro Ser Ile Leu Pro Asn Glu Asn Glu Lys Val Val
    25                  30                  35 cag ctg aat tca tcc ttt tct ctg aga tgc ttt ggg gag agt gaa gtg      559
Gln Leu Asn Ser Ser Phe Ser Leu Arg Cys Phe Gly Glu Ser Glu Val
40                  45                  50                  55 agc tgg cag tac ccc atg tct gaa gaa gag agc tcc gat gtg gaa atc      607
Ser Trp Gln Tyr Pro Met Ser Glu Glu Glu Ser Ser Asp Val Glu Ile
                60                  65                  70 aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
            75                  80                  85 agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
        90                  95                 100 cac act cag aca gaa gag aat gag ctt gaa ggc agg cac att tac atc      751
His Thr Gln Thr Glu Glu Asn Glu Leu Glu Gly Arg His Ile Tyr Ile
    105                 110                 115 tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135 tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150 aca act gat ccc gag act cct gta acc tta cac aac agt gag ggg gtg      895
Thr Thr Asp Pro Glu Thr Pro Val Thr Leu His Asn Ser Glu Gly Val
            155                 160                 165 gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180 gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195 acc atc cca ttt aat gtt tat gct tta aaa gca aca tca gag ctg gat      1039
Thr Ile Pro Phe Asn Val Tyr Ala Leu Lys Ala Thr Ser Glu Leu Asp
200                 205                 210                 215 cta gaa atg gaa gct ctt aaa acc gtg tat aag tca ggg gaa acg att      1087
Leu Glu Met Glu Ala Leu Lys Thr Val Tyr Lys Ser Gly Glu Thr Ile
                220                 225                 230
```

```
gtg gtc acc tgt gct gtt ttt aac aat gag gtg gtt gac ctt caa tgg    1135
Val Val Thr Cys Ala Val Phe Asn Asn Glu Val Val Asp Leu Gln Trp
            235                 240                 245 act tac cct gga gaa gtg aaa ggc aaa ggc atc aca atg ctg gaa gaa    1183
Thr Tyr Pro Gly Glu Val Lys Gly Lys Gly Ile Thr Met Leu Glu Glu
        250                 255                 260 atc aaa gtc cca tcc atc aaa ttg gtg tac act ttg acg gtc ccc gag    1231
Ile Lys Val Pro Ser Ile Lys Leu Val Tyr Thr Leu Thr Val Pro Glu
    265                 270                 275 gcc acg gtg aaa gac agt gga gat tac gaa tgt gct gcc cgc cag gct    1279
Ala Thr Val Lys Asp Ser Gly Asp Tyr Glu Cys Ala Ala Arg Gln Ala
280                 285                 290                 295 acc agg gag gtc aaa gaa atg aag aaa gtc act att tct gtc cat gag    1327
Thr Arg Glu Val Lys Glu Met Lys Lys Val Thr Ile Ser Val His Glu
                300                 305                 310 aaa ggt ttc att gaa atc aaa ccc acc ttc agc cag ttg gaa gct gtc    1375
Lys Gly Phe Ile Glu Ile Lys Pro Thr Phe Ser Gln Leu Glu Ala Val
            315                 320                 325 aac ctg cat gaa gtc aaa cat ttt gtt gta gag gtg cgg gcc tac cca    1423
Asn Leu His Glu Val Lys His Phe Val Val Glu Val Arg Ala Tyr Pro
        330                 335                 340 cct ccc agg ata tcc tgg ctg aaa aac aat ctg act ctg att gaa aat    1471
Pro Pro Arg Ile Ser Trp Leu Lys Asn Asn Leu Thr Leu Ile Glu Asn
    345                 350                 355 ctc act gag atc acc act gat gtg gaa aag att cag gaa ata agg tat    1519
Leu Thr Glu Ile Thr Thr Asp Val Glu Lys Ile Gln Glu Ile Arg Tyr
360                 365                 370                 375 cga agc aaa tta aag ctg atc cgt gct aag gaa gaa gac agt ggc cat    1567
Arg Ser Lys Leu Lys Leu Ile Arg Ala Lys Glu Glu Asp Ser Gly His
                380                 385                 390 tat act att gta gct caa aat gaa gat gct gtg aag agc tat act ttt    1615
Tyr Thr Ile Val Ala Gln Asn Glu Asp Ala Val Lys Ser Tyr Thr Phe
            395                 400                 405 gaa ctg tta act caa gtt cct tca tcc att ctg gac ttg gtc gat gat    1663
Glu Leu Leu Thr Gln Val Pro Ser Ser Ile Leu Asp Leu Val Asp Asp
        410                 415                 420 cac cat ggc tca act ggg gga cag acg gtg agg tgc aca gct gaa ggc    1711
His His Gly Ser Thr Gly Gly Gln Thr Val Arg Cys Thr Ala Glu Gly
    425                 430                 435 acg ccg ctt cct gat att gag tgg atg ata tgc aaa gat att aag aaa    1759
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac    1807
Cys Asn Asn Glu Thr Ser Trp Thr Ile Leu Ala Asn Asn Val Ser Asn
                460                 465                 470 atc atc acg gag atc cac tcc cga gac agg agt acc gtg gag ggc cgt    1855
Ile Ile Thr Glu Ile His Ser Arg Asp Arg Ser Thr Val Glu Gly Arg
            475                 480                 485 gtg act ttc gcc aaa gtg gag gag acc atc gcc gtg cga tgc ctg gct    1903
Val Thr Phe Ala Lys Val Glu Glu Thr Ile Ala Val Arg Cys Leu Ala
        490                 495                 500 aag aat ctc ctt gga gct gag aac cga gag ctg aag ctg gtg gct ccc    1951
Lys Asn Leu Leu Gly Ala Glu Asn Arg Glu Leu Lys Leu Val Ala Pro
    505                 510                 515 acc ctg cgt tct gaa ctc acg gtg gct gct gca gtc ctg gtg ctg ttg    1999
Thr Leu Arg Ser Glu Leu Thr Val Ala Ala Ala Val Leu Val Leu Leu
520                 525                 530                 535 gtg att gtg atc atc tca ctt att gtc ctg gtt gtc att tgg aaa cag    2047
Val Ile Val Ile Ile Ser Leu Ile Val Leu Val Val Ile Trp Lys Gln
                540                 545                 550
```

```
aaa ccg agg tat gaa att cgc tgg agg gtc att gaa tca atc agc ccg     2095
Lys Pro Arg Tyr Glu Ile Arg Trp Arg Val Ile Glu Ser Ile Ser Pro
        555                 560                 565 gat gga cat gaa tat att tat gtg gac ccg atg cag ctg cct tat gac     2143
Asp Gly His Glu Tyr Ile Tyr Val Asp Pro Met Gln Leu Pro Tyr Asp
            570                 575                 580 tca aga tgg gag ttt cca aga gat gga cta gtg ctt ggt cgg gtc ttg     2191
Ser Arg Trp Glu Phe Pro Arg Asp Gly Leu Val Leu Gly Arg Val Leu
585                 590                 595 ggg tct gga gcg ttt ggg aag gtg gtt gaa gga aca gcc tat gga tta     2239
Gly Ser Gly Ala Phe Gly Lys Val Val Glu Gly Thr Ala Tyr Gly Leu
600                 605                 610                 615 agc cgg tcc caa cct gtc atg aaa gtt gca gtg aag atg cta aaa ccc     2287
Ser Arg Ser Gln Pro Val Met Lys Val Ala Val Lys Met Leu Lys Pro
            620                 625                 630 acg gcc aga tcc agt gaa aaa caa gct ctc atg tct gaa ctg aag ata     2335
Thr Ala Arg Ser Ser Glu Lys Gln Ala Leu Met Ser Glu Leu Lys Ile
            635                 640                 645 atg act cac ctg ggg cca cat ttg aac att gta aac ttg ctg gga gcc     2383
Met Thr His Leu Gly Pro His Leu Asn Ile Val Asn Leu Leu Gly Ala
650                 655                 660 tgc acc aag tca ggc ccc att tac atc atc aca gag tat tgc ttc tat     2431
Cys Thr Lys Ser Gly Pro Ile Tyr Ile Ile Thr Glu Tyr Cys Phe Tyr
665                 670                 675 gga gat ttg gtc aac tat ttg cat aag aat agg gat agc ttc ctg agc     2479
Gly Asp Leu Val Asn Tyr Leu His Lys Asn Arg Asp Ser Phe Leu Ser
680                 685                 690                 695 cac cac cca gag aag cca aag aaa gag ctg gat atc ttt gga ttg aac     2527
His His Pro Glu Lys Pro Lys Lys Glu Leu Asp Ile Phe Gly Leu Asn
            700                 705                 710 cct gct gat gaa agc aca cgg agc tat gtt att tta tct ttt gaa aac     2575
Pro Ala Asp Glu Ser Thr Arg Ser Tyr Val Ile Leu Ser Phe Glu Asn
            715                 720                 725 aat ggt gac tac atg gac atg aag cag gct gat act aca cag tat gtc     2623
Asn Gly Asp Tyr Met Asp Met Lys Gln Ala Asp Thr Thr Gln Tyr Val
            730                 735                 740 ccc atg cta gaa agg aaa gag gtt tct aaa tat tcc gac atc cag aga     2671
Pro Met Leu Glu Arg Lys Glu Val Ser Lys Tyr Ser Asp Ile Gln Arg
745                 750                 755 tca ctc tat gat cgt cca gcc tca tat aag aag aaa tct atg tta gac     2719
Ser Leu Tyr Asp Arg Pro Ala Ser Tyr Lys Lys Lys Ser Met Leu Asp
760                 765                 770                 775 tca gaa gtc aaa aac ctc ctt tca gat gat aac tca gaa ggc ctt act     2767
Ser Glu Val Lys Asn Leu Leu Ser Asp Asp Asn Ser Glu Gly Leu Thr
            780                 785                 790 tta ttg gat ttg ttg agc ttc acc tat caa gtt gcc cga gga atg gag     2815
Leu Leu Asp Leu Leu Ser Phe Thr Tyr Gln Val Ala Arg Gly Met Glu
            795                 800                 805 ttt ttg gct tca aaa aat tgt gtc cac cgt gat ctg gct gct cgc aac     2863
Phe Leu Ala Ser Lys Asn Cys Val His Arg Asp Leu Ala Ala Arg Asn
            810                 815                 820 gtc ctc ctg gca caa gga aaa att gtg aag atc tgt gac ttt ggc ctg     2911
Val Leu Leu Ala Gln Gly Lys Ile Val Lys Ile Cys Asp Phe Gly Leu
825                 830                 835 gcc aga gac atc atg cat gat tcg aac tat gtg tcg aaa ggc agt acc     2959
Ala Arg Asp Ile Met His Asp Ser Asn Tyr Val Ser Lys Gly Ser Thr
840                 845                 850                 855 ttt ctg ccc gtg aag tgg atg gct cct gag agc atc ttt gac aac ctc     3007
Phe Leu Pro Val Lys Trp Met Ala Pro Glu Ser Ile Phe Asp Asn Leu
```

-continued

```
                  860                 865                 870
tac acc aca ctg agt gat gtc tgg tct tat ggc att ctg ctc tgg gag      3055
Tyr Thr Thr Leu Ser Asp Val Trp Ser Tyr Gly Ile Leu Leu Trp Glu
            875                 880                 885 atc ttt tcc ctt ggt ggc acc cct tac ccc ggc atg atg gtg gat tct      3103
Ile Phe Ser Leu Gly Gly Thr Pro Tyr Pro Gly Met Met Val Asp Ser
        890                 895                 900 act ttc tac aat aag atc aag agt ggg tac cgg atg gcc aag cct gac      3151
Thr Phe Tyr Asn Lys Ile Lys Ser Gly Tyr Arg Met Ala Lys Pro Asp
    905                 910                 915 cac gct acc agt gaa gtc tac gag atc atg gtg aaa tgc tgg aac agt      3199
His Ala Thr Ser Glu Val Tyr Glu Ile Met Val Lys Cys Trp Asn Ser
920                 925                 930                 935 gag ccg gag aag aga ccc tcc ttt tac cac ctg agt gag att gtg gag      3247
Glu Pro Glu Lys Arg Pro Ser Phe Tyr His Leu Ser Glu Ile Val Glu
                940                 945                 950 aat ctg ctg cct gga caa tat aaa aag agt tat gaa aaa att cac ctg      3295
Asn Leu Leu Pro Gly Gln Tyr Lys Lys Ser Tyr Glu Lys Ile His Leu
            955                 960                 965 gac ttc ctg aag agt gac cat cct gct gtg gca cgc atg cgt gtg gac      3343
Asp Phe Leu Lys Ser Asp His Pro Ala Val Ala Arg Met Arg Val Asp
        970                 975                 980 tca gac aat gca tac att ggt gtc acc tac aaa aac gag gaa gac aag      3391
Ser Asp Asn Ala Tyr Ile Gly Val Thr Tyr Lys Asn Glu Glu Asp Lys
    985                 990                 995 ctg  aag gac tgg gag ggt  ggt ctg gat gag cag  aga ctg agc gct       3436
Leu  Lys Asp Trp Glu Gly  Gly Leu Asp Glu Gln  Arg Leu Ser Ala
1000              1005                1010 gac  agt ggc tac atc att  cct ctg cct gac att  gac cct gtc cct       3481
Asp  Ser Gly Tyr Ile Ile  Pro Leu Pro Asp Ile  Asp Pro Val Pro
1015              1020                1025 gag  gag gag gac ctg ggc  aag agg aac aga cac  agc tcg cag acc       3526
Glu  Glu Glu Asp Leu Gly  Lys Arg Asn Arg His  Ser Ser Gln Thr
1030              1035                1040 tct  gaa gag agt gcc att  gag acg ggt tcc agc  agt tcc acc ttc       3571
Ser  Glu Glu Ser Ala Ile  Glu Thr Gly Ser Ser  Ser Ser Thr Phe
1045              1050                1055 atc  aag aga gag gac gag  acc att gaa gac atc  gac atg atg gac       3616
Ile  Lys Arg Glu Asp Glu  Thr Ile Glu Asp Ile  Asp Met Met Asp
1060              1065                1070 gac  atc ggc ata gac tct  tca gac ctg gtg gaa  gac agc ttc ctg       3661
Asp  Ile Gly Ile Asp Ser  Ser Asp Leu Val Glu  Asp Ser Phe Leu
1075              1080                1085 taa ctggcggatt cgagggttc cttccacttc tggggccacc tctggatccc            3714
gttcagaaaa ccactttatt gcaatgcgga ggttgagagg aggacttggt tgatgtttaa    3774
agagaagttc ccagccaagg gcctcgggga gcgttctaaa tatgaatgaa tgggatattt    3834
tgaaatgaac tttgtcagtg ttgcctctcg caatgcctca gtagcatctc agtggtgtgt    3894
gaagtttgga gatagatgga taagggaata ataggccaca gaaggtgaac tttgtgcttc    3954
aaggacattg tgagagtcc aacagacaca atttatactg cgacagaact tcagcattgt     4014
aattatgtaa ataactctaa ccaaggctgt gtttagattg tattaactat cttctttgga    4074
cttctgaaga gaccactcaa tccatccatg tacttccctc ttgaaacctg atgtcagctg    4134
ctgttgaact ttttaaagaa gtgcatgaaa aaccattttt gaaccttaaa aggtactggt    4194
actatagcat tttgctatct tttttagtgt taagagataa agaataataa ttaaccaacc    4254
ttgtttaata gatttgggtc atttagaagc ctgacaactc attttcatat tgtaatctat    4314
```

-continued

```
gtttataata ctactactgt tatcagtaat gctaaatgtg taataatgta acatgatttc    4374
cctccagaga aagcacaatt taaaacaatc cttactaagt aggtgatgag tttgacagtt    4434
tttgacattt atattaaata acatgtttct ctataaagta tggtaatagc tttagtgaat    4494
taaatttagt tgagcataga aacaaagta aaagtagtgt tgtccaggaa gtcagaattt    4554
ttaactgtac tgaataggtt ccccaatcca tcgtattaaa aaacaattaa ctgccctctg    4614
aaataatggg attagaaaca aacaaaactc ttaagtccta aaagttctca atgtagaggc    4674
ataaacctgt gctgaacata acttctcatg tatattaccc aatggaaaat ataatgatca    4734
gcaaaaagac tggatttgca gaagtttttt ttttttttct tcatgcctga tgaaagcttt    4794
ggcaacccca atatatgtat tttttgaatc tatgaacctg aaaagggtca gaaggatgcc    4854
cagacatcag cctccttctt tcacccctta ccccaaagag aaagagtttg aaactcgaga    4914
ccataaagat attctttagt ggaggctgga tgtgcattag cctggatcct cagttctcaa    4974
atgtgtgtgg cagccaggat gactagatcc tgggtttcca tccttgagat tctgaagtat    5034
gaagtctgag ggaaaccaga gtctgtattt ttctaaactc cctggctgtt ctgatcggcc    5094
agttttcgga aacactgact taggtttcag gaagttgcca tgggaaacaa ataatttgaa    5154
ctttggaaca gggttggaat tcaaccacgc aggaagccta ctatttaaat ccttggcttc    5214
aggttagtga catttaatgc catctagcta gcaattgcga ccttaattta actttccagt    5274
cttagctgag gctgagaaag ctaaagtttg gttttgacag gttttccaaa agtaaagatg    5334
ctacttccca ctgtatgggg gagattgaac tttccccgtc tcccgtcttc tgcctcccac    5394
tccatacccc gccaaggaaa ggcatgtaca aaaattatgc aattcagtgt tccaagtctc    5454
tgtgtaacca gctcagtgtt ttggtggaaa aaacatttta agttttactg ataatttgag    5514
gttagatggg aggatgaatt gtcacatcta tccacactgt caaacaggtt ggtgtgggtt    5574
cattggcatt ctttgcaata ctgcttaatt gctgatacca tatgaatgaa acatgggctg    5634
tgattactgc aatcactgtg ctatcggcag atgatgcttt ggaagatgca gaagcaataa    5694
taaagtactt gactacctac tggtgtaatc tcaatgcaag ccccaacttt cttatccaac    5754
tttttcatag taagtgcgaa gactgagcca gattggccaa ttaaaaacga aaacctgact    5814
aggttctgta gagccaatta gacttgaaat acgtttgtgt ttctagaatc acagctcaag    5874
cattctgttt atcgctcact ctcccttgta cagccttatt ttgttggtgc tttgcatttt    5934
gatattgctg tgagccttgc atgacatcat gaggccggat gaaacttctc agtccagcag    5994
tttccagtcc taacaaatgc tcccacctga atttgtatat gactgcattt gtgggtgtgt    6054
gtgtgttttc agcaaattcc agatttgttt ccttttggcc tcctgcaaag tctccagaag    6114
aaaatttgcc aatctttcct actttctatt tttatgatga caatcaaagc cggcctgaga    6174
aacactattt gtgactttt aaacgattag tgatgtcctt aaaatgtggt ctgccaatct    6234
gtacaaaatg gtcctatttt tgtgaagagg gacataagat aaaatgatgt tatacatcaa    6294
tatgtatata tgtatttcta tatagacttg gagaatactg ccaaaacatt tatgacaagc    6354
tgtatcactg ccttcgttta tatttttta actgtgataa tccccacagg cacattaact    6414
gttgcacttt tgaatgtcca aaattttatat tttagaaata ataaaagaa agatacttac    6474
atgttcccaa acaatggtg tggtgaatgt gtgagaaaaa ctaacttgat agggtctacc    6534
aatacaaaat gtattacgaa tgcccctgtt catgttttg ttttaaaacg tgtaaatgaa    6594
gatctttata tttcaataaa tgatatataa tttaaagtt                            6633
```

<210> SEQ ID NO 2
<211> LENGTH: 1089
<212> TYPE: PRT
<213> ORGANISM: Homo sapiens

<400> SEQUENCE: 2

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ala Ser Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380
```

```
Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
            405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800
```

-continued

```
Gln Val Ala Arg Gly Met Glu Phe Leu Ala Ser Lys Asn Cys Val His
            805                 810                 815

Arg Asp Leu Ala Ala Arg Asn Val Leu Leu Ala Gln Gly Lys Ile Val
        820                 825                 830

Lys Ile Cys Asp Phe Gly Leu Ala Arg Asp Ile Met His Asp Ser Asn
    835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                 1005

Glu Gln  Arg Leu Ser Ala Asp  Ser Gly Tyr Ile Ile  Pro Leu Pro
    1010                 1015                 1020

Asp Ile  Asp Pro Val Pro Glu  Glu Glu Asp Leu Gly  Lys Arg Asn
    1025                 1030                 1035

Arg His  Ser Ser Gln Thr Ser  Glu Glu Ser Ala Ile  Glu Thr Gly
    1040                 1045                 1050

Ser Ser  Ser Ser Thr Phe Ile  Lys Arg Glu Asp Glu  Thr Ile Glu
    1055                 1060                 1065

Asp Ile  Asp Met Met Asp Asp  Ile Gly Ile Asp Ser  Ser Asp Leu
    1070                 1075                 1080

Val Glu  Asp Ser Phe Leu
    1085

<210> SEQ ID NO 3
<211> LENGTH: 6633
<212> TYPE: DNA
<213> ORGANISM: Homo sapiens
<220> FEATURE:
<221> NAME/KEY: CDS
<222> LOCATION: (395)..(3664)

<400> SEQUENCE: 3
ttctccccgc cccccagttg ttgtcgaagt ctgggggttg ggactggacc ccctgattgc       60
gtaagagcaa aaagcgaagg cgcaatctgg acactgggag attcggagcg cagggagttt      120
gagagaaact tttattttga agagaccaag gttgaggggg ggcttattc ctgacagcta      180 tttacttaga gcaaatgatt agttttagaa ggatggacta taacattgaa tcaattacaa      240
aacgcggttt ttgagcccat tactgttgga gctacaggga gagaaacagg aggagactgc      300
aagagatcat ttgggaaggc cgtgggcacg ctctttactc catgtgtggg acattcattg      360
```

-continued

```
cggaataaca tcggaggaga agtttcccag agct atg ggg act tcc cat ccg gcg        415
                                    Met Gly Thr Ser His Pro Ala
                                     1               5 ttc ctg gtc tta ggc tgt ctt ctc aca ggg ctg agc cta atc ctc tgc          463
Phe Leu Val Leu Gly Cys Leu Leu Thr Gly Leu Ser Leu Ile Leu Cys
         10                  15                  20 cag ctt tca tta ccc tct atc ctt cca aat gaa aat gaa aag gtt gtg          511
Gln Leu Ser Leu Pro Ser Ile Leu Pro Asn Glu Asn Glu Lys Val Val
 25                  30                  35 cag ctg aat tca tcc ttt tct ctg aga tgc ttt ggg gag agt gaa gtg          559
Gln Leu Asn Ser Ser Phe Ser Leu Arg Cys Phe Gly Glu Ser Glu Val
 40                  45                  50                  55 agc tgg cag tac ccc atg tct gaa gaa gag agc tcc gat gtg gaa atc          607
Ser Trp Gln Tyr Pro Met Ser Glu Glu Glu Ser Ser Asp Val Glu Ile
                 60                  65                  70 aga aat gaa gaa aac aac agc ggc ctt ttt gtg acg gtc ttg gaa gtg          655
Arg Asn Glu Glu Asn Asn Ser Gly Leu Phe Val Thr Val Leu Glu Val
             75                  80                  85 agc agt gcc tcg gcg gcc cac aca ggg ttg tac act tgc tat tac aac          703
Ser Ser Ala Ser Ala Ala His Thr Gly Leu Tyr Thr Cys Tyr Tyr Asn
         90                  95                 100 cac act cag aca gaa gag aat gag ctt gaa ggc agg cac att tac atc          751
His Thr Gln Thr Glu Glu Asn Glu Leu Glu Gly Arg His Ile Tyr Ile
 105                 110                 115 tat gtg cca gac cca gat gta gcc ttt gta cct cta gga atg acg gat          799
Tyr Val Pro Asp Pro Asp Val Ala Phe Val Pro Leu Gly Met Thr Asp
 120                 125                 130                 135 tat tta gtc atc gtg gag gat gat gat tct gcc att ata cct tgt cgc          847
Tyr Leu Val Ile Val Glu Asp Asp Asp Ser Ala Ile Ile Pro Cys Arg
                 140                 145                 150 aca act gat ccc gag act cct gta acc tta cac aac agt gag ggg gtg          895
Thr Thr Asp Pro Glu Thr Pro Val Thr Leu His Asn Ser Glu Gly Val
             155                 160                 165 gta cct gcc tcc tac gac agc aga cag ggc ttt aat ggg acc ttc act          943
Val Pro Ala Ser Tyr Asp Ser Arg Gln Gly Phe Asn Gly Thr Phe Thr
         170                 175                 180 gta ggg ccc tat atc tgt gag gcc acc gtc aaa gga aag aag ttc cag          991
Val Gly Pro Tyr Ile Cys Glu Ala Thr Val Lys Gly Lys Lys Phe Gln
 185                 190                 195 acc atc cca ttt aat gtt tat gct tta aaa gca aca tca gag ctg gat         1039
Thr Ile Pro Phe Asn Val Tyr Ala Leu Lys Ala Thr Ser Glu Leu Asp
 200                 205                 210                 215 cta gaa atg gaa gct ctt aaa acc gtg tat aag tca ggg gaa acg att         1087
Leu Glu Met Glu Ala Leu Lys Thr Val Tyr Lys Ser Gly Glu Thr Ile
                 220                 225                 230 gtg gtc acc tgt gct gtt ttt aac aat gag gtg gtt gac ctt caa tgg         1135
Val Val Thr Cys Ala Val Phe Asn Asn Glu Val Val Asp Leu Gln Trp
             235                 240                 245 act tac cct gga gaa gtg aaa ggc aaa ggc atc aca atg ctg gaa gaa         1183
Thr Tyr Pro Gly Glu Val Lys Gly Lys Gly Ile Thr Met Leu Glu Glu
         250                 255                 260 atc aaa gtc cca tcc atc aaa ttg gtg tac act ttg acg gtc ccc gag         1231
Ile Lys Val Pro Ser Ile Lys Leu Val Tyr Thr Leu Thr Val Pro Glu
 265                 270                 275 gcc acg gtg aaa gac agt gga gat tac gaa tgt gct gcc cgc cag gct         1279
Ala Thr Val Lys Asp Ser Gly Asp Tyr Glu Cys Ala Ala Arg Gln Ala
 280                 285                 290                 295 acc agg gag gtc aaa gaa atg aag aaa gtc act att tct gtc cat gag         1327
Thr Arg Glu Val Lys Glu Met Lys Lys Val Thr Ile Ser Val His Glu
```

-continued

```
                   300                 305                 310
aaa ggt ttc att gaa atc aaa ccc acc ttc agc cag ttg gaa gct gtc    1375
Lys Gly Phe Ile Glu Ile Lys Pro Thr Phe Ser Gln Leu Glu Ala Val
                315                 320                 325 aac ctg cat gaa gtc aaa cat ttt gtt gta gag gtg cgg gcc tac cca    1423
Asn Leu His Glu Val Lys His Phe Val Val Glu Val Arg Ala Tyr Pro
            330                 335                 340 cct ccc agg ata tcc tgg ctg aaa aac aat ctg act ctg att gaa aat    1471
Pro Pro Arg Ile Ser Trp Leu Lys Asn Asn Leu Thr Leu Ile Glu Asn
        345                 350                 355 ctc act gag atc acc act gat gtg gaa aag att cag gaa ata agg tat    1519
Leu Thr Glu Ile Thr Thr Asp Val Glu Lys Ile Gln Glu Ile Arg Tyr
360                 365                 370                 375 cga agc aaa tta aag ctg atc cgt gct aag gaa gaa gac agt ggc cat    1567
Arg Ser Lys Leu Lys Leu Ile Arg Ala Lys Glu Glu Asp Ser Gly His
                380                 385                 390 tat act att gta gct caa aat gaa gat gct gtg aag agc tat act ttt    1615
Tyr Thr Ile Val Ala Gln Asn Glu Asp Ala Val Lys Ser Tyr Thr Phe
            395                 400                 405 gaa ctg tta act caa gtt cct tca tcc att ctg gac ttg gtc gat gat    1663
Glu Leu Leu Thr Gln Val Pro Ser Ser Ile Leu Asp Leu Val Asp Asp
        410                 415                 420 cac cat ggc tca act ggg gga cag acg gtg agg tgc aca gct gaa ggc    1711
His His Gly Ser Thr Gly Gly Gln Thr Val Arg Cys Thr Ala Glu Gly
425                 430                 435 acg ccg ctt cct gat att gag tgg atg ata tgc aaa gat att aag aaa    1759
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac    1807
Cys Asn Asn Glu Thr Ser Trp Thr Ile Leu Ala Asn Asn Val Ser Asn
                460                 465                 470 atc atc acg gag atc cac tcc cga gac agg agt acc gtg gag ggc cgt    1855
Ile Ile Thr Glu Ile His Ser Arg Asp Arg Ser Thr Val Glu Gly Arg
            475                 480                 485 gtg act ttc gcc aaa gtg gag gag acc atc gcc gtg cga tgc ctg gct    1903
Val Thr Phe Ala Lys Val Glu Glu Thr Ile Ala Val Arg Cys Leu Ala
        490                 495                 500 aag aat ctc ctt gga gct gag aac cga gag ctg aag ctg gtg gct ccc    1951
Lys Asn Leu Leu Gly Ala Glu Asn Arg Glu Leu Lys Leu Val Ala Pro
505                 510                 515 acc ctg cgt tct gaa ctc acg gtg gct gct gca gtc ctg gtg ctg ttg    1999
Thr Leu Arg Ser Glu Leu Thr Val Ala Ala Ala Val Leu Val Leu Leu
520                 525                 530                 535 gtg att gtg atc atc tca ctt att gtc ctg gtt gtc att tgg aaa cag    2047
Val Ile Val Ile Ile Ser Leu Ile Val Leu Val Val Ile Trp Lys Gln
                540                 545                 550 aaa ccg agg tat gaa att cgc tgg agg gtc att gaa tca atc agc ccg    2095
Lys Pro Arg Tyr Glu Ile Arg Trp Arg Val Ile Glu Ser Ile Ser Pro
            555                 560                 565 gat gga cat gaa tat att tat gtg gac ccg atg cag ctg cct tat gac    2143
Asp Gly His Glu Tyr Ile Tyr Val Asp Pro Met Gln Leu Pro Tyr Asp
        570                 575                 580 tca aga tgg gag ttt cca aga gat gga cta gtg ctt ggt cgg gtc ttg    2191
Ser Arg Trp Glu Phe Pro Arg Asp Gly Leu Val Leu Gly Arg Val Leu
585                 590                 595 ggg tct gga gcg ttt ggg aag gtg gtt gaa gga aca gcc tat gga tta    2239
Gly Ser Gly Ala Phe Gly Lys Val Val Glu Gly Thr Ala Tyr Gly Leu
600                 605                 610                 615 agc cgg tcc caa cct gtc atg aaa gtt gca gtg aag atg cta aaa ccc    2287
```

```
Ser Arg Ser Gln Pro Val Met Lys Val Ala Lys Met Leu Lys Pro
            620                 625                 630 acg gcc aga tcc agt gaa aaa caa gct ctc atg tct gaa ctg aag ata    2335
Thr Ala Arg Ser Ser Glu Lys Gln Ala Leu Met Ser Glu Leu Lys Ile
        635                 640                 645 atg act cac ctg ggg cca cat ttg aac att gta aac ttg ctg gga gcc    2383
Met Thr His Leu Gly Pro His Leu Asn Ile Val Asn Leu Leu Gly Ala
        650                 655                 660 tgc acc aag tca ggc ccc att tac atc atc aca gag tat tgc ttc tat    2431
Cys Thr Lys Ser Gly Pro Ile Tyr Ile Ile Thr Glu Tyr Cys Phe Tyr
        665                 670                 675 gga gat ttg gtc aac tat ttg cat aag aat agg gat agc ttc ctg agc    2479
Gly Asp Leu Val Asn Tyr Leu His Lys Asn Arg Asp Ser Phe Leu Ser
680                 685                 690                 695 cac cac cca gag aag cca aag aaa gag ctg gat atc ttt gga ttg aac    2527
His His Pro Glu Lys Pro Lys Lys Glu Leu Asp Ile Phe Gly Leu Asn
                700                 705                 710 cct gct gat gaa agc aca cgg agc tat gtt att tta tct ttt gaa aac    2575
Pro Ala Asp Glu Ser Thr Arg Ser Tyr Val Ile Leu Ser Phe Glu Asn
                715                 720                 725 aat ggt gac tac atg gac atg aag cag gct gat act aca cag tat gtc    2623
Asn Gly Asp Tyr Met Asp Met Lys Gln Ala Asp Thr Thr Gln Tyr Val
            730                 735                 740 ccc atg cta gaa agg aaa gag gtt tct aaa tat tcc gac atc cag aga    2671
Pro Met Leu Glu Arg Lys Glu Val Ser Lys Tyr Ser Asp Ile Gln Arg
        745                 750                 755 tca ctc tat gat cgt cca gcc tca tat aag aag aaa tct atg tta gac    2719
Ser Leu Tyr Asp Arg Pro Ala Ser Tyr Lys Lys Lys Ser Met Leu Asp
760                 765                 770                 775 tca gaa gtc aaa aac ctc ctt tca gat gat aac tca gaa ggc ctt act    2767
Ser Glu Val Lys Asn Leu Leu Ser Asp Asp Asn Ser Glu Gly Leu Thr
                780                 785                 790 tta ttg gat ttg ttg agc ttc acc tat caa gtt gcc cga gga atg gag    2815
Leu Leu Asp Leu Leu Ser Phe Thr Tyr Gln Val Ala Arg Gly Met Glu
                795                 800                 805 ttt ttg gct tca aaa aat tgt gtc cac cgt gat ctg gct gct cgc aac    2863
Phe Leu Ala Ser Lys Asn Cys Val His Arg Asp Leu Ala Ala Arg Asn
            810                 815                 820 gtc ctc ctg gca caa gga aaa att gtg aag atc tgt gac ttt ggc ctg    2911
Val Leu Leu Ala Gln Gly Lys Ile Val Lys Ile Cys Asp Phe Gly Leu
        825                 830                 835 gcc aga gtc atc atg cat gat tcg aac tat gtg tcg aaa ggc agt acc    2959
Ala Arg Val Ile Met His Asp Ser Asn Tyr Val Ser Lys Gly Ser Thr
840                 845                 850                 855 ttt ctg ccc gtg aag tgg atg gct cct gag agc atc ttt gac aac ctc    3007
Phe Leu Pro Val Lys Trp Met Ala Pro Glu Ser Ile Phe Asp Asn Leu
                860                 865                 870 tac acc aca ctg agt gat gtc tgg tct tat ggc att ctg ctc tgg gag    3055
Tyr Thr Thr Leu Ser Asp Val Trp Ser Tyr Gly Ile Leu Leu Trp Glu
            875                 880                 885 atc ttt tcc ctt ggt ggc acc cct tac ccc ggc atg atg gtg gat tct    3103
Ile Phe Ser Leu Gly Gly Thr Pro Tyr Pro Gly Met Met Val Asp Ser
        890                 895                 900 act ttc tac aat aag atc aag agt ggg tac cgg atg gcc aag cct gac    3151
Thr Phe Tyr Asn Lys Ile Lys Ser Gly Tyr Arg Met Ala Lys Pro Asp
        905                 910                 915 cac gct acc agt gaa gtc tac gag atc atg gtg aaa tgc tgg aac agt    3199
His Ala Thr Ser Glu Val Tyr Glu Ile Met Val Lys Cys Trp Asn Ser
920                 925                 930                 935
```

| | |
|---|---|
| gag ccg gag aag aga ccc tcc ttt tac cac ctg agt gag att gtg gag<br>Glu Pro Glu Lys Arg Pro Ser Phe Tyr His Leu Ser Glu Ile Val Glu<br>            940                  945                  950 | 3247 |
| aat ctg ctg cct gga caa tat aaa aag agt tat gaa aaa att cac ctg<br>Asn Leu Leu Pro Gly Gln Tyr Lys Lys Ser Tyr Glu Lys Ile His Leu<br>        955                  960                  965 | 3295 |
| gac ttc ctg aag agt gac cat cct gct gtg gca cgc atg cgt gtg gac<br>Asp Phe Leu Lys Ser Asp His Pro Ala Val Ala Arg Met Arg Val Asp<br>            970                  975                  980 | 3343 |
| tca gac aat gca tac att ggt gtc acc tac aaa aac gag gaa gac aag<br>Ser Asp Asn Ala Tyr Ile Gly Val Thr Tyr Lys Asn Glu Glu Asp Lys<br>        985                  990                  995 | 3391 |
| ctg aag gac tgg gag ggt ggt ctg gat gag cag aga ctg agc gct<br>Leu Lys Asp Trp Glu Gly Gly Leu Asp Glu Gln Arg Leu Ser Ala<br>1000                1005               1010 | 3436 |
| gac agt ggc tac atc att cct ctg cct gac att gac cct gtc cct<br>Asp Ser Gly Tyr Ile Ile Pro Leu Pro Asp Ile Asp Pro Val Pro<br>1015                1020               1025 | 3481 |
| gag gag gag gac ctg ggc aag agg aac aga cac agc tcg cag acc<br>Glu Glu Glu Asp Leu Gly Lys Arg Asn Arg His Ser Ser Gln Thr<br>1030                1035               1040 | 3526 |
| tct gaa gag agt gcc att gag acg ggt tcc agc agt tcc acc ttc<br>Ser Glu Glu Ser Ala Ile Glu Thr Gly Ser Ser Ser Ser Thr Phe<br>1045                1050               1055 | 3571 |
| atc aag aga gag gac gag acc att gaa gac atc gac atg atg gac<br>Ile Lys Arg Glu Asp Glu Thr Ile Glu Asp Ile Asp Met Met Asp<br>1060                1065               1070 | 3616 |
| gac atc ggc ata gac tct tca gac ctg gtg gaa gac agc ttc ctg<br>Asp Ile Gly Ile Asp Ser Ser Asp Leu Val Glu Asp Ser Phe Leu<br>1075                1080               1085 | 3661 |
| taa ctggcggatt cgagggggttc cttccacttc tggggccacc tctggatccc | 3714 |
| gttcagaaaa ccactttatt gcaatgcgga ggttgagagg aggacttggt tgatgtttaa | 3774 |
| agagaagttc ccagccaagg gcctcgggga gcgttctaaa tatgaatgaa tgggatattt | 3834 |
| tgaaatgaac tttgtcagtg ttgcctctcg caatgcctca gtagcatctc agtggtgtgt | 3894 |
| gaagtttgga gatagatgga taagggaata ataggccaca gaaggtgaac tttgtgcttc | 3954 |
| aaggacattg gtgagagtcc aacagacaca atttatactg cgacagaact tcagcattgt | 4014 |
| aattatgtaa ataactctaa ccaaggctgt gtttagattg tattaactat cttctttgga | 4074 |
| cttctgaaga gaccactcaa tccatccatg tacttccctc ttgaaacctg atgtcagctg | 4134 |
| ctgttgaact ttttaaagaa gtgcatgaaa aaccattttt gaaccttaaa aggtactggt | 4194 |
| actatagcat tttgctatct ttttagtgt taagagataa agaataataa ttaaccaacc | 4254 |
| ttgtttaata gatttgggtc atttagaagc ctgacaactc attttcatat tgtaatctat | 4314 |
| gtttataata ctactactgt tatcagtaat gctaaatgtg taataatgta acatgatttc | 4374 |
| cctccagaga aagcacaatt taaaacaatc cttactaagt aggtgatgag tttgacagtg | 4434 |
| tttgacattt atattaaata acatgttttct ctataaagta tggtaatagc tttagtgaat | 4494 |
| taaatttagt tgagcataga gaacaaagta aaagtagtgt tgtccaggaa gtcagaattt | 4554 |
| ttaactgtac tgaataggtt ccccaatcca tcgtattaaa aaacaattaa ctgccctctg | 4614 |
| aaataatggg attagaaaca aacaaaactc ttaagtccta aaagttctca atgtagaggc | 4674 |
| ataaacctgt gctgaacata acttctcatg tatattaccc aatggaaaat ataatgatca | 4734 |
| gcaaaaagac tggatttgca gaagtttttt ttttttttct tcatgcctga tgaaagcttt | 4794 |
| ggcaacccca atatatgtat ttttgaatc tatgaacctg aaaagggtca gaaggatgcc | 4854 |

```
cagacatcag cctccttctt tcaccccctta ccccaaagag aaagagtttg aaactcgaga   4914
ccataaagat attctttagt ggaggctgga tgtgcattag cctggatcct cagttctcaa   4974
atgtgtgtgg cagccaggat gactagatcc tgggtttcca tccttgagat tctgaagtat   5034
gaagtctgag ggaaaccaga gtctgtattt ttctaaactc cctggctgtt ctgatcggcc   5094
agttttcgga acactgact taggtttcag gaagttgcca tgggaaacaa ataatttgaa    5154
ctttggaaca gggttggaat tcaaccacgc aggaagccta ctatttaaat ccttggcttc   5214
aggttagtga catttaatgc catctagcta gcaattgcga ccttaattta actttccagt   5274
cttagctgag gctgagaaag ctaaagtttg gttttgacag gttttccaaa agtaaagatg   5334
ctacttccca ctgtatgggg gagattgaac tttccccgtc tcccgtcttc tgcctcccac   5394
tccatacccc gccaaggaaa ggcatgtaca aaaattatgc aattcagtgt tccaagtctc   5454
tgtgtaacca gctcagtgtt ttggtggaaa aaacatttta agttttactg ataatttgag   5514
gttagatggg aggatgaatt gtcacatcta tccacactgt caaacaggtt ggtgtgggtt   5574
cattggcatt ctttgcaata ctgcttaatt gctgatacca tatgaatgaa acatgggctg   5634
tgattactgc aatcactgtg ctatcggcag atgatgcttt ggaagatgca gaagcaataa   5694
taaagtactt gactacctac tggtgtaatc tcaatgcaag ccccaacttt cttatccaac   5754
tttttcatag taagtgcgaa gactgagcca gattggccaa ttaaaaacga aaacctgact   5814
aggttctgta gagccaatta gacttgaaat acgtttgtgt ttctagaatc acagctcaag   5874
cattctgttt atcgctcact ctcccttgta cagccttatt ttgttggtgc tttgcatttt   5934
gatattgctg tgagccttgc atgacatcat gaggccggat gaaacttctc agtccagcag   5994
tttccagtcc taacaaatgc tcccacctga atttgtatat gactgcattt gtgggtgtgt   6054
gtgtgttttc agcaaattcc agatttgttt ccttttggcc tcctgcaaag tctccagaag   6114
aaaatttgcc aatctttcct actttctatt tttatgatga caatcaaagc cggcctgaga   6174
aacactattt gtgacttttt aaacgattag tgatgtcctt aaaatgtggt ctgccaatct   6234
gtacaaaatg gtcctatttt tgtgaagagg gacataagat aaaatgatgt tatacatcaa   6294
tatgtatata tgtatttcta tatagacttg gagaatactg ccaaaacatt tatgacaagc   6354
tgtatcactg ccttcgttta tattttttta actgtgataa tccccacagg cacattaact   6414
gttgcactt tgaatgtcca aaatttatat tttagaaata ataaaagaa agatacttac     6474
atgttcccaa aacaatggtg tggtgaatgt gtgagaaaaa ctaacttgat agggtctacc   6534
aatacaaaat gtattacgaa tgcccctgtt catgttttg ttttaaaacg tgtaaatgaa    6594
gatctttata tttcaataaa tgatatataa tttaaagtt                          6633
```

<210> SEQ ID NO 4
<211> LENGTH: 1089
<212> TYPE: PRT
<213> ORGANISM: Homo sapiens

<400> SEQUENCE: 4

```
Met Gly Thr Ser His Pro Ala Phe Leu Val Leu Gly Cys Leu Leu Thr
 1               5                  10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
```

-continued

```
            50                  55                  60
Glu Ser Ser Asp Val Glu Ile Arg Asn Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
                100                 105                 110

Glu Gly Arg His Ile Tyr Ile Tyr Val Pro Asp Pro Asp Val Ala Phe
                115                 120                 125

Val Pro Leu Gly Met Thr Asp Tyr Leu Val Ile Val Glu Asp Asp Asp
130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
                180                 185                 190

Val Lys Gly Lys Lys Phe Gln Thr Ile Pro Phe Asn Val Tyr Ala Leu
                195                 200                 205

Lys Ala Thr Ser Glu Leu Asp Leu Glu Met Glu Ala Leu Lys Thr Val
                210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
                260                 265                 270

Tyr Thr Leu Thr Val Pro Glu Ala Thr Val Lys Asp Ser Gly Asp Tyr
                275                 280                 285

Glu Cys Ala Ala Arg Gln Ala Thr Arg Glu Val Lys Glu Met Lys Lys
                290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
                340                 345                 350

Asn Leu Thr Leu Ile Glu Asn Leu Thr Glu Ile Thr Thr Asp Val Glu
                355                 360                 365

Lys Ile Gln Glu Ile Arg Tyr Arg Ser Lys Leu Lys Leu Ile Arg Ala
                370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
                420                 425                 430

Val Arg Cys Thr Ala Glu Gly Thr Pro Leu Pro Asp Ile Glu Trp Met
                435                 440                 445

Ile Cys Lys Asp Ile Lys Lys Cys Asn Asn Glu Thr Ser Trp Thr Ile
                450                 455                 460

Leu Ala Asn Asn Val Ser Asn Ile Ile Thr Glu Ile His Ser Arg Asp
465                 470                 475                 480
```

```
Arg Ser Thr Val Glu Gly Arg Val Thr Phe Ala Lys Val Glu Thr
            485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ser Leu Ile Val
            530                 535                 540

Leu Val Val Ile Trp Lys Gln Lys Pro Arg Tyr Glu Ile Arg Trp
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
                595                 600                 605

Glu Gly Thr Ala Tyr Gly Leu Ser Arg Ser Gln Pro Val Met Lys Val
            610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
            675                 680                 685

Asn Arg Asp Ser Phe Leu Ser His His Pro Glu Lys Pro Lys Lys Glu
            690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
            755                 760                 765

Lys Lys Lys Ser Met Leu Asp Ser Glu Val Lys Asn Leu Leu Ser Asp
            770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Val Ile Met His Asp Ser Asn
            835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895
```

```
Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
            915                 920                 925

Met Val Lys Cys Trp Asn Ser Glu Pro Glu Lys Arg Pro Ser Phe Tyr
            930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
                980                 985                 990

Tyr Lys Asn Glu Glu Asp Lys Leu  Lys Asp Trp Glu Gly  Gly Leu Asp
            995                 1000                1005

Glu Gln  Arg Leu Ser Ala Asp  Ser Gly Tyr Ile Ile  Pro Leu Pro
    1010                1015                1020

Asp Ile  Asp Pro Val Pro Glu  Glu Glu Asp Leu Gly  Lys Arg Asn
    1025                1030                1035

Arg His  Ser Ser Gln Thr Ser  Glu Glu Ser Ala Ile  Glu Thr Gly
    1040                1045                1050

Ser Ser  Ser Ser Thr Phe Ile  Lys Arg Glu Asp Glu  Thr Ile Glu
    1055                1060                1065

Asp Ile  Asp Met Met Asp Asp  Ile Gly Ile Asp Ser  Ser Asp Leu
    1070                1075                1080

Val Glu  Asp Ser Phe Leu
    1085

<210> SEQ ID NO 5
<211> LENGTH: 6621
<212> TYPE: DNA
<213> ORGANISM: Homo sapiens
<220> FEATURE:
<221> NAME/KEY: CDS
<222> LOCATION: (395)..(3652)

<400> SEQUENCE: 5
ttctccccgc cccccagttg ttgtcgaagt ctgggggttg ggactggacc ccctgattgc      60
gtaagagcaa aaagcgaagg cgcaatctgg acactgggag attcggagcg cagggagttt     120
gagagaaact tttatttga agagaccaag gttgagggg ggcttatttc ctgacagcta       180
tttacttaga gcaaatgatt agttttagaa ggatggacta taacattgaa tcaattacaa     240
aacgcggttt ttgagcccat tactgttgga gctacaggga gagaaacagg aggagactgc     300
aagagatcat ttgggaaggc cgtgggcacg ctctttactc catgtgtggg acattcattg     360
```

```
cggaataaca tcggaggaga agtttcccag agct atg ggg act tcc cat ccg gcg     415
                                    Met Gly Thr Ser His Pro Ala
                                    1               5 ttc ctg gtc tta ggc tgt ctt ctc aca ggg ctg agc cta atc ctc tgc       463
Phe Leu Val Leu Gly Cys Leu Leu Thr Gly Leu Ser Leu Ile Leu Cys
        10                  15                  20 cag ctt tca tta ccc tct atc ctt cca aat gaa aat gaa aag gtt gtg       511
Gln Leu Ser Leu Pro Ser Ile Leu Pro Asn Glu Asn Glu Lys Val Val
    25                  30                  35 cag ctg aat tca tcc ttt tct ctg aga tgc ttt ggg gag agt gaa gtg       559
Gln Leu Asn Ser Ser Phe Ser Leu Arg Cys Phe Gly Glu Ser Glu Val
40                  45                  50                  55 agc tgg cag tac ccc atg tct gaa gaa gag agc tcc gat gtg gaa atc       607
```

```
Ser Trp Gln Tyr Pro Met Ser Glu Glu Glu Ser Ser Asp Val Glu Ile
                60                  65                  70 aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
            75                  80                  85 agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
        90                  95                 100 cac act cag aca gaa gag aat gag ctt gaa ggc agg cac att tac atc      751
His Thr Gln Thr Glu Glu Asn Glu Leu Glu Gly Arg His Ile Tyr Ile
    105                 110                 115 tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135 tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150 aca act gat ccc gag act cct gta acc tta cac aac agt gag ggg gtg      895
Thr Thr Asp Pro Glu Thr Pro Val Thr Leu His Asn Ser Glu Gly Val
            155                 160                 165 gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180 gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195 acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215 cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230 gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245 act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260 atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275 gcc acg gtg aaa gac agt gga gat tac gaa tgt gct gcc cgc cag gct     1279
Ala Thr Val Lys Asp Ser Gly Asp Tyr Glu Cys Ala Ala Arg Gln Ala
280                 285                 290                 295 acc agg gag gtc aaa gaa atg aag aaa gtc act att tct gtc cat gag     1327
Thr Arg Glu Val Lys Glu Met Lys Lys Val Thr Ile Ser Val His Glu
                300                 305                 310 aaa ggt ttc att gaa atc aaa ccc acc ttc agc cag ttg gaa gct gtc     1375
Lys Gly Phe Ile Glu Ile Lys Pro Thr Phe Ser Gln Leu Glu Ala Val
            315                 320                 325 aac ctg cat gaa gtc aaa cat ttt gtt gta gag gtg cgg gcc tac cca     1423
Asn Leu His Glu Val Lys His Phe Val Val Glu Val Arg Ala Tyr Pro
        330                 335                 340 cct ccc agg ata tcc tgg ctg aaa aac aat ctg act ctg att gaa aat     1471
Pro Pro Arg Ile Ser Trp Leu Lys Asn Asn Leu Thr Leu Ile Glu Asn
    345                 350                 355 ctc act gag atc acc act gat gtg gaa aag att cag gaa ata agg tat     1519
Leu Thr Glu Ile Thr Thr Asp Val Glu Lys Ile Gln Glu Ile Arg Tyr
360                 365                 370                 375
```

```
cga agc aaa tta aag ctg atc cgt gct aag gaa gaa gac agt ggc cat    1567
Arg Ser Lys Leu Lys Leu Ile Arg Ala Lys Glu Glu Asp Ser Gly His
            380                 385                 390 tat act att gta gct caa aat gaa gat gct gtg aag agc tat act ttt    1615
Tyr Thr Ile Val Ala Gln Asn Glu Asp Ala Val Lys Ser Tyr Thr Phe
            395                 400                 405 gaa ctg tta act caa gtt cct tca tcc att ctg gac ttg gtc gat gat    1663
Glu Leu Leu Thr Gln Val Pro Ser Ser Ile Leu Asp Leu Val Asp Asp
            410                 415                 420 cac cat ggc tca act ggg gga cag acg gtg agg tgc aca gct gaa ggc    1711
His His Gly Ser Thr Gly Gly Gln Thr Val Arg Cys Thr Ala Glu Gly
        425                 430                 435 acg ccg ctt cct gat att gag tgg atg ata tgc aaa gat att aag aaa    1759
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac    1807
Cys Asn Asn Glu Thr Ser Trp Thr Ile Leu Ala Asn Asn Val Ser Asn
            460                 465                 470 atc atc acg gag atc cac tcc cga gac agg agt acc gtg gag ggc cgt    1855
Ile Ile Thr Glu Ile His Ser Arg Asp Arg Ser Thr Val Glu Gly Arg
            475                 480                 485 gtg act ttc gcc aaa gtg gag gag acc atc gcc gtg cga tgc ctg gct    1903
Val Thr Phe Ala Lys Val Glu Glu Thr Ile Ala Val Arg Cys Leu Ala
            490                 495                 500 aag aat ctc ctt gga gct gag aac cga gag ctg aag ctg gtg gct ccc    1951
Lys Asn Leu Leu Gly Ala Glu Asn Arg Glu Leu Lys Leu Val Ala Pro
            505                 510                 515 acc ctg cgt tct gaa ctc acg gtg gct gct gca gtc ctg gtg ctg ttg    1999
Thr Leu Arg Ser Glu Leu Thr Val Ala Ala Ala Val Leu Val Leu Leu
520                 525                 530                 535 gtg att gtg atc atc tca ctt att gtc ctg gtt gtc att tgg aaa cag    2047
Val Ile Val Ile Ile Ser Leu Ile Val Leu Val Val Ile Trp Lys Gln
            540                 545                 550 aaa ccg agg tat gaa att cgc tgg agg gtc att gaa tca atc agc ccg    2095
Lys Pro Arg Tyr Glu Ile Arg Trp Arg Val Ile Glu Ser Ile Ser Pro
            555                 560                 565 gat gga cat gaa tat att tat gtg gac ccg atg cag ctg cct tat gac    2143
Asp Gly His Glu Tyr Ile Tyr Val Asp Pro Met Gln Leu Pro Tyr Asp
            570                 575                 580 tca aga tgg gag ttt cca aga gat gga cta gtg ctt ggt cgg gtc ttg    2191
Ser Arg Trp Glu Phe Pro Arg Asp Gly Leu Val Leu Gly Arg Val Leu
585                 590                 595 ggg tct gga gcg ttt ggg aag gtg gtt gaa gga aca gcc tat gga tta    2239
Gly Ser Gly Ala Phe Gly Lys Val Val Glu Gly Thr Ala Tyr Gly Leu
600                 605                 610                 615 agc cgg tcc caa cct gtc atg aaa gtt gca gtg aag atg cta aaa ccc    2287
Ser Arg Ser Gln Pro Val Met Lys Val Ala Val Lys Met Leu Lys Pro
            620                 625                 630 acg gcc aga tcc agt gaa aaa caa gct ctc atg tct gaa ctg aag ata    2335
Thr Ala Arg Ser Ser Glu Lys Gln Ala Leu Met Ser Glu Leu Lys Ile
            635                 640                 645 atg act cac ctg ggg cca cat ttg aac att gta aac ttg ctg gga gcc    2383
Met Thr His Leu Gly Pro His Leu Asn Ile Val Asn Leu Leu Gly Ala
            650                 655                 660 tgc acc aag tca ggc ccc att tac atc atc aca gag tat tgc ttc tat    2431
Cys Thr Lys Ser Gly Pro Ile Tyr Ile Ile Thr Glu Tyr Cys Phe Tyr
            665                 670                 675 gga gat ttg gtc aac tat ttg cat aag aat agg gat agc ttc ctg agc    2479
Gly Asp Leu Val Asn Tyr Leu His Lys Asn Arg Asp Ser Phe Leu Ser
680                 685                 690                 695
```

```
cac cac cca gag aag cca aag aaa gag ctg gat atc ttt gga ttg aac    2527
His His Pro Glu Lys Pro Lys Lys Glu Leu Asp Ile Phe Gly Leu Asn
            700                 705                 710 cct gct gat gaa agc aca cgg agc tat gtt att tta tct ttt gaa aac    2575
Pro Ala Asp Glu Ser Thr Arg Ser Tyr Val Ile Leu Ser Phe Glu Asn
        715                 720                 725 aat ggt gac tac atg gac atg aag cag gct gat act aca cag tat gtc   2623
Asn Gly Asp Tyr Met Asp Met Lys Gln Ala Asp Thr Thr Gln Tyr Val
    730                 735                 740 ccc atg cta gaa agg aaa gag gtt tct aaa tat tcc gac atc cag aga   2671
Pro Met Leu Glu Arg Lys Glu Val Ser Lys Tyr Ser Asp Ile Gln Arg
745                 750                 755 tca ctc tat gat cgt cca gcc tca tat aag aag aaa tct atg tta gac   2719
Ser Leu Tyr Asp Arg Pro Ala Ser Tyr Lys Lys Lys Ser Met Leu Asp
760                 765                 770                 775 tca gaa gtc aaa aac ctc ctt tca gat gat aac tca gaa ggc ctt act   2767
Ser Glu Val Lys Asn Leu Leu Ser Asp Asp Asn Ser Glu Gly Leu Thr
            780                 785                 790 tta ttg gat ttg ttg agc ttc acc tat caa gtt gcc cga gga atg gag   2815
Leu Leu Asp Leu Leu Ser Phe Thr Tyr Gln Val Ala Arg Gly Met Glu
        795                 800                 805 ttt ttg gct tca aaa aat tgt gtc cac cgt gat ctg gct gct cgc aac   2863
Phe Leu Ala Ser Lys Asn Cys Val His Arg Asp Leu Ala Ala Arg Asn
    810                 815                 820 gtc ctc ctg gca caa gga aaa att gtg aag atc tgt gac ttt ggc ctg   2911
Val Leu Leu Ala Gln Gly Lys Ile Val Lys Ile Cys Asp Phe Gly Leu
825                 830                 835 gcc aga gat tcg aac tat gtg tcg aaa ggc agt acc ttt ctg ccc gtg   2959
Ala Arg Asp Ser Asn Tyr Val Ser Lys Gly Ser Thr Phe Leu Pro Val
840                 845                 850                 855 aag tgg atg gct cct gag agc atc ttt gac aac ctc tac acc aca ctg   3007
Lys Trp Met Ala Pro Glu Ser Ile Phe Asp Asn Leu Tyr Thr Thr Leu
            860                 865                 870 agt gat gtc tgg tct tat ggc att ctg ctc tgg gag atc ttt tcc ctt   3055
Ser Asp Val Trp Ser Tyr Gly Ile Leu Leu Trp Glu Ile Phe Ser Leu
        875                 880                 885 ggt ggc acc cct tac ccc ggc atg atg gtg gat tct act ttc tac aat   3103
Gly Gly Thr Pro Tyr Pro Gly Met Met Val Asp Ser Thr Phe Tyr Asn
    890                 895                 900 aag atc aag agt ggg tac cgg atg gcc aag cct gac cac gct acc agt   3151
Lys Ile Lys Ser Gly Tyr Arg Met Ala Lys Pro Asp His Ala Thr Ser
905                 910                 915 gaa gtc tac gag atc atg gtg aaa tgc tgg aac agt gag ccg gag aag   3199
Glu Val Tyr Glu Ile Met Val Lys Cys Trp Asn Ser Glu Pro Glu Lys
920                 925                 930                 935 aga ccc tcc ttt tac cac ctg agt gag att gtg gag aat ctg ctg cct   3247
Arg Pro Ser Phe Tyr His Leu Ser Glu Ile Val Glu Asn Leu Leu Pro
            940                 945                 950 gga caa tat aaa aag agt tat gaa aaa att cac ctg gac ttc ctg aag   3295
Gly Gln Tyr Lys Lys Ser Tyr Glu Lys Ile His Leu Asp Phe Leu Lys
        955                 960                 965 agt gac cat cct gct gtg gca cgc atg cgt gtg gac tca gac aat gca   3343
Ser Asp His Pro Ala Val Ala Arg Met Arg Val Asp Ser Asp Asn Ala
    970                 975                 980 tac att ggt gtc acc tac aaa aac gag gaa gac aag ctg aag gac tgg   3391
Tyr Ile Gly Val Thr Tyr Lys Asn Glu Glu Asp Lys Leu Lys Asp Trp
985                 990                 995 gag  ggt ggt ctg gat gag  cag aga ctg agc gct  gac agt ggc tac    3436
Glu  Gly Gly Leu Asp Glu  Gln Arg Leu Ser Ala  Asp Ser Gly Tyr
```

-continued

| | | | | | | | | | | | | | | |
|---|---|---|---|---|---|---|---|---|---|---|---|---|---|---|
| | 1000 | | | | 1005 | | | | | 1010 | | | | |
| atc | att | cct | ctg | cct | gac | att | gac | cct | gtc | cct | gag | gag | gag | gac | 3481 |
| Ile | Ile | Pro | Leu | Pro | Asp | Ile | Asp | Pro | Val | Pro | Glu | Glu | Glu | Asp | |
| 1015 | | | | | 1020 | | | | | 1025 | | | | | |
| ctg | ggc | aag | agg | aac | aga | cac | agc | tcg | cag | acc | tct | gaa | gag | agt | 3526 |
| Leu | Gly | Lys | Arg | Asn | Arg | His | Ser | Ser | Gln | Thr | Ser | Glu | Glu | Ser | |
| 1030 | | | | | 1035 | | | | | 1040 | | | | | |
| gcc | att | gag | acg | ggt | tcc | agc | agt | tcc | acc | ttc | atc | aag | aga | gag | 3571 |
| Ala | Ile | Glu | Thr | Gly | Ser | Ser | Ser | Ser | Thr | Phe | Ile | Lys | Arg | Glu | |
| 1045 | | | | | 1050 | | | | | 1055 | | | | | |
| gac | gag | acc | att | gaa | gac | atc | gac | atg | atg | gac | gac | atc | ggc | ata | 3616 |
| Asp | Glu | Thr | Ile | Glu | Asp | Ile | Asp | Met | Met | Asp | Asp | Ile | Gly | Ile | |
| 1060 | | | | | 1065 | | | | | 1070 | | | | | |
| gac | tct | tca | gac | ctg | gtg | gaa | gac | agc | ttc | ctg | taa ctggcggatt | | | | 3662 |
| Asp | Ser | Ser | Asp | Leu | Val | Glu | Asp | Ser | Phe | Leu | | | | | |
| 1075 | | | | | 1080 | | | | | 1085 | | | | | |

```
cgaggggttc cttccacttc tggggccacc tctggatccc gttcagaaaa ccactttatt    3722
gcaatgcgga ggttgagagg aggacttggt tgatgtttaa agagaagttc ccagccaagg    3782
gcctcgggga gcgttctaaa tatgaatgaa tgggatattt tgaaatgaac tttgtcagtg    3842
ttgcctctcg caatgcctca gtagcatctc agtggtgtgt gaagtttgga gatagatgga    3902
taagggaata ataggccaca gaaggtgaac tttgtgcttc aaggacattg gtgagagtcc    3962
aacagacaca atttatactg cgacagaact tcagcattgt aattatgtaa ataactctaa    4022
ccaaggctgt gtttagattg tattaactat cttctttgga cttctgaaga gaccactcaa    4082
tccatccatg tacttccctc ttgaaacctg atgtcagctg ctgttgaact ttttaaagaa    4142
gtgcatgaaa aaccattttt gaaccttaaa aggtactggt actatagcat tttgctatct    4202
ttttagtgt taagagataa agaataataa ttaaccaacc ttgtttaata gatttgggtc    4262
atttagaagc ctgacaactc attttcatat tgtaatctat gtttataata ctactactgt    4322
tatcagtaat gctaaatgtg taataatgta acatgatttc cctccagaga aagcacaatt    4382
taaaacaatc cttactaagt aggtgatgag tttgacagtt tttgacattt atattaaata    4442
acatgtttct ctataaagta tggtaatagc tttagtgaat taaatttagt tgagcataga    4502
gaacaaagta aaagtagtgt tgtccaggaa gtcagaattt ttaactgtac tgaataggtt    4562
ccccaatcca tcgtattaaa aaacaattaa ctgccctctg aaataatggg attagaaaca    4622
aacaaaactc ttaagtccta aaagttctca atgtagaggc ataaacctgt gctgaacata    4682
acttctcatg tatattaccc aatggaaaat ataatgatca gcaaaaagac tggatttgca    4742
gaagttttt ttttttttct tcatgcctga tgaaagcttt ggcaacccca atatatgtat    4802
ttttgaatc tatgaacctg aaaagggtca gaaggatgcc cagacatcag cctccttctt    4862
tcaccccta ccccaaagag aaagagtttg aaactcgaga ccataaagat attctttagt    4922
ggaggctgga tgtgcattag cctggatcct cagttctcaa atgtgtgtgg cagccaggat    4982
gactagatcc tgggtttcca tccttgagat tctgaagtat gaagtctgag ggaaaccaga    5042
gtctgtattt ttctaaactc cctggctgtt ctgatcggcc agttttcgga aacactgact    5102
taggtttcag gaagttgcca tgggaaacaa ataatttgaa ctttggaaca gggttggaat    5162
tcaaccacgc aggaagccta ctatttaaat ccttggcttc aggttagtga catttaatgc    5222
catctagcta gcaattgcga ccttaattta actttccagt cttagctgag gctgagaaag    5282
ctaaagtttg gttttgacag gttttccaaa agtaaagatg ctacttccca ctgtatgggg    5342
gagattgaac tttccccgtc tcccgtcttc tgcctccac tccataccc gccaaggaaa    5402
```

-continued

```
ggcatgtaca aaaattatgc aattcagtgt tccaagtctc tgtgtaacca gctcagtgtt      5462
ttggtggaaa aaacatttta agttttactg ataatttgag gttagatggg aggatgaatt      5522
gtcacatcta tccacactgt caaacaggtt ggtgtgggtt cattggcatt ctttgcaata      5582
ctgcttaatt gctgatacca tatgaatgaa acatgggctg tgattactgc aatcactgtg      5642
ctatcggcag atgatgcttt ggaagatgca gaagcaataa taaagtactt gactacctac      5702
tggtgtaatc tcaatgcaag ccccaacttt cttatccaac ttttttcatag taagtgcgaa      5762 gactgagcca gattggccaa ttaaaaacga aaacctgact aggttctgta gagccaatta      5822
gacttgaaat acgtttgtgt tctagaatc acagctcaag cattctgttt atcgctcact       5882
ctcccttgta cagccttatt ttgttggtgc tttgcatttt gatattgctg tgagccttgc      5942
atgacatcat gaggccggat gaaacttctc agtccagcag tttccagtcc taacaaatgc      6002
tcccacctga atttgtatat gactgcattt gtgggtgtgt gtgtgttttc agcaaattcc      6062
agatttgttt ccttttggcc tcctgcaaag tctccagaag aaaatttgcc aatctttcct      6122
actttctatt tttatgatga caatcaaagc cggcctgaga acactatttt gtgacttttt      6182
aaacgattag tgatgtcctt aaaatgtggt ctgccaatct gtacaaaatg gtcctatttt      6242
tgtgaagagg gacataagat aaaatgatgt tatacatcaa tatgtatata tgtatttcta      6302
tatagacttg gagaatactg ccaaaacatt tatgacaagc tgtatcactg ccttcgtta       6362 tatttttta actgtgataa tccccacagg cacattaact gttgcacttt tgaatgtcca      6422
aaatttatat tttagaaata ataaaagaa agatacttac atgttcccaa acaatggtg       6482 tggtgaatgt gtgagaaaaa ctaacttgat agggtctacc aatacaaaat gtattacgaa      6542
tgcccctgtt catgttttg ttttaaaacg tgtaaatgaa gatctttata tttcaataaa       6602
tgatatataa tttaaagtt                                                   6621
```

<210> SEQ ID NO 6
<211> LENGTH: 1085
<212> TYPE: PRT
<213> ORGANISM: Homo sapiens

<400> SEQUENCE: 6

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
```

-continued

```
            145                 150                 155                 160
Leu His Asn Ser Glu Val Val Pro Ala Ser Tyr Asp Ser Arg Gln
                    165                 170                 175
Gly Phe Asn Gly Thr Phe Thr Val Gly Pro Tyr Ile Cys Glu Ala Thr
                180                 185                 190
Val Lys Gly Lys Lys Phe Gln Thr Ile Pro Phe Asn Val Tyr Ala Leu
            195                 200                 205
Lys Ala Thr Ser Glu Leu Asp Leu Glu Met Glu Ala Leu Lys Thr Val
        210                 215                 220
Tyr Lys Ser Gly Glu Thr Ile Val Val Thr Cys Ala Val Phe Asn Asn
225                 230                 235                 240
Glu Val Val Asp Leu Gln Trp Thr Tyr Pro Gly Glu Val Lys Gly Lys
                245                 250                 255
Gly Ile Thr Met Leu Glu Glu Ile Lys Val Pro Ser Ile Lys Leu Val
            260                 265                 270
Tyr Thr Leu Thr Val Pro Glu Ala Thr Val Lys Asp Ser Gly Asp Tyr
        275                 280                 285
Glu Cys Ala Ala Arg Gln Ala Thr Arg Glu Val Lys Glu Met Lys Lys
    290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
                325                 330                 335
Val Glu Val Arg Ala Tyr Pro Pro Pro Arg Ile Ser Trp Leu Lys Asn
            340                 345                 350
Asn Leu Thr Leu Ile Glu Asn Leu Thr Glu Ile Thr Thr Asp Val Glu
        355                 360                 365
Lys Ile Gln Glu Ile Arg Tyr Arg Ser Lys Leu Lys Leu Ile Arg Ala
    370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp Asp His Gly Ser Thr Gly Gly Gln Thr
            420                 425                 430
Val Arg Cys Thr Ala Glu Gly Thr Pro Leu Pro Asp Ile Glu Trp Met
        435                 440                 445
Ile Cys Lys Asp Ile Lys Lys Cys Asn Asn Glu Thr Ser Trp Thr Ile
    450                 455                 460
Leu Ala Asn Asn Val Ser Asn Ile Ile Thr Glu Ile His Ser Arg Asp
465                 470                 475                 480
Arg Ser Thr Val Glu Gly Arg Val Thr Phe Ala Lys Val Glu Glu Thr
                485                 490                 495
Ile Ala Val Arg Cys Leu Ala Lys Asn Leu Leu Gly Ala Glu Asn Arg
            500                 505                 510
Glu Leu Lys Leu Val Ala Pro Thr Leu Arg Ser Glu Leu Thr Val Ala
        515                 520                 525
Ala Ala Val Leu Val Leu Leu Val Ile Val Ile Ile Ser Leu Ile Val
    530                 535                 540
Leu Val Val Ile Trp Lys Gln Lys Pro Arg Tyr Glu Ile Arg Trp Arg
545                 550                 555                 560
Val Ile Glu Ser Ile Ser Pro Asp Gly His Glu Tyr Ile Tyr Val Asp
                565                 570                 575
```

```
Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ser Asn Tyr Val Ser Lys
        835                 840                 845

Gly Ser Thr Phe Leu Pro Val Lys Trp Met Ala Pro Glu Ser Ile Phe
    850                 855                 860

Asp Asn Leu Tyr Thr Thr Leu Ser Asp Val Trp Ser Tyr Gly Ile Leu
865                 870                 875                 880

Leu Trp Glu Ile Phe Ser Leu Gly Gly Thr Pro Tyr Pro Gly Met Met
                885                 890                 895

Val Asp Ser Thr Phe Tyr Asn Lys Ile Lys Ser Gly Tyr Arg Met Ala
            900                 905                 910

Lys Pro Asp His Ala Thr Ser Glu Val Tyr Glu Ile Met Val Lys Cys
        915                 920                 925

Trp Asn Ser Glu Pro Glu Lys Arg Pro Ser Phe Tyr His Leu Ser Glu
    930                 935                 940

Ile Val Glu Asn Leu Leu Pro Gly Gln Tyr Lys Lys Ser Tyr Glu Lys
945                 950                 955                 960

Ile His Leu Asp Phe Leu Lys Ser Asp His Pro Ala Val Ala Arg Met
                965                 970                 975

Arg Val Asp Ser Asp Asn Ala Tyr Ile Gly Val Thr Tyr Lys Asn Glu
            980                 985                 990
```

```
                Glu Asp Lys Leu Lys Asp Trp Glu  Gly Gly Leu Asp Glu  Gln Arg Leu
                    995                 1000                1005

Ser Ala Asp Ser Gly Tyr Ile  Ile Pro Leu Pro Asp  Ile Asp Pro
                    1010                1015                1020

Val Pro Glu Glu Glu Asp Leu  Gly Lys Arg Asn Arg  His Ser Ser
                    1025                1030                1035

Gln Thr Ser Glu Glu Ser Ala  Ile Glu Thr Gly Ser  Ser Ser Ser
                    1040                1045                1050

Thr Phe Ile Lys Arg Glu Asp  Glu Thr Ile Glu Asp  Ile Asp Met
                    1055                1060                1065

Met Asp Asp Ile Gly Ile Asp  Ser Ser Asp Leu Val  Glu Asp Ser
                    1070                1075                1080

Phe Leu
                    1085

<210> SEQ ID NO 7
<211> LENGTH: 6624
<212> TYPE: DNA
<213> ORGANISM: Homo sapiens
<220> FEATURE:
<221> NAME/KEY: CDS
<222> LOCATION: (395)..(3655)

<400> SEQUENCE: 7
ttctccccgc cccccagttg ttgtcgaagt ctggggttg ggactggacc ccctgattgc      60
gtaagagcaa aaagcgaagg cgcaatctgg acactgggag attcggagcg cagggagttt    120
gagagaaact tttattttga agagaccaag gttgagggg ggcttatttc ctgacagcta    180
tttacttaga gcaaatgatt agttttagaa ggatggacta taacattgaa tcaattacaa    240
aacgcggttt ttgagcccat tactgttgga gctacaggga gagaaacagg aggagactgc    300
aagagatcat ttgggaaggc cgtgggcacg ctctttactc catgtgtggg acattcattg    360
cggaataaca tcggaggaga agtttcccag agct atg ggg act tcc cat ccg gcg   415
                                    Met Gly Thr Ser His Pro Ala
                                      1               5
```

```
ttc ctg gtc tta ggc tgt ctt ctc aca ggg ctg agc cta atc ctc tgc    463
Phe Leu Val Leu Gly Cys Leu Leu Thr Gly Leu Ser Leu Ile Leu Cys
         10                  15                  20 cag ctt tca tta ccc tct atc ctt cca aat gaa aat gaa aag gtt gtg    511
Gln Leu Ser Leu Pro Ser Ile Leu Pro Asn Glu Asn Glu Lys Val Val
    25                  30                  35 cag ctg aat tca tcc ttt tct ctg aga tgc ttt ggg gag agt gaa gtg    559
Gln Leu Asn Ser Ser Phe Ser Leu Arg Cys Phe Gly Glu Ser Glu Val
40                  45                  50                  55 agc tgg cag tac ccc atg tct gaa gaa gag agc tcc gat gtg gaa atc    607
Ser Trp Gln Tyr Pro Met Ser Glu Glu Glu Ser Ser Asp Val Glu Ile
                60                  65                  70 aga aat gaa gaa aac aac agc ggc ctt ttt gtg acg gtc ttg gaa gtg    655
Arg Asn Glu Glu Asn Asn Ser Gly Leu Phe Val Thr Val Leu Glu Val
            75                  80                  85 agc agt gcc tcg gcg gcc cac aca ggg ttg tac act tgc tat tac aac    703
Ser Ser Ala Ser Ala Ala His Thr Gly Leu Tyr Thr Cys Tyr Tyr Asn
        90                  95                 100 cac act cag aca gaa gag aat gag ctt gaa ggc agg cac att tac atc    751
His Thr Gln Thr Glu Glu Asn Glu Leu Glu Gly Arg His Ile Tyr Ile
    105                 110                 115 tat gtg cca gac cca gat gta gcc ttt gta cct cta gga atg acg gat    799
Tyr Val Pro Asp Pro Asp Val Ala Phe Val Pro Leu Gly Met Thr Asp
120                 125                 130                 135
```

-continued

| | | |
|---|---|---|
| tat tta gtc atc gtg gag gat gat gat tct gcc att ata cct tgt cgc<br>Tyr Leu Val Ile Val Glu Asp Asp Asp Ser Ala Ile Ile Pro Cys Arg<br>140 145 150 | 847 | |
| aca act gat ccc gag act cct gta acc tta cac aac agt gag ggg gtg<br>Thr Thr Asp Pro Glu Thr Pro Val Thr Leu His Asn Ser Glu Gly Val<br>155 160 165 | 895 | |
| gta cct gcc tcc tac gac agc aga cag ggc ttt aat ggg acc ttc act<br>Val Pro Ala Ser Tyr Asp Ser Arg Gln Gly Phe Asn Gly Thr Phe Thr<br>170 175 180 | 943 | |
| gta ggg ccc tat atc tgt gag gcc acc gtc aaa gga aag aag ttc cag<br>Val Gly Pro Tyr Ile Cys Glu Ala Thr Val Lys Gly Lys Lys Phe Gln<br>185 190 195 | 991 | |
| acc atc cca ttt aat gtt tat gct tta aaa gca aca tca gag ctg gat<br>Thr Ile Pro Phe Asn Val Tyr Ala Leu Lys Ala Thr Ser Glu Leu Asp<br>200 205 210 215 | 1039 | |
| cta gaa atg gaa gct ctt aaa acc gtg tat aag tca ggg gaa acg att<br>Leu Glu Met Glu Ala Leu Lys Thr Val Tyr Lys Ser Gly Glu Thr Ile<br>220 225 230 | 1087 | |
| gtg gtc acc tgt gct gtt ttt aac aat gag gtg gtt gac ctt caa tgg<br>Val Val Thr Cys Ala Val Phe Asn Asn Glu Val Val Asp Leu Gln Trp<br>235 240 245 | 1135 | |
| act tac cct gga gaa gtg aaa ggc aaa ggc atc aca atg ctg gaa gaa<br>Thr Tyr Pro Gly Glu Val Lys Gly Lys Gly Ile Thr Met Leu Glu Glu<br>250 255 260 | 1183 | |
| atc aaa gtc cca tcc atc aaa ttg gtg tac act ttg acg gtc ccc gag<br>Ile Lys Val Pro Ser Ile Lys Leu Val Tyr Thr Leu Thr Val Pro Glu<br>265 270 275 | 1231 | |
| gcc acg gtg aaa gac agt gga gat tac gaa tgt gct gcc cgc cag gct<br>Ala Thr Val Lys Asp Ser Gly Asp Tyr Glu Cys Ala Ala Arg Gln Ala<br>280 285 290 295 | 1279 | |
| acc agg gag gtc aaa gaa atg aag aaa gtc act att tct gtc cat gag<br>Thr Arg Glu Val Lys Glu Met Lys Lys Val Thr Ile Ser Val His Glu<br>300 305 310 | 1327 | |
| aaa ggt ttc att gaa atc aaa ccc acc ttc agc cag ttg gaa gct gtc<br>Lys Gly Phe Ile Glu Ile Lys Pro Thr Phe Ser Gln Leu Glu Ala Val<br>315 320 325 | 1375 | |
| aac ctg cat gaa gtc aaa cat ttt gtt gta gag gtg cgg gcc tac cca<br>Asn Leu His Glu Val Lys His Phe Val Val Glu Val Arg Ala Tyr Pro<br>330 335 340 | 1423 | |
| cct ccc agg ata tcc tgg ctg aaa aac aat ctg act ctg att gaa aat<br>Pro Pro Arg Ile Ser Trp Leu Lys Asn Asn Leu Thr Leu Ile Glu Asn<br>345 350 355 | 1471 | |
| ctc act gag atc acc act gat gtg gaa aag att cag gaa ata agg tat<br>Leu Thr Glu Ile Thr Thr Asp Val Glu Lys Ile Gln Glu Ile Arg Tyr<br>360 365 370 375 | 1519 | |
| cga agc aaa tta aag ctg atc cgt gct aag gaa gaa gac agt ggc cat<br>Arg Ser Lys Leu Lys Leu Ile Arg Ala Lys Glu Glu Asp Ser Gly His<br>380 385 390 | 1567 | |
| tat act att gta gct caa aat gaa gat gct gtg aag agc tat act ttt<br>Tyr Thr Ile Val Ala Gln Asn Glu Asp Ala Val Lys Ser Tyr Thr Phe<br>395 400 405 | 1615 | |
| gaa ctg tta act caa gtt cct tca tcc att ctg gac ttg gtc gat gat<br>Glu Leu Leu Thr Gln Val Pro Ser Ser Ile Leu Asp Leu Val Asp Asp<br>410 415 420 | 1663 | |
| cac cat ggc tca act ggg gga cag acg gtg agg tgc aca gct gaa ggc<br>His His Gly Ser Thr Gly Gly Gln Thr Val Arg Cys Thr Ala Glu Gly<br>425 430 435 | 1711 | |
| acg ccg ctt cct gat att gag tgg atg ata tgc aaa gat att aag aaa<br>Thr Pro Leu Pro Asp Ile Glu Trp Met Ile Cys Lys Asp Ile Lys Lys | 1759 | |

```
                440              445              450              455 tgt aat aat gaa act tcc tgg act att ttg gcc aac aat gtc tca aac    1807
Cys Asn Asn Glu Thr Ser Trp Thr Ile Leu Ala Asn Asn Val Ser Asn
            460                      465                      470 atc atc acg gag atc cac tcc cga gac agg agt acc gtg gag ggc cgt    1855
Ile Ile Thr Glu Ile His Ser Arg Asp Arg Ser Thr Val Glu Gly Arg
            475                      480                      485 gtg act ttc gcc aaa gtg gag gag acc atc gcc gtg cga tgc ctg gct    1903
Val Thr Phe Ala Lys Val Glu Glu Thr Ile Ala Val Arg Cys Leu Ala
            490                      495                      500 aag aat ctc ctt gga gct gag aac cga gag ctg aag ctg gtg gct ccc    1951
Lys Asn Leu Leu Gly Ala Glu Asn Arg Glu Leu Lys Leu Val Ala Pro
            505                      510                      515 acc ctg cgt tct gaa ctc acg gtg gct gct gca gtc ctg gtg ctg ttg    1999
Thr Leu Arg Ser Glu Leu Thr Val Ala Ala Ala Val Leu Val Leu Leu
            520                      525                      530                     535 gtg att gtg atc atc tca ctt att gtc ctg gtt gtc att tgg aaa cag    2047
Val Ile Val Ile Ile Ser Leu Ile Val Leu Val Val Ile Trp Lys Gln
                        540                      545                      550 aaa ccg agg tat gaa att cgc tgg agg gtc att gaa tca atc agc ccg    2095
Lys Pro Arg Tyr Glu Ile Arg Trp Arg Val Ile Glu Ser Ile Ser Pro
            555                      560                      565 gat gga cat gaa tat att tat gtg gac ccg atg cag ctg cct tat gac    2143
Asp Gly His Glu Tyr Ile Tyr Val Asp Pro Met Gln Leu Pro Tyr Asp
            570                      575                      580 tca aga tgg gag ttt cca aga gat gga cta gtg ctt ggt cgg gtc ttg    2191
Ser Arg Trp Glu Phe Pro Arg Asp Gly Leu Val Leu Gly Arg Val Leu
            585                      590                      595 ggg tct gga gcg ttt ggg aag gtg gtt gaa gga aca gcc tat gga tta    2239
Gly Ser Gly Ala Phe Gly Lys Val Val Glu Gly Thr Ala Tyr Gly Leu
600                      605                      610                      615 agc cgg tcc caa cct gtc atg aaa gtt gca gtg aag atg cta aaa ccc    2287
Ser Arg Ser Gln Pro Val Met Lys Val Ala Val Lys Met Leu Lys Pro
                        620                      625                      630 acg gcc aga tcc agt gaa aaa caa gct ctc atg tct gaa ctg aag ata    2335
Thr Ala Arg Ser Ser Glu Lys Gln Ala Leu Met Ser Glu Leu Lys Ile
            635                      640                      645 atg act cac ctg ggg cca cat ttg aac att gta aac ttg ctg gga gcc    2383
Met Thr His Leu Gly Pro His Leu Asn Ile Val Asn Leu Leu Gly Ala
            650                      655                      660 tgc acc aag tca ggc ccc att tac atc atc aca gag tat tgc ttc tat    2431
Cys Thr Lys Ser Gly Pro Ile Tyr Ile Ile Thr Glu Tyr Cys Phe Tyr
            665                      670                      675 gga gat ttg gtc aac tat ttg cat aag aat agg gat agc ttc ctg agc    2479
Gly Asp Leu Val Asn Tyr Leu His Lys Asn Arg Asp Ser Phe Leu Ser
680                      685                      690                      695 cac cac cca gag aag cca aag aaa gag ctg gat atc ttt gga ttg aac    2527
His His Pro Glu Lys Pro Lys Lys Glu Leu Asp Ile Phe Gly Leu Asn
                        700                      705                      710 cct gct gat gaa agc aca cgg agc tat gtt att tta tct ttt gaa aac    2575
Pro Ala Asp Glu Ser Thr Arg Ser Tyr Val Ile Leu Ser Phe Glu Asn
            715                      720                      725 aat ggt gac tac atg gac atg aag cag gct gat act aca cag tat gtc    2623
Asn Gly Asp Tyr Met Asp Met Lys Gln Ala Asp Thr Thr Gln Tyr Val
            730                      735                      740 ccc atg cta gaa agg aaa gag gtt tct aaa tat tcc gac atc cag aga    2671
Pro Met Leu Glu Arg Lys Glu Val Ser Lys Tyr Ser Asp Ile Gln Arg
            745                      750                      755 tca ctc tat gat cgt cca gcc tca tat aag aag aaa tct atg tta gac    2719
```

```
Ser Leu Tyr Asp Arg Pro Ala Ser Tyr Lys Lys Lys Ser Met Leu Asp
760                 765                 770                 775 tca gaa gtc aaa aac ctc ctt tca gat gat aac tca gaa ggc ctt act    2767
Ser Glu Val Lys Asn Leu Leu Ser Asp Asp Asn Ser Glu Gly Leu Thr
            780                 785                 790 tta ttg gat ttg ttg agc ttc acc tat caa gtt gcc cga gga atg gag    2815
Leu Leu Asp Leu Leu Ser Phe Thr Tyr Gln Val Ala Arg Gly Met Glu
        795                 800                 805 ttt ttg gct tca aaa aat tgt gtc cac cgt gat ctg gct gct cgc aac    2863
Phe Leu Ala Ser Lys Asn Cys Val His Arg Asp Leu Ala Ala Arg Asn
    810                 815                 820 gtc ctc ctg gca caa gga aaa att gtg aag atc tgt gac ttt ggc ctg    2911
Val Leu Leu Ala Gln Gly Lys Ile Val Lys Ile Cys Asp Phe Gly Leu
825                 830                 835 gcc aga gac atc atg ccc tat gtg tcg aaa ggc agt acc ttt ctg ccc    2959
Ala Arg Asp Ile Met Pro Tyr Val Ser Lys Gly Ser Thr Phe Leu Pro
840                 845                 850                 855 gtg aag tgg atg gct cct gag agc atc ttt gac aac ctc tac acc aca    3007
Val Lys Trp Met Ala Pro Glu Ser Ile Phe Asp Asn Leu Tyr Thr Thr
            860                 865                 870 ctg agt gat gtc tgg tct tat ggc att ctg ctc tgg gag atc ttt tcc    3055
Leu Ser Asp Val Trp Ser Tyr Gly Ile Leu Leu Trp Glu Ile Phe Ser
        875                 880                 885 ctt ggt ggc acc cct tac ccc ggc atg atg gtg gat tct act ttc tac    3103
Leu Gly Gly Thr Pro Tyr Pro Gly Met Met Val Asp Ser Thr Phe Tyr
    890                 895                 900 aat aag atc aag agt ggg tac cgg atg gcc aag cct gac cac gct acc    3151
Asn Lys Ile Lys Ser Gly Tyr Arg Met Ala Lys Pro Asp His Ala Thr
905                 910                 915 agt gaa gtc tac gag atc atg gtg aaa tgc tgg aac agt gag ccg gag    3199
Ser Glu Val Tyr Glu Ile Met Val Lys Cys Trp Asn Ser Glu Pro Glu
920                 925                 930                 935 aag aga ccc tcc ttt tac cac ctg agt gag att gtg gag aat ctg ctg    3247
Lys Arg Pro Ser Phe Tyr His Leu Ser Glu Ile Val Glu Asn Leu Leu
            940                 945                 950 cct gga caa tat aaa aag agt tat gaa aaa att cac ctg gac ttc ctg    3295
Pro Gly Gln Tyr Lys Lys Ser Tyr Glu Lys Ile His Leu Asp Phe Leu
        955                 960                 965 aag agt gac cat cct gct gtg gca cgc atg cgt gtg gac tca gac aat    3343
Lys Ser Asp His Pro Ala Val Ala Arg Met Arg Val Asp Ser Asp Asn
    970                 975                 980 gca tac att ggt gtc acc tac aaa aac gag gaa gac aag ctg aag gac    3391
Ala Tyr Ile Gly Val Thr Tyr Lys Asn Glu Glu Asp Lys Leu Lys Asp
985                 990                 995 tgg gag ggt ggt ctg gat  gag cag aga ctg agc  gct gac agt ggc      3436
Trp Glu Gly Gly Leu Asp  Glu Gln Arg Leu Ser  Ala Asp Ser Gly
1000                1005                 1010 tac atc att cct ctg cct  gac att gac cct gtc  cct gag gag gag      3481
Tyr Ile Ile Pro Leu Pro  Asp Ile Asp Pro Val  Pro Glu Glu Glu
1015                1020                 1025 gac ctg ggc aag agg aac  aga cac agc tcg cag  acc tct gaa gag      3526
Asp Leu Gly Lys Arg Asn  Arg His Ser Ser Gln  Thr Ser Glu Glu
1030                1035                 1040 agt gcc att gag acg ggt  tcc agc agt tcc acc  ttc atc aag aga      3571
Ser Ala Ile Glu Thr Gly  Ser Ser Ser Ser Thr  Phe Ile Lys Arg
1045                1050                 1055 gag gac gag acc att gaa  gac atc gac atg atg  gac gac atc ggc      3616
Glu Asp Glu Thr Ile Glu  Asp Ile Asp Met Met  Asp Asp Ile Gly
1060                1065                 1070
```

```
ata gac tct tca gac ctg  gtg gaa gac agc ttc  ctg taa ctggcggatt          3665
Ile Asp Ser Ser Asp Leu  Val Glu Asp Ser Phe  Leu
1075             1080                 1085 cgagggqttc cttccacttc tggggccacc tctggatccc gttcagaaaa ccactttatt        3725
gcaatgcgga ggttgagagg aggacttggt tgatgtttaa agagaagttc ccagccaagg        3785
gcctcgggga gcgttctaaa tatgaatgaa tgggatattt tgaaatgaac tttgtcagtg        3845
ttgcctctcg caatgcctca gtagcatctc agtggtgtgt gaagtttgga gatagatgga        3905
taagggaata ataggccaca gaaggtgaac tttgtgcttc aaggacattg gtgagagtcc        3965
aacagacaca atttatactg cgacagaact tcagcattga aattatgtaa ataactctaa        4025
ccaaggctgt gtttagattg tattaactat cttctttgga cttctgaaga gaccactcaa        4085
tccatccatg tacttccctc ttgaaacctg atgtcagctg ctgttgaact ttttaaagaa        4145
gtgcatgaaa aaccatttit gaaccttaaa aggtactggt actatagcat tttgctatct        4205
tttttagtgt taagagataa agaataataa ttaaccaacc ttgtttaata gatttgggtc        4265
atttagaagc ctgacaactc attttcatat tgtaatctat gtttataata ctactactgt        4325
tatcagtaat gctaaatgtg taataatgta acatgatttc cctccagaga aagcacaatt        4385
taaaacaatc cttactaagt aggtgatgag tttgacagtt tttgacattt atattaaata        4445
acatgtttct ctataaagta tggtaatagc tttagtgaat taaatttagt tgagcataga        4505
gaacaaagta aaagtagtgt tgtccaggaa gtcagaattt ttaactgtac tgaataggtt        4565
ccccaatcca tcgtattaaa aaacaattaa ctgccctctg aaataatggg attagaaaca        4625
aacaaaactc ttaagtccta aaagttctca atgtagaggc ataaacctgt gctgaacata        4685
acttctcatg tatattaccc aatggaaaat ataatgatca gcaaaaagac tggatttgca        4745 gaagttttti tttttttict tcatgcctga tgaaagcttt ggcaaccccca atatatgtat        4805 tttttgaatc tatgaacctg aaaagggtca gaaggatgcc cagacatcag cctccttctt        4865
tcacccctta ccccaaagag aaagagtttg aaactcgaga ccataaagat attctttagt        4925
ggaggctgga tgtgcattag cctggatcct cagttctcaa atgtgtgtgg cagccaggat        4985
gactagatcc tgggtttcca tccttgagat tctgaagtat gaagtctgag ggaaaccaga        5045
gtctgtattt ttctaaactc cctggctgtt ctgatcggcc agttttcgga aacactgact        5105
taggtttcag gaagttgcca tgggaaacaa ataatttgaa ctttggaaca gggttggaat        5165
tcaaccacgc aggaagccta ctatttaaat ccttggcttc aggttagtga catttaatgc        5225
catctagcta gcaattgcga ccttaatita actttccagt cttagctgag gctgagaaag        5285
ctaaagtttg gttttgacag gttttccaaa agtaaagatg ctacttccca ctgtatgggg        5345
gagattgaac tttccccgtc tcccgtcttc tgcctcccac tccatacccc gccaaggaaa        5405
ggcatgtaca aaaattatgc aattcagtgt tccaagtctc tgtgtaacca gctcagtgtt        5465
ttggtggaaa aaacatttta agttttactg ataatttgag gttagatggg aggatgaatt        5525
gtcacatcta tccacactgt caaacaggtt ggtgtgggtt cattggcatt ctttgcaata        5585
ctgcttaatt gctgatacca tatgaatgaa acatgggctg tgattactgc aatcactgtg        5645
ctatcggcag atgatgcttt ggaagatgca gaagcaataa taaagtactt gactacctac        5705
tggtgtaatc tcaatgcaag cccccaacttt cttatccaac tttttcatag taagtgcgaa        5765
gactgagcca gattggccaa ttaaaaacga aaacctgact aggttctgta gagccaatta        5825
gacttgaaat acgtttgtgt ttctagaatc acagctcaag cattctgttt atcgctcact        5885
ctcccttgta cagccttatt tgttggtgc tttgcatttt gatattgctg tgagccttgc         5945
```

```
atgacatcat gaggccggat gaaacttctc agtccagcag tttccagtcc taacaaatgc    6005
tcccacctga atttgtatat gactgcattt gtgggtgtgt gtgtgttttc agcaaattcc    6065
agatttgttt cctttggcc tcctgcaaag tctccagaag aaaatttgcc aatctttcct     6125
actttctatt tttatgatga caatcaaagc cggcctgaga acactatttt gtgacttttt    6185
aaacgattag tgatgtcctt aaaatgtggt ctgccaatct gtacaaaatg gtcctatttt    6245
tgtgaagagg gacataagat aaaatgatgt tatacatcaa tatgtatata tgtatttcta    6305
tatagacttg gagaatactg ccaaaacatt tatgacaagc tgtatcactg ccttcgttta    6365
tattttttta actgtgataa tccccacagg cacattaact gttgcacttt tgaatgtcca    6425
aaatttatat tttagaaata ataaaaagaa agatacttac atgttcccaa acaatggtg     6485 tggtgaatgt gtgagaaaaa ctaacttgat agggtctacc aatacaaaat gtattacgaa    6545 tgccctgtt catgttttg tttaaaacg tgtaaatgaa gatctttata tttcaataaa       6605
tgatatataa tttaaagtt                                                  6624
```

<210> SEQ ID NO 8
<211> LENGTH: 1086
<212> TYPE: PRT
<213> ORGANISM: Homo sapiens

<400> SEQUENCE: 8

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
```

-continued

```
                245                 250                 255
Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
            275                 280                 285

Glu Cys Ala Ala Arg Gln Ala Thr Arg Glu Val Lys Glu Met Lys Lys
            290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
            325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
            370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
            405                 410                 415

Ile Leu Asp Leu Val Asp Asp His Gly Ser Thr Gly Gly Gln Thr
            420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
            450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
            485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
            530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
            565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
            595                 600                 605

Glu Gly Thr Ala Tyr Gly Leu Ser Arg Ser Gln Pro Val Met Lys Val
            610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
            645                 650                 655

Ile Val Asn Leu Leu Gly Ala Cys Thr Lys Ser Gly Pro Ile Tyr Ile
            660                 665                 670
```

```
Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
        690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
        770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met Pro Tyr Val Ser
        835                 840                 845

Lys Gly Ser Thr Phe Leu Pro Val Lys Trp Met Ala Pro Glu Ser Ile
        850                 855                 860

Phe Asp Asn Leu Tyr Thr Thr Leu Ser Asp Val Trp Ser Tyr Gly Ile
865                 870                 875                 880

Leu Leu Trp Glu Ile Phe Ser Leu Gly Gly Thr Pro Tyr Pro Gly Met
                885                 890                 895

Met Val Asp Ser Thr Phe Tyr Asn Lys Ile Lys Ser Gly Tyr Arg Met
            900                 905                 910

Ala Lys Pro Asp His Ala Thr Ser Glu Val Tyr Glu Ile Met Val Lys
        915                 920                 925

Cys Trp Asn Ser Glu Pro Glu Lys Arg Pro Ser Phe Tyr His Leu Ser
930                 935                 940

Glu Ile Val Glu Asn Leu Leu Pro Gly Gln Tyr Lys Lys Ser Tyr Glu
945                 950                 955                 960

Lys Ile His Leu Asp Phe Leu Lys Ser Asp His Pro Ala Val Ala Arg
                965                 970                 975

Met Arg Val Asp Ser Asp Asn Ala Tyr Ile Gly Val Thr Tyr Lys Asn
            980                 985                 990

Glu Glu Asp Lys Leu Lys Asp Trp Glu Gly Gly Leu Asp Glu Gln Arg
        995                 1000                1005

Leu Ser Ala Asp Ser Gly Tyr Ile Ile Pro Leu Pro Asp Ile Asp
        1010                1015                1020

Pro Val Pro Glu Glu Glu Asp Leu Gly Lys Arg Asn Arg His Ser
        1025                1030                1035

Ser Gln Thr Ser Glu Glu Ser Ala Ile Glu Thr Gly Ser Ser Ser
        1040                1045                1050

Ser Thr Phe Ile Lys Arg Glu Asp Glu Thr Ile Glu Asp Ile Asp
        1055                1060                1065

Met Met Asp Asp Ile Gly Ile Asp Ser Ser Asp Leu Val Glu Asp
        1070                1075                1080
```

```
Ser Phe Leu
    1085

<210> SEQ ID NO 9
<211> LENGTH: 6639
<212> TYPE: DNA
<213> ORGANISM: Homo sapiens
<220> FEATURE:
<221> NAME/KEY: CDS
<222> LOCATION: (395)..(3664)

<400> SEQUENCE: 9
ttctccccgc cccccagttg ttgtcgaagt ctgggggttg ggactggacc ccctgattgc      60
gtaagagcaa aaagcgaagg cgcaatctgg acactgggag attcggagcg cagggagttt     120
gagagaaact tttattttga agagaccaag gttgaggggg ggcttatttc ctgcagcta      180 tttacttaga gcaaatgatt agttttagaa ggatggacta taacattgaa tcaattacaa     240
aacgcggttt ttgagcccat tactgttgga gctacaggga gagaaacagg aggagactgc     300
aagagatcat ttgggaaggc cgtgggcacg ctctttactc catgtgtggg acattcattg     360
cggaataaca tcggaggaga agtttcccag agct atg ggg act tcc cat ccg gcg     415
                                      Met Gly Thr Ser His Pro Ala
                                      1               5 ttc ctg gtc tta ggc tgt ctt ctc aca ggg ctg agc cta atc ctc tgc       463
Phe Leu Val Leu Gly Cys Leu Leu Thr Gly Leu Ser Leu Ile Leu Cys
        10                  15                  20 cag ctt tca tta ccc tct atc ctt cca aat gaa aat gaa aag gtt gtg       511
Gln Leu Ser Leu Pro Ser Ile Leu Pro Asn Glu Asn Glu Lys Val Val
25                  30                  35 cag ctg aat tca tcc ttt tct ctg aga tgc ttt ggg gag agt gaa gtg       559
Gln Leu Asn Ser Ser Phe Ser Leu Arg Cys Phe Gly Glu Ser Glu Val
40                  45                  50                  55 agc tgg cag tac ccc atg tct gaa gaa gag agc tcc gat gtg gaa atc       607
Ser Trp Gln Tyr Pro Met Ser Glu Glu Glu Ser Ser Asp Val Glu Ile
                60                  65                  70 aga aat gaa gaa aac aac agc ggc ctt ttt gtg acg gtc ttg gaa gtg       655
Arg Asn Glu Glu Asn Asn Ser Gly Leu Phe Val Thr Val Leu Glu Val
            75                  80                  85 agc agt gcc tcg gcg gcc cac aca ggg ttg tac act tgc tat tac aac       703
Ser Ser Ala Ser Ala Ala His Thr Gly Leu Tyr Thr Cys Tyr Tyr Asn
        90                  95                 100 cac act cag aca gaa gag aat gag ctt gaa ggc agg cac att tac atc       751
His Thr Gln Thr Glu Glu Asn Glu Leu Glu Gly Arg His Ile Tyr Ile
    105                 110                 115 tat gtg cca gac cca gat gta gcc ttt gta cct cta gga atg acg gat       799
Tyr Val Pro Asp Pro Asp Val Ala Phe Val Pro Leu Gly Met Thr Asp
120                 125                 130                 135 tat tta gtc atc gtg gag gat gat gat tct gcc att ata cct tgt cgc       847
Tyr Leu Val Ile Val Glu Asp Asp Asp Ser Ala Ile Ile Pro Cys Arg
                140                 145                 150 aca act gat ccc gag act cct gta acc tta cac aac agt gag ggg gtg       895
Thr Thr Asp Pro Glu Thr Pro Val Thr Leu His Asn Ser Glu Gly Val
            155                 160                 165 gta cct gcc tcc tac gac agc aga cag ggc ttt aat ggg acc ttc act       943
Val Pro Ala Ser Tyr Asp Ser Arg Gln Gly Phe Asn Gly Thr Phe Thr
        170                 175                 180 gta ggg ccc tat atc tgt gag gcc acc gtc aaa gga aag aag ttc cag       991
Val Gly Pro Tyr Ile Cys Glu Ala Thr Val Lys Gly Lys Lys Phe Gln
    185                 190                 195 acc atc cca ttt aat gtt tat gct tta aaa gca aca tca gag ctg gat      1039
```

```
Thr Ile Pro Phe Asn Val Tyr Ala Leu Lys Ala Thr Ser Glu Leu Asp
200                 205                 210                 215 cta gaa atg gaa gct ctt aaa acc gtg tat aag tca ggg gaa acg att         1087
Leu Glu Met Glu Ala Leu Lys Thr Val Tyr Lys Ser Gly Glu Thr Ile
            220                 225                 230 gtg gtc acc tgt gct gtt ttt aac aat gag gtg gtt gac ctt caa tgg         1135
Val Val Thr Cys Ala Val Phe Asn Asn Glu Val Val Asp Leu Gln Trp
                235                 240                 245 act tac cct gga gaa gtg aaa ggc aaa ggc atc aca atg ctg gaa gaa         1183
Thr Tyr Pro Gly Glu Val Lys Gly Lys Gly Ile Thr Met Leu Glu Glu
            250                 255                 260 atc aaa gtc cca tcc atc aaa ttg gtg tac act ttg acg gtc ccc gag         1231
Ile Lys Val Pro Ser Ile Lys Leu Val Tyr Thr Leu Thr Val Pro Glu
265                 270                 275 gcc acg gtg aaa gac agt gga gat tac gaa tgt gct gcc cgc cag gct         1279
Ala Thr Val Lys Asp Ser Gly Asp Tyr Glu Cys Ala Ala Arg Gln Ala
280                 285                 290                 295 acc agg gag gtc aaa gaa atg aag aaa gtc act att tct gtc cat gag         1327
Thr Arg Glu Val Lys Glu Met Lys Lys Val Thr Ile Ser Val His Glu
            300                 305                 310 aaa ggt ttc att gaa atc aaa ccc acc ttc agc cag ttg gaa gct gtc         1375
Lys Gly Phe Ile Glu Ile Lys Pro Thr Phe Ser Gln Leu Glu Ala Val
                315                 320                 325 aac ctg cat gaa gtc aaa cat ttt gtt gta gag gtg cgg gcc tac cca         1423
Asn Leu His Glu Val Lys His Phe Val Val Glu Val Arg Ala Tyr Pro
            330                 335                 340 cct ccc agg ata tcc tgg ctg aaa aac aat ctg act ctg att gaa aat         1471
Pro Pro Arg Ile Ser Trp Leu Lys Asn Asn Leu Thr Leu Ile Glu Asn
345                 350                 355 ctc act gag atc acc act gat gtg gaa aag att cag gaa ata agg tat         1519
Leu Thr Glu Ile Thr Thr Asp Val Glu Lys Ile Gln Glu Ile Arg Tyr
360                 365                 370                 375 cga agc aaa tta aag ctg atc cgt gct aag gaa gaa gac agt ggc cat         1567
Arg Ser Lys Leu Lys Leu Ile Arg Ala Lys Glu Glu Asp Ser Gly His
            380                 385                 390 tat act att gta gct caa aat gaa gat gct gtg aag agc tat act ttt         1615
Tyr Thr Ile Val Ala Gln Asn Glu Asp Ala Val Lys Ser Tyr Thr Phe
                395                 400                 405 gaa ctg tta act caa gtt cct tca tcc att ctg gac ttg gtc gat gat         1663
Glu Leu Leu Thr Gln Val Pro Ser Ser Ile Leu Asp Leu Val Asp Asp
            410                 415                 420 cac cat ggc tca act ggg gga cag acg gtg agg tgc aca gct gaa ggc         1711
His His Gly Ser Thr Gly Gly Gln Thr Val Arg Cys Thr Ala Glu Gly
425                 430                 435 acg ccg ctt cct gat att gag tgg atg ata tgc aaa gat att aag aaa         1759
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac         1807
Cys Asn Asn Glu Thr Ser Trp Thr Ile Leu Ala Asn Asn Val Ser Asn
            460                 465                 470 atc atc acg gag atc cac tcc cga gac agg agt acc gtg gag ggc cgt         1855
Ile Ile Thr Glu Ile His Ser Arg Asp Arg Ser Thr Val Glu Gly Arg
                475                 480                 485 gtg act ttc gcc aaa gtg gag gag acc atc gcc gtg cga tgc ctg gct         1903
Val Thr Phe Ala Lys Val Glu Glu Thr Ile Ala Val Arg Cys Leu Ala
            490                 495                 500 aag aat ctc ctt gga gct gag aac cga gag ctg aag ctg gtg gct ccc         1951
Lys Asn Leu Leu Gly Ala Glu Asn Arg Glu Leu Lys Leu Val Ala Pro
505                 510                 515
```

-continued

| | |
|---|---|
| acc ctg cgt tct gaa ctc acg gtg gct gct gca gtc ctg gtg ctg ttg<br>Thr Leu Arg Ser Glu Leu Thr Val Ala Ala Ala Val Leu Val Leu Leu<br>520                           525                           530                           535 | 1999 |
| gtg att gtg atc atc tca ctt att gtc ctg gtt gtc att tgg aaa cag<br>Val Ile Val Ile Ile Ser Leu Ile Val Leu Val Val Ile Trp Lys Gln<br>                   540                           545                           550 | 2047 |
| aaa ccg agg tat gaa att cgc tgg agg gag agg gtc att gaa tca atc<br>Lys Pro Arg Tyr Glu Ile Arg Trp Arg Glu Arg Val Ile Glu Ser Ile<br>                555                           560                           565 | 2095 |
| agc ccg gat gga cat gaa tat att tat gtg gac ccg atg cag ctg cct<br>Ser Pro Asp Gly His Glu Tyr Ile Tyr Val Asp Pro Met Gln Leu Pro<br>570                           575                           580 | 2143 |
| tat gac tca aga tgg gag ttt cca aga gat gga cta gtg ctt ggt cgg<br>Tyr Asp Ser Arg Trp Glu Phe Pro Arg Asp Gly Leu Val Leu Gly Arg<br>     585                          590                           595 | 2191 |
| gtc ttg ggg tct gga gcg ttt ggg aag gtg gtt gaa gga aca gcc tat<br>Val Leu Gly Ser Gly Ala Phe Gly Lys Val Val Glu Gly Thr Ala Tyr<br>600                           605                           610                           615 | 2239 |
| gga tta agc cgg tcc caa cct gtc atg aaa gtt gca gtg aag atg cta<br>Gly Leu Ser Arg Ser Gln Pro Val Met Lys Val Ala Val Lys Met Leu<br>                   620                           625                           630 | 2287 |
| aaa ccc acg gcc aga tcc agt gaa aaa caa gct ctc atg tct gaa ctg<br>Lys Pro Thr Ala Arg Ser Ser Glu Lys Gln Ala Leu Met Ser Glu Leu<br>635                           640                           645 | 2335 |
| aag ata atg act cac ctg ggg cca cat ttg aac att gta aac ttg ctg<br>Lys Ile Met Thr His Leu Gly Pro His Leu Asn Ile Val Asn Leu Leu<br>                   650                           655                           660 | 2383 |
| gga gcc tgc acc aag tca ggc ccc att tac atc atc aca gag tat tgc<br>Gly Ala Cys Thr Lys Ser Gly Pro Ile Tyr Ile Ile Thr Glu Tyr Cys<br>665                           670                           675 | 2431 |
| ttc tat gga gat ttg gtc aac tat ttg cat aag aat agg gat agc ttc<br>Phe Tyr Gly Asp Leu Val Asn Tyr Leu His Lys Asn Arg Asp Ser Phe<br>680                           685                           690                           695 | 2479 |
| ctg agc cac cac cca gag aag cca aag aaa gag ctg gat atc ttt gga<br>Leu Ser His His Pro Glu Lys Pro Lys Lys Glu Leu Asp Ile Phe Gly<br>                   700                           705                           710 | 2527 |
| ttg aac cct gct gat gaa agc aca cgg agc tat gtt att tta tct ttt<br>Leu Asn Pro Ala Asp Glu Ser Thr Arg Ser Tyr Val Ile Leu Ser Phe<br>715                           720                           725 | 2575 |
| gaa aac aat ggt gac tac atg gac atg aag cag gct gat act aca cag<br>Glu Asn Asn Gly Asp Tyr Met Asp Met Lys Gln Ala Asp Thr Thr Gln<br>                   730                           735                           740 | 2623 |
| tat gtc ccc atg cta gaa agg aaa gag gtt tct aaa tat tcc gac atc<br>Tyr Val Pro Met Leu Glu Arg Lys Glu Val Ser Lys Tyr Ser Asp Ile<br>745                           750                           755 | 2671 |
| cag aga tca ctc tat gat cgt cca gcc tca tat aag aag aaa tct atg<br>Gln Arg Ser Leu Tyr Asp Arg Pro Ala Ser Tyr Lys Lys Lys Ser Met<br>760                           765                           770                           775 | 2719 |
| tta gac tca gaa gtc aaa aac ctc ctt tca gat gat aac tca gaa ggc<br>Leu Asp Ser Glu Val Lys Asn Leu Leu Ser Asp Asp Asn Ser Glu Gly<br>                   780                           785                           790 | 2767 |
| ctt act tta ttg gat ttg ttg agc ttc acc tat caa gtt gcc cga gga<br>Leu Thr Leu Leu Asp Leu Leu Ser Phe Thr Tyr Gln Val Ala Arg Gly<br>795                           800                           805 | 2815 |
| atg gag ttt ttg gct tca aaa aat tgt gtc cac cgt gat ctg gct gct<br>Met Glu Phe Leu Ala Ser Lys Asn Cys Val His Arg Asp Leu Ala Ala<br>                   810                           815                           820 | 2863 |
| cgc aac gtc ctc ctg gca caa gga aaa att gtg aag atc tgt gac ttt<br>Arg Asn Val Leu Leu Ala Gln Gly Lys Ile Val Lys Ile Cys Asp Phe<br>825                           830                           835 | 2911 |

```
ggc ctg gcc aga gac atc atg cat gat tcg aac tat gtg tcg aaa ggc     2959
Gly Leu Ala Arg Asp Ile Met His Asp Ser Asn Tyr Val Ser Lys Gly
840                 845                 850                 855 agt acc ttt ctg ccc gtg aag tgg atg gct cct gag agc atc ttt gac     3007
Ser Thr Phe Leu Pro Val Lys Trp Met Ala Pro Glu Ser Ile Phe Asp
                860                 865                 870 aac ctc tac acc aca ctg agt gat gtc tgg tct tat ggc att ctg ctc     3055
Asn Leu Tyr Thr Thr Leu Ser Asp Val Trp Ser Tyr Gly Ile Leu Leu
            875                 880                 885 tgg gag atc ttt tcc ctt ggt ggc acc cct tac ccc ggc atg atg gtg     3103
Trp Glu Ile Phe Ser Leu Gly Gly Thr Pro Tyr Pro Gly Met Met Val
        890                 895                 900 gat tct act ttc tac aat aag atc aag agt ggg tac cgg atg gcc aag     3151
Asp Ser Thr Phe Tyr Asn Lys Ile Lys Ser Gly Tyr Arg Met Ala Lys
    905                 910                 915 cct gac cac gct acc agt gaa gtc tac gag atc atg gtg aaa tgc tgg     3199
Pro Asp His Ala Thr Ser Glu Val Tyr Glu Ile Met Val Lys Cys Trp
920                 925                 930                 935 aac agt gag ccg gag aag aga ccc tcc ttt tac cac ctg agt gag att     3247
Asn Ser Glu Pro Glu Lys Arg Pro Ser Phe Tyr His Leu Ser Glu Ile
                940                 945                 950 gtg gag aat ctg ctg cct gga caa tat aaa aag agt tat gaa aaa att     3295
Val Glu Asn Leu Leu Pro Gly Gln Tyr Lys Lys Ser Tyr Glu Lys Ile
            955                 960                 965 cac ctg gac ttc ctg aag agt gac cat cct gct gtg gca cgc atg cgt     3343
His Leu Asp Phe Leu Lys Ser Asp His Pro Ala Val Ala Arg Met Arg
        970                 975                 980 gtg gac tca gac aat gca tac att ggt gtc acc tac aaa aac gag gaa     3391
Val Asp Ser Asp Asn Ala Tyr Ile Gly Val Thr Tyr Lys Asn Glu Glu
    985                 990                 995 gac aag ctg aag gac tgg gag ggt ggt ctg gat gag cag aga ctg         3436
Asp Lys Leu Lys Asp Trp Glu Gly Gly Leu Asp Glu Gln Arg Leu
1000                1005                1010 agc gct gac agt ggc tac atc att cct ctg cct gac att gac cct         3481
Ser Ala Asp Ser Gly Tyr Ile Ile Pro Leu Pro Asp Ile Asp Pro
1015                1020                1025 gtc cct gag gag gag gac ctg ggc aag agg aac aga cac agc tcg         3526
Val Pro Glu Glu Glu Asp Leu Gly Lys Arg Asn Arg His Ser Ser
1030                1035                1040 cag acc tct gaa gag agt gcc att gag acg ggt tcc agc agt tcc         3571
Gln Thr Ser Glu Glu Ser Ala Ile Glu Thr Gly Ser Ser Ser Ser
1045                1050                1055 acc ttc atc aag aga gag gac gag acc att gaa gac atc gac atg         3616
Thr Phe Ile Lys Arg Glu Asp Glu Thr Ile Glu Asp Ile Asp Met
1060                1065                1070 atg gac gac atc ggc ata gac tct tca gac ctg gtg gaa gac agc         3661
Met Asp Asp Ile Gly Ile Asp Ser Ser Asp Leu Val Glu Asp Ser
1075                1080                1085 ttc     ctgtaactgg cggattcgag gggttccttc cacttctggg gccacctctg      3714
Phe
1090 gatcccgttc agaaaaccac tttattgcaa tgcggaggtt gagaggagga cttggttgat   3774 gtttaaagag aagttcccag ccaagggcct cggggagcgt tctaaatatg aatgaatggg   3834 atattttgaa atgaactttg tcagtgttgc ctctcgcaat gcctcagtag catctcagtg   3894 gtgtgtgaag tttggagata gatggataag ggaataatag gccacagaag gtgaactttg   3954 tgcttcaagg acattggtga gagtccaaca gacacaattt atactgcgac agaacttcag   4014
```

```
cattgtaatt atgtaaataa ctctaaccaa ggctgtgttt agattgtatt aactatcttc   4074
tttggacttc tgaagagacc actcaatcca tccatgtact tccctcttga aacctgatgt   4134
cagctgctgt tgaactttt aaagaagtgc atgaaaaacc attttgaac cttaaaggt     4194 actggtacta tagcattttg ctatcttttt tagtgttaag agataaagaa taataattaa   4254
ccaaccttgt ttaatagatt tgggtcattt agaagcctga caactcattt tcatattgta   4314
atctatgttt ataatactac tactgttatc agtaatgcta aatgtgtaat aatgtaacat   4374
gatttccctc cagagaaagc acaatttaaa acaatcctta ctaagtaggt gatgagtttg   4434 acagttttg acatttatat taaataacat gtttctctat aaagtatggt aatagcttta    4494
gtgaattaaa tttagttgag catagagaac aaagtaaaag tagtgttgtc caggaagtca   4554
gaatttttaa ctgtactgaa taggttcccc aatccatcgt attaaaaaac aattaactgc   4614
cctctgaaat aatgggatta gaaacaaaca aaactcttaa gtcctaaaag ttctcaatgt   4674
agaggcataa acctgtgctg aacataactt ctcatgtata ttacccaatg gaaaatataa   4734
tgatcagcaa aaagactgga tttgcagaag tttttttttt ttttcttcat gcctgatgaa   4794
agctttggca accccaatat atgtattttt tgaatctatg aacctgaaaa gggtcagaag   4854
gatgcccaga catcagcctc cttctttcac cccttacccc aaagagaaag agtttgaaac   4914
tcgagaccat aaagatattc tttagtggag gctggatgtg cattagcctg gatcctcagt   4974
tctcaaatgt gtgtggcagc caggatgact agatcctggg tttccatcct tgagattctg   5034
aagtatgaag tctgagggaa accagagtct gtatttttct aaactccctg gctgttctga   5094
tcggccagtt ttcggaaaca ctgacttagg tttcaggaag ttgccatggg aaacaaataa   5154 tttgaactt ggaacagggt tggaattcaa ccacgcagga agcctactat ttaaatcctt    5214
ggcttcaggt tagtgacatt taatgccatc tagctagcaa ttgcgacctt aatttaactt   5274
tccagtctta gctgaggctg agaaagctaa agtttggttt tgacaggttt tccaaaagta   5334
aagatgctac ttcccactgt atgggggaga ttgaactttc cccgtctccc gtcttctgcc   5394
tcccactcca taccccgcca aggaaaggca tgtacaaaaa ttatgcaatt cagtgttcca   5454
agtctctgtg taaccagctc agtgttttgg tggaaaaaac attttaagtt ttactgataa   5514
tttgaggtta gatgggagga tgaattgtca catctatcca cactgtcaaa caggttggtg   5574
tgggttcatt ggcattcttt gcaatactgc ttaattgctg ataccatatg aatgaaacat   5634
gggctgtgat tactgcaatc actgtgctat cggcagatga tgctttggaa gatgcagaag   5694
caataataaa gtacttgact acctactggt gtaatctcaa tgcaagcccc aactttctta   5754
tccaactttt tcatagtaag tgcgaagact gagccagatt ggccaattaa aaacgaaaac   5814
ctgactaggt tctgtagagc caattagact tgaaatacgt ttgtgtttct agaatcacag   5874
ctcaagcatt ctgtttatcg ctcactctcc cttgtacagc cttattttgt tggtgctttg   5934 catttgata ttgctgtgag ccttgcatga catcatgagg ccggatgaaa cttctcagtc    5994
cagcagtttc cagtcctaac aaatgctccc acctgaattt gtatatgact gcatttgtgg   6054
gtgtgtgtgt gttttcagca aattccagat ttgtttcctt ttggcctcct gcaaagtctc   6114
cagaagaaaa tttgccaatc tttcctactt tctatttta tgatgacaat caaagccggc    6174
ctgagaaaca ctatttgtga cttttaaac gattagtgat gtccttaaaa tgtggtctgc    6234
caatctgtac aaaatggtcc tattttgtg aagagggaca taagataaaa tgatgttata    6294
catcaatatg tatatatgta tttctatata gacttggaga atactgccaa aacatttatg   6354
acaagctgta tcactgcctt cgtttatatt ttttaactg tgataatccc cacaggcaca    6414
```

```
ttaactgttg cacttttgaa tgtccaaaat ttatatttta gaataataa aaagaaagat    6474 acttacatgt tcccaaaaca atggtgtggt gaatgtgtga gaaaaactaa cttgataggg    6534
tctaccaata caaatgtat tacgaatgcc cctgttcatg tttttgtttt aaaacgtgta    6594
aatgaagatc tttatatttc aataaatgat atataattta aagtt                  6639
```

<210> SEQ ID NO 10
<211> LENGTH: 1090
<212> TYPE: PRT
<213> ORGANISM: Homo sapiens

<400> SEQUENCE: 10

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335
```

-continued

```
Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
            370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp His His Gly Ser Thr Gly Gly Gln Thr
            420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
            450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
            530                 535                 540

Leu Val Val Ile Trp Lys Gln Lys Pro Arg Tyr Glu Ile Arg Trp Arg
545                 550                 555                 560

Glu Arg Val Ile Glu Ser Ile Ser Pro Asp Gly His Glu Tyr Ile Tyr
                565                 570                 575

Val Asp Pro Met Gln Leu Pro Tyr Asp Ser Arg Trp Glu Phe Pro Arg
            580                 585                 590

Asp Gly Leu Val Leu Gly Arg Val Leu Gly Ser Gly Ala Phe Gly Lys
            595                 600                 605

Val Val Glu Gly Thr Ala Tyr Gly Leu Ser Arg Ser Gln Pro Val Met
            610                 615                 620

Lys Val Ala Val Lys Met Leu Lys Pro Thr Ala Arg Ser Ser Glu Lys
625                 630                 635                 640

Gln Ala Leu Met Ser Glu Leu Lys Ile Met Thr His Leu Gly Pro His
                645                 650                 655

Leu Asn Ile Val Asn Leu Leu Gly Ala Cys Thr Lys Ser Gly Pro Ile
            660                 665                 670

Tyr Ile Ile Thr Glu Tyr Cys Phe Tyr Gly Asp Leu Val Asn Tyr Leu
            675                 680                 685

His Lys Asn Arg Asp Ser Phe Leu Ser His His Pro Glu Lys Pro Lys
            690                 695                 700

Lys Glu Leu Asp Ile Phe Gly Leu Asn Pro Ala Asp Glu Ser Thr Arg
705                 710                 715                 720

Ser Tyr Val Ile Leu Ser Phe Glu Asn Asn Gly Asp Tyr Met Asp Met
                725                 730                 735

Lys Gln Ala Asp Thr Thr Gln Tyr Val Pro Met Leu Glu Arg Lys Glu
            740                 745                 750
```

```
Val Ser Lys Tyr Ser Asp Ile Gln Arg Ser Leu Tyr Asp Arg Pro Ala
        755                 760                 765
Ser Tyr Lys Lys Lys Ser Met Leu Asp Ser Glu Val Lys Asn Leu Leu
    770                 775                 780
Ser Asp Asp Asn Ser Glu Gly Leu Thr Leu Leu Asp Leu Leu Ser Phe
785                 790                 795                 800
Thr Tyr Gln Val Ala Arg Gly Met Glu Phe Leu Ala Ser Lys Asn Cys
                805                 810                 815
Val His Arg Asp Leu Ala Ala Arg Asn Val Leu Leu Ala Gln Gly Lys
            820                 825                 830
Ile Val Lys Ile Cys Asp Phe Gly Leu Ala Arg Asp Ile Met His Asp
        835                 840                 845
Ser Asn Tyr Val Ser Lys Gly Ser Thr Phe Leu Pro Val Lys Trp Met
850                 855                 860
Ala Pro Glu Ser Ile Phe Asp Asn Leu Tyr Thr Thr Leu Ser Asp Val
865                 870                 875                 880
Trp Ser Tyr Gly Ile Leu Leu Trp Glu Ile Phe Ser Leu Gly Gly Thr
                885                 890                 895
Pro Tyr Pro Gly Met Met Val Asp Ser Thr Phe Tyr Asn Lys Ile Lys
                900                 905                 910
Ser Gly Tyr Arg Met Ala Lys Pro Asp His Ala Thr Ser Glu Val Tyr
            915                 920                 925
Glu Ile Met Val Lys Cys Trp Asn Ser Glu Pro Glu Lys Arg Pro Ser
        930                 935                 940
Phe Tyr His Leu Ser Glu Ile Val Glu Asn Leu Leu Pro Gly Gln Tyr
945                 950                 955                 960
Lys Lys Ser Tyr Glu Lys Ile His Leu Asp Phe Leu Lys Ser Asp His
                965                 970                 975
Pro Ala Val Ala Arg Met Arg Val Asp Ser Asp Asn Ala Tyr Ile Gly
            980                 985                 990
Val Thr Tyr Lys Asn Glu Glu Asp Lys Leu Lys Asp Trp Glu Gly Gly
        995                 1000                1005
Leu Asp Glu Gln Arg Leu Ser Ala Asp Ser Gly Tyr Ile Ile Pro
    1010                1015                1020
Leu Pro Asp Ile Asp Pro Val Pro Glu Glu Glu Asp Leu Gly Lys
    1025                1030                1035
Arg Asn Arg His Ser Ser Gln Thr Ser Glu Glu Ser Ala Ile Glu
    1040                1045                1050
Thr Gly Ser Ser Ser Ser Thr Phe Ile Lys Arg Glu Asp Glu Thr
    1055                1060                1065
Ile Glu Asp Ile Asp Met Met Asp Asp Ile Gly Ile Asp Ser Ser
    1070                1075                1080
Asp Leu Val Glu Asp Ser Phe
    1085                1090

<210> SEQ ID NO 11
<211> LENGTH: 6618
<212> TYPE: DNA
<213> ORGANISM: Homo sapiens
<220> FEATURE:
<221> NAME/KEY: CDS
<222> LOCATION: (395)..(3649)

<400> SEQUENCE: 11
ttctccccgc cccccagttg ttgtcgaagt ctgggggttg ggactggacc ccctgattgc    60
```

```
gtaagagcaa aaagcgaagg cgcaatctgg acactgggag attcggagcg cagggagttt      120
gagagaaact tttattttga agagaccaag gttgagggg ggcttatttc ctgacagcta       180
tttacttaga gcaaatgatt agttttagaa ggatggacta taacattgaa tcaattacaa     240
aacgcggttt ttgagcccat tactgttgga gctacaggga gagaaacagg aggagactgc     300
aagagatcat ttgggaaggc cgtgggcacg ctctttactc catgtgtggg acattcattg     360
cggaataaca tcggaggaga agtttcccag agct atg ggg act tcc cat ccg gcg    415
                                   Met Gly Thr Ser His Pro Ala
                                    1               5
```

| | | | | | | | | | | | | | | | | |
|---|---|---|---|---|---|---|---|---|---|---|---|---|---|---|---|---|
| ttc | ctg | gtc | tta | ggc | tgt | ctt | ctc | aca | ggg | ctg | agc | cta | atc | ctc | tgc | 463 |
| Phe | Leu | Val | Leu | Gly | Cys | Leu | Leu | Thr | Gly | Leu | Ser | Leu | Ile | Leu | Cys | |
| | 10 | | | | 15 | | | | | 20 | | | | | | |
| cag | ctt | tca | tta | ccc | tct | atc | ctt | cca | aat | gaa | aat | gaa | aag | gtt | gtg | 511 |
| Gln | Leu | Ser | Leu | Pro | Ser | Ile | Leu | Pro | Asn | Glu | Asn | Glu | Lys | Val | Val | |
| | 25 | | | | 30 | | | | | 35 | | | | | | |
| cag | ctg | aat | tca | tcc | ttt | tct | ctg | aga | tgc | ttt | ggg | gag | agt | gaa | gtg | 559 |
| Gln | Leu | Asn | Ser | Ser | Phe | Ser | Leu | Arg | Cys | Phe | Gly | Glu | Ser | Glu | Val | |
| 40 | | | | | 45 | | | | | 50 | | | | | 55 | |
| agc | tgg | cag | tac | ccc | atg | tct | gaa | gaa | gag | agc | tcc | gat | gtg | gaa | atc | 607 |
| Ser | Trp | Gln | Tyr | Pro | Met | Ser | Glu | Glu | Glu | Ser | Ser | Asp | Val | Glu | Ile | |
| | | | | 60 | | | | | 65 | | | | | 70 | | |
| aga | aat | gaa | gaa | aac | aac | agc | ggc | ctt | ttt | gtg | acg | gtc | ttg | gaa | gtg | 655 |
| Arg | Asn | Glu | Glu | Asn | Asn | Ser | Gly | Leu | Phe | Val | Thr | Val | Leu | Glu | Val | |
| | | 75 | | | | | 80 | | | | | 85 | | | | |
| agc | agt | gcc | tcg | gcg | gcc | cac | aca | ggg | ttg | tac | act | tgc | tat | tac | aac | 703 |
| Ser | Ser | Ala | Ser | Ala | Ala | His | Thr | Gly | Leu | Tyr | Thr | Cys | Tyr | Tyr | Asn | |
| | | 90 | | | | | 95 | | | | | 100 | | | | |
| cac | act | cag | aca | gaa | gag | aat | gag | ctt | gaa | ggc | agg | cac | att | tac | atc | 751 |
| His | Thr | Gln | Thr | Glu | Glu | Asn | Glu | Leu | Glu | Gly | Arg | His | Ile | Tyr | Ile | |
| | 105 | | | | | 110 | | | | | 115 | | | | | |
| tat | gtg | cca | gac | cca | gat | gta | gcc | ttt | gta | cct | cta | gga | atg | acg | gat | 799 |
| Tyr | Val | Pro | Asp | Pro | Asp | Val | Ala | Phe | Val | Pro | Leu | Gly | Met | Thr | Asp | |
| 120 | | | | | 125 | | | | | 130 | | | | | 135 | |
| tat | tta | gtc | atc | gtg | gag | gat | gat | gat | tct | gcc | att | ata | cct | tgt | cgc | 847 |
| Tyr | Leu | Val | Ile | Val | Glu | Asp | Asp | Asp | Ser | Ala | Ile | Ile | Pro | Cys | Arg | |
| | | | 140 | | | | | 145 | | | | | 150 | | | |
| aca | act | gat | ccc | gag | act | cct | gta | acc | tta | cac | aac | agt | gag | ggg | gtg | 895 |
| Thr | Thr | Asp | Pro | Glu | Thr | Pro | Val | Thr | Leu | His | Asn | Ser | Glu | Gly | Val | |
| | | | 155 | | | | | 160 | | | | | 165 | | | |
| gta | cct | gcc | tcc | tac | gac | agc | aga | cag | ggc | ttt | aat | ggg | acc | ttc | act | 943 |
| Val | Pro | Ala | Ser | Tyr | Asp | Ser | Arg | Gln | Gly | Phe | Asn | Gly | Thr | Phe | Thr | |
| | | 170 | | | | | 175 | | | | | 180 | | | | |
| gta | ggg | ccc | tat | atc | tgt | gag | gcc | acc | gtc | aaa | gga | aag | aag | ttc | cag | 991 |
| Val | Gly | Pro | Tyr | Ile | Cys | Glu | Ala | Thr | Val | Lys | Gly | Lys | Lys | Phe | Gln | |
| | 185 | | | | | 190 | | | | | 195 | | | | | |
| acc | atc | cca | ttt | aat | gtt | tat | gct | tta | aaa | gca | aca | tca | gag | ctg | gat | 1039 |
| Thr | Ile | Pro | Phe | Asn | Val | Tyr | Ala | Leu | Lys | Ala | Thr | Ser | Glu | Leu | Asp | |
| 200 | | | | | 205 | | | | | 210 | | | | | 215 | |
| cta | gaa | atg | gaa | gct | ctt | aaa | acc | gtg | tat | aag | tca | ggg | gaa | acg | att | 1087 |
| Leu | Glu | Met | Glu | Ala | Leu | Lys | Thr | Val | Tyr | Lys | Ser | Gly | Glu | Thr | Ile | |
| | | | 220 | | | | | 225 | | | | | 230 | | | |
| gtg | gtc | acc | tgt | gct | gtt | ttt | aac | aat | gag | gtg | gtt | gac | ctt | caa | tgg | 1135 |
| Val | Val | Thr | Cys | Ala | Val | Phe | Asn | Asn | Glu | Val | Val | Asp | Leu | Gln | Trp | |
| | | | 235 | | | | | 240 | | | | | 245 | | | |
| act | tac | cct | gga | gaa | gtg | aaa | ggc | aaa | ggc | atc | aca | atg | ctg | gaa | gaa | 1183 |
| Thr | Tyr | Pro | Gly | Glu | Val | Lys | Gly | Lys | Gly | Ile | Thr | Met | Leu | Glu | Glu | |
| | | 250 | | | | | 255 | | | | | 260 | | | | |
| atc | aaa | gtc | cca | tcc | atc | aaa | ttg | gtg | tac | act | ttg | acg | gtc | ccc | gag | 1231 |

```
                    Ile Lys Val Pro Ser Ile Lys Leu Val Tyr Thr Leu Thr Val Pro Glu
                        265                 270                 275 gcc acg gtg aaa gac agt gga gat tac gaa tgt gct gcc cgc cag gct        1279
Ala Thr Val Lys Asp Ser Gly Asp Tyr Glu Cys Ala Ala Arg Gln Ala
280                 285                 290                 295 acc agg gag gtc aaa gaa atg aag aaa gtc act att tct gtc cat gag        1327
Thr Arg Glu Val Lys Glu Met Lys Lys Val Thr Ile Ser Val His Glu
                300                 305                 310 aaa ggt ttc att gaa atc aaa ccc acc ttc agc cag ttg gaa gct gtc        1375
Lys Gly Phe Ile Glu Ile Lys Pro Thr Phe Ser Gln Leu Glu Ala Val
                        315                 320                 325 aac ctg cat gaa gtc aaa cat ttt gtt gta gag gtg cgg gcc tac cca        1423
Asn Leu His Glu Val Lys His Phe Val Val Glu Val Arg Ala Tyr Pro
            330                 335                 340 cct ccc agg ata tcc tgg ctg aaa aac aat ctg act ctg att gaa aat        1471
Pro Pro Arg Ile Ser Trp Leu Lys Asn Asn Leu Thr Leu Ile Glu Asn
345                 350                 355 ctc act gag atc acc act gat gtg gaa aag att cag gaa ata agg tat        1519
Leu Thr Glu Ile Thr Thr Asp Val Glu Lys Ile Gln Glu Ile Arg Tyr
360                 365                 370                 375 cga agc aaa tta aag ctg atc cgt gct aag gaa gaa gac agt ggc cat        1567
Arg Ser Lys Leu Lys Leu Ile Arg Ala Lys Glu Glu Asp Ser Gly His
                380                 385                 390 tat act att gta gct caa aat gaa gat gct gtg aag agc tat act ttt        1615
Tyr Thr Ile Val Ala Gln Asn Glu Asp Ala Val Lys Ser Tyr Thr Phe
                        395                 400                 405 gaa ctg tta act caa gtt cct tca tcc att ctg gac ttg gtc gat gat        1663
Glu Leu Leu Thr Gln Val Pro Ser Ser Ile Leu Asp Leu Val Asp Asp
            410                 415                 420 cac cat ggc tca act ggg gga cag acg gtg agg tgc aca gct gaa ggc        1711
His His Gly Ser Thr Gly Gly Gln Thr Val Arg Cys Thr Ala Glu Gly
425                 430                 435 acg ccg ctt cct gat att gag tgg atg ata tgc aaa gat att aag aaa        1759
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac        1807
Cys Asn Asn Glu Thr Ser Trp Thr Ile Leu Ala Asn Asn Val Ser Asn
                460                 465                 470 atc atc acg gag atc cac tcc cga gac agg agt acc gtg gag ggc cgt        1855
Ile Ile Thr Glu Ile His Ser Arg Asp Arg Ser Thr Val Glu Gly Arg
                        475                 480                 485 gtg act ttc gcc aaa gtg gag gag acc atc gcc gtg cga tgc ctg gct        1903
Val Thr Phe Ala Lys Val Glu Glu Thr Ile Ala Val Arg Cys Leu Ala
            490                 495                 500 aag aat ctc ctt gga gct gag aac cga gag ctg aag ctg gtg gct ccc        1951
Lys Asn Leu Leu Gly Ala Glu Asn Arg Glu Leu Lys Leu Val Ala Pro
505                 510                 515 acc ctg cgt tct gaa ctc acg gtg gct gct gca gtc ctg gtg ctg ttg        1999
Thr Leu Arg Ser Glu Leu Thr Val Ala Ala Ala Val Leu Val Leu Leu
520                 525                 530                 535 gtg att gtg atc atc tca ctt att gtc ctg gtt gtc att tgg aaa cag        2047
Val Ile Val Ile Ile Ser Leu Ile Val Leu Val Val Ile Trp Lys Gln
                540                 545                 550 aaa ccg agg tat gaa att cgc tgg agg gtc att gaa tca atc ccg tat        2095
Lys Pro Arg Tyr Glu Ile Arg Trp Arg Val Ile Glu Ser Ile Pro Tyr
                        555                 560                 565 att tat gtg gac ccg atg cag ctg cct tat gac tca aga tgg gag ttt        2143
Ile Tyr Val Asp Pro Met Gln Leu Pro Tyr Asp Ser Arg Trp Glu Phe
            570                 575                 580
```

```
cca aga gat gga cta gtg ctt ggt cgg gtc ttg ggg tct gga gcg ttt         2191
Pro Arg Asp Gly Leu Val Leu Gly Arg Val Leu Gly Ser Gly Ala Phe
    585                 590                 595 ggg aag gtg gtt gaa gga aca gcc tat gga tta agc cgg tcc caa cct         2239
Gly Lys Val Val Glu Gly Thr Ala Tyr Gly Leu Ser Arg Ser Gln Pro
600                 605                 610                 615 gtc atg aaa gtt gca gtg aag atg cta aaa ccc acg gcc aga tcc agt         2287
Val Met Lys Val Ala Val Lys Met Leu Lys Pro Thr Ala Arg Ser Ser
                620                 625                 630 gaa aaa caa gct ctc atg tct gaa ctg aag ata atg act cac ctg ggg         2335
Glu Lys Gln Ala Leu Met Ser Glu Leu Lys Ile Met Thr His Leu Gly
            635                 640                 645 cca cat ttg aac att gta aac ttg ctg gga gcc tgc acc aag tca ggc         2383
Pro His Leu Asn Ile Val Asn Leu Leu Gly Ala Cys Thr Lys Ser Gly
        650                 655                 660 ccc att tac atc atc aca gag tat tgc ttc tat gga gat ttg gtc aac         2431
Pro Ile Tyr Ile Ile Thr Glu Tyr Cys Phe Tyr Gly Asp Leu Val Asn
    665                 670                 675 tat ttg cat aag aat agg gat agc ttc ctg agc cac cac cca gag aag         2479
Tyr Leu His Lys Asn Arg Asp Ser Phe Leu Ser His His Pro Glu Lys
680                 685                 690                 695 cca aag aaa gag ctg gat atc ttt gga ttg aac cct gct gat gaa agc         2527
Pro Lys Lys Glu Leu Asp Ile Phe Gly Leu Asn Pro Ala Asp Glu Ser
                700                 705                 710 aca cgg agc tat gtt att tta tct ttt gaa aac aat ggt gac tac atg         2575
Thr Arg Ser Tyr Val Ile Leu Ser Phe Glu Asn Asn Gly Asp Tyr Met
            715                 720                 725 gac atg aag cag gct gat act aca cag tat gtc ccc atg cta gaa agg         2623
Asp Met Lys Gln Ala Asp Thr Thr Gln Tyr Val Pro Met Leu Glu Arg
        730                 735                 740 aaa gag gtt tct aaa tat tcc gac atc cag aga tca ctc tat gat cgt         2671
Lys Glu Val Ser Lys Tyr Ser Asp Ile Gln Arg Ser Leu Tyr Asp Arg
    745                 750                 755 cca gcc tca tat aag aag aaa tct atg tta gac tca gaa gtc aaa aac         2719
Pro Ala Ser Tyr Lys Lys Lys Ser Met Leu Asp Ser Glu Val Lys Asn
760                 765                 770                 775 ctc ctt tca gat gat aac tca gaa ggc ctt act tta ttg gat ttg ttg         2767
Leu Leu Ser Asp Asp Asn Ser Glu Gly Leu Thr Leu Leu Asp Leu Leu
                780                 785                 790 agc ttc acc tat caa gtt gcc cga gga atg gag ttt ttg gct tca aaa         2815
Ser Phe Thr Tyr Gln Val Ala Arg Gly Met Glu Phe Leu Ala Ser Lys
            795                 800                 805 aat tgt gtc cac cgt gat ctg gct gct cgc aac gtc ctc ctg gca caa         2863
Asn Cys Val His Arg Asp Leu Ala Ala Arg Asn Val Leu Leu Ala Gln
        810                 815                 820 gga aaa att gtg aag atc tgt gac ttt ggc ctg gcc aga gac atc atg         2911
Gly Lys Ile Val Lys Ile Cys Asp Phe Gly Leu Ala Arg Asp Ile Met
    825                 830                 835 cat gat tcg aac tat gtg tcg aaa ggc agt acc ttt ctg ccc gtg aag         2959
His Asp Ser Asn Tyr Val Ser Lys Gly Ser Thr Phe Leu Pro Val Lys
840                 845                 850                 855 tgg atg gct cct gag agc atc ttt gac aac ctc tac acc aca ctg agt         3007
Trp Met Ala Pro Glu Ser Ile Phe Asp Asn Leu Tyr Thr Thr Leu Ser
                860                 865                 870 gat gtc tgg tct tat ggc att ctg ctc tgg gag atc ttt tcc ctt ggt         3055
Asp Val Trp Ser Tyr Gly Ile Leu Leu Trp Glu Ile Phe Ser Leu Gly
            875                 880                 885 ggc acc cct tac ccc ggc atg atg gtg gat tct act ttc tac aat aag         3103
Gly Thr Pro Tyr Pro Gly Met Met Val Asp Ser Thr Phe Tyr Asn Lys
        890                 895                 900
```

| | |
|---|---|
| atc aag agt ggg tac cgg atg gcc aag cct gac cac gct acc agt gaa<br>Ile Lys Ser Gly Tyr Arg Met Ala Lys Pro Asp His Ala Thr Ser Glu<br>905                910                915 | 3151 |
| gtc tac gag atc atg gtg aaa tgc tgg aac agt gag ccg gag aag aga<br>Val Tyr Glu Ile Met Val Lys Cys Trp Asn Ser Glu Pro Glu Lys Arg<br>920                925                930                935 | 3199 |
| ccc tcc ttt tac cac ctg agt gag att gtg gag aat ctg ctg cct gga<br>Pro Ser Phe Tyr His Leu Ser Glu Ile Val Glu Asn Leu Leu Pro Gly<br>                940                945                950 | 3247 |
| caa tat aaa aag agt tat gaa aaa att cac ctg gac ttc ctg aag agt<br>Gln Tyr Lys Lys Ser Tyr Glu Lys Ile His Leu Asp Phe Leu Lys Ser<br>955                960                965 | 3295 |
| gac cat cct gct gtg gca cgc atg cgt gtg gac tca gac aat gca tac<br>Asp His Pro Ala Val Ala Arg Met Arg Val Asp Ser Asp Asn Ala Tyr<br>                970                975                980 | 3343 |
| att ggt gtc acc tac aaa aac gag gaa gac aag ctg aag gac tgg gag<br>Ile Gly Val Thr Tyr Lys Asn Glu Glu Asp Lys Leu Lys Asp Trp Glu<br>985                990                995 | 3391 |
| ggt ggt ctg gat gag cag aga ctg agc gct gac agt ggc tac atc<br>Gly Gly Leu Asp Glu Gln Arg Leu Ser Ala Asp Ser Gly Tyr Ile<br>1000               1005               1010 | 3436 |
| att cct ctg cct gac att gac cct gtc cct gag gag gag gac ctg<br>Ile Pro Leu Pro Asp Ile Asp Pro Val Pro Glu Glu Glu Asp Leu<br>1015               1020               1025 | 3481 |
| ggc aag agg aac aga cac agc tcg cag acc tct gaa gag agt gcc<br>Gly Lys Arg Asn Arg His Ser Ser Gln Thr Ser Glu Glu Ser Ala<br>1030               1035               1040 | 3526 |
| att gag acg ggt tcc agc agt tcc acc ttc atc aag aga gag gac<br>Ile Glu Thr Gly Ser Ser Ser Thr Phe Ile Lys Arg Glu Asp<br>1045               1050               1055 | 3571 |
| gag acc att gaa gac atc gac atg atg gac gac atc ggc ata gac<br>Glu Thr Ile Glu Asp Ile Asp Met Met Asp Asp Ile Gly Ile Asp<br>1060               1065               1070 | 3616 |
| tct tca gac ctg gtg gaa gac agc ttc ctg taa ctggcggatt<br>Ser Ser Asp Leu Val Glu Asp Ser Phe Leu<br>1075               1080 | 3659 |
| cgaggggttc cttccacttc tggggccacc tctggatccc gttcagaaaa ccactttatt | 3719 |
| gcaatgcgga ggttgagagg aggacttggt tgatgtttaa agagaagttc ccagccaagg | 3779 |
| gcctcgggga gcgttctaaa tatgaatgaa tgggatattt tgaaatgaac tttgtcagtg | 3839 |
| ttgcctctcg caatgcctca gtagcatctc agtggtgtgt gaagtttgga gatagatgga | 3899 |
| taagggaata ataggccaca gaaggtgaac tttgtgcttc aaggacattg gtgagagtcc | 3959 |
| aacagacaca atttatactg cgacagaact tcagcattgt aattatgtaa ataactctaa | 4019 |
| ccaaggctgt gtttagattg tattaactat cttctttgga cttctgaaga gaccactcaa | 4079 |
| tccatccatg tacttccctc ttgaaacctg atgtcagctg ctgttgaact ttttaaagaa | 4139 |
| gtgcatgaaa aaccattttt gaaccttaaa aggtactggt actatagcat tttgctatct | 4199 |
| tttttagtgt taagagataa agaataataa ttaaccaacc ttgtttaata gatttgggtc | 4259 |
| atttagaagc ctgacaactc attttcatat tgtaatctat gtttataata ctactactgt | 4319 |
| tatcagtaat gctaaatgtg taataatgta acatgatttc cctccagaga aagcacaatt | 4379 |
| taaaacaatc cttactaagt aggtgatgag tttgacagtg tttgacattt atattaaata | 4439 |
| acatgtttct ctataaagta tggtaatagc tttagtgaat taaatttagt tgagcataga | 4499 |
| gaacaaagta aaagtagtgt tgtccaggaa gtcagaattt ttaactgtac tgaataggtt | 4559 |

```
ccccaatcca tcgtattaaa aaacaattaa ctgccctctg aaataatggg attagaaaca    4619
aacaaaactc ttaagtccta aaagttctca atgtagaggc ataaacctgt gctgaacata    4679
acttctcatg tatattaccc aatggaaaat ataatgatca gcaaaaagac tggatttgca    4739 gaagttttt ttttttttct tcatgcctga tgaaagcttt ggcaacccca atatatgtat    4799
tttttgaatc tatgaacctg aaaagggtca gaaggatgcc cagacatcag cctccttctt    4859
tcacccctta ccccaaagag aaagagtttg aaactcgaga ccataaagat attctttagt    4919
ggaggctgga tgtgcattag cctggatcct cagttctcaa atgtgtgtgg cagccaggat    4979
gactagatcc tgggtttcca tccttgagat tctgaagtat gaagtctgag ggaaaccaga    5039
gtctgtattt ttctaaactc cctggctgtt ctgatcggcc agttttcgga aacactgact    5099
taggtttcag gaagttgcca tgggaaacaa ataatttgaa ctttggaaca gggttggaat    5159
tcaaccacgc aggaagccta ctatttaaat ccttggcttc aggttagtga catttaatgc    5219
catctagcta gcaattgcga ccttaattta actttccagt cttagctgag gctgagaaag    5279
ctaaagtttg gttttgacag gttttccaaa agtaaagatg ctacttccca ctgtatgggg    5339
gagattgaac tttccccgtc tcccgtcttc tgcctcccac tccataccc gccaaggaaa    5399 ggcatgtaca aaattatgc aattcagtgt tccaagtctc tgtgtaacca gctcagtgtt    5459
ttggtggaaa aaacatttta agttttactg ataatttgag gttagatggg aggatgaatt    5519
gtcacatcta tccacactgt caaacaggtt ggtgtgggtt cattggcatt ctttgcaata    5579
ctgcttaatt gctgatacca tatgaatgaa acatgggctg tgattactgc aatcactgtg    5639
ctatcggcag atgatgcttt ggaagatgca gaagcaataa taaagtactt gactacctac    5699
tggtgtaatc tcaatgcaag ccccaacttt cttatccaac ttttcatag taagtgcgaa    5759 gactgagcca gattggccaa ttaaaaacga aaacctgact aggttctgta gagccaatta    5819
gacttgaaat acgtttgtgt ttctagaatc acagctcaag cattctgttt atcgctcact    5879
ctcccttgta cagccttatt tgttggtgc tttgcatttt gatattgctg tgagccttgc    5939
atgacatcat gaggccggat gaaacttctc agtccagcag tttccagtcc taacaaatgc    5999
tcccacctga atttgtatat gactgcattt gtgggtgtgt gtgtgttttc agcaaattcc    6059
agatttgttt cctttggcc tcctgcaaag tctccagaag aaaatttgcc aatctttcct    6119
actttctatt tttatgatga caatcaaagc cggcctgaga acactatt gtgacttttt    6179 aaacgattag tgatgtcctt aaaatgtggt ctgccaatct gtacaaaatg gtcctatttt    6239
tgtgaagagg gacataagat aaaatgatgt tatacatcaa tatgtatata tgtatttcta    6299
tatagacttg gagaatactg ccaaaacatt tatgacaagc tgtatcactg ccttcgttta    6359 tatttttta actgtgataa tccccacagg cacattaact gttgcacttt tgaatgtcca    6419
aaatttatat tttagaaata ataaaagaa agatacttac atgttcccaa aacaatggtg    6479
tggtgaatgt gtgagaaaaa ctaacttgat agggtctacc aatacaaaat gtattacgaa    6539
tgcccctgtt catgtttttg ttttaaaacg tgtaaatgaa gatctttata tttcaataaa    6599
tgatatataa tttaaagtt                                                 6618
```

<210> SEQ ID NO 12
<211> LENGTH: 1084
<212> TYPE: PRT
<213> ORGANISM: Homo sapiens

<400> SEQUENCE: 12

Met Gly Thr Ser His Pro Ala Phe Leu Val Leu Gly Cys Leu Leu Thr

-continued

```
1               5                  10                 15
Gly Leu Ser Leu Ile Leu Cys Gln Leu Ser Leu Pro Ser Ile Leu Pro
                20                 25                 30
Asn Glu Asn Glu Lys Val Val Gln Leu Asn Ser Ser Phe Ser Leu Arg
                35                 40                 45
Cys Phe Gly Glu Ser Glu Val Ser Trp Gln Tyr Pro Met Ser Glu Glu
                50                 55                 60
Glu Ser Ser Asp Val Glu Ile Arg Asn Glu Glu Asn Asn Ser Gly Leu
65                       70                 75                 80
Phe Val Thr Val Leu Glu Val Ser Ser Ala Ser Ala Ala His Thr Gly
                85                 90                 95
Leu Tyr Thr Cys Tyr Tyr Asn His Thr Gln Thr Glu Glu Asn Glu Leu
                100                105                110
Glu Gly Arg His Ile Tyr Ile Tyr Val Pro Asp Pro Asp Val Ala Phe
                115                120                125
Val Pro Leu Gly Met Thr Asp Tyr Leu Val Ile Val Glu Asp Asp Asp
                130                135                140
Ser Ala Ile Ile Pro Cys Arg Thr Thr Asp Pro Glu Thr Pro Val Thr
145                      150                155                160
Leu His Asn Ser Glu Gly Val Val Pro Ala Ser Tyr Asp Ser Arg Gln
                165                170                175
Gly Phe Asn Gly Thr Phe Thr Val Gly Pro Tyr Ile Cys Glu Ala Thr
                180                185                190
Val Lys Gly Lys Lys Phe Gln Thr Ile Pro Phe Asn Val Tyr Ala Leu
                195                200                205
Lys Ala Thr Ser Glu Leu Asp Leu Glu Met Glu Ala Leu Lys Thr Val
                210                215                220
Tyr Lys Ser Gly Glu Thr Ile Val Val Thr Cys Ala Val Phe Asn Asn
225                      230                235                240
Glu Val Val Asp Leu Gln Trp Thr Tyr Pro Gly Glu Val Lys Gly Lys
                245                250                255
Gly Ile Thr Met Leu Glu Glu Ile Lys Val Pro Ser Ile Lys Leu Val
                260                265                270
Tyr Thr Leu Thr Val Pro Glu Ala Thr Val Lys Asp Ser Gly Asp Tyr
                275                280                285
Glu Cys Ala Ala Arg Gln Ala Thr Arg Glu Val Lys Glu Met Lys Lys
                290                295                300
Val Thr Ile Ser Val His Glu Lys Gly Phe Ile Glu Ile Lys Pro Thr
305                      310                315                320
Phe Ser Gln Leu Glu Ala Val Asn Leu His Glu Val Lys His Phe Val
                325                330                335
Val Glu Val Arg Ala Tyr Pro Pro Pro Arg Ile Ser Trp Leu Lys Asn
                340                345                350
Asn Leu Thr Leu Ile Glu Asn Leu Thr Glu Ile Thr Thr Asp Val Glu
                355                360                365
Lys Ile Gln Glu Ile Arg Tyr Arg Ser Lys Leu Lys Leu Ile Arg Ala
                370                375                380
Lys Glu Glu Asp Ser Gly His Tyr Thr Ile Val Ala Gln Asn Glu Asp
385                      390                395                400
Ala Val Lys Ser Tyr Thr Phe Glu Leu Leu Thr Gln Val Pro Ser Ser
                405                410                415
Ile Leu Asp Leu Val Asp Asp His His Gly Ser Thr Gly Gly Gln Thr
                420                425                430
```

```
Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
                500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
        530                 535                 540

Leu Val Val Ile Trp Lys Gln Lys Pro Arg Tyr Glu Ile Arg Trp Arg
545                 550                 555                 560

Val Ile Glu Ser Ile Pro Tyr Ile Tyr Val Asp Pro Met Gln Leu Pro
                565                 570                 575

Tyr Asp Ser Arg Trp Glu Phe Pro Arg Asp Gly Leu Val Leu Gly Arg
                580                 585                 590

Val Leu Gly Ser Gly Ala Phe Gly Lys Val Val Glu Gly Thr Ala Tyr
            595                 600                 605

Gly Leu Ser Arg Ser Gln Pro Val Met Lys Val Ala Val Lys Met Leu
        610                 615                 620

Lys Pro Thr Ala Arg Ser Ser Glu Lys Gln Ala Leu Met Ser Glu Leu
625                 630                 635                 640

Lys Ile Met Thr His Leu Gly Pro His Leu Asn Ile Val Asn Leu Leu
                645                 650                 655

Gly Ala Cys Thr Lys Ser Gly Pro Ile Tyr Ile Ile Thr Glu Tyr Cys
                660                 665                 670

Phe Tyr Gly Asp Leu Val Asn Tyr Leu His Lys Asn Arg Asp Ser Phe
            675                 680                 685

Leu Ser His His Pro Glu Lys Pro Lys Lys Glu Leu Asp Ile Phe Gly
        690                 695                 700

Leu Asn Pro Ala Asp Glu Ser Thr Arg Ser Tyr Val Ile Leu Ser Phe
705                 710                 715                 720

Glu Asn Asn Gly Asp Tyr Met Asp Met Lys Gln Ala Asp Thr Thr Gln
                725                 730                 735

Tyr Val Pro Met Leu Glu Arg Lys Glu Val Ser Lys Tyr Ser Asp Ile
            740                 745                 750

Gln Arg Ser Leu Tyr Asp Arg Pro Ala Ser Tyr Lys Lys Lys Ser Met
        755                 760                 765

Leu Asp Ser Glu Val Lys Asn Leu Leu Ser Asp Asn Ser Glu Gly
        770                 775                 780

Leu Thr Leu Leu Asp Leu Leu Ser Phe Thr Tyr Gln Val Ala Arg Gly
785                 790                 795                 800

Met Glu Phe Leu Ala Ser Lys Asn Cys Val His Arg Asp Leu Ala Ala
                805                 810                 815

Arg Asn Val Leu Leu Ala Gln Gly Lys Ile Val Lys Ile Cys Asp Phe
            820                 825                 830

Gly Leu Ala Arg Asp Ile Met His Asp Ser Asn Tyr Val Ser Lys Gly
        835                 840                 845
```

```
Ser Thr Phe Leu Pro Val Lys Trp Met Ala Pro Glu Ser Ile Phe Asp
    850                 855                 860

Asn Leu Tyr Thr Thr Leu Ser Asp Val Trp Ser Tyr Gly Ile Leu Leu
865                 870                 875                 880

Trp Glu Ile Phe Ser Leu Gly Gly Thr Pro Tyr Pro Gly Met Met Val
                885                 890                 895

Asp Ser Thr Phe Tyr Asn Lys Ile Lys Ser Gly Tyr Arg Met Ala Lys
            900                 905                 910

Pro Asp His Ala Thr Ser Glu Val Tyr Glu Ile Met Val Lys Cys Trp
        915                 920                 925

Asn Ser Glu Pro Glu Lys Arg Pro Ser Phe Tyr His Leu Ser Glu Ile
    930                 935                 940

Val Glu Asn Leu Leu Pro Gly Gln Tyr Lys Lys Ser Tyr Glu Lys Ile
945                 950                 955                 960

His Leu Asp Phe Leu Lys Ser Asp His Pro Ala Val Ala Arg Met Arg
                965                 970                 975

Val Asp Ser Asp Asn Ala Tyr Ile Gly Val Thr Tyr Lys Asn Glu Glu
            980                 985                 990

Asp Lys Leu Lys Asp Trp Glu Gly Gly Leu Asp Glu Gln Arg Leu Ser
        995                 1000                1005

Ala Asp Ser Gly Tyr Ile Ile Pro Leu Pro Asp Ile Asp Pro Val
        1010                1015                1020

Pro Glu Glu Glu Asp Leu Gly Lys Arg Asn Arg His Ser Ser Gln
    1025                1030                1035

Thr Ser Glu Glu Ser Ala Ile Glu Thr Gly Ser Ser Ser Ser Thr
    1040                1045                1050

Phe Ile Lys Arg Glu Asp Glu Thr Ile Glu Asp Ile Asp Met Met
    1055                1060                1065

Asp Asp Ile Gly Ile Asp Ser Ser Asp Leu Val Glu Asp Ser Phe
    1070                1075                1080

Leu

<210> SEQ ID NO 13
<211> LENGTH: 12
<212> TYPE: PRT
<213> ORGANISM: Homo sapiens

<400> SEQUENCE: 13

Tyr Val His Arg Asp Leu Ala Ala Arg Asn Ile Leu
1               5                   10

<210> SEQ ID NO 14
<211> LENGTH: 12
<212> TYPE: PRT
<213> ORGANISM: Homo sapiens

<400> SEQUENCE: 14

Cys Ile His Arg Asp Leu Ala Ala Arg Asn Val Leu
1               5                   10

<210> SEQ ID NO 15
<211> LENGTH: 12
<212> TYPE: PRT
<213> ORGANISM: Homo sapiens

<400> SEQUENCE: 15

Phe Val His Arg Asp Leu Ala Ala Arg Asn Cys Met
1               5                   10
```

```
<210> SEQ ID NO 16
<211> LENGTH: 12
<212> TYPE: PRT
<213> ORGANISM: Homo sapiens

<400> SEQUENCE: 16

Leu Val His Arg Asp Leu Ala Ala Arg Asn Val Leu
1               5                   10

<210> SEQ ID NO 17
<211> LENGTH: 12
<212> TYPE: PRT
<213> ORGANISM: Homo sapiens

<400> SEQUENCE: 17

Phe Ile His Arg Asp Ile Ala Ala Arg Asn Cys Leu
1               5                   10

<210> SEQ ID NO 18
<211> LENGTH: 12
<212> TYPE: PRT
<213> ORGANISM: Homo sapiens

<400> SEQUENCE: 18

Phe Val His Arg Asp Leu Ala Thr Arg Asn Cys Leu
1               5                   10

<210> SEQ ID NO 19
<211> LENGTH: 191150
<212> TYPE: DNA
<213> ORGANISM: Homo sapiens
<220> FEATURE:
<221> NAME/KEY: exon
<222> LOCATION: (1)..(49)
<220> FEATURE:
<221> NAME/KEY: Intron
<222> LOCATION: (50)..(2330)
<220> FEATURE:
<221> NAME/KEY: exon
<222> LOCATION: (2331)..(2648)
<220> FEATURE:
<221> NAME/KEY: Intron
<222> LOCATION: (2649)..(4902)
<220> FEATURE:
<221> NAME/KEY: exon
<222> LOCATION: (4903)..(5163)
<220> FEATURE:
<221> NAME/KEY: Intron
<222> LOCATION: (5164)..(6154)
<220> FEATURE:
<221> NAME/KEY: exon
<222> LOCATION: (6155)..(6285)
<220> FEATURE:
<221> NAME/KEY: Intron
<222> LOCATION: (6286)..(8524)
<220> FEATURE:
<221> NAME/KEY: exon
<222> LOCATION: (8525)..(8696)
<220> FEATURE:
<221> NAME/KEY: Intron
<222> LOCATION: (8697)..(8787)
<220> FEATURE:
<221> NAME/KEY: exon
<222> LOCATION: (8788)..(8977)
<220> FEATURE:
<221> NAME/KEY: Intron
<222> LOCATION: (8978)..(166510)
<220> FEATURE:
<221> NAME/KEY: Unsure
<222> LOCATION: (10577)..(10676)
<223> OTHER INFORMATION: n = any nucleic acid
```

```
<220> FEATURE:
<221> NAME/KEY: misc_feature
<222> LOCATION: (10577)..(10676)
<223> OTHER INFORMATION: n is a, c, g, or t
<220> FEATURE:
<221> NAME/KEY: Unsure
<222> LOCATION: (14335)..(14434)
<223> OTHER INFORMATION: n = any nucleic acid
<220> FEATURE:
<221> NAME/KEY: misc_feature
<222> LOCATION: (14335)..(14434)
<223> OTHER INFORMATION: n is a, c, g, or t
<220> FEATURE:
<221> NAME/KEY: Unsure
<222> LOCATION: (16247)..(16346)
<223> OTHER INFORMATION: n = any nucleic acid
<220> FEATURE:
<221> NAME/KEY: misc_feature
<222> LOCATION: (16247)..(16346)
<223> OTHER INFORMATION: n is a, c, g, or t
<220> FEATURE:
<221> NAME/KEY: misc_feature
<222> LOCATION: (17457)..(17457)
<223> OTHER INFORMATION: n is a, c, g, or t
<220> FEATURE:
<221> NAME/KEY: misc_feature
<222> LOCATION: (21818)..(21818)
<223> OTHER INFORMATION: n is a, c, g, or t
<220> FEATURE:
<221> NAME/KEY: misc_feature
<222> LOCATION: (36293)..(36298)
<223> OTHER INFORMATION: n is a, c, g, or t
<220> FEATURE:
<221> NAME/KEY: misc_feature
<222> LOCATION: (36314)..(36314)
<223> OTHER INFORMATION: n is a, c, g, or t
<220> FEATURE:
<221> NAME/KEY: misc_feature
<222> LOCATION: (36316)..(36316)
<223> OTHER INFORMATION: n is a, c, g, or t
<220> FEATURE:
<221> NAME/KEY: misc_feature
<222> LOCATION: (36432)..(36433)
<223> OTHER INFORMATION: n is a, c, g, or t
<220> FEATURE:
<221> NAME/KEY: Unsure
<222> LOCATION: (36774)..(36873)
<223> OTHER INFORMATION: n = any nucleic acid
<220> FEATURE:
<221> NAME/KEY: misc_feature
<222> LOCATION: (36774)..(36873)
<223> OTHER INFORMATION: n is a, c, g, or t
<220> FEATURE:
<221> NAME/KEY: Unsure
<222> LOCATION: (59740)..(59740)
<223> OTHER INFORMATION: n = any nucleic acid
<220> FEATURE:
<221> NAME/KEY: misc_feature
<222> LOCATION: (59740)..(59740)
<223> OTHER INFORMATION: n is a, c, g, or t
<220> FEATURE:
<221> NAME/KEY: Unsure
<222> LOCATION: (59742)..(59742)
<223> OTHER INFORMATION: n = any nucleic acid
<220> FEATURE:
<221> NAME/KEY: misc_feature
<222> LOCATION: (59742)..(59744)
<223> OTHER INFORMATION: n is a, c, g, or t
<220> FEATURE:
<221> NAME/KEY: Unsure
<222> LOCATION: (59744)..(59744)
<223> OTHER INFORMATION: n = any nucleic acid
<220> FEATURE:
<221> NAME/KEY: Unsure
<222> LOCATION: (59749)..(59755)
<223> OTHER INFORMATION: n = any nucleic acid
<220> FEATURE:
<221> NAME/KEY: misc_feature
<222> LOCATION: (59749)..(59755)
```

-continued

```
<223> OTHER INFORMATION: n is a, c, g, or t
<220> FEATURE:
<221> NAME/KEY: Unsure
<222> LOCATION: (59759)..(59760)
<223> OTHER INFORMATION: n = any nucleic acid
<220> FEATURE:
<221> NAME/KEY: misc_feature
<222> LOCATION: (59759)..(59760)
<223> OTHER INFORMATION: n is a, c, g, or t
<220> FEATURE:
<221> NAME/KEY: misc_feature
<222> LOCATION: (59765)..(59766)
<223> OTHER INFORMATION: n is a, c, g, or t
<220> FEATURE:
<221> NAME/KEY: Unsure
<222> LOCATION: (59776)..(59875)
<223> OTHER INFORMATION: n = any nucleic acid
<220> FEATURE:
<221> NAME/KEY: misc_feature
<222> LOCATION: (59776)..(59875)
<223> OTHER INFORMATION: n is a, c, g, or t
<220> FEATURE:
<221> NAME/KEY: Unsure
<222> LOCATION: (82745)..(82844)
<223> OTHER INFORMATION: n = any nucleic acid
<220> FEATURE:
<221> NAME/KEY: misc_feature
<222> LOCATION: (82745)..(82844)
<223> OTHER INFORMATION: n is a, c, g, or t
<220> FEATURE:
<221> NAME/KEY: Unsure
<222> LOCATION: (96508)..(96607)
<223> OTHER INFORMATION: n = any nucleic acid
<220> FEATURE:
<221> NAME/KEY: misc_feature
<222> LOCATION: (96508)..(96607)
<223> OTHER INFORMATION: n is a, c, g, or t
<220> FEATURE:
<221> NAME/KEY: Unsure
<222> LOCATION: (147675)..(147774)
<223> OTHER INFORMATION: n = any nucleic acid
<220> FEATURE:
<221> NAME/KEY: misc_feature
<222> LOCATION: (147675)..(147774)
<223> OTHER INFORMATION: n is a, c, g, or t
<220> FEATURE:
<221> NAME/KEY: Unsure
<222> LOCATION: (157152)..(157251)
<223> OTHER INFORMATION: n = any nucleic acid
<220> FEATURE:
<221> NAME/KEY: misc_feature
<222> LOCATION: (157152)..(157251)
<223> OTHER INFORMATION: n is a, c, g, or t
<220> FEATURE:
<221> NAME/KEY: misc_feature
<222> LOCATION: (161475)..(161574)
<223> OTHER INFORMATION: n is a, c, g, or t
<220> FEATURE:
<221> NAME/KEY: Unsure
<222> LOCATION: (165240)..(165339)
<223> OTHER INFORMATION: n = any nucleic acid
<220> FEATURE:
<221> NAME/KEY: misc_feature
<222> LOCATION: (165240)..(165339)
<223> OTHER INFORMATION: n is a, c, g, or t
<220> FEATURE:
<221> NAME/KEY: exon
<222> LOCATION: (166511)..(166626)
<220> FEATURE:
<221> NAME/KEY: Intron
<222> LOCATION: (166627)..(168271)
<220> FEATURE:
<221> NAME/KEY: exon
<222> LOCATION: (168272)..(168398)
<220> FEATURE:
<221> NAME/KEY: Intron
<222> LOCATION: (168399)..(169414)
<220> FEATURE:
<221> NAME/KEY: exon
```

```
<222> LOCATION: (169415)..(169608)
<220> FEATURE:
<221> NAME/KEY: Intron
<222> LOCATION: (169609)..(170408)
<220> FEATURE:
<221> NAME/KEY: exon
<222> LOCATION: (170409)..(170503)
<220> FEATURE:
<221> NAME/KEY: Intron
<222> LOCATION: (170504)..(170718)
<220> FEATURE:
<221> NAME/KEY: exon
<222> LOCATION: (170719)..(170851)
<220> FEATURE:
<221> NAME/KEY: Intron
<222> LOCATION: (170852)..(173265)
<220> FEATURE:
<221> NAME/KEY: exon
<222> LOCATION: (173266)..(173370)
<220> FEATURE:
<221> NAME/KEY: Intron
<222> LOCATION: (173371)..(173773)
<220> FEATURE:
<221> NAME/KEY: exon
<222> LOCATION: (173774)..(173884)
<220> FEATURE:
<221> NAME/KEY: Intron
<222> LOCATION: (173885)..(174239)
<220> FEATURE:
<221> NAME/KEY: exon
<222> LOCATION: (174240)..(174393)
<220> FEATURE:
<221> NAME/KEY: Intron
<222> LOCATION: (174394)..(176193)
<220> FEATURE:
<221> NAME/KEY: exon
<222> LOCATION: (176194)..(176360)
<220> FEATURE:
<221> NAME/KEY: Intron
<222> LOCATION: (176361)..(181248)
<220> FEATURE:
<221> NAME/KEY: exon
<222> LOCATION: (181249)..(181364)
<220> FEATURE:
<221> NAME/KEY: Intron
<222> LOCATION: (181365)..(181718)
<220> FEATURE:
<221> NAME/KEY: exon
<222> LOCATION: (181719)..(181841)
<220> FEATURE:
<221> NAME/KEY: Intron
<222> LOCATION: (181842)..(183307)
<220> FEATURE:
<221> NAME/KEY: exon
<222> LOCATION: (183308)..(183419)
<220> FEATURE:
<221> NAME/KEY: Intron
<222> LOCATION: (183420)..(184676)
<220> FEATURE:
<221> NAME/KEY: exon
<222> LOCATION: (184677)..(184776)
<220> FEATURE:
<221> NAME/KEY: Intron
<222> LOCATION: (184777)..(184886)
<220> FEATURE:
<221> NAME/KEY: exon
<222> LOCATION: (184887)..(184992)
<220> FEATURE:
<221> NAME/KEY: Intron
<222> LOCATION: (184993)..(186190)
<220> FEATURE:
<221> NAME/KEY: exon
<222> LOCATION: (186191)..(186432)
<220> FEATURE:
<221> NAME/KEY: Intron
<222> LOCATION: (186433)..(191002)
<220> FEATURE:
<221> NAME/KEY: exon
<222> LOCATION: (191003)..(191150)
```

<400> SEQUENCE: 19

```
atg ggg act tcc cat ccg gcg ttc ctg gtc tta ggc tgt ctt ctc aca g      49
Met Gly Thr Ser His Pro Ala Phe Leu Val Leu Gly Cys Leu Leu Thr
1               5                   10                  15 gtacggagcc cagtcctctc tgagttcctt gtttgggtgt cttgtttttt taagctttgt     109
gctgcatggg tttattacca gtactctgca tacacagtcc aaaagagtga aagaaaatag     169
aaaactatag gacgttatcc agaatgacca caaaccttca gttccctttg ctgtattgca     229
cttactccat ttcaaaagga atgctctcca gtggcagttt tagtacatat ataatgttgg     289
cattgaaatg ttgttagtaa taatgtctaa atttacttac tactctcttc cttttcctag     349
gacaaggctt ctattagagc tggattagat aaattcagga atggtcagct gtgggaggtg     409
gcacatctgt tgtcccagcc ccttgagcag ctgaggtggg atgatcccct taaggccagg     469
agttcaaggg ttgcagtgca ctgtgattat gcctgtgact agccaccaca ctccagcaac     529
atagcaagac ctcatttaaa aaaaatgttc aaaggaaata aataatagaa aattcttgcc     589
caagaaatca tacttgtctt aaatcataac tctcttgagg aaagatgctt acattgcttc     649
taaatctcag agtcaccttt atcttctcta ggaatcaaat tgatagatga atgtttggct     709
cttggaaaat cttaaaaact ttcccaccaa aaggatcatt ggggtaattt gttgaagtgt     769
gtattggact gtcttagttt tcctccagat atttatgcac tgcagatgtt cgccatgaaa     829
ccagtgctct tctattctga ggagttagct cagcccgtta gtgtctttgt cttacccatt     889
tggatatggt agaattgagc aagaccgag attcaacagt tctaagctcc actaagtata     949
ccccatctac agagtaatag gtgatccaga tgtacttaca aatcctatct taacaagctt    1009
taggaattat agtggtcata tattgaagtt gggtgggagt ctcacaccag gttccaaggg    1069
agattacaaa tcactaatta ataattaagt cataatatct cttctatcag tctcgggttt    1129
cttgttttct aagttctgtg ctccatgggt ttattatctg tactctgctt acacagtcca    1189
aaagagtgaa aagaaataga aaactacagg acgttatcca gaatgaccac aaaccttcag    1249
ttcctttgct gcattgcact tactctattg caaaaggagt aagtgcaatt tcagtctaaa    1309
taagcgagac tgaaatttga gcttcgaaga tgaacttaga gttttcactc ttgggtttta    1369
cttaccaatt gtgaattaaa atccgtatca tctggcacca ctgcactcca gcctgggtga    1429
cagagcaaga ctccatctca taaaaataaa gaaataaata aacaaataaa tccacatcat    1489
cctgctttgg ccctggaagt catgaggag agacggcatg cccgagggct ataagaaatg    1549
gaagatgtgg aattcttgag cacagatgtg ctttgtgttt tcttcagtct gtgtccttgc    1609
ctccattctt attccatgtg ggtttttttt tttttttttt tttttttttt tgagacaggt    1669
tttttttcct ttattgccca gggggagtg caaaggctga ctgcaacctc aatcccctgg    1729
gctccagtga tcctcccacc tcagcctcca aagtagctag gactacaggt gtacaccagc    1789
acacctggct aatttttttta tttttttatt tttgggggag accaggtctc actacgttgc    1849
ccaggctggt ctcgaactcc tgagctcaag cgatcctccc acttccacct aacaaagtgc    1909
tgggattata acatgagcc tttgcgcccc agccttttttt tttttaact aaaggaaacc    1969
tttgcagtga ttgtgaacca taagaaccc atatgtgctt gagcccgtgc catcttggga    2029
tattttatg gttacacata agagtctgaa atatggaatt ggaatcagac atcctctgtc    2089
tatttgagtg tttggagggg tgaatctagt ggggcttggt ggagctattt ggaacatttg    2149
ctgctctcag cagatgcagt ggctgttata atgggggagc tttcatgggc atccaggcta    2209
```

```
acggattttt gtgtagaaat ggtcattgtt catctaagct gctactgttg cttctctcag    2269
ttgtcgggat gagactgtcc tttctgactg catcctattc agagcgtgct tccttttgca    2329 g gg  ctg agc cta atc ctc tgc cag ctt tca tta ccc tct atc ctt cca    2377
  Gly Leu Ser Leu Ile Leu Cys Gln Leu Ser Leu Pro Ser Ile Leu Pro
         20                  25                  30 aat gaa aat gaa aag gtt gtg cag ctg aat tca tcc ttt tct ctg aga      2425
Asn Glu Asn Glu Lys Val Val Gln Leu Asn Ser Ser Phe Ser Leu Arg
         35                  40                  45 tgc ttt ggg gag agt gaa gtg agc tgg cag tac ccc atg tct gaa gaa      2473
Cys Phe Gly Glu Ser Glu Val Ser Trp Gln Tyr Pro Met Ser Glu Glu
 50                  55                  60 gag agc tcc gat gtg gaa atc aga aat gaa gaa aac aac agc ggc ctt      2521
Glu Ser Ser Asp Val Glu Ile Arg Asn Glu Glu Asn Asn Ser Gly Leu
 65                  70                  75                  80 ttt gtg acg gtc ttg gaa gtg agc agt gcc tcg gcg gcc cac aca ggg      2569
Phe Val Thr Val Leu Glu Val Ser Ser Ala Ser Ala Ala His Thr Gly
                 85                  90                  95 ttg tac act tgc tat tac aac cac act cag aca gaa gag aat gag ctt      2617
Leu Tyr Thr Cys Tyr Tyr Asn His Thr Gln Thr Glu Glu Asn Glu Leu
                100                 105                 110 gaa ggc agg cac att tac atc tat gtg cca g gtgagttggc tgggtctcca      2668
Glu Gly Arg His Ile Tyr Ile Tyr Val Pro
         115                 120 ggaccaagct tcttctcttc ctgtctctcc tgttaaatgt actaaggttt taaacatata    2728
tataaataat taatatttat tgcgggaagt ttgaaaaatg taagcgaaca cacacaaaaa    2788
tcatttgtaa tattatcaag aaatattcat tgttagcatt tcagagctgt attaagtttg    2848
gaaagtcatc tttgttatga catgtcctgt attgatactg tataaacaat ctgaaatata    2908
ctcatctcta ttcagttcat tcaagttgca cacatactca cagtgtgtcc agcactgggc    2968
taagtgttga gtacacaaaa attaataggt aagccctgtc ttggagttgc tgatagttca    3028
ttataatatc ttccaaataa acactcgatt tttcagattc actatcaaca tacatttatt    3088
cttggagagt tggaaggaat tttctttttc cttttaaaaa agttacatat atatatatat    3148
atatatatat atatatatat tttttttttt tttggtaaca gggtctcact ctgttgccca    3208
ggctggaatg cagtggcatg atcatcatag cttactgcaa tctcaactcc cttggttcaa    3268
gcgattctcc cacttcagcc tccccagtag ctgggattac aggcatgcac caccacgccc    3328
agctaatttt tatattagtt gagacggggg tttcaccata ttgaccaggc tggtcttgaa    3388
ctcctgacct taagtgatct gcctgcttcg gcctcccaaa atgctgggat tacaggcgtg    3448
agccactgtg ccctaatttt tattttattt tttgtagaga tagggtttca ctgtgttgcc    3508
caggctggtc tcaaactcct gggctcaagt gatccacagc cacctcagcc tcccaaagtt    3568
ctgggattac aggcacgagc cactgggcct ggcctactcc tgcattttaa ttaaaaggac    3628
aaaagggtcg agcacaagtg atggcaattt cagtatgcag ttgggtaaat taaaaggac    3688 tatggctaga atccttggtt ttagaacaaa acctaaactg tttatgattc ttgccatcct    3748
tgctgttttg gcataggtgt gtcttcctac ctttctgcct tttctttttc agttttaat    3808 gggctcctct ttctaccctg tataactacg agtgtcccca gggatctaga ccctctttac    3868
tttttcatga tactcttatt catatgaacc ttccttctta acaattaaaa aaaaccaaaa    3928 actttgttttt gaaaagggaa ggtatttaga atgtcactcc aacttcattc acacttagat    3988
tccttcagga aaatcctcta ggtgtggagg gattttcccc tgctgtgaag agaatggtag    4048
gaacgtgaat gtgttaaagg cacacgagtc cctgaagttt taatccgtgt aagattgtcc    4108
```

```
aaaaatttttt cttgttccag cacagatgcc atccaagtag cccctgcatc gctgtctgac    4168
tgagatcttt ttattcgcaa tcatgcagac gtaggggccc tttctgcagc tgatgtttga    4228
gactgttaga acttcttacc accgtagctt aagtagctgt tttctttttg gaaaggaaat    4288
tctcaggctc cttctccttc tttaaatttt atgtatttct caaaggatta cttttaata    4348 aacagatttc tatgctattt ttgaatcata ctgactatag gtggtaagag tttttaaaag    4408
catttcataa taaaactcga aatatttttt cctgttttaa acagagttgg actgtattat    4468
tttattgtta attttttgttt ttagttgttt aaattttgat ttagattcct ggttagtatt    4528
tatttattta tttgtagaga cagggtctct ctatgttgcc caggctggtc tcaaactcct    4588
gaacacaagc aaccctccca ccttggcttc ccaaagtgct gggattacag gcatgagcca    4648
caactcctgt ccagtattga tatttatcat cagtattatc catcaggaga caggcaattt    4708
ggtattattc atacttaaaa atcactttgt agctgtcatg ataactaatg ccagtggggc    4768
aattcttctg gatatatgtg taaaggtgaa cttcatacct aatatcaata atgccagtgg    4828
gatagttttt ctggatttat gtgtaaaggt gaaattaatg tctaatagag tcttcattct    4888
tttttaaacc acag ac cca gat gta gcc ttt gta cct cta gga atg acg       4937
               Asp Pro Asp Val Ala Phe Val Pro Leu Gly Met Thr
                   125                 130 gat tat tta gtc atc gtg gag gat gat gat tct gcc att ata cct tgt       4985
Asp Tyr Leu Val Ile Val Glu Asp Asp Asp Ser Ala Ile Ile Pro Cys
135                 140                 145                 150 cgc aca act gat ccc gag act cct gta acc tta cac aac agt gag ggg       5033
Arg Thr Thr Asp Pro Glu Thr Pro Val Thr Leu His Asn Ser Glu Gly
                155                 160                 165 gtg gta cct gcc tcc tac gac agc aga cag ggc ttt aat ggg acc ttc       5081
Val Val Pro Ala Ser Tyr Asp Ser Arg Gln Gly Phe Asn Gly Thr Phe
            170                 175                 180 act gta ggg ccc tat atc tgt gag gcc acc gtc aaa gga aag aag ttc       5129
Thr Val Gly Pro Tyr Ile Cys Glu Ala Thr Val Lys Gly Lys Lys Phe
        185                 190                 195 cag acc atc cca ttt aat gtt tat gct tta aaa g gtacttgtat              5173
Gln Thr Ile Pro Phe Asn Val Tyr Ala Leu Lys
    200                 205 catctccttc cttctttaaa taagagtaac aggcaaaatc ataaggtgcg tgtaggattt    5233
tttttttttt ttaaatcatc atcactggtg atcctaaatt ctgatttggg gatttaggac    5293
cccagctaat acaatgtctg tggctataat aataagctta aaattactaa aggccaaagc    5353
ttgattaccc atgcaagatt tcatgtttca tcagttgact tcaaaatact gtaaggaatt    5413
cttttcttac ataagcctct tactttcatt cacattcctg actatggcgg ccctaaaaac    5473
aaacatacac ccaggggggtt agatgcctag attaatttta gtaacttaag aaaagtgatt    5533
tgaagaaagt agtttagact tcaaccctttt gatgtccaca gttagtacgc ttggggaagt    5593
ataatacatg ctgaggtcaa cagatatttc ctgaacacta tattacatgg aggaatgggt    5653
agcagcaaga gtacactgtt ttaaaatcag agcacagcta attttgtgcc aggcactgtg    5713
ctaggttctg ggaaagtact gagaataact gaggagcaga gtggaagaga agaagagaag    5773
aaacaattgg atagaaacaa agtgtctaga gcagtgtgga tcagcaaatg ttggttgatt    5833
aaatgaataa atttattagt caaggagatt gtggacgagt ataaccataa ctaacccact    5893
gctgaggaat gcggtgttct gtttgattgg aatttatttt tattgttatt attttgtaat    5953
tctgtattat aactatatgc ctaattgttg tacaccatct cacaatcaag ccttgtgaga    6013
```

-continued

```
ttttccaaat tttatcttga tcaaactggt ttgcaaatta ttttttcaggg ttttcttaaa      6073 aaaaaaaaaa aaaacccaaa ctttataaga tcctggctat cctgtggatt tttaggccct      6133
tgtatttgtt ctttttata g ca  aca tca gag ctg gat cta gaa atg gaa         6183
                        Ala Thr Ser Glu Leu Asp Leu Glu Met Glu
                        210                 215 gct ctt aaa acc gtg tat aag tca ggg gaa acg att gtg gtc acc tgt        6231
Ala Leu Lys Thr Val Tyr Lys Ser Gly Glu Thr Ile Val Val Thr Cys
220                 225                 230                 235 gct gtt ttt aac aat gag gtg gtt gac ctt caa tgg act tac cct gga        6279
Ala Val Phe Asn Asn Glu Val Val Asp Leu Gln Trp Thr Tyr Pro Gly
                240                 245                 250 gaa gtg gtaggtaccc tcaaaacgtg caatggcttg agcagagca acagggctca          6335
Glu Val
```

```
gaagacctgc atttgagctc ggtctgtcac tgatgggcac atcactgagt ttctctagac      6395
cttagcttcc cacctctggg atgaacacat ttgattaaat ggcctttagg actccttgat      6455
caatgggaga gtttgaaatg atagttcctg gaccaggccc ttcagaatac ataaagagtg      6515
tgccgtaagc cttctttttc agaagtcaga cagaaatagg aaggttctct ggctacaaga      6575
tatcaaccaa aaaattagaa gagcaaaaaa accactggat tttactattg cggagacagt      6635
gattgattct catcgtcttg gcttctgtgc cctgaggttt gattcatctg atagtgttga      6695
ttgcccgcac cccttcctct tctgccttgt tggcacccag acaatgtgt cttcctgttc       6755 cacctcctat gtgcctgacc tttgcatggc tcaccttcag tgaaccgtta tgatgtaatc      6815
attcagcaaa ggtttaatga agtttgctca atcccaagca ctgtaccaga agctggttca     6875
gtattgcagg aagaagggag gaggggagat ggaagtgggg aaggggagcc accatgctgc     6935
ctcttggtca ctggagattt acagagtctc agtcattcta atgcattgtc actaagtgtg     6995
taagacagcc atgtgtaaga ggctatgaat gcccaaatgc aggaatgact aatattctta     7055
tggagaacaa aaacgagata tatatatttc ttgcctccac tcctgacttg taaatttctg     7115
ctccctgttc ttttaggcat ttgacagctt tctgtccttc tatccattga tctccctcct     7175
tttatccgtt tctctctccc atgcatttgc cgctgctttt catttgtcct ggggcatctg     7235
ataggaagtt gggcattttc actattgcct cacaaacttc acacagtgaa gggacattta    7295
cagtccaaca aatgtacatc ttccctgaaa tatgaagtga tttggttctt ctgttcatac     7355
ttgattgact ttaatcctta acacataaac actgctttct atttatagga cacagcaatt    7415 ttttttttcca aaccgaagta catgctattt ggcttacaaa tatataatca agtattgtt    7475 tcatacagta tgttttttcc gattataaaa gtaatgcagg tttattgcag aaactttgta    7535
aaatatggag agacaaagga aaggctactt cccagagcat cactgtttat attttaggga    7595
gataaagctt ttattttttca tttgtatttc tttcttttt ttttcttttt tctttttttt    7655
ttttgttgtg gagatgagga tctcactaca ttgcccaggc tggtctcaaa ctcctgggct    7715
taagtgatcc tcccaccttg gcctttcaaa gtgttgggat tgattacaca tgtgagcctc    7775
tgagcttgac tgagataaag ctcttaagta tttcttatcc atagataaac attgaataat    7835
aggtgttatt ctttaaatgg taatttatta cattctttat ccttcagcag tatagcacaa    7895
acacctatta tgtgtcatta actgtccttt taaaaaatgg gctgggtgtg gtggctcatg    7955
cctgtaatcc cagtactttg ggaggctgag gcaggagagt cacttgaggc caggagtttg    8015
agatcagcct gggcaatgta tcaagactcc gtctctacaa aaattttta aaattagcca    8075 ggtgtggtgg catgagcctg tagccccagc tactcaggag actgaggtgg gaggatcact    8135
```

```
tgaacccagg aggttggggc tgcagtgagc catgattgtg ccactgcact ccagcctggg      8195
cagcagagtg agattctgtc tctaaaaaaa ttaaaaacaa aataaaaaat ctcatgattt      8255
tctaagcagc tagcttttat tctttaggtt ttatctttta gagcagtttt aggtttacag      8315
caaaattgag aggtacagag atttcccatg tgttccctac acccacacat gtgtagcctc      8375
ccaccttgtc aacatcccta ccatccattt gttataactg ctgaacctcc attgacacat      8435
ccatatcatc cagagtccat agtttatctt agagttcact cctaggagcg agcttttaa       8495 aagtcggttt tcttcccctt ttgctgtag aaa ggc aaa ggc atc aca atg ctg        8548
                                 Lys Gly Lys Gly Ile Thr Met Leu
                                     255             260 gaa gaa atc aaa gtc cca tcc atc aaa ttg gtg tac act ttg acg gtc        8596
Glu Glu Ile Lys Val Pro Ser Ile Lys Leu Val Tyr Thr Leu Thr Val
            265                 270                 275 ccc gag gcc acg gtg aaa gac agt gga gat tac gaa tgt gct gcc cgc        8644
Pro Glu Ala Thr Val Lys Asp Ser Gly Asp Tyr Glu Cys Ala Ala Arg
        280                 285                 290 cag gct acc agg gag gtc aaa gaa atg aag aaa gtc act att tct gtc        8692
Gln Ala Thr Arg Glu Val Lys Glu Met Lys Lys Val Thr Ile Ser Val
    295                 300                 305 cat g gtacattccg ctttctaaaa tgtcagttgt ccatgctgct cgggatccat           8746
His
310 atgtggtaat cattatttaa tggaaactct tccctgtaca g ag  aaa ggt ttc att      8801
                                             Glu Lys Gly Phe Ile
                                                             315 gaa atc aaa ccc acc ttc agc cag ttg gaa gct gtc aac ctg cat gaa        8849
Glu Ile Lys Pro Thr Phe Ser Gln Leu Glu Ala Val Asn Leu His Glu
                320                 325                 330 gtc aaa cat ttt gtt gta gag gtg cgg gcc tac cca cct ccc agg ata        8897
Val Lys His Phe Val Val Glu Val Arg Ala Tyr Pro Pro Pro Arg Ile
            335                 340                 345 tcc tgg ctg aaa aac aat ctg act ctg att gaa aat ctc act gag atc        8945
Ser Trp Leu Lys Asn Asn Leu Thr Leu Ile Glu Asn Leu Thr Glu Ile
        350                 355                 360 acc act gat gtg gaa aag att cag gaa ata ag  gtaaagaaac tctctgccca      8997
Thr Thr Asp Val Glu Lys Ile Gln Glu Ile Arg
    365                 370 agtatgcctt ttttagtgt gcatcagagg cggactgagg tttgtgtgtg tcttacaacc       9057
cagacccaaa gtcagtctag aaaatgtaac aatctgagtt aagagatgct tgaaatcaca      9117 tcccttaat gataacattg caaagtggta ttagtatgct ggtaagtatt taatgagaag       9177
atgagaagaa agaactaaaa gctctggccc ctggggaaag acaggtcact ggattcagct      9237
agggtggaag aaaggaagta aaattggact caccaggatt gaatgattg aatatattcc       9297 ctgatgttca tcatccatat cgcaagtaga cagatatggt gattaccc atgaggcagt        9357 tatcacatca ccttacgtga aagttaacgt cataggctta atctggaacc catttgcccc      9417
aattgaggac tccacaggaa agaagagtag agcctggcta atcaggagag agatgtgcag      9477
tgagttgctt ggatccctac cttttaatca gaatggtaga ttgctctcat ctcttaattg      9537
gtggtggagt tttgaatgag tcacccctca gccacagttt cctcatctac aatgtaggat      9597
aaacaatacc ttatgtcctt caaggcaagg aattggatca gatgatatca tgaggcctct      9657
taaggtttta agctgtgatt agaacccaag agtcagaaga tacatctcac agcacccagc     9717
taaccagccc tatactttg tcagaaatca tctcagaaag acaaagtcag tcctgtattt      9777
caagccttca ggaggaagaa cagagccttt ctcatcagtt ccattcacct caggatttgc      9837
```

```
tttcttcttt gtgaactaaa ttccacgtgt aattgagaag caatgtctga gaaaatggaa    9897
ttttacagcc tctatagaat agtaaaggaa aaatgaagtg ggatactgaa tctggaaggc    9957
tttctgttga cacaaaatga aggtgtacaa caaggagggc agctttccac gaggaacttc   10017
catgaggctg tgcagccaga gaggaatagg gtaacaaccc tggtacagct aacacctcca   10077
acacgtgtgt gagcactgtc tgcaagccat aatccatagc agtggcagga caggctcgcc   10137
aactgagtgg ttctggaaag ctgccttttc cttttagtga ttcaaggatg cttcaacgtg   10197
gatttttag ttcctgttat gagccagtga atacaaagat gaacatggta gatgggggat    10257
ctggcttcct ggagcttaaa actccaggat gggggatctg gctttcctgg agcaagaaaa   10317
ccagtggttt tcttggccga agaagtgaag agaacaaaca gcagaggata atttggtaat   10377
cagcatccta gtgtgcccca gggtactctc ttaaggaaat ccagtcctgg agcacaccca   10437
gtatggtcca gcctgctgtc ttcgtaggtc tgagtgcccc agtatttgca aagtgttttg   10497
gagcctatga aatgctttca cacatacaat ctcctttaat taactctcac aatgactctg   10557
tgctatgtgt acaattatcn nnnnnnnnnn nnnnnnnnnn nnnnnnnnnn nnnnnnnnnn   10617
nnnnnnnnnn nnnnnnnnnn nnnnnnnnnn nnnnnnnnnn nnnnnnnnnn nnnnnnnnng   10677
tatgaaaccc acttgatcat agtggattat cttttgata tgttgttgga ttgaggtagc    10737
tagtattttg ttaaggattt tagcatctat gttcatcaag gatttcagcc tgtagctttc   10797
tttcttggac gtgtcctttt ctggttttgg tattagggtg atgttggctt cacagaatga   10857
attaggaagg gttccttctt tctctatctt gtggaatagt gtcaaaagga ttggtaccaa   10917
ttcttctctg aatgtctgtt aggattctgc tgtgaatcca tctggtcccg gacattttt    10977
tggttggtaa tttcttaatt accattccag tcttgctgct tgttattggt ctgttcagga   11037
tatccagtgc ttcctgattt aggctaggag ggttgtattt ttacaagaat ctatctatct   11097
cttctaggtt ttctagtttta tatgtgtaaa ggtgttcatt atagccttgc attatctttt   11157
atatttcagt agtgtcactt gtaatatcgc ctgtttaatt tcttagtgag gttatttgga   11217
ttttctctct tcttttcttg gttaatcttg ctaatggtct atctatttaa tttatctttt   11277
caaaaaacca gttttgtct catttattat tgtgtgttt tgtttgttt caatttcatt      11337
tagttctgct ctgaccttttg ttatttcctt tcttctgctg ggtttgggtt tggtttgttt   11397
ttgtttctct aattccttga ggtgtgacct tagattgtca gtttgtgctc tttcagactt   11457
tttgatgtag gcatttactg ctttgaactt tcctcttagc actgcctttg ctgtatccta   11517
gaggttttga taggttatgt cattattatc attcagttca aagaattttt taatttctac   11577
cttgattttg tttcgaccc aatgctcatt caggagcagg ttatttaatt tccatgtatt    11637
tggatggttt tgaaggtttc ttttggaatt gatttccagt tttatttcac tgtggtccga   11697
gagagtgctt gatatatttt caattttctt aaatttatcg aggctcattt tatggcctat   11757
catatggtct atcttggaga aagttccatg tgctgttgaa tgtgtactct gtggttgttg   11817
gataaaatgt tctgtatata tttgttaggt ccatttgctc caagaaacaa tccaatgttt   11877
ctttgttaac tttctgtctt gatgacctgt ctagtgctgt cagtggagta ttgaagtccc   11937
ctactattat attgctctct atctcatttc ttaggtctgt tagtaattgt tttataaatt   11997
tgggatctcc agtgttaggt gcatatatgt ttaggattgt gacattttcc tattggacaa   12057
ggccttttat cattatataa tgtccctctt tgtctctttt taccattgtt gctttaaagt   12117
ttgttatgtg tgtactttg ttttttgtt tttggttttt gctttataac ttgtattttt     12177
```

```
gtttcatagg tcctgtgtga tttatgcttt aaagaggttc tgttttcatg tgtttccagg    12237
atttgtttca agatttaggg ctcctttttg cagttcttgt agtggcggta atggcaaatt    12297
ctctcatcat ttgtttgtct gaaaagacct gtatctttcc ttcatatatg atgcttagtt    12357
tcactggata caagattctt ggctgataat tgttttgttt gaggaggctg aagataggcc    12417
ccgaatccct tctagcttgt agggtttctg ctgagaactc tgctgttaat ttgatagatg    12477
tacctttata ggttacctgg tgcttctgtc tcacagctct taagattctt tccttcatct    12537
taactttgga taaccttatg acaatgtacc taggtgaaga tcttttttgca gtcaatttcc    12597 caggtgttct ttgtgcttct tttatttggt tgtctaggtc tctcacaagg ccagggaagt    12657
tttcctcaat tagtcccca gatatatttt gtaggctttt agaattctct tctttttcag    12717
gaacattgat tattcttagg tttggttgtt aacataatc ccagacttct tggagccttt    12777
gttcatattt tcttattatt tttttctttg tctttgttgg attgggttaa ttcaaagact    12837
ttgtctttga gctctgaatt tctttcttct acttgttcaa ttctattgct gagacttttcc    12897 acagcatttc gcatttctaa aagtatgtcc aaagtttcct gaatttatga ttgttttttc    12957
tttaagctat ctatttcctt gaatatatct cccgtcactt cttctattat tcttggattt    13017
ccttgcatcg tgctttgtct ttctccgatc cctccctgat caccctaata actaacctcc    13077
tgaattcttt ttcaggtaaa tcagaaattt cttcttggtt tggatccatt gctggtgaac    13137
tagtgtgatt atttgggggt gttgtagagc cttgttttgt catattacca gggttggttt    13197
tctgattcat tctcatttgg gtaggctctg tcagagggaa ggtctaaggc tgaaggctgt    13257
tgttcagatt cttttgtccc acggggtgtt cctttgatgt agtactctcc ccttttccta    13317
tggatgtggc ttcctgtgag ccgaacttca gtgactgttg tctctcttct gaatctagcc    13377
acccagcgag tctacctggc tctaggctgg taccaagggt tgtctgcaca gaatccagtg    13437
atgtgaacca tctatgggtc tctcagtcat ggataccagc acctgttcca gtggaggtgt    13497
tggagggtgc aatgaactct gagagggtcc ttagcttcgg tggtttaatg ctctattttt    13557
gtgctggttg gcctcctgcc aggaggtggt gctttccaga aagcattaac tgcagtagtg    13617
tgaagaggaa ccggcggtga gctgggccct agattcccaa gattacatgc cctttgtctt    13677
cactactagg gtgtataggg aagtaccatc aggttgggc agggctaggt gtgtctgagc    13737
tcagactctc cttgggtgga tcttgttgca cctgctgtca gggatggagg tgagattctc    13797
aggtcactgg agttgtgtac ctaggaggat tatggctgcc tctgctgagt cttgcaggtt    13857
gtcagggaag cagggtaaag ccagcagtca caggcctcac ccagctccca tgcaaactga    13917
acggccagta ttacttccac cgtgaccccc aaccagtatc cctgagtata tttccaggta    13977
gagggcgaga agggcttgaa aacttgcctg aggctatctg tctccaagct gtggggaaa    14037 aaaagggctt aagttcttcc cctgcctatg aagtctgtac tccagatttg caccctcccc    14097
cgagttctgg ccaggaggct tcccgcccgt tccaattgtt acaaagttca gctagagaat    14157
tctttctccc tgtggagttt taccacctgc ccctctggcc gccctcccta tggatccccg    14217
tggtgccagt caggaattgg ctgcttgggg acccagcgag ctcccagggc ttttctgctg    14277
cttactacta cccctgtat ttgctcagct gtctacttga ctcagtttca ggtaaagnnn    14337 nnnnnnnnn nnnnnnnnnn nnnnnnnnnn nnnnnnnnnn nnnnnnnnnn nnnnnnnnnn    14397
nnnnnnnnnn nnnnnnnnnn nnnnnnnnnn nnnnnnatt aggaaaagaa ggaagtcata    14457
ttgtctctgt ttgcagatga catgattgta taattagaaa accccatcgt ctcagcccaa    14517
aatctcctta agctgataaa cagcttcagc aaagtctcag gatacaaaac tcaaaatgca    14577
```

-continued

```
aaaatccaag cattcctata caccaagaac agacaaacag agagccaaat catgagtgaa    14637
ctcccattca caattgctgc aatgagaata aaatacctag gaatccaaat tataagggat    14697
gggagggaac tcttcaagga gaactacaaa ccactgctca atgaaataac agatgacaca    14757
aacaaatgga agaacattct gtgctcatag atgggaagaa tcaatattac aaaaatggcc    14817
atattgccca aagtgattta tagattcaat gctattccca ccaagcttca cagaattgga    14877
taaaaactac tttaaatttc atatggagct aaaaaagagc ctgcatagcc aagacaatct    14937
taagcaaaaa gaacaaagct ggaggcatca tgctacctaa cttcaaatta tactacaagg    14997
ctacagtaac caaaacagca tggtactggt accaaaacag atatatagac caatggaaca    15057
gaacagaggc ctcagaaata acaccacaca ccacacatct acaaccatct gatctttgac    15117
aaacctgaca aaaacaagca gtggggaaag gattccctat ttaataaatg gtgctaggac    15177
aactggctag ccatatgtag aaagctgaaa ctggatccct tccttacacc ttacacaaaa    15237
attaactcaa gatgaattaa agacttaagc atgagaccta aaaccacaaa aaccctagaa    15297
gaaagcctag gcaataccat tcaggacata ggcatgggca aagacttcat gactaaaaca    15357
ccaaaagcaa tggcaacaaa agccaaaata gacaaatggg atctaattaa actaaagagc    15417
ttctgcacag caaaagaaac tgtcatcaga gtgaagaggc aacctacaga atgggagaaa    15477
atttttgcaa tctatccatc tgacaaagga ctaatatcca gagtatacaa gaacttaag    15537
caaatttaca agaaaaaaac aactccatca aaaagcgggc aaagaatatg aacaaacact    15597
tctcaaaaga aaacatttat gcagccaaca gacacatgaa aaaatgctca tcatcactgg    15657
tcataagaga aaagcaaatc aaaaccacaa taagatacca tctcacacca gttagaatgg    15717
cgatcattaa aatgtcagga acaaacatgc tggagaggat gtggagaaat aagaacactt    15777
ttacactgtt ggtgggagtg taaattaatt taatcattat ggaatacagt gtggtgattc    15837
ctcaaggatc tagaactaga aatattattt gacccagcga tcccattact gggtatatac    15897
ccaaagaatt ataaaacatg ctgctatgaa gacatatgca catgtatgtt tattgcgcac    15957
tattcacaat agcaaagact tgaaacaaac ccaaatgccc atcaataata gactggatta    16017
agaaaatgtg gcacatatac accatggaat actatgcagc cattaaacag gatgagttca    16077
tgtcctttgt agggacatgg atgaagctgg aaaccatcat tctcagcaaa ctatcacaag    16137
gacagaaaac caaataccac atgttctcac tcataagtgg gagttgaaca atgaaaacac    16197
atggacacag gaaggggaac atcccacacc agggcttgtt gggggtgggn nnnnnnnnn    16257
nnnnnnnnnn nnnnnnnnnn nnnnnnnnnn nnnnnnnnnn nnnnnnnnnn nnnnnnnnnn    16317
nnnnnnnnnn nnnnnnnnnn nnnnnnnnna aggtatgtag ggtatctagt aggaaaagca    16377
ccctgggagg ctaaagcagg aggatcactt gagctcagga gttcaagact agccttggca    16437
acacattgag atgctgtctc tacaaaaaaa attaaacatt agccaagtgt ggtggtgcat    16497
acctatagtc ccagctactt gggaggctga ggcagaaggg ttgcttgaga ccaggggtg    16557
gaacctgcag taagccatga ttgtgccact gtactccagc ctgcgtgaca agagagaac    16617
ttaaacaaac aaaaacctca tagattctga caaaaagac acgatgcaaa ataatactgg    16677
tgtgagggc aattacggga gacactcatt tatgttttgt cttctctgtt taggagtgt    16737
ggtgtaagga gtgacatttc ggcccctcac actgttatt cttttgcagg tgggtgagat    16797
agaagtctat aaaggggaaa gagaagaagc tgatgctgaa acttaagaga tatttctcca    16857
agactagaga aagacaagaa gaaaggagcc tctgagagtg ataagaggcc caaggtttgc    16917
```

```
atgcatggag caccagtaag agatggcttc aggaagccag agagctaggc cggggacaca   16977
gataccttgg gaaccacagc gagagtgtcc gtgggctgag gcagtggtca gtggagagac   17037
ccattgagag gtgacaacat gctagtagcc ctgcctcgct ctcggcacct cctcaagcca   17097
cggtgtccac tctggccgcg cttgaggaac ccttctgctt gcagggaggt gtggagggag   17157
aggcgcgggc gggaaccggg gccgtgcccc gtgctcgccg gccagcgcga gttccggatg   17217
ggcgtgggct cggcgggccc cgcacttgga gcggccggcc ggcgccaccg caccagtcag   17277
tgagggcttt agcacccggg ccagcatctg cagagggtgc gccgggtccc tcagcagtgc   17337
tggcccaccg ggtcggcgct cgaattctcg tcgggcctca gctgccttcc tcccccggct   17397
cccccgactc ccatggctgg cgactggcag cccgccatgc gcgagccccc ggagcccccgn   17457
cgccccgccc cctccccacc ccctgctccg cggcgcccgg ccccatcgat gcccaacggc   17517
tgaggagtgc gggcacatgg cggggcactg gtgggcagct ctgccagcag ccttggggcg   17577
ggaatccact aggcaaagcc agctgggttc ctgagtggga tggggacttg gagaactttt   17637
atgtctagct ggaggattgt aaatgcacca atcagcactc tgtgtctagc attggtgggg   17697
ggcaggggtt cgtagacgca ccaatcagca ccctgtgtca agctcaaggt ttataaatgc   17757
accaatcagt gctctgtgtc tagctaatct agtagggact tggagcactt ttatgtctag   17817
ctagaggatt gtaaatacac caatcagcac tctgtgtcta gctcagggat tgtaaacgca   17877
ccaatcagca ccctgtcaaa acggaccaat cagctctcta taaaacagac caatcagctc   17937
tttgtaaaat ggaccaatca gctctctgta aatgggcga atcagcagga tgtgggtgga   17997
gtgagataag ggaataaaag cagggtgcca gagccagcag cggcaatctg cttgggtcgt   18057
ctaccatgtt gtggcaggtt tgttcttttg ttcttcctaa taagacttgt ggctgctcac   18117
tttttggagc cttgctgcct ttatgagctg tgacactcac ctgaaggtat gtagcttcac   18177
tcctgaagct agtgagatca tgaacccact gagaggaatg aacaactcca gtgctgcctt   18237
aagaggtgta acactcccag cgaatgtctg tagcttcact cctgaagcta gtgggaccag   18297
gaacccagca gaaggaagaa actccgaaca cgtccaaaca tcagaaggaa caaactccag   18357
tcacactatg tttaagaact gttaacagtc accatgaggg tctgcagctt gattattgaa   18417
gtcagtgaga ccaagaaccc accaattacg gacataccat gggaacagtg tccctcagcc   18477
tgctgaaaga atccctgtgc aagggcaggg agggctggtc tgagtaacaa agtcctgtag   18537
cagagcagac tgaggcaatg aaacccaatg cttccagtta agactgggcc ccgcccact    18597
ggctggatag gacaacgacc cttcccaact tcgattatat tttctgtatt tatttatta   18657
ttttgagatg gagttttgct cttgttgccc aagctggact acaatggcat gatcttagct   18717
cactgcaacc tccacatcct gggttcaagc gattctcctg cttcagcctc ctgagtagat   18777
gggattacag gcaagcgcca ccaggcccag ctaattttt gaatttttag tagaaacggg   18837
gtttcaccat gttagccagg ctggtctcaa attcctgacc tcaggtgttc tgccctcctt   18897
ggcctcccaa attgctggga ttacaggcgt gagccactgc gcccagctta ttttgaagag   18957
gaactactca gactgtgttc tctccctttt actctcccca aggaagcgaa gaaaattatc   19017
aatagaaaat ggcaggccga gcatagtggc tcatacctgt aattccagca ctttaagaga   19077
ctgaggcagg tggaatactt aaggttagaa gttcaagacc accctggcca acagagcggt   19137
tttcatttaa aaaaaaaaa aaagcaagtt tattaaggta aatgaataaa acaatggcta   19197
ctccataggc agagcagctg aaaccctgtc tctactaaaa tacaaaaatt agccaagcgt   19257
ggtggcacat gactatagtc ccagctactc aggaggctat ggcaggagaa tcgcttgaac   19317
```

```
ccgggaggca gaggttgcag tgagctgaga tcgcaccact gcactccaga ctgggcaaca    19377
gagtgagact ctgtctcaaa aaaaaaaatc aataagtaaa atcttaaagt agcaaatgac    19437
agttgcagcc aagtaattcc aaaagccagc ttcactcgga gaaccctgtg cttcctctta    19497
tttccagcga tccacatatt tagagaaact tttccagtaa taaaccatag aaattatacc    19557
tggaagtaga gtcttcaact tggattttta ggtgaccta acaaaagggg gaaatttccc     19617
aaaacatatc cgaaatggac tttctcactg ctttggctag tcgaggttaa gaatcagagg    19677
taattttaga acatatagat gaggtgacaa ctcatacacc caagtatgta gagcaactca    19737
tatctacccc actgcatttg gagggaaagt gtttccctgg tgaacttgtg agtataaata    19797
gatggaagaa gatgtactca aaacagcaaa cttctaatta tacaaaatgt tatattttct    19857
gcttagtgaa gccacatcca tgtagattat gatgctctaa tcattacacc tgtcaacaca    19917
atgaaatagc tcaaatctct gaaaaacttt gcttcactct taatgatgtc aaaaattaca    19977
actcaaatta aatcttcatg tctctaatga aacctcaact ctgcaaattt ccttatttaa    20037
aaatgctgtt ttagccaaag aaatgtttca aaaattctgt attcaggcca ggcacggtgg    20097
cttacgcctg taatcccagc actttgggag gccaaggtgg gtggattgct tgaggtcagg    20157
agttcgagac cagcctggct gacatggtga accccgtctc tactaaaaaa tacaaaaagc    20217
cggatgtggt ggtgcatgcc tgtagtccca gctactcagg agactgaggc aggagaatca    20277
cttgaacgca ggaggcggag gttgcagtga gccgagattg tgccactgca ctccagcctg    20337
ggtgacagag cgacgctccc tctgaaaaaa gaaaaaaaaa ttctgtattc acaaatagct    20397
tgatactagc aatcacttgt ttacattgta ataggcagc aggctgaaaa ttttgatga     20457
cttaattgca ggttcacagc tatgaaggca agccaaaggg ctaccttgcc aggtctgtaa    20517
aactgatgta catagtatga gctgcttgat ctttgagtaa tcacaaaaga caaatcaggc    20577
tgggcatggt ggctcatgcc tgtaatccca gtgctttggg aggccgaggc aggtggatta    20637
cttaaggtca ggcattggag accagcctgg ccaacatggt gaaatcccat ttctataaaa    20697
aaaacaaaag ttagctgggc atggtggtgt gtgcctgtag tcccagctac tcaggaagca    20757
gaggcaggag aaccgcttga acccgggaag tggagtttgc agtgagccga gatcatgcga    20817
ctgcactcca gcctgggaga cagagtgaaa ctctgtctca aagaaaaaaa aaaaaggaa    20877
agaaataaaa gacaaatcag caaaagagg aattcataaa aagagaataa agctttgcaa     20937
aaaagaaccc tgtctttgga tcttcagaag tgactaaaat attttaatag gtccctttta    20997
gtgcctcttt ttgcttgcct atgaaatatt gacagatctt cccaactggg ggaaaaaaaa    21057
cccaaaattc attaaactca ctgtgtctta tttggttaaa taaaagagg tagaaagact     21117
attatgagaa aagagaagca atagaaactg tggaaattgg agttccaaac atcaatctta    21177
atttgattga atagtagaaa gtatataaac tatggaaatt gatgttccaa acatcaatcc    21237
gcattcctga gcaattttca aattggtcac cagctctcca ctcctcctgt catgagtcac    21297
ttatacctta aaaagtatat cctctgagaa ttctgaaagg tatccagacc ttccattaga    21357
caacttccaa tccatatgtg cctcaaagtt gtgtcttcat tttcctcctg ttccatttcc    21417
ttcagatttc caccaagata tgcatgttga gctttgtttt gagactacat ccagatgtca    21477
cctacctctc ctgtggcctt aaaaagattc tataagcaca gagagatcag cctgagacat    21537
ctgaagacct aagcctgcat ccttcctggt ttttggatta agggaatgta aagatgagag    21597
gaaaatgagc aaggcgaggt gataactcat ttctaaataa aacaggaata ttttaaaaa    21657
```

```
tctgacactg ctaaaggcca agtcatacag taggattccc accaggccag gctgtaaata    21717
ttgattctcc tctctgcaac cccagtgttc aggcttcaga gtaacagtct tagttcctcc    21777
aaccacattt ctaaccacaa ggtcactgca cacttcacca nctggcctct tctttagcac    21837
aacaattgta agtttagaga tgttatcatt tatttgcagt cgtcccacag atgttgggac    21897
ttggaaaaac ctcctttata atcaaatagt tccggtgttt tgtagtttga aaagcactgt    21957
tcgaaagtta tctcatttaa tctttacaac tgttgacttt acagataaag aaaactgcag    22017
gatcagaaaa gttaaataaa tgcccaagga cacacaactt gtaagaaaag aagccagggc    22077
taggctaggc cggctgcagt ggctcacgcc tgtaatccca gaaccttggg aggccaagac    22137
aggcggatca tctgatgtca ggagttcgag accagcctgg ccaacatggt gaaacccgt     22197
ctctaccaaa aatacaaaaa ttagctgggt gtggtggtgg gaacctgtaa tcccagctac    22257
tcaggaggct gaggcaggag aatcacttga acccaggagg tggaggttgc agtgagccaa    22317
gatcgtgcac tccagcctag gcaacaaaag tgaaactccg tttcaaaaaa gaaaaaaaaa    22377
aaaagaagcc agggctaaaa cccacctgtg cccttcatct tctagttctg ggttcttttc    22437
atgccaccaa ttgcacttca aagaagtgga aacattttga agttttgat aagactagta     22497
gcaaggctta ttttcaaata gtctatgaat ttttatagct tgtagaaggt ctgaggaaga    22557
tataatttca tttgtatcac ttcagaagca atacaaaaaa aagtattatc ctatttcttt    22617
attttatatt ctaggcctat tagagaacaa taaattagat aaactcaaaa tccacttagg    22677
ccttcatgta tccttttttt tttttttttt tttgagacca gtctcactc tgtcacccag      22737
gctggagtgc aatggcatga tctaggctca ctgcaacctc ctggtttcaa gcgattctct    22797
caactctgcc tccggagtag ctgggactgc aggcacgtgc caccatgccc agctaatttt    22857
tgtatttag tagagatggg gtttcacagt gttggccagg ctggtcttga actcctgacc      22917
tcaagtgatg agcctgcctc agcctcccaa agtgctggga ttatagacgt cagccaccac    22977
accccacctg ctctgatatt tattatttct tttcttctgc taattttgag tttggtttgc    23037
tcttgctttt gtagttcttt aacacgtacc attaggttat ttatgattat tagattagtt    23097
tttcttcttt ttaaatgtag ataccctataa ttataaaatt ccctcttagt actgcttttg   23157
ctgtattcca tagttttggt atgttctgtt tccattatca tttgtttcaa caaatttttc    23217
aatttccctc ttaatttctt cattgaccca ctggtcattc agaagcatat tgtttaattg    23277
ctgtgtattt ttatagcttc caaatctctt gttttgttac attgtggtca gagaagatgc    23337
ctgatgttat ttcaattttt ttgaattttt taaagccttg ttttgtgatt taacatatgg    23397
tctattcttg agaataatcc atgtgctgag gagaagaatg tgtattctgc agccttcaga    23457
tgaaatgctc tgtaaatatc tattaggtcc atttgttcta tagtgcagtt taagcctgat    23517
gtttccttgt tgattttctg tctagaagat ctgtccattg gtgaaagtgg gatgttaaaa    23577
tctccagcta ttattgtact gagggctgtc ttttacctt aaataatatt tgctgcttca     23637
tatatctgga tgctccagtg ttgggtgcat ataattgt tatatcttct tgctaaactg      23697
actccttgat tattatataa tgaccttctt tgtttctgcc gcctatagag acaaagaagg    23757
ttattatata atgatgaaag agtccagttt tttgttgttg ttgtcatttt ttgagatgaa    23817
gtctcactct ttcacccagg ctggagtgca gtggcacaat cttggctcac tgcaatctct    23877
gcctctaggt tcaagtgatt cccctgcctc agcctcccga gtagctggga ctacaggtgc    23937
ccactaccac acttggctaa ttttttgtatt tttagtagag acaggttttt caccatgttg    23997
gccaggctgg tctccaactc ctcatatcaa gcgatccgtc cgtctcagcc ccccaaagtg    24057
```

```
ctgggattac aggcgtgagc cactgtgcct ggcccattgt atgtttttca atttggggtt    24117
accatgaggc ttgcaactac tgtttcataa cccattgttt caaactgatg acaacttaac    24177
actgattgca taaacaaaca aataagcaaa aagaaaacta ataaaaactc ttaacttcat    24237
cctcctgctt tttaactttt tgttgtttct cttcatgtct tattgtactg tctgtcatga    24297
caaattgctg tagttattat ttttgattag ttcattgctt agtctttctg cttaagagta    24357
ttttgaacac cgtaattaaa gtgttataat attctatgtc tttctgtgtg ctattaccag    24417
tgagttttgt agcttcacgt gacttcctat tgctcatcaa tgtccttttc tttcagatgt    24477
aagaactttc tttagcattt cttttttttt ttttgagatg gagtctcact cttttgccca    24537
ggctggagtg cagtagcatg atctcagctc actgcaacct ctgcctccca tgttcaagca    24597
attatagtgc ctcagcctcc caagtagttg ggtctacagg catgcgccac cacacccagc    24657
taatttttgt attttagta gagacacctg accatgttgg tcaggctggt ctggaactcc    24717
tggcctcaag caatccaccc gcctcagcct cacaaactgc tgggattaca cgcatgagcc    24777
accacgcttg gcctccttta gcatttctta taggacaggt ctagtgttga tgaaaatccc    24837
ttagcttttg tttgtctggg aaggtcttta tttccccttc atgcttaaaa gatatatttt    24897
gctgaatata ctattctagg gttaaagttt ttttttttccc ttcagcattt aaaatatgtc    24957
atgctagttt ctcctggcct ataaggtttc cactgaaaag tctgaggcca gatgtattgg    25017
agctctatta tattttattt gtttctttc tgttgctgtt tttaagatcc tttctttatc    25077
tttgaccttt gggagtttga ttattaaatg ccttgaggtt gtctttttg gattaaatct    25137 gcctgatgtt ctataacttt cttgtacttg aatattgata tctttctctg ggtttgggaa    25197
gttctttgtt attatcccctt tcaataaact ttctatcccc atctcttcct caacctcctc    25257
tttttggcca atagtgctta gatttgccct tttaaggcta ttttctatat cttgtagaca    25317
tgcttcattg tttttttactc tttcttttg tctcctctga ctgtggattt tcaaatagcc    25377
tgtcttcaag ctcattaatt ctttcttctg cttgatcacg tctgttatta agagacccag    25437
atgcattctt cagcatggca gttgtacttt tcagcactag aatttcattt ctttttaata    25497
acttcaatct ctttgttaaa tttgtctgat agaattctga attcctggcc aggcgcagtg    25557
gctcacacct gtaatcgcag cactttggga ggctgatcac ttgaggtcag gagttcaaga    25617
ccagcctagc caaaatggca aaactccatg tctactaaaa acataaaaat tagttgggtg    25677
tggtggcaca tacctgtaat tccagctact taggaggctg aggtgggaag atcacttgaa    25737
cccaggaggc agaggttgca gtgagccaag atcgtaccac tacactccag cctgggcgtt    25797
catctcaaga aaaaaaaaa agaattctga atttctgttt tgtgtttctt ggatttcttt    25857
gagtttcctc gacacagcta ctttgaattc tctgtctgaa aggtcacata tctgtttctc    25917
caggattggt ccctggttcc ttatttattt tgtttggtga ggtcattttc tcctggatgg    25977
tcttgatgct tgtagatgtt cgttaatgtc tgggcattga agagttaggc gcttattgta    26037
gtcttcacag tctgggctta tttgtgccca tcctccttgg aaaggctttc cgggtatttt    26097
gaaggaactt gggccccaag tccaataata ttatgtttct tgcagactca tagaggtgct    26157
gctctggtag tcttggataa gatctggaag aattctctag attaccaggc agacactttt    26217
atttttttct cttattttt cacaagcagc gtctctccct gactctgtgc tgagtctcct    26277
ggaactggag gtggagggac acaagtaccc tgtagccacc accaccagga ctgtgctggc    26337
tgagacatga aaccagcaca gcactgggcc ccacccaagg cctgctgtaa ctactatctg    26397
```

```
gctaccacct aagttcactc taggacctag ggctttatga tcagcatatg gcaaagccag   26457
tctgatttat gtccctccat tcagggcagt gagttcctcc agacctaggt tggtccgag    26517 atgttgtctg agagccaggg atttaagtca aataccttag aaatttaccg ggtattctac   26577
tctactgcag caaagctggc actcaaacca taagacaaag tccttcccac ttttctctcc   26637
ctgtggccac caccataagc accccacgag gggttctgcc aggctaccgc tgatgttcac   26697
ttaaagccca agggcccttt tgtcagcttg tgatgagtgc tgccagacct gacactcact   26757
cttcagagta gtgggcttcc ttctggtcca tggcaggtcc agaaatgcta accaagagcc   26817
taggcttgga cgtggggacc tgaagagtct gcttattgct ccaccccact gtggctgagc   26877
tggtacctga agtgcaagac ggagtcccct ttactttccc ccctgttttt ctcaaacaga   26937
aagatctttc gctgtagcca ccacagctgg gaatgtgctg ggtcacactt gaagccagca   26997
tgtctcagag cccaaggccc atagtgtatt acctgggtat tgctggtggt tattcagggc   27057
ctaggggctc ttttgtcagc aggagatgaa tcctgccagg tctccactgt gagacggcag   27117
cactaagttc aatgtaaagt ccccggttg ctgtgctctc cctctcccaa gcacaaagat    27177
ttctctgcac cacatggcca ctgctggggg gtgagggaag ggtgacaaaa gcaccctccc   27237
aagccacccc ggctggtgtc tcagtaggtt tcatgcctgc ccagtccact ggctctgagc   27297
ccagctcagc actaggactt gcctaggaat tgcactcctt gtgacctaga ctgcccctta   27357
agttcactta gtgccccaga gcactccagc ccacggtaat gaggcttgct ggaactcaag   27417
ctcccaccag tgggatggac aatttctctc tggctagagc tgggccaaat gaacatcagc   27477
tgagtagaac ctggttctgc tttccactgt aacagggag cactgggttc aatgaaaagc    27537
ctcacaattg ctgcactttc cctctcccaa gcacccagat tctctgtgct acatggccgc   27597
tgctggggga tgaaggaggg gtggcgtcag tgcttcaatg ctgtcttcc tgccctcttc    27657 aatgtctctt tcagtgatat aaagttaaaa tcaggtacta tgattgctca cctgattttt   27717
ggttcttatg atggtgcttg ttgtgtgtag ttagtagtta aaatttggtg ttgctatgtg   27777
gaggatgaac agtataagcc tctatcagcc gtcttgctct accccattct ctgttaattt   27837
ctcaggcacc aataagtgtg tgtaactgta atatgcccat tacccaatgt gcacagcaag   27897
tcaacgtgct gatatattgg attgcagcag agaaagaggt ttaagcgaag ggttgctgaa   27957
tgaggaaatg agagtaaacc taaaatccat ctccctgaga aatttggggc taggattgtt   28017
aagggttttg gagttggctg aagtgtggag atattgattg gtcgaagagt gcagggtgaa   28077
atcatggccc aggaagatga aaaaatgtgt tttcatgctg attcagttct gctgtggggg   28137
tcttcaaact ggttggcatc agccattcca ctggaattca gagtctgctt aagcaattct   28197
taaacaagtc ttatgaatct aatgtcagaa atcctatcta taggaaaaac aggggttgcaa  28257 attgtgagta tctagtgcta tgtgactttt ggttacaaag aagtgggtca aaatatagca   28317
tgattaatgc ttaattatag ctatatttct gtccaaaatt cttattaacc ctgtgagaat   28377
ggctttatta gtaattggta agtcaagtct gtgctttcta gcaatagcac tgggtatttc   28437
taccctagta gaaggcacgc acatatagcc aatgtcttat ccttgcttct ctgctcttct   28497
atgtgttgaa ttaattttag ctgggctggg aacagtgacc ttcagcatgg ctccaatcac   28557
tttatactta ccagggaagc ttttaaaca tttcattcct aggctttgct ttatatgtac    28617
ataagtcaaa gttcctggag gtggtggtct aaaatctgta tctttatctt tatcttcctg   28677
aataatttta ggaccatatt tagcatttga aaacctctgg cataggctat gcaaacagaa   28737
actctcttat ccgacctcta cttaactggc ttttcaattt tgtaaaatgt aagaaatgag   28797
```

```
gctcacagca tgttgctacc cttcctgtat tctccagtgg taattattgc ttagtgtgta   28857
ttctttcagg ccacttctaa tgtacttcaa tggataaata tgtgcttatt aaatatatat   28917
agtagaaaat atgcttttaa gaaaatggca tgcctgatga atccttctgc aacttgcttt   28977
ttacacctac caatggaatt tggagatctt cccagataag aatacatggc tccatctcat   29037
ccttattaat agctgcctag tttttcaaag ttggacctgg tttatttagg tggtcattta   29097
ttgatggaca ttttaagctt aacatctctt cctatttaa acaatggtcc aatgaatatg   29157
cttgtacatt tttccttgtg tgcatggagg ttaaaatgca gtcattgagt gtgcatttta   29217
aacatttcag tagaatctgt caaattccgc ttacaggtta ctgcaccaat atatattccc   29277
accagcagag catgaaatat ctattttatc catgggcttg ccagtatttg ataatatcaa   29337
acttgattat ttatttattt atttgacaca gggtcttgct ctgtcaccca ggctggagtg   29397
cagtggtgcg atcactgctc actgcagcct caatcttcca ggttcaagtg atcttcccac   29457
ctcagctttc caaggagccg ggactacagg tatgcaccac tatgtccagc taattttgt    29517 atttttttgc agagatgggg ttttgccgtg ttgcccaggc tggtctcaaa ctcctcagct   29577
caagcaatct gcccacctca gcctcctaaa gtgttgggat tacagacata agccactgca   29637
tttggcccaa acttgatttt tttttcttg ccgatatatc taataagtgt tacttcattt    29697
taataaaaat ttgcattttg ccattttaa tgaggctgtg ttttgcata tgtttattga     29757 ccatttctat ttccactttt ttgaactgcc tgttgatgca ttcttataca taattgtgtc   29817
agtaatattt tgtttttga aaattaaact tttctcttaa tttttaattt ttaaaaatgt    29877
acatttgggg catatgtgat aatttaatac atttatatta tttgtaaaga tcaaatcagt   29937
gtaattgaga tatccattac cttaaatatt tgtcttttat ttatgctaga aacacttgca   29997
ttattgtttt ctagctattt tgaaatatgc aataaactat tgtaagctat agtttacaaa   30057
tatagtcact ctactgatct agcaaacact agatcctatt tcttctatca gactgtatat   30117
ttgtacccat taacccagct ttcttcattc ccctcaccct tcctggcctc tggtaatgac   30177
aaatttattt tcatcttcat gagatccact ttttaagctc ccacataaga atgagaacat   30237
gtgatatttg cctttctgtg cttggcttat tttgcttaac atagtaacct ctagttccat   30297
ccaagttcct acaaatgaca ggatgtcatt ctgttttata gattaacaat attccattgt   30357
gtatatatac cacattttct ttatcctttc gcccaatgat gggtacttag gttgattcca   30417
tagtttggtt attgtgaata gtgctccagt aaacatgaaa gtgcagatat cccttttgaca  30477 tattgatttt gcttcttttg tatatatacc cagtagtgaa attgctggat catatagcag   30537
tttttagtta tttgagaaac ctctatatag ttttccataa tagccgtact aatttacatt   30597
ctcaccacca gtgtatgagt gttcctcttt ctccacattc tcaacagagt ctgatattcc   30657
ctgtcttttt aataaaagcc attttaactg acttgtgata attcattgtg gttttgattt   30717
gcatttctct gataatgagt gatgttgaac atttttttat atacctgttg gctatatgta   30777 tgtattttt tttgagaaat gtctattcag attgcttgcc cattaaaaca attgaatcat   30837
ttgtgtgggt tttaaattt aaattaattt aattttttt ttttttttacc attgagttgt    30897 ttgagctcct tatatattct ggttattaat ttccttgttag gtggatagcc gtaaatattt   30957
tctcccattc tgtgggttgt ctctttgctc tgttgcttgt ttcttttgct gtgcagaagc   31017
cttttcagct tgatataatc tcatttgtca atggcagctt ggttggcctg tgttctggag   31077
gttcttacac aaaaatcttt gcccagacca atatcttgga gagtttcccc aatgttttct   31137
```

```
tccagtagtt tcatgtctta gatttaagtc tttaatctat tttggttagt tctgttgtat    31197
acggtaagaa ataggggtct agtttcattc ttttgcatat ggttatccag ttttcccagc    31257
accatttatt gaagagactg tcctttacct aaggtatgtt cttggtgcct ttgtcaaaaa    31317
tgagttggct gtaaatgtgt ggattatatc tgggttccct attttattcc actggtgtat    31377
tgtgtttgtt tttatgccag tactatgctg atttggttac tatagctttg tagtacattt    31437
tgaagtcagg taatgtgatg cctccagctt tgttctcttt aattaaaaaa aaaatttaga    31497
ggcaggttct ttctctgtca ctctggctgg agtgcagtgg tgctatcatg gctcacggca    31557
gcctcaacct tctgggctga aatattcctc ctgccttggc ctgccgaagt gctgagatta    31617
caggttcaag ccatcacacc tggcctagct ttggtttatt ttgctcacga ctgctttgcc    31677
tatgtaaggt cttttgtggt ttcatgtaaa ttttaggatt ttgtttctat ttctgtgaag    31737
aatgtcattg gtattttgat tgagattgca ttggatctat aaattgtttg gagtaagatt    31797
atcattttca taatattaat gatttcaatt catgagcctg aacatccttt ccactctttg    31857
tgtcctcttc aatttcttta atcagtactt tatagttttc cttatatata tatctttaac    31917
ttctatggat atattggttc ctagatattt tatattcttt gtagccattg taaatgagat    31977
tgcttttttg atttgttttt cagattgtta ctgcccactt acagtagctt atgtaagtgc    32037
tactgatttt tgtatgttga ttttgtatcc cacaattgta ctgactttgt tatttctaac    32097
aatgtttagg tgaagtcttt aggttttttct aagtataaga ttatattggc taggcatggt    32157
ggctcatgcc tataatccta gtactttggg aggccaaagt gggtggatca cttgaaccca    32217
ggagttcgag accagcctgg gcaacaaggc aaaatcccat ctctatgaaa aatacaaaaa    32277
ttagccagac ataatggtgt gggcctgtag tcccaactac tcaggaggct gaggcaggag    32337
gattgcttga gcctggaagg ttgaggctgg tgtgcagtta ccactgtat ctccagcctg     32397
ggtgagacag agagggagac cctgtctcaa aaaataaaaa ataaaaatga aaataaaatt    32457
atgtcatctg tgaaccagac tgagttgact tcttcctttg ccatttggaa gcccttatt    32517
tctatctctt gcctaattgc tctggccaaa ataaaactct ttttaacctt agagaaaact    32577
gagcagccat agtctaccaa tgagttaggc tttggagatg gtgtgtcctg tgttctgaat    32637
atttgcatcc ctcaccaaat ccaaatgttg aaatcctaat ccctaaggca atggtactag    32697
gtggtcaaag cctttaggag gtgattatat tacaaaagtt gaaccctcat gaatgagatt    32757
tgtgtcctta taaaataggc ctgagacccc ttacttccac cttgtgagga catagtgaga    32817
agtttccctc cattaggaag gtggccctca accagacacc aaatctgctg ttgccttaat    32877
cttggacttc ccagtttcag aactgtgaga aataaaattt ctgttatcta taagcgaccc    32937
agtttatgat atttttgtgat ggcagcctga gtgaactaaa atggtggggt atgacatctt   32997
tgagctcatc aggatatgct gcagtacagt taagactgat tgaatttgca acagtaggac    33057
tgatccattg attacgtggc ctattgcagt atgcagaaag acaaaggggt agaatccctc    33117
accttacacc aattagtacc tgtcagggtt tagtgcagga aaaagctatt ttaatcagga    33177
aggaacttag tagagaaagt tagatgctta caaaaccatt gaaagatggt tttgaaagga    33237
gcaaaaattg gtcactagga ctaggctttt ggcttcaagg tgatacattg ccacttctgg    33297
ggtccagagg tcaggaagcc actgtggcag tagaataggc aatgttgccc agcactgccc    33357
acactcacat ctattggagc ctacatgtgc tcctgcacct ccacaggaat acaatggggc    33417
tccacctctc ttccgctttc ttttccttcc ttcgtccctc cctccctccc ctctctctct    33477
ctttctctct ctgttttctt ttctttcttc tttctttctt tctttcttc tttctttctt    33537
```

```
tctttcttc  tctctctctc  tctctctctc  tctctctctc  tatttcttt  ttgacaaggt  33597
ctcactatgt  tgccaaggct  ggtctcagac  tcctaagttc  aagtgatctg  cctacttcag  33657
cctcccaaag  tgttaggatt  ataggcgtga  gccaccgtgc  ccagcctagc  cactgtgcct  33717
cactttcttc  tattttcaaa  tgtcatgtaa  ctgcctcaag  ggcagagact  acatctaaac  33777
tcctagctgc  aagggagcct  ggatactgta  gtttttagct  atcaatgcaa  aaaatagagc  33837
atgtgaagag  aatagcagta  gatgctgaat  atcaaaagtc  tccatccttc  caaaatacag  33897
tcatgtgcca  cataaccatg  ttttggtcaa  tgatgaacca  catgtatgat  ggtgatacca  33957
taagattata  atggagcaca  tatagaaacc  tgatacctgg  cacaagatac  tggcactgca  34017
cattaagtgg  gggaaaagat  tgatattcaa  taatggtgat  agggcattta  gttttccatg  34077
tgaagaatat  atataaataa  taatatatat  accttctagg  tctgtggaag  tacatgctac  34137
gatctttgca  caatgacaaa  atctagtgat  gcgtttctca  gaatgtgtcc  cagttgttaa  34197
gctccgcatg  actgtattga  aacttaagtt  gccatctggc  acttactagg  tgcctacctc  34257
ctgcaaagca  ttctcattta  tctaatagat  gaatgaataa  tcacttaata  ggtagaattt  34317
ccattaagtg  tatcaaactc  tgctgataga  cagtactcag  tatctgtagt  actctgcaaa  34377
tctccccatt  ccccatttaa  ggtatcaggg  tctggcaggt  gcagaagtga  atgggaggc   34437
aacagaagct  ctcttagtcc  cttcctctct  caaatcagat  ccctttacag  ctgctcatct  34497
tcaggtcaga  ggcagtgcaa  ctgtataact  tgaaatcatg  atagtctatt  ttctaacatt  34557
ttattatcag  tagatcatgt  tttctttact  caaacacact  atgtgtaata  gtcctcttct  34617
agccactctc  atggcatatt  actctatgaa  acactttaat  caaagataaa  atgtgactct  34677
ttttgacatc  ttaaaggcat  ctaccccaa   aaggtatcta  cagcaaacat  ttattgctgg  34737
tgaaatcttt  ctagtagatt  acagttaata  cattattggt  ttattatcat  ttgcatatgt  34797
atgggcaaca  ctacgttttt  tcaaaaaagg  caacctagaa  ataccatttg  acccagccat  34857
cccattactg  ggtatatacc  caaaggacta  taattcatgc  taccataaag  acacatgcac  34917
acgtatgttt  attgcggcac  tattcagaat  agcaaagact  tggaaccaac  ccaaatgtcc  34977
aacaatgata  gactggatta  agaaaatgtg  acacatatac  accatggaat  actatgcagc  35037
cataaaaaat  gatgagttca  tgtcctttgt  agggacatgg  aagaaattgg  aaatcatcat  35097
tctcagtaaa  ctattgcaag  aacaaaaaac  caaacaccgc  atgttctcac  tcataggtgg  35157
gaattgaaca  atgagaacac  atggacacag  gaagggaaac  atcacactct  ggggactgtt  35217
gtggggtggg  ggtaggggg   agggatagca  ttaggagata  tacctaatgc  taaatgacga  35277
gttaatgggt  gcagcacacc  agcatggcac  atgtatacat  atgtaactaa  cctgcacatt  35337
atgcacatgt  accctaaaac  ttaaagtata  ataataataa  aataaaataa  gaaaattaaa  35397
aaaataaaaa  taaaaaaata  aaataaaata  agatcatatc  attaaaaaaa  aaaaaaaaaa  35457
ggctagcttg  gaacccaggc  accacacgcc  attactggct  tcctgagtac  acatccttta  35517
gctcttacct  acaattctct  cctagaaatt  attgtttgaa  tgctgtgtcc  agaaggtaac  35577
atatatatgt  gtatacacac  acacatacac  acatgtatga  aaaactaaat  tgctgcttag  35637
acatatagaa  aagttttcca  aattttgaa   ttcataagt   ctatcaacct  gatagcattt  35697
ctcaaaaaat  ttttcaatg   ggtagaggac  ttgtgcttt   cttttattct  attgagaaat  35757
tctcaaacct  ctaagaaatt  gtgcaaagga  aatttaaatc  atatgaagga  catagtcaaa  35817
atgtgtagct  acaaggacta  cacatttcaa  ttgttgagaa  acagtttact  ctcaataatt  35877
```

```
tgtgaatgtt tgttttaatc tgccaaattc tgaggaagat agtgtaaaaa gatataattt   35937
ttaaggtatt tttaataaat ctggtaactt tttgatcaga ggacattcaa ataaaatgta   35997
gagtatagag cagaaattca gatgcagttt ttttaaaatg taatgtatgg gccgggcttg   36057
gtggctcaca cctgtaatcc cagctaggag ttcaagacca gcctggccaa catggtgaaa   36117
cccagtctct actaaaaata caaaaattag ctgggtatgg tgacgtgcac ttgtaatccc   36177
agctacacaa gaggctgagg caggagaata gcttgaaccc aggaggtgga ggttgcactg   36237
agccaaaatc acacctctgt gcctcctgag tgacacagcc agattctatc taaggnnnnn   36297
ntttgggggg gcccccnana aaaaattctg gccccagtgg gtggtttttt tttggcccga   36357
aaattccaaa aatttgccca aaaaaaaagt gggtttttg aaattttaaa ttgggcggtt    36417 tttttcccc cctcnnggtt gtggggaggg gggccccct tttttcttct cccctttgaa    36477
aagggggggt ttcccctgt ttccccgaa ttttcccggg tcttttggg tatctcttgc     36537 caccggtttc ccccccctt ggaaggttta agggggggtg gggtaaaatt ttttaaagcc   36597
cttttcaacc ctccttcccc gggttttggg cccttggggg ggagtcctaa aactcttgcc   36657
cggcccccct tcccctattt tgtgtggaac taaaaggccc gtctttctat aggggtctc    36717 cccgccgggg taaaaagccc ccacacccca aaaaactctg ttgtgtggtt ggttttnnnn   36777
nnnnnnnnnn nnnnnnnnnn nnnnnnnnnn nnnnnnnnnn nnnnnnnnnn nnnnnnnnnn   36837
nnnnnnnnnn nnnnnnnnnn nnnnnnnnnn nnnnnnacag cctttaaaa ataatattct    36897 aatattgtca tgcacacatt aattatttct tgattaaaag aatcaaaatg gtttcagttt   36957
ctttattcaa tttctataca tatagtttta caatttattt ttaatatttt tagggaggaa   37017
aaaaaacagg ttgtcctggg atattgatcg tgaagctgat cattcctctt gctgtgtgaa   37077
gagcttttat gacaaaatgc attctcccaa aacaaagtac ataatgatta taaatgcagc   37137
aaaattgcac actatgaaaa accaaaatgc aatgagggat gaaaaaagaa acccttttca   37197
acatttaaac aataatgtag caaaaccctg tgtacattat aaggagcagc tttactaagg   37257
atttgtaaga attctaactt gtgatatgac aaagataaac agaaaagtgg acagtctact   37317
tagtacttgg ttcagttagt ccttaggata aaatgatact ggggttggtc aagtatccaa   37377
cttcaacctg gttgatctca tcgtccctct gcctgcttag tctcccttat tcttctgaat   37437
gaagagattc agaagattca tgttatagga taatgtggat attggttcac atagcccggc   37497
cagtattcat tcactcttct tggagttaag taaaggtgtc cttcctttct cttgggaaat   37557
tttgtcccct gcccattgtc agtccctgta gctgagtaag tggggtcaac cacattctca   37617
gctccttttg ttgactgtta actaagacca gaccaatcgg agcatccctt cccttagcca   37677
cagtgactga ttcaggaatg gcacccaccc aatcagaccc actctgaacc aatcccacaa   37737
ctattgctga agggaccaga aaagaggtat tattttttt gttgctggat gaaagttgtg    37797
aagattaggc cagctgttct gctgggcttc acctttctga cgatgacctt ccagagagta   37857
aagtgtacat gagggaaatt ctagccaaga gatggacctg actcagtaac ataattgaat   37917
cccgaaatcc ggctgtgtgc aaactggtct gtgttaaaag ccagtagaga tccccatttt   37977
gctatgggaa attttattaa tagagttttt ctagcctttg caactacaag aatccaaaca   38037
aagagaagga aaggggaggc caagttgcat gccttgaaga gaaagagcac atttctctat   38097
gcccattcaa atctcactag ggtagggaca gtgccattgg tttcatcata ttccctacac   38157
tgcaaagaca ttatttcta gaaatttgat acacgtatat taatatgact taacagcaaa    38217
gcaagtgaaa gcagccattc acagtccatg tggtatgcag tgaagatcta ggtagttggt   38277
```

```
taatacgggc aaagtgcaaa aatgagataa gaaaatgcaa tgtccagatg cccctgcagt    38337
ttctgtacct gccagctaat aattctgccc cagccaagca aaaggatctc cttccactgg    38397
gtaggagagg cactctctga tgatccagac tggttagctg cttctttctt gtgaggaaac    38457
acaacacaaa gcatttttc aacttttatt ttatgttcag gagatacatg tgtaggtttc     38517
ttacttgaca tattgcatga cactgaggtt tggggtacag atagtcccat cacccaggta    38577
gtaagcatag tgctctatag gtcattttcc aggccttgcc tctctccatc tgtccttcta    38637
gcagttgtca gtgtctactg ttcccatctt tatgtccata tctacccaat gtttagcttc    38697
catttaaagt gaaaacatgc agtatttggt tttctgctcc tgtgttaact tccttaggat    38757
catggcctcc aactgcatcc atattgctac aaaggacatg atttcattct tttttatggc    38817
tgtattgtat tccatgctgt atatgtatca cgttttcttt atccagttca ctgctgatgg    38877
gtatctaggt tgattccata tatttgctgt tgtgaatagt gctgtaatga acatacaagt    38937
gcctgtgtct ttttggtaga acaatttatt ctcttttgga tatataccca gtaatgagat    38997
tgctggatgg aatggtagtt ctattttag ttctttgaga aatctccaaa ctgctttcca     39057
tagaggctga accaatttac attcccacct tcagtatata agcattccct tttctccgca    39117
gcctctccag catctgttat tttatgtttt ttgagaccaa gtttcgctct tgttgcccag    39177
gctggagtgc aatggcatga tctcggctca ccacaacctc tgccttcctg gttcaagcga    39237
ttctcctgct tcagcctccc tagtagctgg gattacaggc atgtaccacc acgcccggct    39297 attttttgtat tttagtgtt tgcgggattt ctccatgttg tcaggctgg tcttgaactc     39357 cccacttcag atgatctgcc tgcctcagcc tcccaaagtg ctaggattac aggcgtgagc    39417
tgctgcaacc agccagcatc tgttattttt tgtctttta atagtaacca ctctactggt     39477
ataaggtggt atctcattgt ggttttgatt tgcatttctc tgaagattag tagttttgag    39537 catttttca tatgtttgtt ggccactgt atgtcttctt ctgagaagtg tctgttcatg      39597
ttctttgctc attttttaat aaggttgttt tttgcttgtt aagttcctca cagattctag    39657
acattagact tttgtcaaat gcatagtttg caaaaattt ctcccattct gtgggttatc     39717
tgtttagtct gttgagagtt tctttgctgt gcaaaacctt tttagtttag ttaggttcca    39777
cttgtcaatt ttttttat gcaattgctt ttgaggactt aatcaaaagt tctttgctaa      39837
ggccaatgtc cagaatggta tttcctaggt tttcttccgg gattttatt gtttgaggta     39897 ttacacttaa attttaatc catcttgagt taattttgt atatgatgaa agggagggat      39957
ccagtttcat tcttctgcat atggctagcc agtaattcca gcacctttta ttttattaaa    40017
tagagaatcc tctccccatt gttgtttttg tcaactttat tgaagatcag atggttgtag    40077
gtgtgcagct ttatttctgg ggttttcatt ctgttccatt ggtctgtgtg tctgttttta    40137
taccagtgtc atgctgtgtt ggttcttct aaccttatag tataatttga agttgtataa     40197
tgtgatgtct ctggctttgt tctttttgct taggattgct gtagctattc aagctttttt    40257
tttcttttgt tttttttgg ttccatatga atttgagggc cgggcacagt ggctcacacc     40317
tgtaagtgtg cctcagcctc agacgccgag gtgggtggat cacctgaggt caggagttca    40377
agaccagcct ggccaacagg gtgaaacccc gtctctacta aaatacaaa atttgctgg      40437 gcatgttggt gggtgcctat aatcctagct acttgggagg ctgaagcaga aaaattgctt    40497
gagtctggga ggcagaggtt gcagtgagct gagatcacac cattgcactg agcgagactc    40557
cgtctcaaaa aaaaaaaaa agaaaaaaga aaaaaagaa ttctgggata gttttttct       40617
```

```
aattctgtaa aaaatgacat tggtagtttg ataggaatag tgttgaatct gtagattgct   40677
ttgggcagta tggccattcg aatgatatta attcttgcaa tccatgagca tggaatgttt   40737
ttccatttgt ttttatcatc tatgatttta aatatttttt tagaacaaag gaatcattgg   40797
atgtcctgcc aaaaccagat gggagaaagc catgtgtatc tatcaattgt gactttgcat   40857
tttttcttgt gaagttgctc ttgtgttgta aagaagaaaa aggaaaagga aataaaaaag   40917
aatcatggtt ttgactatta caactgaaac agagcttcat aatcattttg ttccatcttt   40977
tttccatccc tccctttctt ttcttcctcc ttccctcctt cctttactcc ctttctccct   41037
tcatcactct cccttctttt ccctctcttc ttctctttt tcgcccaccc ttccctccct   41097
ccctccttcc ttccttcctt ccttcctttc ctctctctct ctctctctca atcactcact   41157
ctctctccct cccttccttc ctcttctgag gtctgacagt gagatacgcc caagggcaca   41217
tagctaactt gttggcaggg ccaggactca agtgaactca gctgaccact gattctgtta   41277
cattgttttc tccatattt gacagacact aaggaccatc aaaagctgtt ctaaatgtgc    41337
aaatcaacca gtctgttggt ttatatccta atggtataaa agagtaagga actggctggg   41397
cgccatggct cgcacctgta atcccagcac tttgggaggc tgagagggc agatcacctg    41457 aggtcaggag ttcgagatca gtctggccaa catggtgaaa ccctgtctcc actaaaaata   41517
taaaaaatta gcccgcgtgg tggtgcatgc ttgtagctcc agctaccag gaggctaagg    41577 caggagaatc tcttgaaccc aggtggtgga ggttaaaatg ggcaaagatc acaccactat   41637
actcctgcct gggtgacaaa aggagactct ttcaaaaaaa aaaaaaaaaa aaggaaagaa   41697
aataaagaaa caaaaagaa aagaaaggtc aggtgtggtg gctcactcct gtaatttcag    41757
cacttcggga ggctgaggtg ggtggatcac ctgaggtcag gagttcaaaa ccagcctgac   41817
caacatggag aaaccctgtc tctactaaaa atacaaaaca ttagccaggc atggtggcac   41877
atgcctgtaa tcccagttac tcggtaggct gaggcaggtg aattgcttga acctgggagg   41937
cggaagttgt ggtgagccaa gatcatgcca ttgcactcca gcctgggcaa caagagcgaa   41997
actctgtctc aaaaataaat aaataaataa ataagaaata aaacaataaa aaaaaagtag   42057
ggaatagtcc agtatgatat gtgagttgaa agattactaa acttttcaac acaggacaaa   42117
ccatgatttc acctttccct taattcctca gagctgatga ttcccagaag aaaaatctgg   42177
gctctactca gagttcccca tacctcacgc atttctctag gaaatgttgt caggccactt   42237
accttttagc acccatttct ttttcttgcaa gatacaaagt gtcttgatct aagcatatac   42297
ttcccttcct gtctcatggg gctcagagta agcttggcta ccaggtgtta tgaaatgtat   42357
tcaaccacag gaaaataagg ctatttgtgt ttgctggtca ttgaagggct gcagatgaca   42417
agcattgtag aaattacaaa tatttattat gggtgggttg tggtggctca cgcgtgtaat   42477
tgcaacactt tgagaggctg aggcaggagg atcatttgag cccaggagtt agagaacagc   42537
ccgggcaata tagtgagacc ctgtctcaac aaaacatcaa aaaaaaaaag aaaattagct   42597
gggtgtggtg gcatgcgctt gtagtcccag ctactcagga ggctgaggtg agaggatggc   42657
ttaagcccag gaggcagagg tttcagtaag ctggcgttgc atgctgcact ccaggctgga   42717
tgacagagca agctcctgtc tcaaaaaaaa aaaaaaaaa attactgtat gaactagttt    42777
cattttaagg tctagactaa tggggttgttg tcatatccaa ctgtgacaag aatttttgta   42837
acttaatttc tgccttggca tgttacataa gcttaataac caaacaaat cttaaatatt    42897 aaaatatttc acaggcagtt tccaaagaaa atcgtattta ttaactgttg agagacttct   42957
tagaatgtca agacatttga aaaatactac ccactgcctt ttttcctgtg cagagtttag   43017
```

```
ttctcttttt cctctgattt ttttttttcag tgttatggtg tttgagagta ctatacatcc    43077
accttataat tccatttgct gaagctgccg cttgttttt gtgttgttgt ggttttgaga      43137
caggttcttg ctttgttgcc taggctgggt ctccaactac tgggctcgaa cgatccttct    43197
gcctcagcct tctgagtagc cgggactata gatatgcacc actgcacctg gccatatcca    43257
tccttacgaa tgggattatt gttcttataa aaaaaaaata aggggtgct gggcacggtg      43317 gctcatgcct gtaatcccag cattttggga ggtggaggca ggcagatcac ttgaggtcag    43377
gagttcgaga ccagcttggc caacatggtg aaaccctgtc tctactaaaa atacaaaaat    43437
tagcctggtg tggtggcagg cgcctgtaat cccagctact gggaggctg tggcaggaga     43497 atctcttgaa cccaggaggc agaggttgca gtgagccaag atcacgcctt cagatttcag    43557
cctgagcaac tgagggagac tccatcaaaa ataaaaaggt tgaagagagc accctagtct    43617
cttttgtcta ccatcacttc caccacatga aacatagtg ttcattccct ctggaggatg     43677
tagcaacaag gctgctgttt ccaagcaaca tcttggaaaa cagagacagg gtccctacaa    43737
gacaccaaat ctatctgagc ctttaacctg gtcttccaga tatatatatt tggaacagca    43797
ttgtatgacc acacatttga aaatgaagat ggaaatggga aatagcagcc cttttgattca   43857 aaatacatga acagggaaag gagaaccatc tcttatcaga taaaaagatt aagaatttga    43917
agaagccaag agagtagagg aactaggaaa aaatgaaaaa gggaagagaa aaaaagggaa    43977
cagaacagga agggtaaata caaaatgcac ctcagtgtca ttaatctatc caataaaaat    44037
atgcggagca ccatctaagt gcctggcact gttagattct gggatacaat gctgtgcaaa    44097
atcagtgttg agcctcacct ttgcagaact tatgagtaac aaggaagaca taaataatcc    44157
aaataatcac ataagcagat gtaaggaag tgctactcag tacccagaag gtccatcaga     44217
gatagtggga gaaaaggcag aaaaaccaac aaagtggatc catcacccgc cctgagttcc    44277
agggtggaat ggaggctggc acgatagagc tgccaaatag aggtactgac tggactggca    44337
caatgtccaa gaaacacaac ggatttggct ctcagggttt tgttcggaaa tggtcagctc    44397
ctgtgacttg caatccaggt aggctaaatg agagggaatc cagccgcaga cactacacag    44457
agggcaggtg aggccagggg atctggaact caatcccctg atctgcaggg caaaactcca    44517
gtgccctatg gcaggactgg caagaggaaa gcaaagcagc aggagctcaa ttctaggcag    44577
ggatttggag cagggtttca gtcagtaggg cctgaaccag taggggccag gatcccagat    44637
acagacagga aaggatcaga ggtggaggat agagactggg agcactgtga ggccagccca    44697
tccctcaggc cactgagttc aggactttag atacttaggg gttccaggag ggtgaggcca    44757
agacaggcgg atcacctgag gtcaggagtt tgagaccagc ctggccaaca tagtgaaacc    44817
ccgtctctac taaaaataca aaaattagcc tggaatggtg gcacacgcct gtagtcccca    44877
ctacttggga ggctgaggca ggagaatcac ttgaacctgg gaggtggtgg ttgcaatgag    44937
ctgatattgt gccactgcac tccagcctgg gtgacagagc aagactctgt ctcagaaaaa    44997
aaaaaaaaaa agggtaataa taatacctac ctctagaaga ctgtgagaag taaatgtcaa    45057
gtgcttagaa cagtgaacag tacctggcac agagaaaaat actaagtaag tgtctgttga    45117
atgaatggat gaatgaacaa atacatagat aatatgggca gaggcttcca aatgtaaatg    45177
gatgaagcct taagaaagtc tcagaatgac tctggactaa cgggagttta gggatgggag    45237
caaatggaaa aggaagtaac taaacagctg agctgagtca ttaaagcatt ctagggtcat    45297
tctagaaatt gcatccaagt cttaacagtc ttactgcttc cccgttgccc tctctaatcc    45357
```

```
attttctggt ctgcagtcac atcatcttta aaacataggt cagattatgt catctcaatg    45417
aattcccata aaacttgagg gaaaaaatcc aaactatggg ccatatgagg caccaaataa    45477
aagactgtaa actagtgacc cccccaagt cataaagagt tcacaaatgg agttaaatac     45537
tcagtttggg ttttttgtt tttgttttt ttcaaggcag ggtctcactc tgtcacccat      45597
gcttgagtgc agtggcgcca tcatagctta ctgcagcctc aacctttccg gctcaagcaa    45657
tcctcccacc tcatcctccc aagtagctgc agccacagac acatgccacc acacctggct    45717
aatttctgta ttttttgtaa agacggggtt ttgccatgta gcccaggcta attttttttt    45777
ttttgaggtg gagtcttgcc ctgtcacccc aggttcaact gattctcctg cctcagcctc    45837
ccgagtagct gggattactg gtgcacacca ccacgcccgg ctagtttttt gtacctttag    45897
tagagatggg gtttcaccat gctggccagg caggtcctga cctcatgatc tgcctgcctt    45957
ggcctcccaa agtgccggga ttacaggcgt gagccacgac gcctggccac ccaggctaat    46017
cttgaactct tgaactcttg aactcaaggg atccacccgc ctctgcctcc caaagtgctg    46077
agattacagg cgtgagccac tgggccctgt caatttactc agtttttttt tttttaatct    46137
ttccaaataa gtgaccaaaa tttaaaaatt gggagagttc atgttaaaaa gtgggtttat    46197
ggcttctcct gaaaccctat gagacaagta ttatgtttaa cctccatttt atagatgaga    46257
caactgaaaa attgaactcg aagcttacat gaaatcacag cgttagcaga ggcagagtgg    46317
agacttgaac caggtcaatc tggttcctga gtctgtactc tttaactccc atgtcatatc    46377
cctgccagtt agatggggtt agtgctctcc agccctcctc tctccctgtc cccccatcct    46437
gggaccctct catacacaca gttctctctt tcctgggaca ctccctctac tctaaggctg    46497
cctggctctt cctcatcttt ctgccaactt taatgtcacc tccttggaac acacttctct    46557
gggcaaacac agagagtcct acctaatttt tctctgttgc tgacatttgt gcttccttga    46617
taaaacctat cactgtttct aattaattct tgtttgtgac tctattttat ctgtgtcggc    46677
tccaaaaagg taaacaccat tcctgtgatt gctatggttt gaatgtgtcc ctccaaaatt    46737
catgttggaa cttaacccct aaggcaatga catcaatagg tggggcttgg gccaggcttg    46797
gtggcacatg ccagtaattc cagcattttt tgggaggcca aggtggaagg tttgcttgag    46857
cccaggagtt caagaccagc ctgggcaaca tagtgagacc cccatctcta caaaaacaat    46917 tttttttaaat tagccaggta taatggtgca catctgtagt cccagctact caggaaattg    46977
aggtaagagg atcgtttcgg tttgagactg cggtgagcca tgatcatgcc actgcattcc    47037
agcctggttg acagaatgag accctgtctc aaaaaaaaaa aaagaggtg gggctttggg    47097 gaggtgatta ggtcatgagg gctctatgaa taggataaat ctccttataa aaaagctca    47157 agtgagttgc agagccctt ttttgtcctt ccaccatgtg cagacatggt attcatcccc     47217
tctggaagat acggcaacaa ggcaccatcc gaaagcagag agcagccctc gccaggcact    47277
gaccctgcca gcaccttaat cttggacttc tcagcctcta gaactgtaag aaataaattt    47337
ctcttgttta taaattacct agttttggat attttgttat agcagcacaa atggactaac    47397
agtgatttac tctgagcctc tggcagacaa tagaccttca acaagtaact gttgaataaa    47457
gcaataaatg gtctcattta actggatgta caggtgagga atatcataga tgcagcgtta    47517
aagagctggg atgtcatccc attagggca gattctcaag actagttttt ccccttcctt    47577
aattaactga actctaggca aaagtcctca gaggcaggaa agggttttcc ttctttaaca    47637
catgaaatca gcgacatcca gcaggctttg aggtatggac cttatgagaa gggaagagaa    47697
atgaaaatat ctacatataa gattcccact tgcctatgat ttgaatgtgt gtttttctcc    47757
```

```
aaaattcatg ttggaaccta acacccaatg tgataacagt aagaggtggg ggccttttgg    47817
gaagcaatta agtcataagc actccatcct taggaatgag attagtgttc ttataaaaaa    47877
ggttgaagac agcatcttag tctcttttat cctacaatcc tttccaccag gtaagaacat    47937
agcgttcatc ctctctggag gatatagcaa caaggcgcta tcttggaaac agacagtggg    47997
tccccaccag acaccaaatg tgtctgagcc ttgaacttgg actccccagt ctccaaaact    48057
aggagaaata aatttctaat atttataatt actcagtctg tggcatttta ttacagcagc    48117
aggaatgcac taagacacgt cccccatca aaataacat aatctttaaa agttttacca    48177
tcttttcttt tgagtactgg gtgttacctg aatagtatcc tcttttatt ctattttat    48237 tttatgtatt tattttatg tatttttttt tttgagacag gatctctttt tgtcactcag    48297
gctggagtgc ggtgaacaat catagctcac tgcagcctcc aactcctggc ctcaagcaat    48357
cctcccacct taacctccca gtagctagg atcacaggca catgccacca tccctggcta    48417
ttttgtgtgt gtgtgtgtat tttttgtaga gatgaggttt caccatgttg cccaggctgg    48477
tcttgaactc ctgggctcaa gagaatcacc caaagtgcta ggattacagg cataagccac    48537
tgtgcctggc cttgaatact atcactttat tctccagaca tccattcttc accaatcatc    48597 caggcttttgg gaagtagacc atgtactgca gcaatttcct gactcctgga acaccgtctt    48657
caaggtaggg gtctatatgt acccattgta aatttgaatt gcaaaaaaaa ttctaattca    48717
ttagggcctg acaattttc ctaacattcg gtagtttaaa aacatccaca catgtgaata    48777
ctgcagacaa attcatgaaa agactaatgg tttctctaga gtgacagaaa atcaattgt    48837 gaaaatcatg agttatcacc tacaaggaat ttatgtgatt ctttagggga tcattggtca    48897
atgtggaaat gtcaagtata agcccttttc agttccccta ggtaaggtta gctattcttt    48957
ttctgtctgt ggctccacta aagccattat catattgaat tgcaataatt gcctttgtg    49017 tctatatccc catgtgagca acttaaaagc agtgagcaca ccacaaacca atttgtaacc    49077
ccagcagagg gccaaaaaca ttccagaggt actcagtcac tatggaatga ataagtaaat    49137
gacatagtcc ctgactccag gaatgtacaa tctagctgga aactaagaca tagaaaagtg    49197 gaaaataat tccaagacag ttatttgcta agaagtaaaa gagagattta caataattac    49257
taaagagaga aaagagagac atcagtgtgt gctgcaatcc acaggaagat gtgtaggagg    49317
agatagtgaa gagagagaga aaggctgtcc agatataggga aatcgcatgg ccaagatatt    49377
caggcaggaa aacacaaggc atttaatgag tttaatagat acagatggag tggagtggat    49437
ggttgactct gttgagatta atcaactgat atggaaacta aaaatgtcgg ctagtgctgt    49497
ggtttgaata tttgcatccc tccaaaattc atgtcaaaat gtaatctccg gctgggtgcg    49557
gtggctcatg cctgtaatcc caacactttc caaggctgag gcaggtgaat catttgaggt    49617
caggagttca tgaccagctt gaccaacatg gtgagacccc tgtctctact gaaaatacaa    49677
aacttagcca gccgtggtgg catgcacctg taatcccagc tactcgggag gctgaggtag    49737
gagaatcgct tgaaacggga ggcagaggtt gcagtgagct gagatcgtgc cattgtactc    49797
cagcctgggc aacaagagtg aaactccagg ttgaaaaaaa aaaaaattaa tcctcatcgt    49857
ggtggtatta agaggtgggg catttgggaa agtgattaac tctcaaacaa tggaattaat    49917
aatggccttt tacaagtcca ttagagagct tcctggcctt tccatctctt ctgccatgtg    49977
atggcacagc atttgttccc acttttgccc ttctgccatg tgaggacaca gagtttgccc    50037
cttccaccgt gtgaggacac agcaagagat gtcatctatg aaccagaggg taagccttta    50097
```

```
ccagactcaa atctgctagt gccttgatcg gggacttccc agccttcaga actgtggaaa   50157
aatacgtttc tcttatttat aatttaccca gtctaagata ttttgttata gtattccaaa   50217
caaactaaga gtaaggaata gatcaagagg gcctctgaca tttagctaag aattttagaa   50277
attatttaat aagctagagg gtattggaaa ggaaagtgac agaagatatt ttaagtttag   50337
tttagcaaga tagaacagta tgaattggag gtagaggtaa aaatattaag agtctaagtt   50397
ggaataatga caataaaaga gatgaaaagt aaaagctacc ttatatttct taagcctgag   50457
ttactgagga gtaggagttt catacagaag gactgatcag ccatagcaca actaagaaaa   50517
gtatccacta cagctggaag tgtggagatg gagcttagaa gagaagtctt tatacgagat   50577
gttagaaaag aaactttggc caggcacagt ggctcacgcc tgtaatccca gcactttagg   50637
aggccgagac gtgcggatca cttgaggtca ggaattcaag atcagcctgg ccaacatgat   50697
gaaactccat ctctactaaa aatataaaaa ttagcagggc atggtggcag gcgcctgtaa   50757
tcccagctac tctggaggct gaggcaggaa aatcacttga actcgggagg tggaagttgc   50817
agtgagccga gatcatgcca ctgcactcca gcttgggcaa ccgagtgaga caccatctca   50877
aaaataaata aataaataaa ataaaaatac aaaagttagc cagatatggt ggtacccacc   50937
tgtaatccca actacttggg aggctgaggc aggagaatca cttgaatccg ggaggcagaa   50997
gttgcagtga actgagatca cgccactgcc ctccagccta ggtgacagag tgagaccttα   51057
tctgaaaaaa aaaaaaaaat catagagtca aaaagtggaa tggtggttgc caggggcttg   51117
gagaaggaag gaatgggaag ttactgttta atgggatgga gtttcagttt gggaagataa   51177
aagttctgga gatgtgtgat ggtggtgatg gttgcacaat aatgtcactg aaatgtatgc   51237
ttaaaatggc taaaatagta cattttatgt tatatataaa atacacaatg ttacatataa   51297
gaacacaaac atagtaagat gatagttcta ccaaccatct ttatgaaagg aatcattgat   51357
cccacgggag aggtgagagc tctgaggaag aaaattagga gcaagaaaag gacagagtct   51417
tagggatgcc cacattgagg ggaaggagaa ggaagtgggg tttagtcaaa ccttccaaga   51477
tttgacatcc ctaccaatca aagttctacc ctacaagtta agaggaaaat ctgagtccta   51537
ttgattattc ctgagatgtc cagtgaagca ctgaaatgca aaattgctgt gggatagcaa   51597
ggatggtagt gattttaaac tactttccaa gttgttagag tggcaagcta tgaatatgtt   51657
ttgaacaaat accagtagct acttggcaag aaaggagtta ttaatggtca ctggcttcta   51717
gacagttttt cttgcagaac ttggagagaa aaataaatac atcatgaaac atattcattt   51777
cagtcagttg taaatttgtg gttctgtgca tgagggaggt agaaaaggat gagtatatgt   51837
ttagatgtga agaggaatat aagacatggg atgattttag gctttaatta caaaataaaa   51897
cacccagcac ccatgattat gtttatttag aaaaagtttg tctagggaag caggagtatt   51957
aaaatggttt agttcagttt tcagcaagaa aagctggttc tttgtcactc caaccagta   52017
ggcagctaaa acaataggcc tctataaata gcaaataagg ctttcatatg aaaagatgaa   52077
aaaattgtca atttaaaata caacaaattt ttcctggaaa acatactcat agctgtattc   52137
tctggcagat cctattgcta gagaagcaag ttgtagggag aaaatggttg tgtttctcca   52197
agaatacagg gcaaaattcg tatatgtttg tgtgataaaa acattagaac ttgtatgttt   52257
gagttgtttt gtctatttcc ttaattatct ggagataata ctaatacatc tgtctttgca   52317
gtggaaaatc tacacttaga cataactgtc ctctaaaatt aatccaccat gtctcattct   52377
actggatgaa ctgtttttat attttctttt ctttctttct tttttttttt tctttttttg   52437
agatggcatc tcactctgtc aaccaggctg gagtgaagtg gcacaatctc ggctcactgc   52497
```

```
aacctctgcc tcccaggttc aaacgattct cctgcctcag cctcccaagt agctgggaat    52557
acaggtgccc acgaccatgc ctggataatt ttttgtatt tttagtagag atggggtttt     52617
accatgttgg ccaggctggt ttcaaactcc tgacctcaag tgatccaccc acctcgggct    52677
gccaaagtgt tcggattaca ggcatgatcc tagcccttc taactttggc aaaatatctg     52737
attaaaacat cttataataa actggcaatc aaatttaaaa ttgtattaac ttttaagaat    52797 tgattttct tagcttcagg aagtcctctt ttcttttat ttattttag ttactttact       52857 tatttattta ttttgataca gtcttgctct gtcgcacagg ctcctggagt gcagtggcgc    52917
gatctcggct cactgcaacc tctgcctccg aggctcaagt gattctcatg cctcagcctc    52977
ccaagtagct gggattacag gtgcgcacca ccacacctgg ctaatttttt gtaggaagct    53037
gtcttttctg aactgagtta ggttaagtac tgtttgggcc ttattaccta acacgaagca    53097
gctggatgac attggagact gaaaactagt ggtccatgga ctgaattaag gaaaagata     53157 tattttgtca ggcctgagct gtgctttgaa agatttttaa atgattagcc aacagaaaat    53217
actgggaaat acacataagg atctgaattt caggattctt ttagaaaaga aaggaaaat     53277 ctgacaacca ggactcaaat tcttgaatgg tgtcagtaga atagagttga tttgtggttc    53337
cccctgccct ccagatcaca atagtcccca tctggctgac tttacttgtt aaaattacct    53397
gcttgactct cgtgaaacaa gaaactgatg actgggctgg aaagcatagg gatctcatga    53457
tgctaaaatt tcaaagccct atcagagaaa agaaactgga tcatgcctaa gacatacaat    53517
accataagtg gattgaactg aaatcaacaa agtggcaac cccaagttct gattagactg      53577
aagagattac ccccaaccaa acctagcttc ctgatagagg aaagggaatc atcttggtgc    53637
agtggggagc aggggtggtg gtggtaaata ttatttataa atactcatac acacacggaa    53697
gtctaaaaca agaaatgcaa aatatgtaaa aaaaggggg ggaaatatga cccataatga      53757
aaagaaaaaa aactcaataa aagcagactc acaggtaacc ctagtgttag aattagcaga    53817 caaaattt caaataacta ttacaaatat gttaaacaat ttagataaaa agatgagtga       53877
aacaagagat aagagaatct cagctaaaat aagaaaatga actaaaaaaa taacaatatc    53937
taaaatgaag tattgattgt ataagtttaa taacaaatca atatagcaga aaaagaata     53997 agtgaactgc aagataggtc agtaaaaatt attcaaattg aaaacagaat aaaagaatga    54057
ggaaaacaaa aatggggaac aaagaatcag agactaaaag taaatattag gcaactgagt    54117
tgtcttttag tctgttttat gctgctataa cagagtaccc atgactgcat aatgtataaa    54177
taacagagat ttatttctta catttctgaa gtctgggaag tccaaggttg aaaggcctgc    54237
atgagttgag gaccttcttg ctgcgttatt tcatgacaga aggtgaaagg gcaagagagc    54297
aggtatatgc atgagaatga cagagagtga gagagctaaa attgatttcc tcataaacta    54357
atgctcacta taataaaccc actctctgat tatattagt ccattcacaa gggcagagcc     54417
cttgcgactt aatcaccttg taaatattct acctctcaac attgttgcat tgggattaa     54477 gttttctatt ttcttttttt cttttgaga cagagtctca ctctgtctct gaggatggag     54537
tgcactgaca cagtctcggc tcactgcaac ctccgcctcc caggtccaag cggttctcct    54597
gcctcatcct cctgagtagt tgggactaca ggcatgcacc accacaccta gctaattttt    54657 gtattttag tagagatggg gtttcactat gttgggccag tctagtctca aatttctgac      54717
cttgtgatcc atccaccttg gcctcctaca gtgctggtat tacaggcatt agccactgtg    54777
cccagccaag gattaagttt tcaatacgtg aactctggag gacacattca aaccatatat    54837
```

```
ctagcataca ggtaattgga atccaggaac agaggagaaa ctggggcaaa ataaatattt    54897
taaaagatag tggccaagag ttttctaaaa ttgatgaaag atatgaaccc atatatccaa    54957
taatcacagt gaacactaag ctagatttaa aaaaaaaaaa ctatacctag agatatttta    55017
aaagaagcca gggcagggga aaggatctat tatgcttatg aatagaaaaa taagaatgtt    55077
ggttaacttc ttaagagaaa aaaaacggaa gacagaaaat gatggaacga catctggaaa    55137
acaaacaaac aaacaaaacc tgtcaaccta gaaatctata ccttcaaaag cacccttaa     55197 aaatgaaagc taaataaaaa cagaaacaga aaaaaattgt cacttgcaga ccagcattat    55257
gagtaacact caacgaagtt tttctccagg aatctgtgaa cgccaccaga atgggcaaag    55317
atgtgaaaaa acataaagta ctctttagaa actttcttta ggagactatt gaccatttaa    55377
agcaaataga atagcaaaat aatcgataat gaaaaaatac atgacatttg cacaaggggca   55437 gaagggtaat aaaattatac tgtagtaagt ttcttacatt gtttatgaaa tgataaaata    55497
aggaaaaggt aagaacacat attgtaatct ttagtaacca ctaaaaaaat accaagagat    55557
attactagaa aaacaatagg taagataaaa tagaatactg gctgggcaca gtggctcatg    55617
cctatacttt cagcactttg ggaggctgag gtaggcagat cacttgaaac caggggtttg    55677
agactagcct gggcaacaaa gtgaaacccc atctctaata catacatata tatatatata    55737
cacacacata tacatgacta ctgaataatc cttatgtaac atataatata taatactgat    55797
atattgagaa tagtgaataa ttcttaattt ttactttttt ttacctttt ttttttttga     55857 gatgtagtct cgccctgttg cccaggctgg agtgcagtgg cgcgatctcg gctcactgca    55917
agctccgcct tccgggttca cgccattctc ctgcctcagc ctccctagta gctgggatca    55977
caggcgccgg ccatcacgcc cagctaattt ttgtattt tagtagagac ggggtttcac      56037
cgtgttagcc aggatggtct caatctcctg accttgtgat ccgctcgcct cggcctccca    56097
aagtgctggg attacaggcg tgagccaccg cgcccagcct attctcatcc atccttaaga    56157
ctggactctt tggtcattgt taactgactt tttcgtatag gataaattct taaacatgag    56217
atagtagtca attctgccaa cattcagttg ttgtttctga atttcccaca ttgcttaagg    56277
tcaactccac catgacgcta taaaaacact tttctccatt ttttcatata tttgtatagg    56337
tttgttttta catttaagtg aatttttaaag ataaaactta cctatctata tggaatgagg   56397
aaggaaacct cttactttca tatacataac caattatgtt acactattta ttacataaac    56457
catactttat caatgattgc agtgccatct ttgtcatata ttaagtccta acaaatacct    56517
aaatatgttc ctacaatctc tattctattt acagatctac ttgacagctg tcgaaccaat    56577
acatgccatt ctgaccataa tacctttaag ataagtttga ccatttaaca taagaagtaa    56637
taaccagacc gggctcagtg gctcacgcct gtaatcccag cactttggga gtccgaggtg    56697
ggtggatcac ctgaggtcgg aagttcaaga ccagcctgac caacatggga gaaacccat     56757 ttctactaaa aatacaaaat tagctgggcg tggtggcaca tgactatagt cccagcaact    56817
caggaggctg aggcaggaga atcgcttgaa cccgggaggc agaggttgca gtgagctgag    56877
atcgcaccac tgcactccag cctgggcaac agagtgaaat tgtctcaaaa aaaaaaatca    56937
ataagtaaaa tcttaaagta gcaaatgaca gttgcagcca agtaattcca aaagccagct    56997
tcactcggag aaccctgtgc ttcctcttat ttccagcgat ccacatattt agagaaactt    57057
ttccagtaat aaaccataga aattatacct ggaagtagag tcttcaactt ggatttttag    57117
gtgaccctaa caaagggggg aaatttccca aaacatatcc gaaatggact ttctcactgc    57177
tttggctagt cgaggttaag aatcagaggt aattttagaa catatagatg aggtgacaac    57237
```

```
tcatacaccc aagtatgtag agcaactcat atctacccca ctgcatttgg agggaaagtg   57297
tttccctggt gaacttgtga gtataaatag atggaagaag atgtactcaa aacagcaaac   57357
ttctaattat acaaaatgtt atattttctg cttagtgaag ccacatccat gtagattatg   57417
atgctctaat cattacacct gtcaacacaa tgaaatagct caaatctctg aaaaactttg   57477
cttcactctt aatgatgtca aaaattacaa ctcaaattaa atcttcatgt ctctaatgaa   57537
acctcaactc tgcaaatttc cttatttaaa aatgctgttt tagccaaaga atgtttcaa    57597
aaattctgta ttcaggccag gcacggtggc ttacgcctgt aatcccagca ctttgggagg   57657
ccaaggtggg tggattgctt gaggtcagga gttcgagacc agcctggctg acatggggga   57717
aaccccgtct ctactaaaaa tacaaaaagc cggatgtggt ggtgcatgcc tgtagtccca   57777
gctactcagg agactgaggc aggagaatca cttgaacgca ggaggcggag gttgcagtga   57837
gccgagattg tgccactgca ctccagcctg ggtgacagag cgacgctccc tctgaaaaaa   57897
gaaaaaaaa ttctgtattc acaaatagct tgatactagc aatcacttgt ttacattgta   57957
aataggcagc aggctgaaaa ttttttgatga cttaattgca ggttcacagc tatgaaggca   58017
agccaaaggg ctaccttgcc aggtctgtaa aactgatgta catagtatga gctgcttgat   58077
ctttgagtaa tcacaaaaga caaatcaggc tgggcatggt ggctcatgcc tgtaatccca   58137
gtgctttggg aggccgaggc aggtggatta cttaaggtca ggcattggag accagcctgg   58197
ccaacatggt gaaatcccat ttctataaaa aaacaaaag ttagctgggc atggtggtgt    58257
gtgcctgtag tcccagctac tcaggaagca gaggcaggag aaccgcttga acccgggaag   58317
tggagtttgc agtgagccga gatcatgcga ctgcactcca gcctgggaga cagagtgaaa   58377
ctctgtctca aaagaaaaaa aaaaaaggaa agaaataaaa gacaaatcag caaaagagg    58437
aattcataaa aagagaataa agcttttgcaa aaaagaaacc tgtctttgga tcttcagaag   58497
tgactaaaat attttaatag gtcccttta gtgcctctt ttgcttgcct atgaaatatt     58557
gacagatctt cccaactggg ggaaaaaaaa cccaaaattc attaaactca ctgtgtctta   58617
tttggttaaa taaaagagg tagaaagact attatgagaa aagagaagca atagaaactg    58677
tggaaattgg agttccaaac atcaatctta atttgattga atagtagaaa gtatataaac   58737
tatgaaaatt gatgttccaa acatcaatcc gcattcctga gcaattttca aattggtcac   58797
cagctctcca ctcctcctgt catgagtcac ttatacctta aaagtatat cctctgagaa    58857
ttctgaaagg tatccagacc ttccattaga caacttccaa tccatatgtg cctcaaagtt   58917
gtgtcttcat tttcctcctg ttccatttcc ttcagatttc caccaagata tgcatgttga   58977
gctttgtttt gagactacat ccagatgtca cctacctctc ctgtggcctt aaaaagattc   59037
tataagcaca gagagatcag cctgagacat ctgaagacct aagcctgcat ccttcctggt   59097
ttttggatta agggaatgta aagatgagag gaaaatgagc aaggcgaggt gataactcat   59157
ttctaaataa aacaggaata ttttaaaaa tctgacactg ctaaaggcca agtcatacag    59217
taggattccc accaggccag gctgtaaata ttgattctcc tctctgcaac cccagtgttc   59277
aggcttcaga gtaacagtct tagttcctcc aaccacattt ctaaccacaa ggtcactgca   59337
cacttcacca tcctggccat cttccttag cacatacaat tgtaagttta aaaatttat    59397
cttttatttt cagtcctccc acagctgttg ggacttggac aaacctacct tataatcaaa   59457
tatttgcggt gttttctagt ttgaaaagca ctgttcaaaa gttatctcat ttaatcttta   59517
caactgttga ctttacagat aaagaaaact gcagatcaga aaagttaaat aaatgcccaa   59577
```

```
ggacacacaa cttgtaagaa aagaagccag ggctaggcta ggccggctgc agtggctcac   59637
gcctgtaatc ccagaacctt gggaggccaa gacaggcgga tcatctgatg tcaggagttc   59697
gagaccagcc tggccaacat ggttaaaccc cgttttttacc ccncnnnccc cnnnnnnncc   59757
cnnggggnng ggcggggcnn nnnnnnnnnn nnnnnnnnnn nnnnnnnnnn nnnnnnnnnn   59817
nnnnnnnnnn nnnnnnnnnn nnnnnnnnnn nnnnnnnnnn nnnnnnnnnn nnnnnnnntt   59877 tttcttttttc ctttttttttt tttttttttt tgagacggag tctcgctgtg tccccccaggc   59937 tggagtacaa tggcatgatc tcggctcact gcaacctctg cctcccaggt ttcaagcgat   59997
tttcctgcct cagcctcccg agtagctggg attacaggca cccaccaccg tgcccagcta   60057
atttttgtat ctttaataga gatggggttt caccatcttg gccaggctgg tcttgaactc   60117
ctgacctcat gatccaccca cctcagtctc ccaaagtgct gggattacag gcatgagcca   60177
ccatgcccgg ccccaaaact atttctaaga gaagtgttga agtgaggct tggctccttc   60237 cgactgctta tagtaaaata acagaagaga gaaatgactt aaatatgaaa ttgttaggta   60297
aaaaaggaag cagaacgtaa agatttagaa aattcttaga ctatccatat tgcaaaacaa   60357
gataacagta aagatgtgac caagcaacca tttgctaatg aaatttgtat ggatcagcca   60417
tctcaacaga agccaggtat gatcctctaa gacaatggaa gaatgacccc aaagatgatt   60477
ccagagatca tcagggctgc cttccttggt ttcaaaaggg aagaccatca ttgcacaatc   60537
agccagatct cctccaccca aaatagtgac agcaggactg ccaaaaggct tggagcctaa   60597
gccctgcctg acagagccgt gggagcagaa cctctaacct agcagttctt gaaggcagga   60657
gtcccactgt agtgggcctg gaaggagcat caagccaaaa aagattttttc tcaagcctta   60717 agatctcatg gagtttggct tgtagcctgg acttacatgg gattttgttac ccttttcttc   60777 tttgctatttt ctccctttttg gaatggatat gtctattcta tccctgtccc accactgtat   60837 tttgaagca tatggcttat ttggtttcac agtgtcacag ctagggagca atttgcctca   60897
agatgaatca tatcttgagt ctcacccata tctgatttag atgatattta ggtgagactg   60957 tgggtttttaa attttaggtt gatgctgaaa tgaatcaaga ttttgaggac tgttgggatg   61017 caatgtctttt tgcttgtgag aaaaacataa attttgggag gcaagggtg gcaggctatg   61077 gattgaatat gtatccccca aaattcatat gttgaaatac taatctccaa tgtgctggca   61137
ttaggaagtg ggcactttgg taggtgataa ggccatgagg gcagagtcct tatgaatgga   61197
attagtgctg ttataaaaga gactctggat agcacccccta cttcttctat catgtgagaa   61257
cttagcaaga cactatctgt gaacctggaa gaaggccctc accagacacc aaatctgctg   61317
gcactttgat ataggaattc ccagtctcca gaactgtgag aaataaatct gttactacaa   61377
gctacctagt ctatggtagt ttgtaatagc agttccaaca gactaaggca aatgtctatt   61437
aaattttttg ttcatttttt aaatggttta tcttttatt ggtcagtttt aagagttcct   61497
tatctattct gaatactaga ctgttacctg atatatggtt tacaaatatt tttccagctc   61557
ttttaattgc cttttcgctt tattgctagt gtcctttgaa gcaaaaagtt tctaattttg   61617
atgaagtcca attgtgctga actgttttga accacaaaat ttctttatga aaattttcat   61677
catgatgcag gtaactaaaa ttaaaatgca gggctttta taattattca tttgacaaat   61737
aactgaatat ggaatcagct tacaattttct ctgctggtac aaaagtcaaa tttcttttaat   61797 ttgtaaaaga gacaaataac tataaagtag gcaaattaaa tatttaatag tcaaaagata   61857
ccaaattaat tttgtcatga ggcattcata acaaagagatt tttttctata caggctagga   61917
aaaaattgct tgaaagggat caaaataaat ataatcaatt tcttgccaat ggatagaggt   61977
```

```
taaggccatc tctagatgtc ccgtttgtag aatttctata ttcttaaatt agttttggaa    62037
tctacatctg gactaaatgc taatattatt aattcacaga acatgtttgc ttgccatcat    62097
ttcttaagat gtgaagttat acaaacatat ttcccctgca gcatttcaaa acatactcaa    62157
ccattaaaag gaaattaatt ttaaagacat ctgtgccaaa atgtatgata tatttgcttc    62217
ttctgcagag agctacaaaa gacagaactt tgctttggta ataataaaat gtgttgactt    62277
ccaagcactg catagttttg caatggaaaa caagctggag aagcttttga aggtttgtca    62337
gaaactatga tgtctgggtg gcaagtggga tttcactaat ccccaggdac attgcaaaac    62397
tgtcttccca accatctgtt gctaggactc tagtcaaaaa gaggatgaca agtgaaaact    62457 atttggcaa cagaacaaaa aataagaaat ccaaaacaaa cctctcacaa acagttgggc    62517
tttctattag attcaaatca tacatgacca cattttagaa aatgcacata ttcaactcac    62577
tgaaaatgcc aaaagagata gaatggaaaa ggaaaggtaa ccaggagggg acacctcttc    62637
tggaagaaac ctgtctatta atacttgttc atatgacaga aaagttcatt gagggcagtg    62697
attgtattct tagaatgtca gtgctggcta aatgaatatg tgaagagaga gtacaagaaa    62757
ggatcataag atccagatag gaaagaaatc agcttgaaaa tatccacagt atgtgacttg    62817
ggataaggaa agaacactga gcatggcagt ggtattctca agtgggatct ttagtaacca    62877
ttcattcact tattcaacaa atatttgtga aactacaatg ggtaccatct tagacactag    62937
ggatgcagct aaacaaaaca gactagatcc ctgccctcat ggagcttaca ttgaaaagct    62997
aataattatg gagcactgaa gtgtgccaag cattgtgttc agagcttcat atatattctc    63057
tctgatcttc acaccacccc tatgggataa gcactatcat cattcccatt ttacagagga    63117
gacaattgaa gtttacataa agggacttgt ttacgtccaa gaattgataa caaacacagg    63177
tctgcctaac cactgaaact ctaatcttca ccactgcaca actcccctca cagattcatc    63237
acatgactct aagatcatac ttctatatta ataactgcta tgccatgttg tttatttttg    63297
gatggcaatt atgcaaatgg gtgttatacc atttcatact atattatact attatagtca    63357
ttcacagatg agagaaaaat cttccatatt ggtaaagttt aaatctatgg gctgaagaaa    63417
ggaaattttt tgtctctgaa gattgctgaa agaggagaca gtgaggagat acaaagttaa    63477
aagagatgca catagcagaa aggaataatg ctatgagttt ttctaagatg gaagagagct    63537
gtctcccact agagataaag aattaactct cagcacccag gcaaaagagg aaactaggtt    63597
aaaaaaaaaa aaagaactct ggcaactctg tgctaggatg gtgtgtaagt cttaaagtaa    63657
ttattaatga gattcagaat attaaaaaac taagaaaatc atttgagtat atattgtctc    63717
tgatgatttt ccagtaattc agaatctaga aaataacata taaaatatta acatgacccct   63777 ccagggatat ctacataaat cttattgcta aataagttaa ttatgactta ttattccata    63837
aaatgtcaat ttagctcaac tttcaactgt tcaaattcag aacacctaaa gtctctccag    63897
agtcctgtag atacaacttt catagaaact gcttaggtga cctgtgatat aacacaggca    63957
gacatgaaga tttctgggag gagagatgca ctctgaaaaa tagggctatg gagtctgttc    64017
cttctacatt cattttagca atgctacatc ttcactatta gacactctag atcatgctca    64077
cttcccactt ccaataattt atagcttttc ttttaaaaat aatttttatta attgatatta    64137 tgctggaata tcaaaactct taaaagattc aattactaaa cacttaaaga aatataaatc    64197
ttccagagtc aatatcagta tcactgtgag ttttttaggca gatgtgacag aaaagaagac    64257
gtcaaaatta gaacaggaag caaaataatc tcattaaatc aaagctatat tagaaattgt    64317
```

```
catatgacat attgtgcaaa ttacagtgca tatttgtgct tcatttcatt caataaatat   64377
ttacagaata caataggcca agccttgtgc tagaagcata tatacaggac aaaatgacat   64437
agtctgagct tttggtggat ttacattata atttgcctga taaaacacgt catatgacac   64497
ataacaggtc gtattttta acatcttgta agaaaaaaat tttaggtcta aggaaataac   64557
ctcaaaattg ttagttgaaa tgtataatgg tacagccact ctgaaaaaca gttgggcaat   64617
ttctttaaaa aataaacata cacttaccaa acaaactagc aattcactc tcatgcattt    64677 aactcagaga agtaaaaatt tacaactcca caaaaacatg tacatgaata ttcatagtag   64737
ctttattttt aaagccccca aattggaaac aacctacatg tccaataaga gataaatggt   64797
taaacaaact gtgctacata tataccacgg aatactactc aacaatataa aggaactgat   64857
tgatatatga tataaaaaga actatggata tatgaaacaa ccttgacaga tctcaagggt   64917
atttaagggg aaaaaagcta acctcaaaag gccacttaat gtatgattcc atttatataa   64977
caatcttgaa atgacaaaat tattaagaga gaaaacagat taatgatttc catgaggtag   65037
gtagggatga tgaaaataaa aatacagtat gtcagatggt aatgttatca aaaaaataaa   65097
gcagactaaa aaaacaaaac agagggccca aatggggaag gagattattg ctactgtaca   65157
taggttggtg agaaaggctg ctctgaagga ggtacaagag tgagtcacgt ggatattcga   65217
agcagagagg acagaagagt agtgtccatg gctggagtgt gcacagtgcc tttcagaggg   65277
ctcagtgtgg ttgaatgagg gaggacagag gagcaggaga tactgttaaa acattgggaa   65337
aaagaggaga gttgatcata agtggtcttg taggcaactg tatggatttt gactttttt    65397 tgctgactga cctagggaag ctgctgaaaa gtttggagca cagggtttat accagtgccc   65457
aaaacagtga ctgcaaatga taggtgttca gcaaatagtt gttcaaggga tggcatgttt   65517
tgacttatat tttaaaaaa ggatcaccat ggctgctgaa agaagaatga aatgtgttaa    65577
ggcaagagtc tgaagaaaca gtattgatgt gagagtaaat cagtgcaatt tccattgaga   65637
gcaatttggc aataatttgg caatatctgt caaaaatatc aatatatata acttttgatc   65697
caggaattct tcttctagga atatatccta cagatgtact cacacatgtg tgaaataatg   65757
tatctggaag gcttctgtgt aatagcaata gatttttaaac aacttcaatg gccactgtga   65817
gataagttag agaaactata gaatacccat acaacagaat accacgcaac cataaaaatt   65877
taatagaaag ctctttacat gctgatataa aacagtctcc aagatatata ttaaatgaaa   65937
aaccaaggca gatttcaatg ctatgatttg tattttaaaa ggtaatagaa aaaaaatatg   65997
tatttgtgtg tgtgtagaga tgtatatctt tgcaggagca ctcaagaaac ggtagcatca   66057
gtcatctcca ggaagaatag cagggtgaag gggctaggga tgggtggggg ccaggatgga   66117
gggaaaacat ttcactgtat gtaattttta aacttttgga ttttgaacta tgtaactaaa   66177
aaatgaataa cattgaaatt ttcttttaata ttttttaaaat agattattta tataccttag   66237
ttaggaactg gggaaagaaa cacgagactt aaagttacaa ggatgtaggt ttaagaccac   66297
ttccagcatt agtaggggta taacattaga aaagtcacat aacctttga gcctcagttt     66357 cctaactggt gaatggaatt gttgtagagt agcctaactc ttaaccaaag ttcatctttc   66417
cactgtgcat cacattccat cctttctcct ctactcaatt atgtggcttg tattagtttg   66477
ctacggatgc cataacaaat atcacagaca ggtgccctaa acaacagaaa tttatttcct   66537
tacaattctg gagtctagaa gtccaagatc aaggtatcaa cagggttgtt tttctaagtc   66597
tctgtctcct tggcttgtag gtggccatgt gtctccccat gatctttcct ctgtgtatat   66657 ctgtgcccctt atttcataag gatggtatga gataccaatc tcattggatt atcgcccacc   66717
```

```
taatgacctc atgcagccat cattaacctc tttaatgacc ctatctccaa atacagttcc    66777
attttgaggt actgagggtg aggactttaa catataacat caggaggatc acaattcagc    66837
ccataacaaa gtattggcaa ctctgctctt tttcccaatg tcatcaattt ctttaatctc    66897
tgttggacca ttttcatcag tgtacaatgt gcttttattt cttttatctt aaaaaaaaaa    66957
atctctgact ccacttctcc gttcagcaac caccctattt tctgggtctc ctttacagca    67017
taagtcttcc aaagagttgt ccatattcac tgtctcaaat tcctctttta ttctcttaca    67077
ctcattccaa caaagctttt gcccctcac tccactgaag ctgctattgc ttttgtcacc     67137
aatcaactct atgtcacaaa atacaatggt caaaactcag tcctcacctt aacttgtcct    67197
gttagcatta ctgatgtact tttacttggc tttaaagaca catattctat tagtttttcct   67257 cctaattcat tggttgctgc ttctcaattt ccatttctgg tttctttctt cttccctct    67317 attgaacgtt acttcttgaa cttctttctt tctctaacta tactcaatcc cttagtgata    67377
tcattgtctc atgactttga ataatgtcta cattccaata gctcttgcat ttttgccttg    67437
gatgttcaat agatgtgtta cattcagcat gccccaaagt gaacttatgt tcttcccta    67497 aaaaccggct cacacatagc ctcccctatt ccagctgact ttaactccaa tccctctagc    67557
tgctcaagtc aagtaatctt tgacatcgtt cttttcctta tatctcacat ctaatcctcc    67617
agagaatgcc taaggcataa tctgctatat atatatataa tctgatctct ttttacctcc    67677
ttcaccacta ccatcctggt tcaagctttc atcacctctc acttagatta ctctaaaagc    67737
ctcctaacaa gagtccatgc tcccagtctt actcccctct tcagtatctt cttgacatga    67797
tagacactgt gatcctttaa aaatgtatga cagataattt cactcctctg ctgaacacac    67857
tccaacagct ctacatttca ttcagggtta aaacctaagt gcttaaaata ccctaagact    67917
cttcatgacc tactactaca ttttctctc ttgctcattt ttttttattt atactttaag    67977
ttctagggta catgtgcaca acgtgcagat ttgttacata tgtatacatg tgccacgttg    68037
gtgtgctgca cccattaact cgtcatttac attaggtata tatcctaatg ctatccctcc    68097
ccccatcccg accccacaac aggccccggt gtgtgatgtt ccccttcctg tgcccaggtg    68157
ttctcattgt tcaattccca cctattagtg agaacatgcg gtgtttggtt ttttgtcctt    68217
gcggtagttt gctgagaatg atggtttcca gcttcatcca tgtccctaca aaggacatga    68277
actcatcatt ttttatggct gcgtagtatt ccatggtgta tatgtgccac atttctcttaa    68337 tccagtctat catagatgga catttgggtt ggttccaatt cactatttgt gaacagtgcc    68397
tcaaaaaaca taagtgtgca tgtgtcttta tagcggcatg atttataatt ctttgggtat    68457 atcccagta atgggatggc tgggtcaaat ggtatttcta gttctagatc cttgaggaat    68517
cgccatgctg tcttccacaa tggttgaact agtttacagt cccaccaaca gtgtcaaagt    68577
gttcttattt ctccacatcc tctccagcac ctgttgtttc ctgactttt aatgattgcc    68637 attctaactg gtgtgagatg gtatctcatt gtggttttga cttgcatttc tctgatggcc    68697
agtgatgatg agcatttgtt catgtgtctg ttggctgcat aaatgtcttc ttttgagaag    68757
tgtctgttca tatcctttgc ccacttttg atggggttgt ttttttcttg taaatttgtt    68817
tgagttcttt gtagattctg gatattagcc ctttgtcaga tgagtagatt gcaaaaattt    68877
tctcccattc tgtaggttgc ctgttcactt tgatgatagc ttcttttgct gtgcagaagc    68937
tctttcattt aattagatcc catttgtcaa ttttggcttt tgttgccatt gcttttggtg    68997
ttttagtcag gaagtccttg cccatgccta tgtcctgaat ggtactgcct aggttttctt    69057
```

```
ctagggtttt tatggtttta ggtctaacat gtaagtcttt aatccatctt gaattaattt    69117
ttgtataagg tgtaaggaag ggatccagtt tcagctttct acatatggct agccagtttt    69177
cccagcacca tttattaaat agggaatcct ttcctcattt cttgttttg tcaggtttgt    69237 caaagatcag atggttgtag atgtgtggta ttatttctga gggatctgtt ctgttccatt    69297
ggtctatatc tctgttttgg tatgagtacc atgctgtttt ggttactgta gccttgtagt    69357
atagtttgaa gttaggtagc gtgatgcctc cagctttgtt cttttggctt aggattgtct    69417
tggcaatggg ggctctcttt tggttccata tgaactttaa agttgttttt tccaattctg    69477
tgaagaaagg cattggtagc ttgatgggga tggcattgaa tctataaatt accttgggca    69537
gtatggctat tttcacgata ttgattcttg ctatccatga gcatggaatg ttcttccatt    69597
tgtttgtgtc ctctttatt tcattgagca atggtttgta gttctccttg aagaggtcct    69657
tcacatccct tgtaaattgg attcctaggt attttattct ctttgaagca attgtgaata    69717
ggagttcact catgatttgg ctctcttttt gactgttatt ggtgtataag aatgcttgtg    69777 attttttgcac attgattttg tatcctgaga ctttgctgaa gttgcttatc agctgaagga    69837
gattttgggc tgagacgatg gggttttcta aatacacaat catgttgtct gcaaagagag    69897
acaatttgac ttcctctatt cctaattgaa tacactttat ttctttctcc tgcctgattg    69957
ccctggccag aacttccaat actatgttga ataggagtgg tgagagggg catccctgtc    70017 ttgtgccagt tttcaaaggc aatgcttcca gttttgtcc attcagtatg atattggctg    70077
tgggtttgtc ataaatagct cttattattt tgagatatgt ccaatcaata cttaatttat    70137
tgagagttgt tagcatgaag ggctgttgaa ttttgtcaaa ggccttttct gcatctattg    70197
agataatcat gtggcttttg tctttggttc tgtttacatg ctggtttacg tttactgatt    70257
tgcctatgtt gaaccagcct tgcatcccag ggatgaagcc cacttgatca tggtggataa    70317 gcttttgat gtgctgctgg atttggttta ccagtatttt attgaggatt tttgcatcga    70377
tgttcatcag ggatattggt ctaaaattct cttttttgt tgtgtctctg ccaggatttg    70437
gtatcaggat gatgctggcc tcataaaatg agttagggag gattccctct ttttctattg    70497
attggaatag tttcagaagg aatggtacca gctcctcctt gtacctctgg tagaattcgg    70557
ctgtgaatcc gtcaggtcct ggactttttt tggttggtag gctattaatt attgcttcaa    70617
tttcggagca tgttattggt ctattcagga attcaacttc tttgtggttt agtcttggag    70677
ggtgtatgtg tccaggaatt tgtccatttc ttctagattt tgtagtttat ttgcgcagag    70737
gtgtttatag tattctctga cggtagtttg tatttctgtg ggattggtgg tgatatccca    70797
ttttgttctt taaacattcc agactcactg ctgctttaga gactgctcta actgttccct    70857
ctctctggaa agctcttccc ctagatagcc acttggttat ctcctcagta cttaagatc    70917 aatgagcctc ttccctgaca tctctatta tacttccta catgcatgtg tgtgtgcaca    70977
cacatacaca cacactctct ctgactccct taatgactat atgattactc acacacacac    71037
atgcacgcac acattctgac ttccttaacc actatatgat tattttttc ttagtctcat    71097 caactcccct aaaactgtaa tattatttgt ttccatagac ctattcttct aacatactct    71157
atcattcatc tagctttgta tgtacctatc tatcaatcat gtttactgtt tattggctgt    71217
ctcctccagc taaactgtaa gctctgtaag ggaagtgaat cattgtctgc tttgttcact    71277
ggtatatctc aaacacccag aacagtgtct ggcgctcagt aagtattcaa aaactgtttg    71337
ttaagtgaat gaatacaagc actggtacta ttgcttctat cacttctacc accaccattc    71397
atattagaaa tatacaaaca gtaaacaatg acaagtcttc gccagttttc caaatcacta    71457
```

```
aggatgtcta taagactact tctacaatct cctttgtca catgaggtca caaaatttca    71517
caaagcggag agttgaaaga gaaaagagta agttatcatt acattccttt taacttgtaa    71577
ccatcaaacc cataattatt agcccatttc ctcattaaat atcctctaat gggtagtaat    71637
cttttgaggg catcttagcc tactttgtgt tgctatgaag gaatatctaa ggctgggtaa    71697
tttatcaaga aaagaggttt attttgctca aggttctgca ggttgtacaa gacgcatggc    71757
gccagcatct gcttggcttc tggtgagggc ctcatgctgc ttccattcat ggtggaaggt    71817
gaagggagc cagcatgtgc agagatcaca ttgtgagaga ggaagcaaga gagtctgagg     71877
agaggtgtca gcctgttttt aacaagcagc tctagaagga actattagag caagtactta    71937
ctccccctac ccacttaggg agggcattag tcttattcat gaggtatctg tccccatgcc    71997
tcaaacaaac acctcccatt agggactacc tccaacaccg gggatcaaat ttcaacatga    72057
ggtttggagg ggtcaaacat ccaaaccata gcagaggatt tttgtcctta attttttaaa    72117
aaattattta tgggtaagag gtatgtgaaa gtttataaaa tactggaaaa gacactgaat    72177
tgaacctcat tctagttcag tggacaagga aaatatgaac aaaaaactaa tttggaagtc    72237
tcataaatac caataaataa tggtataagc aaactaaaag gaaatcagaa tggacatcag    72297
gaaactgatg aagaaaacaa taataataat agcaatctgt tgcttgtcat gttagtaatc    72357
ttagccttca cttcttctaa ttgttactca tgtggtagtt aagagctcag gaattaaatt    72417
gccaacattt actacctggt tgaacttggg caagttattt aatttgcctc agttctctca    72477
tctgttcaat gtaggataat aatagcaact acttactagg gcttctaaga agaataaata    72537
ccttgtttat aatagtgtct ggcacctagt gatggtcctg aagtcaataa tcagaagtac    72597
catcatagtt atgaaatact aaataaatta tacaaacaaa aaataaatgt gtacacatgc    72657
atgtgtgcat atgtgaatga atggatagaa atggtttcat aacgtgatta tttaattagc    72717
cataagaacc acttcctatc cacgctagat agcaaaatta cattacccttt gttaaattag   72777
gtgttgaaag gtcattagtt ctatattaca aattcttatt attaaaaagt tgcttttata   72837
actattccaa caaagcgtac tgtaagaata aaatctggag caggaaagaa tgaacagaca   72897
cataaggctc cctatggaat cagcccaaac ccagtaagtg ttcaagatta cagaaactga   72957
atttctggct ttacttcagc attattctgg gtcccaaaaa tttgctttct ttttaagtat   73017
ttttcagtat ctcttttta gtgaatgtag gatataacca acgttagaag taaattgtaa   73077
aaaatggttt gcaagttttc attaaaatct catgactatg caaatactca gaattttgc    73137
ataaataatc accacgaccc ccaaatgatg ttttcgaatg aatcatgcaa acccacagtt   73197
gagagattaa gtataaaaaa agacagatat ccacctctgg cacaacttca aatgcgtcga   73257
tggagacaga aaatgtcaa acacaaagat tacatgaagc actgcagctt ccatggacag    73317
ggaagaaact accaatactt tctgtatggt aaaatactta aacacacttc agcttttcatg  73377
cattataaag aggattgact tgtagaaact caggaccagt ggctttatgg atctgcaaca   73437
gggaccccta tgctgtatat gaacctagtc aaagagctgc acttccaaat gctgacatac   73497
tgctaaggag attggggctt ctctctggtc ctgttcctct ctttgactct tgactctct    73557
ttgattcaaa gagcaactca gagttttcag aatgatattc taatttgata gtagttgatc   73617
ttttaaattc tagatagtga agggttccag tagattctag ttaacagtaa tgtgtgaagt   73677
ttaaaatgta tctgctgata gagaggaaat tactcatgga agaaatatct ctgatgcata   73737
acacacagtc tggctgtact gagatagttg tttcaaatgg aaaagaatgc agttggtagt   73797
```

```
gcttttaatc agaactttaa gaaccactgg gtgacttaaa agatataatg gtagagaaaa    73857
acctcatttg caacaacaat ggaaaaaaga gataatactt ggaaataaac tccaaatgtt    73917
tcaaacctat aggaccaaca ctttaataaa acactctgca aaacacaaat gtagacttga    73977
acaaatggaa agacattcct ggttcttgat taggatgtct caatgtcatc aaaagatgtt    74037
tgtactcact aagtcaattt ataaattttg tgacatccca attaaaaaaa aaccaataag    74097 cttttttctcc cctgggaaat aaacaaatga actttactac acatgaattt tcacatgaaa    74157
caatagccaa aagagaatat caagaaaaac aatgaaaaga aagagttgtg aggagataac    74217
agccacatca gatattaaaa cctaccacaa aatctgtata agtaaaacgg tgtggtcctg    74277
gaacatgaat gcacatgcaa atcaatgaag cagaacagca agtccagcaa aagacctgac    74337
cacaggtgga aattattcta gtatatgata caggtgcaac tcaaaatgct ggggcagcaa    74397
agaacatttt aataagtgct gttgggacaa ttggaaagcc atttccaaaa gataaatttt    74457
catccattcc tcatgtcatc cagtaagcac aaacttcaaa tagatcagat ttttaataag    74517
taaaagtata caagtaattt ttgatggata aattcctcta taattcctct ataatctgag    74577
ggtagaaaag gccttctgtg actaaaaatc cagatgcagt ttttaaaaat tgacatattt    74637
gactaaaaaa aattgaatgg caaaacacc ataagcaaaa tgataggaca aataaattag    74697
aagaaaatat ttgcaaataa tataaagaac taatattcat aatttataaa gaacttttaa    74757
aagttgatga aaggagatca aaagtactct agaaaatggg caaaagacag gaatagaaaa    74817
tacacaaaaa agatataaaa ttacattaaa atatgaaaat atgttcaatt ttacataaaa    74877
ggaaaattca tattaaaatt atattgaaaa caatttctca tccatcagtt tgacaaaaaa    74937
acaaaagctt gttggtgagg ctgaagaaaa acaggcccat ttttatacat gattttcagg    74997
aaggcaaaag ggtgtaaatc ttatgtaggg gaatttcaca atgtctaaca aaaatatagg    75057
aaccagcttg caggagctct tacttgacaa atgtaaaaca ataaggtacc caaattcatt    75117
cattacaact cattgaatta agaatccatg agtctatact tataataaat aaatacatac    75177
atacataggc agacagctgg agagaaggaa aggctcttcc ttctggtaga atgtcaactg    75237
atgagtgcag ggtgtaatgg aattgaaaat cacccttta aaccatcact gtaagattgt    75297
gggaagaatc aatggggaaa agtttgatga gaagcaggat gtttgtatgg tctcaaagaa    75357
aatgaccaca cattgcttat ttcttgcaag ggagaacata ataaatataa atcaatgtct    75417
tgactgggtg atcaaaatta acataactga agggagatga ttagcaaagg gctctggata    75477
taacacccca agaaggctac attacttagt attgtgggtg agtaggggtt gggagtctga    75537
actgaatcta aacaaataaa tggatggaga attatgggag ccaagttttt cactgttggt    75597
gtggaagtgt gcagatgaac aaggacataa ggctataatc catctattca cacagaatgc    75657
tccacctggt aatggattac agctgaagac attagtataa acaaatgttt agcttaatct    75717
ggatatagaa tgtttcataa aaatatttat agatatctat attttcatgg ttttttatata    75777 tattatatat aaatatatat taatttttct tgctctgtca actaagagga tgtagaagaa    75837
caatgacatt ccagtagcaa tgagcatatc tagtaccaga tcttgatttt caatatcctc    75897
cagtgaaagg aagcagggtt ccctgaagaa atagctgatt ctaggacaaa ggcaggaaat    75957
atacatgagt ctgggtcttg tagttccaga agtaaggaa gtaaaaaaaa aaaaaaaaa    76017 aaaaggcatg gggtagggga tgggagaaaa gaaaaaaaaa tgccgtaagg gttgacaaca    76077
cagatgccac tgaaagagct cccaatggcc aaagctggaa caatatgagc taaaaaaaaa    76137
aaaaaaaaaa gaaaatgacg tattggagta taacccaaaa tacaaaataa atatgtatca    76197
```

-continued

```
gtccatactg atataaataa ataattgatt aagtaaataa agggagaaga gaaaactatc   76257
ttgtgcagaa gaattcctaa taattatgct gaggttttat agatgttatg tatgtatatt   76317
gccttcaagg aggtggagca taactcctta tttattaagt gtgggctact tcctaaagag   76377
ttgagtatga aagcaggagt agtgggggaa gagtaattgt acagtagaga aaactgaaaa   76437
atgcttcttc agccaggtga taaaggtcaa catcatgtca atggtatata ctcttgatac   76497
gatgtaatga aaatgacact ttacctctgc agtctttctc cccaaaattt atatcaccaa   76557
tctaataatg agaaaaacat cagactcatc ccagctaaga gcatacaaaa tgctaaatag   76617
tgttcctcaa tactgtcatg gtcaccaaaa ataaagaaag tctaagaaac tgccataacc   76677
aagagaagcc aaaggtgacg tgatgagtaa atgtaatatg gcaccctgga tggaatccta   76737
gaacagaata aggatattag gtagaaacta aggaaatctt taaaaagtcc acactttagt   76797
taataatact gtattgttac ttgtaaatgt accatactaa cgtaagatgt aaataataag   76857
aaaaactgga tacaggttat atggaaactc tgtattagct ttgaattatt ctgtacatct   76917
aaaaccattc taaaaaacaa agtttattta aactaaaaac aaatccatgt cagctgaaca   76977
gcttgtgcta atcattactg cagaatatca tcacaaaaca cagatgacct gacgtttcct   77037
cacagttagt tctccacagc tcatggggtc atacagcgca gcctaattaa gagatttggt   77097
agtaaaaaga gaattagaga gtggctggca agatggctga ataggaacag ctccggtctg   77157
caggtcccag tgagatcaac acaaaaggaa ggtgatttct gcatttccaa gtgaggtacc   77217
tgcctcatgt cattgggagt ggtcagacaa tgggtgcagc tcacaaaggg cgagctgaag   77277
tggggtgggg cattgcctta ccccagaagt gcaagcggtc ggggaactcc ctcctctagc   77337
caaggaagcc atgagggact gtgccatgag gaatggtgca ctccggccca gatactatgc   77397
ttttcccaga ttcttcacaa cctgcagacc aggagattca cttccgtgcc tacaccacca   77457
gtgccctggg tttcaagcac aaaactgcgc ggccgtttgg gcagacaccg agctagcttt   77517
aggagttttt tttcataccc cagtggcacc tggaatacca ccgagacaga gccgttcact   77577
cccctggaaa gggggctgaa gccagggagc caagtggtct agctcagcag atcccacccc   77637
catggagccc agcatgctag gatccactgg cttgaaattc tcactgacag cacagcagtc   77697
tgaagtccac ctgggaccct cgaccttggt cggggaggg gtgtttacca tttctgacac   77757
ttgaaaaggt ggttttcccc taacagtgta aacaaagcca cagggaagtt caaacaagat   77817
ggagcccact gcagctccgc aaagccgcag tagtcagatt gcctctctag attcctcctc   77877
tttgggcagg gcatgtctga agtaaggca gcagccccag tcaggggctt atagataaaa   77937
ctcccatctc cctgggacag tacacctggg ggaaggagcg gctgtgggcg cagcttcagc   77997
agacttaaat gtccctgcct gcaggctctg aagagagcag cagaagtcct aacacagtgc   78057
tcgtgctctg ctaagggaca gactgcctcc tcaattgggt ccctgacccc ccaccccccc   78117
gcctcctgac tgggagacac ttcccagcag gggttgacag acacctcaca caggagagct   78177
ctggctggca tctggtgggt gcccctctgg gacgaagctt ccagaggaag gaacaggcag   78237
taatctttgc tgttctgcag gctccactgg tgatacccag tcaaacaggg tctggagtgg   78297
acccagtcaa acagggtctg gagtggacct gcaaacacta gcagacctgc agcagagggg   78357
cctgactgtt tagaaggaaa acaaataaac agaaggaat agcatcaaca tcaacaaaaa   78417
ggatgtccac acaaaaaccc gatctgaagg tcaccaacat caaagaccaa aggtagataa   78477
atccatgaag atgaggaaaa accagcacaa aaaggctgaa aattccaaaa accaggacac   78537
```

```
ctcttctcct ccaaacggtc acaactgctt gccagcaagg gaacaaaaat ggacggagta    78597
tgagtttgac gaattgccag aagtaggctt cagaaggtgg gtaataagaa actcctctga    78657
gttaaaggag catgttctaa cccaatgcaa ggaagccaag aaccttgaaa aaaggttaga    78717
ggaattgata actagaataa ccgtttagag aagaacataa atgatctgat ggagctgaaa    78777
aacacagaga acttcgtgaa gcatacacaa gtatcaatag ccgaatgatc aagaggaaga    78837
aaggatatca gagattgaag atcaacttaa tgaaataaac agtgaagaaa agattagaga    78897
aaagagaatg aaaacaaaca aacaaagcct ccaaggaata ggggactatg tgaaaagacc    78957
aaacctacat ttgattgtac ctgaaagtgt acctgaaagt gatggagaga atgaaaccaa    79017
gttggaaaac actgttcagg atattatcca ggagaacttc cccaacctag caagacaggc    79077
caacattcaa attcagaaaa tacacagaac accacaaaga taccctcga gaagagcaac    79137
cccaagacat gtaatcatca gattcaccaa aattgaaacg aaggaaaaaa tgttatgggc    79197
agccagagag aaaggtcggg ttacccacaa agggaagccc atcagactaa cagcagatat    79257
cttggcagac accctaaaag ccagaagaga gtggggcca atattcaaca ttcttaaaga    79317
aaagaatttt caacccagaa tttcatattc agccaaacta agcttcataa gcacaggaga    79377
aataaaatcc tttacaaaca agcaaatgct gagagatttt gtcaccacca ggcctgcctt    79437
acaagaactc ctgaaggaag cactaaacat ggaaaggaaa aaccggtact atccactgca    79497
aaaacatacc aaattgtaaa caccattgac actatgaaga aactgcatcc agtaatgggc    79557
aaaataacca gctagcatca taatgacagg attaaattca cacataacga tattaacctt    79617
aaacataaat gggccaaatg ccccaaataa aatacacaga ctggcaaatt ggataaagag    79677
tcaagaccca ttggtgtgct gtattcagga gatctacctc atgtgcaaag acactcacag    79737
gctcaaaata aagagatgga gggatattta acaaacaaat ggaaagcaaa aaaaagcagg    79797
ggttgtgatc ctagtcccg attaaacaga ctttaaacca acaaagatca aaaaagaaaa    79857
gaagggcatt acatagtggt aaagggatca atgcaacaag aagagctaac tatcctaaat    79917
atatatgcac ccaatacaga agcacccaga ttcataaaat aagttcttac agatctgcaa    79977
agagacttag atgcccacac aatcatagtg gaagacttta cacccccact gtcaatatta    80037
gacagatgaa tgagacagaa aattaacaag aatattcagg acttgaactc agttctggat    80097
caagtggacc taactgacat ctacagaatt ctccaccca aatcaacaga atataccttc    80157
ttcacagcac cacatcgcac ttattctaaa attgatcaca taattggaag taaaatactc    80217
agcaaatgca aaagaacgga aatcagaaca acagtctttc agaccacagt gcaatcaaac    80277
tagaactcag gattaagaaa ctcactcaaa accccacaac tacatgaaag ctgaacaacc    80337
tgctcctgaa tgactactgg gtaaataatg aaattaaggc agaaataaat aagttctttg    80397
aaatcaatga gaacaaagac acaatgtacc agaatcaacg ggacacaact aaagcagtgt    80457
ttagagtgaa atttatagca ctatatgccc acaggagaaa gtaggaaaga tgtaaagttg    80517
acatcctaac atcaccatta aaagaactag agaagcaaga gcaaacaaat tcaaaagcta    80577
acagaagaca agaaataact acagcagaag tgaaggagat atagagacac gaaaaaccct    80637
taaaaaatca ataaatccag gaggtgcttt ttttaaaga ttaacaaaat agataagtga    80697
ctagtcagac taataaagaa gaaagagag aagaatcaaa tagacacaat aaaaatgata    80757
aagggaatat caccactgat cccacagaaa tacaaactac catcagagaa tactataaac    80817
acctctacac aaataaacta gaaaatctag aagaatgga taaactcctg aacacataca    80877
ccctcccaag actaaaccag gaataagttt aattcctgac tagaccaata acaagttctg    80937
```

```
aaattgaggc agtaattaat agcctaccaa ccaaaaaaag cccaggacca gacagagtca    80997
cagctgaatt ctaccagagg tacaaagagg agctggcacc attccttctg aaactattcc    81057
aaacaatgga aaagagggac tcccctctaa ctcacttgat gaggccagca tcatcctgac    81117
accaaaacct ggcagagaca caacaaaaaa agaaaagttc aggccaatat ccctgatgaa    81177
catcgatgag aaaatcctca ataaaatact agtaaagcaa atccagcagc acattgaaaa    81237
gctcatctac catgatcaag tcagcttcat acctgggatg caagactggt tcaacatatg    81297
caaatcaaca aatgtaatcc atcacataaa cagaaccagt gacaaaaacc acatgattat    81357
ctcaacagat acagaaaagg ccttcgataa aattcaacac cccttcatgc taaaaactct    81417 ccataaaacta ggtattgata aaagtatct caaaataatg agagctatct atgcaaacc     81477 cacagccaat atcatactga atgggcaaaa actggaagca ttccctttga aaccagcac    81537 aagacaagga tgccttctct caccactcct attcaacata atattggaag ttctggccag    81597
ggcaatcagg caagagaaat aaataaacgg tattcaaata ggaagagagg aagtcaaatt    81657
gtctctgctt gcagatgaca tgattgtata tttagaaaac cccatcgtct ctcagcccaa    81717
aatctcctta agctgataag caacttcagc aaagtctcag gataaaaaat caatgtgcaa    81777
aaatcacaag cattcctata caccaataat agaaaaacag agagccaaat catgagtgaa    81837
ctcccattca caattgctac aaagagtata aaatacctag gaatacaact cacaacgaat    81897
gtgaaggacg tcttcaagga gaactacaaa ccactgctca aggaaataag agaggacaca    81957
aacaaatgga aaaacattcc atgcttatta ataggaagaa tcaatatcat gaaaatggcc    82017
atattgtcca aagtaattta tagcttcaat gctataaatc aagctatcac tgacttcctt    82077
cacagaatta gaaaaaatta ctttaaattt cacatggaac taaaaaagag cctgtatagc    82137
caagacaatc ctaagccaaa aaaataaat aaataaatct ggaggtatca cactacctga    82197
cttcaaacta tactcaaagg ctacagtaac caaaacagca tggtactggt accaaaacag    82257
atatacagac caatggaaca gaacagaaca gaacagaaca gaggcctcag aaataacacg    82317
acacacctac aaccatctga tctttaacaa atctgacaaa acatgcaat ggggaaagaa     82377 ttccctactt aataaacagt gttgggaaaa ctggctagct atatgcagaa aactgaaact    82437
ggatcccttc cttacacctt acacaaaaat taactcaaga tggattaaaa tattaaatgt    82497
aagacctaac accataaaaa ccctagagga aaacctaggc aatagcattc aggagatagg    82557
catgggcaaa gacttcatga ccaaaacacc aaaagcaatg gaacaaaag ccaaaattga     82617 caaatgggat ctaattaaac taaagagcac agcacagcaa aagaaattat catcagagtg    82677
aatgggcaac ttacacaatg ggagaaaatt tttgcaatct gtccatctga caagggcta     82737 atatccannn nnnnnnnnn nnnnnnnnnn nnnnnnnnnn nnnnnnnnnn nnnnnnnnnn    82797
nnnnnnnnnn nnnnnnnnnn nnnnnnnnnn nnnnnnnnnn nnnnnnggc tgaggtggca    82857 gaattgcttg agccctggag gtctaggttg cagtgagtca tgatcatgcc actgcactcc    82917
aaactgggca acagagtgag accctgtttc aatttattta tttatttaa agaagagtga    82977 tattgttttg aatgcaggtt aatagtcctt aatccctga ggtcggtgtt gcccagtgcc     83037
ataactttag gactaccttc tttcacaaaa tagatgagaa aggaaaaaac agagtggctc    83097
acgcctgtaa tccctacact tgggaggctg aggcaggtgg atcacttgag gtcaggagtt    83157
caagaccagc ctggccaaca tagtgaaacc ccatctctac taaaaataca aaaattagcc    83217
aggcatggca acaggtatct gtagtcccag ctacctggga ggctgaagca ggagaatcac    83277
```

```
ttggacctgg gaggcggagg ttgcagtgag ccaagattgc accactgcac tctagcctcg   83337
gcaacggagc gagactccat ctcaaaagaa aaaaaaaaaa agaaagaaag aaagaaagaa   83397
aagaaaggaa aaaacagaaa aaaatatcct gaagaactca gaacagtctc taagtgctta   83457
gttgtgtatg ttcatagcca tgctgatgct gacaacaaat ccaaaggat cacaccaaac    83517 attttttcaa ttaaaaatta taataaataa cgtaaggtaa tacataggct aattagcttg   83577
atttagccac tccaaatttc aaaacattat gttgtatgcc ataaatatat acaattttta   83637
tttgtcaatt aaaaaataga agataaaata attaggtaaa taggctcaaa aacatttaag   83697
aaattacacg tgaatggggc ttcattaaaa aaaattccat cctagccagg cacggtggtt   83757
tatgcctgta atcccagcac tttgggaggc caaggcgggt ggatcacccg cggtgaggag   83817
ttcgagacca gcctggccaa gatggtgaaa cctcatctct actgaaaata taaaaattag   83877
ccgggcgtgg tggtgggcac ctgtaatccc agctacttgg gaggctgagg cagagaactg   83937
cctgaacctg ggaggtggag gttacagtga gctgagatcg tgccactgca ctccagcctg   83997
ggtagtaaag caagacatca tctcaaaaaa aaagaaaaa aaaattccat cctaagtaaa    84057
tctttgggaa taaaggctag gtttttttccc ccctgctttt atgtctattg agtttcttcg   84117
ctttagaatg agcctctgca ttaataagat cctctgggat catatccaca aaagggtatt   84177
aaatccttga agggttgtta taaatcttct gtcttggcca cactaataga aatccagcct   84237
aggaacacct tcctcacccc tgagccccctt ctctaaggaa ctctacagtg tcagtcagtc   84297
atccaaatca atgactttac ccatcaccta caggcagcca gtctgcctgg ctgaaccatg   84357
gcagtcattc tgcctcagaa ataactctga tggacaaccc gggcagggag gaatacggga   84417
aattataaga aggacctagg catggaggta gaccagctga aagttttcca ggaacatttg   84477
aaacactctt ttttacactt gagacaagtg acatggtttt cttaatgagc acatgcagcc   84537
aaaatcccag ttcatatact ggaaggaaaa gtctcataga acaagcagca gacctctgag   84597
gaatggattc agaaacaatt ccagacccag aatgtgaaaa gttagcttta aataccctgc   84657
tctcagacca cccaggaatg gtatccagac ctcatcctgg cctctagaga attcccaggg   84717
ccacctgtca aagtggcttg tcaggcatgg ataaaaatgc cattggggga aggaaaatgc   84777
aacataaagc cttctagcag aggaaatatg aagaatagta ttttctacac gactgcgcta   84837
aagggttcat ttaaagaaaa aaacacttct aactattagg gaaaattcca ggttaactat   84897
acttaaaaaa aaaaaaaaag cccaaaaatc tagtaaatat tttgctggga aattcacact   84957
taaagaaatg gtctttcagg cccctgggga gaaggcatta agctgacaca tttttcaaat   85017
caaaatggct gctctaaaaa cataaacctt caaaatgaac accacagaga gccccttcct   85077
tcctgtgctg agcacgctca ctacccactc agagcgccct gtgccaaggc gaagtcaaac   85137
cccatagaaa cctgatcccc actgtggaga aaactgtgca gcgcccttgt tttctgtcgt   85197
gctttgtttt gtatttcaga tgtgctggtc acatctgttc tttatctccc ctcttccact   85257
gtgattttgt ttacaggatc ccagaacaat ggggactgca gaatctccac acagatgaca   85317
ggagacaagg ctctcagggg gtagtcactg tctgcaaaac gtggagccaa aggcgtggtt   85377
ttcagagtag ctgccaacac tccaagttac tcaggctcat ggaccaggaa tgactggaaa   85437
ggagactgcc ttgtctgggg aagatccaga cccacagatg caattttttg aaagtaatct   85497
ctttacaatg gcctgcccat ctcctctctc tgcttagaag ttttttgtgtt ctgtaaggag   85557 ccttctaatg ggcttctgtc tgcctgggct tctgtccctt tggttctccc agtctgctct   85617
ctgtctcttt tgtttctttc atccctggat tccaggaagt caaggtcagg gcagcttacc   85677
```

```
agtccctaaa caccattatt ttggcaggat gctttggcag tggaatgaat gcctgcagaa    85737
ggcctcacct agtcacccac aaattcatga acacagctgt gacttttcga agcagaagcc    85797
agactcttag tctttgtttt ttatcttttt tttcttttt ttttttttt gagacggagt      85857 ctcactctgt cgcctaggct ggagtgcggt gacaccatct tggctcactg caacttctgc    85917
ctcctgggtt caagcagttc tcctgcctca gcctcccgag taggtgggat tacaggcacc    85977
caccactaca cctggctaag ttttgtattt ttagtagaga tggggtttca ccatcttggc    86037
caggctggtc ttgaactcct gacctcatga tctgcccacc tcggcctccc aaagtgctgg    86097
gactagaggt gtgagccacc gcacctggcc tgttttcat cttatttta aaagtcatat      86157 gtcgagcaag aaaaaatcta gactacagtg ttactcaaac tgtgggttgc taacagacag    86217
tgctcctcat ggctcttact actggtcagt ggagaaacga agaaattgag agaatgcatt    86277
tagaaaattt catagtgctt tcacagaata atcttatgtc tcttgaatct aataataaaa    86337
attggggagc ctatatttta catgtctttg gtttgctatt tcacttttct atttattcat    86397
ttttagtata tttataagaa tgtcagtcca taatggcatg gaaataattc aagaagaagg    86457
aaaccctatc acacatagta tgaaaagcaa accacagacg atacaaaaaa agaaagaaaa    86517
aaaacccacc aaacactcat ttagccatta cccagccttt gtcaaaactt aacattttat    86577
catgtttgcc tttgctttt taattttat tgattggttg attgattgag acagactctc       86637
actttatcac ccaggctaga gtacagaggc ccacatggct cattgcagcc tcaacctcct    86697
gagctcaagg gatcctcaca cctcagcctc caattagct gggactaaag ctcatgccac       86757
catgtttggc taattaaaaa ttttttttg tagagacagg gtctcactat gttgtccagg      86817
ctggtctcaa actcatgtga tcctcccacc ttggcctccc aacgtgctgg gattataggc    86877
atgagccatc gcacctggac attgccttt tttctttttt tttttgaga cggagtttag        86937 ctctgtcacc cccaggctgg agtgcagtgg cccaatcttg gctcactgca acctccgcct    86997
tcctagttca agcaatactc ctgcctcagc ctttcgagta gctgggacta caggcatgca    87057
tcaccatgcc cagctaattt ttgtattttt agtagagaca gtgtttcacc atgttggcca    87117
ggctggtctt gaactcttga cttcaagtga tccgcctgtc ttggcttccc aaagtgctgg    87177
gattacaggc gtgagccacc atgcccagcc tagccattgc cttttttaaa gagattaaaa    87237
attacacatt tttcctcacc tttcctctct tccacccttc tctttaccct tccctccctc    87297
ttcattctct ttcttttccc cctcttcctc ctctcttcca ttctccttct acccacccca    87357
cttctcttct attccctccc ctccctcctt catctgcctt ccacttctca cttccctaca    87417
cttctacctc ccttctctct tctccccctc cctctaattt ttaggtaaat tgagcatggt    87477
agacctccaa ggttgggaga cagaggaatc cacagtggcc cagcatgagg aagcagagcc    87537
tgggcaggat gcataagtgg gatgccaggt gaagggatgt ggggtgtcag cacccaggag    87597
aggtgagcaa gttgtccatg aagcagggca gcctctggca tgggaagtca ggactcaaac    87657
aggagagaaa gcctgtcaca tgggagaatg agatgggata ttagccgtac tccagaggat    87717
tgatcaaata ataaatgcg ataagaataa tgacagccag gtctctatgg aaataaggaa     87777
aactaggata aattctgaat tgttaacca gaattagatg tgttggtgaa aacttaaagt       87837
ttatcatata tagagatcaa cgaataatat agttttaaat gtgtatatat gcatatacat    87897
ttctattccc tagctccgtg tgccgagagc agcgacaccc catgagcaat gaacacacct    87957
agtgctcaga tctggtttct aaatattgtt tttcactaaa aggaatgagg acttcttgga    88017
```

```
gagctggcag attctagagt taagactgag aatgcacacg atgagcctgg aacatcttgt    88077
accagaaatc aagacagtac tccaacaatg atgaggatcg gtcaaaggac acagaagtga    88137
acttgaatgg gcttcccctg gccggtgtgg tcaggatttg aacattaaat taaataatta    88197
tagtaacaaa ttataatcta tttgctaaaa tagaaatcat gagcccattc agatgtacat    88257
taaaacatga gtaaattaag agtttgaagg gatgggacat ttacatagtt attcattata    88317
aaggaaaaga gagtctcttt acagtgaaaa agcgggcaga caccacagta atcatgtgat    88377
ccagctgaac atcatcattg cttgagccca agagtttgag cctgcagtga actgcgatca    88437
tgtcactaga ctccagcctg agtgacagac caagatccta tctctaaaac aacaacatta    88497
ttctggtttc ttagagtgtg ttaaaaaaat tatacaaaat gaacatcatc agtgttaatt    88557
aaataaaact taataggagg gcattggttc agactgggct cctaccctag gcctaacaga    88617
ccaaaatgga gttaaaccaa gccaaaacta agttgtttat ctgaccttcc aagaaatcag    88677
gaaagaaaaa tagccaaatc cctaaacagg ccagttttat acagcatgat aaggaagtcc    88737
cctctgcttt aacccttaca aaaaggtaat ctggactggg tgtggtagct catgtctgta    88797
atttcagcac tttgggaagc cgaggtgggt ggatcgtttg agaccaggag tttgagacca    88857
gcctggccaa catggcgaaa ccccacctct actaaaaata caaaaattag ccgggtgtgg    88917
tggcacacac ctgtagtccc agctactgtg gaggctgagg catgagaatc gctggaaccc    88977
aggaggagga ggttgcagtg agccaagatc atgccactgc actccagctg gctacagag    89037
tgagactttg tctcaaaaaa aaaaaaaaa aagaaagaaa gaaaagggaa aaaagtaacc    89097
tgaagtaact tgacattggt caatcagctt tatttctatt gttctgtttc cttgttctca    89157
ccttacaaaa cccacttctc ttttgccccc tgccaatcta ttcttctatt ttgtagaata    89217
gaggctatct taactcataa attccaaata aaagccaatt aggtctataa ctaaactcat    89277
gattttgtct tttgacatca gtaatgggac aaattgaaac tgtgcaccat tggtaccata    89337
caatgagaag tacacgacat cacttctgtg atcatcctgc tacatgaatc taatcacaag    89397
gaaatatcag aaaaacccaa attgaagggc attttacaaa ataagctaac tacaagcttc    89457
aaaattatca gggtcataaa agtcaataga agaccaagga atctttcttt tttatgtata    89517
tattctccaa tttaaaactt ttaattaaaa agtaaacttt aatgtcgaaa atgcaaactt    89577
ggggaagaca gaaaagatca cacacaaggc tgtcacttca cacttggaag gttgcacaat    89637
ggccggacag aggcgctcct cacttccag atggggtggc tgggcagagg cgctccttac    89697
ttcccagacg gttggcagcc aggcagaggc gcctgctcct cgcttcctag acggttggca    89757
gccgggtaga ggcgctcctc acatcccagt cagttggcag ccagacagag gcgctcctca    89817
cttcccagac ggggcagtgg ccaggcggag gcgctcctca cttcccagac ggttggcggc    89877
cggggcagag gcactaacca aggaaacttt ctataatgga gtaggttaaa ggaacatgat    89937
aaactaaaca taatgcttga tttggcattg aatccttttg atctaagtgg caaaacttga    89997
atggggtatg aatatgagat actagcaatg tcaatattaa tttcttcttt ttttttttt    90057
tttctgatga tggagtctcg ctctgttacc caggctggag tgcagtggtg caattttggc    90117
taactgcaac ctctgcctcc cgggtccaag agattctcct gcctcagcct tctgagtagc    90177
tgtgactaca ggtgcccgct accatgcctg gttaattttt gtattttag tagacacggg    90237
tttctccatg ttagcaaagc tggtctcgaa cccctgacct caggtgatct accagctcag    90297
cctcccaaag tgctgggatt acaggcatga gccatgcacc cagcctatt atttatttga    90357
gatggagtct tgctctgtca cccaggctgg tgtgcagcag ggcaatttca gctcactgca    90417
```

```
acctccacct ctggggctca agtgatcctc ctacctcagc ctcccgagta gctgggacca   90477
caggcgcatg ccaccatgcc caactaattt ttgtattttt tggtagagat ggagtttcac   90537
catgttggcc aggctggtct caaactcctg acctcaactg atctgcctgc ctcagcctcc   90597
caaagtgctg ggattacagg tgtgagccac tggacccagc cctcagcctc gttttttctt   90657
ttcttttctt ttctttcttt ctttttttt tttttttttt tagaggtgga agcttggcta   90717
tgttgtccag gctggcctca aaccctggg tttgaactcc tgggctcaag ggatcctcct   90777
gcctcagccc ctggagttgc tgggaccaca gggatgtatt accacacaca gctcattttc   90837
ttaatctcct cacctttaat aattttgtct ctaccctatc ttaaccatac actcccatgg   90897
gcctctctgg attttgtctt tcttaatatt ttcttaagcc ttttttctata gcctcaatca   90957
agcatcccat tttcatattt ccagctcatt cccattcctt tccatattca gacctgcatt   91017
cttctggttg ctcagatcaa atactttgga accattcttg atccattcct tgtggcagag   91077
gagaggaaat gtgtaaagga gggtgaggcc ctacagtcaa gaggtgggat agcatgaatg   91137
caaagaagag tagcactggg gccagccaca gtggctcaca cctgtaatct cagcactttg   91197
agaggccaag gcatgcagat cacctgacca gtctggccaa catgttgaaa ccccatctgt   91257
actaaaaata caaaaattag ccaggcatgg tggctcgaac ctgtaatccc tgctactcag   91317
gaggctgagg cagcagaatc acttgaacct ggaaggcgga ggttgcagtg agctgagatc   91377
gcaccactgc actccagcct gggtgacaga gtgaggctcc gtctaaaaaa aaaaaaagag   91437
tagcattgga tttgggaatg taagcttata ggtgaacttg caaacaggaa tgttattgga   91497
aggtggggac aaaatcctga ttttttcaat gttttggaga tagtctgtca ctaaggctgg   91557
agtacagtgg tgcaatcatg gctcactgta gcctcaaaat gttgggctca agctatcctc   91617
ctgcctcagc ctccagagta acagggtcta caggtgcacc accacacctg actaattttt   91677
attgtttatg gatatggggg tctcactatg ttgccaaggc tggtcttgaa ctcctggcct   91737
caagcagtcc tccctgtctt ggcttccgaa agtattggga ttacaggcat gcccagccaa   91797
tcctgatttg aattgaggaa ataatcatag tatttctcaa ggaattgctt gaatctgaat   91857
actcaagaag cacttattaa gcaatcaaat gatgtgggct aagtcatttt cgaaagtctt   91917
gaacctttag ccttgaaagt cggaccaatg agtttgtgcc ttatttgttt ctgaaggtct   91977
ttttgagtct tgcgttagga aattaatccg gcaaaagcag gcacaaaaga tcttgtgggt   92037
tgaggagtca gtaaaaagac tactggaata gcccgggtac aagcttatga gacactgaga   92097
tgggagccgg ggggttaggg ggtgggcaga agcgggaaga gcagtggcac tgggaatcaa   92157
tacaagagga aggaaaatca acaaccatac catagaaaat gagtcagatt tggaactgat   92217
tagatgtgga tggggagaca gaagaatcag agaataagtc aaagctagcc aggagtgttt   92277
caacctggat tcctgagaat cctgttacct aggaggagac actgtttctt agatttagtt   92337
tgaggagaag atgatagctt tggtcttaaa ttgcttttt tttgttgttt ttttttctcg   92397
agatggagtt ttgctctgtc tccgggggctg gagttcaatg gcatgatctg gctcactgc   92457
aacctccacc ccctgggttc aagtgattct cctgcctcag cctcctgagt agctgggatt   92517
acaggcatgc accaccacgc ctggctaatt ttttgtattt ttagtagaga tgggggtttca   92577
ccatgttgac caggctgatc tcgaactcct gacctcgtga tccacccgct tcggcctccc   92637
aaagtgctgg gattataggc atgagccacc gcgcctggcc ttaaattgtt ttttgttg   92697
ttttcagac agagttttgc tctgttgccc aggctagaag ctcagtggtg ccatcttggc   92757
```

```
tcactgcaac ctccgcctcc tgggttcaag cgattctcct gcctcagcct cccaagtagc    92817
tgggattaca ggtgcatacc accacacccg gctaattttt tgcatttta gtagagacgg    92877 ggtttcacca tgttggccag gctagtctgg aactcctgac ctcaggtgat ccaccccct    92937 cggcctccca aaatgcaagg atcacaggtg tgaaccactg tgcctggcaa aaatatttt    92997 taattttaat tttttaaatt tgttttgag acaggaactc actctgtcac ccacactgga    93057
gtgcagtggc atgatcacag ctcactgcag cctcaacttc ctgggctcat gcgatcctgc    93117
tatccacccg agtagctgga ataacaggtg tgtgccacca tgcctggcta attttttaat    93177
tttttgtaga gatgaggtct cattatgttg cccaggctaa tctcaaactc ctgagctcaa    93237
gggatccttc caccttggcc tcccaaagtg ctgggatgag agacgtgagc cacctcatcc    93297
tctagtattt ttcactgata gagctagaag acaacctggg aaaggcagca attagaaatt    93357
aggtcataga agtagaaaga gtacttgagg ctgcagtctg tcaagctgca tggaaatgaa    93417
agttgaagcc ctaagatatg atgaaccaca gtcataacta taacttcctt ttaataaggc    93477
ttgctttctt ccaacagctg ccttaaatat ttgaaatatt tctctcccag tcgttatggt    93537
acagtgtaag taagtgttgt taactcagta ctgcagacca gaaagctaag gttcagggga    93597
atcaaataac ttgtcatgtt aacagaactc acaagtaaag aactagatct tgaacccaga    93657
tccacctgat cccatgcagt ttgatgtcag aatttggtag tcaaaggagt caatgaaaca    93717
gacagagaag aatttgttag gagaaagaaa attatgtatt tatttttaatt ttatttattt    93777 ttatttttat tttttttgaga tggagtcttg ttctgttgcc caggcgggag tgcagtggcg    93837
caatcttggc tcactgcaac ctctgtctcc tgggttcaag tgattctcct gtctcagcct    93897
ccatagtagc tgggactaca ggcgtgtgcc accatgcctg gctaattttt tttgtatttt    93957
taaaagagac agggtttcac catattggcc aggctgccct cgagctcctg acctcgcgat    94017
ccacccacct cagcctccca aagagctgag attacaggcg tgagccaccg aacccagctt    94077
atatatttat ttatttattg tatttatttta tttatttgta gatagagtct cactctgtca    94137
tccaggttgg agtgcagtgg tgtgatatcg gcttactgca acctccacct cccaagttca    94197
agtaattatc gtgtctcagc ctcctgagta gcacagaaac ccccaccat acccggccat    94257 accgtacacc ataccattac agaagcaccc caccataccc agccatactg tacaccctac    94317
cattacagaa gtacccacc ataccccagcc atactgtaca ccctaccatt acagaagtac    94377
cccaccatac ccggccatac cgtacaccat accattacag aagcacccca ccatagctgg    94437 ccaattttg tatttttagt agagacacag ttttgccata ttggccaggc tggtctcgaa    94497
cttctgacct caagtgatcc acctgcctca atctcccaaa gtgttgggat tcaggcatg    94557 agccacctag aagaaataaa attataactt tgtggggcta ctgagggtga agaaagaaac    94617
caaggaattt caagaaggaa aagttcacca gtcaaatgct ccagaactaa gaaaacacaa    94677 caaaaccccac tgagtttagg tgttagtgtt ggtttcagtg gatggaggag aaaggcagat    94737
tcctaaggtt aaatctgaac ataagcccag agtaaggaga ggatcctctt ggtattatgg    94797
tcaccaactg tcctaatgcg tctaggactg tccccttttt agcacagaaa gtcacacatt    94857
tcaggaaact cctatgtcct gggtaaccca gggccaccct acccatggca gctagtgtaa    94917
ccaccctacc cccggcctct cctttttct gagacagagt ctgctctgtg acccaggctg    94977
gagtgcagtg caacctccac cacccaaatt caagtgattc tcctgcctca gcctccttag    95037
tagctgggat tacaagcgtg tgccaccatg cctagctcat atttgtattt ttagtagaga    95097
tggcgtttca ccacattggt caggctggtc tcgacctgac ctcaagtaat ctgcccatct    95157
```

```
tggcctccca aaatactggg attacaggcg cgaaccatgg cgcctggcct tggtgtaaac   95217
cccttttaag agaggttgag caaggaagag ctgaaagata aggggggttgc ttccaagtgt   95277 agcaaggtca aggaaaggtt ttttattttt tttgataaag aaaacttgcg tctgttaata   95337
aactgggaga ggagattggg aagtacaatc gtcgttggac ttgatcccag aggaagcgaa   95397
actgcattgt tctgaaaggc aggcggcagt gtcccatgtt tctcacagcc ctcactgtgc   95457
tggctcagag ttgccctgtc ctgggactct gaacaggcag tgagtgctgg attccagcct   95517
ctgtgcatgc cttcacccga cagcgctgcg agcagagtg ttggataaaa gtcggacaca   95577
ttagggttct gcactactgt gactgtggct gtcacacctt tctgggcctc agtttcctca   95637
actgtaaaag ccaatattac cagataaaag tggggagcac agtgcctaac acatgacagg   95697
aacaggtaga gtgtccctta ttcctttatc caaaatgctt ggtactggag tgggtttttt   95757
gttgttgttt ttgttttttgt ttttgagatg aagtcttact ctgtcaccca ggctggaatg   95817
cagtggcaca atcttagttc acggcaacct ccacctccca ggttcaagcg attctcctac   95877
ctcagcctcc cgagtagctg ggattacaga tgtgtgctac cacacctggc taattttgt   95937 attttagta gagatggggt ttcaccatgt tggccaggct ggtctttaac tcccgatctc   95997
aggtgatctg cctgcctcgg cctcccaaag tgctgggatt acaggcatca gccaatgagc   96057
aagaaataaa ttctttatca gatacatgtt ttacaaagaa tttctcccag tcttgtcttt   96117
tcattccctt aagagtcata ctgtggccag acacacctgt aatcccagca attttggaag   96177
ctgaggtggt ggattgcttg ggcccagtg tttaagacct gtttggcaac atggcaaaac   96237
cctgtctcta ccaaaaaaaa atataaaaag acaaaaacaa aaacaaaaa tttaccgggc   96297 atggtggcac acgcctgtaa tcccaactac tcggaggct gaggtggcag aattgcttca   96357
gccctggagg tataggttgc agtgagtcat gatcatgcca ctgcactcca aactgggcaa   96417
cagagtgaga ccctgtttca atttatttat ttattttaaa gaagagtgat attgtttga   96477 atgcaggtta atagtcctta atcccctgag nnnnnnnnnn nnnnnnnnnn nnnnnnnnnn   96537
nnnnnnnnnn nnnnnnnnnn nnnnnnnnnn nnnnnnnnnn nnnnnnnnnn nnnnnnnnnn   96597
nnnnnnnnnn gtgaaaccct atctctaata aaaatacaaa agttagctgg gcatggtggc   96657
ttgttcctgt aatcccagct actcgggagg ctgaggcagg agaatcgctt gaacccagga   96717
ggtggaggtt gcagtgagcc gagatcatgc cactgcactc tagcctgggc cgtagagcaa   96777
aactctgctt ccaaaaaaaa aaaaaaaatc tattgggttt taaattatac aatcattcta   96837
gaaaatgtct tacaatacaa tgttgtataa gctaagtata aaaagtaaaa agagtaaaaa   96897
tggccaggcg tggtggttca cacctgtaat ccaagcactt tgggaggcca acgtgggcgg   96957
atcacaagct caggagttcg agaccaacct ggccaatatg gcgaaaccct gtctctacta   97017
aaatacaaaa attagctggg cgtggtggcg cacacctgta gtcccagcta ctcaggagac   97077
tgaggcagaa gaatcgcttg aaccggggag gcagaggttg cagtgagctg aggtcacacc   97137
actgcactcc agcctcggtg acagagtgag actgcatctc aaaaaaaaag gaagcgtaaa   97197
aatttacaaa atccacttcc ttccagcccc aattctacaa agcaaaggcc accactgctg   97257
ttgatatgta tatataagct tcatgagggt ttgtctgttt tctttaacat tatatcccta   97317 attttttggca gtgtctaatg catagtaatc attcaataaa tattcattga ttaaatgatt   97377
aaagtaatgt tctgcatgta tattttttac tttagtatca catttagtgt gtatatataa   97437
gattacattg tattctatat aattaatata ttatacatta tttaaccaat gcctgaactt   97497
```

```
ttaggctgtt tataattttt cctatagcaa acaatgctga tacaatcaac cttttatgca   97557
catctttgta cttgtgtgat tctttctgaa gaacaatttt tagaactgga attacagtgt   97617
caatgtgcaa acatattaaa cttttttag  tatttctttc ctctattttt ctatttaggg   97677
ggcttttttt ctaattacaa aagtagtgca tgttgtctgt aacaagtcta attataatgc   97737
taaaagttac caaacattta ttgtgtacca gtcactatgc caggattttt tgtgtattac   97797
cttatgtact ggctggctag gccaagggag ggtagcccat ggaaagcccc aaagtaagga   97857
aaattaaaaa aaaaattctt ccgcatgaga acagatgagg aaatattgtt tcaatgacaa   97917
tacagcaaga attacatgtt ctagaatgca gccatttggt tcgggatga  tgtgcctttc   97977 caaggatggt tacttttta  aatagtaagt ataattttgg gagctgacct tcttgaggat   98037
ataaaagacc taaattctac attgttgtga ttctctcacc aggcagacat ctcattctat   98097
atctatgcta caactaatt  gttagcatct ctgacctttg gagactttc  cataaaaga   98157 caaaggaggc aatgggaaac cacatctacc tacttgcatt tttatcttac atagaccttc   98217
aaggtaactt agtttaagca gacttaaaca gaatccagat cattattctc attcatcttt   98277
ttgtttttgt ttttgttttt gttttttttc tgagatgtag tctcgccctg ttgcccaggc   98337
tggagtgcag tggcgcgatc tcggctcact gcaagctccg ccttccgggt tcacgccatt   98397
ctcctgcctc agcctcccta gtagctggga tcacaggcgc cggccatcac gcccagctaa   98457 tttttttgtat ttttagtaga cgggggttt  caccgtgtta gccaggatgg tctcaatctc   98517
ctgaccttgt gatccgctcg cctcggcctc ccaaagtgct gggattacag gcgtgagcca   98577
ccgcgcccag cctattctca tccatcctta agactggact ctttggtcat tgttaactga   98637 cttttttcgta taggataaat tcttaaacat gagatagtag tcaattctgc caacattcag   98697
ttgttgtttc tgaatttccc acattgctta aggtcaactc caccatgacg ctataaaaac   98757
acttttctcc atttttttcat atatttgtat aggtttgttt ttacatttaa gtgaattta   98817 aagataaaac ttacctatct atatggaatg aggaaggaaa cctcttactt tcatatacat   98877
aaccaattat gttacactat ttattacata aaccatactt tatcaatgat tgcagtgcca   98937
tctttgtcat atattaagtc ctaacaaata cctaaatatg ttcctacaat ctctattcta   98997
tttacagatc tacttgacag ctgtcgaacc aatacatgcc attctgacca taatacccttt  99057 aagataagtt tgaccattta acataagaag taataaccag accgggctca gtggctcacg   99117
cctgtaatcc cagcactttg ggagtccgag gtgggtggat cacctgaggt cggaagttca   99177
agaccagcct gaccaacatg gagaaacccc atttctacta aaaatacaaa attagctggg   99237
cgtggtggca catgcctgta gtcccagcaa ctcaggaggc tgaggcagga aaatcgcttg   99297
aacccgggag ccggaggtta cagtgagctg agatcgcacc attgcactcc agcctgggca   99357
acaagagtga aattgtctca aaaaaaaaaa aaaaaaaaaa aatgtgggga aaaaaatctt   99417
cctcagctga agaagaaaa  aaaaaacaaa tctgacgtgg tagacaaaat agtctaaagg   99477
aattccctac tacaaaataa tgagatcctg cacaaaacaa aatgtttatt gctgggcttc   99537
caggaaataa ggtaaacctc tgacagtagg tccaaacctt gaactgacac cagaatagaa   99597
gtcctaagat gcttaaaaag tcagcttgtc ctgcaggcat atgtgatatc agctctgcaa   99657
tgtagagttc aaatttgggg tcaatagaaa aaaaatagaa gctgaagctg agctttcctg   99717
attaaagaaa gggaacaaaa gtgactccta gcagaagcta ttccgctcac agtttcattc   99777
gacggatttt ctacaagtta aggttaatga aatctgactg ccaagcatac gtgttaatga   99837
gtttcttctg agtgagagcc agctgaaatc acaaacaaca gatttggaca cccttaatta   99897
```

```
ttttaattat gtataagatg ttttaaataa ataggagatc ttttttgtag ttcataaatg   99957
cgatgattgg gttttcatgt ttatgtgtga gatgtgcttc cctcaaacct tgttatgatg  100017
tcagtacgtt atccatctga tgtggaagaa aagaaaaca aacaagaaga aataaatagg  100077
agtcataaag caataaatta cagaaacaca aatatgagga ataaaagatt atccaaagtg  100137
gccagacttt agaagaagcc aaagtgaatt tttagttttt aaaaattgtt gaagtaaaaa  100197
tttgaatata tggataaaaa ttagatacag cttaaaacag aattagtaaa ctggaagttg  100257
ggtagaataa attatccaga atacagccct ctcactccca aatggatagt atgataagag  100317
atagaagtgt atatatctaa ttcaaatcca gaagtagaga acagataaga ctgagaagtg  100377
gcaatatttg aagctatttg ccaggcacgg tggctcacgc ctgtaatccc agcactttgg  100437
gaggctgagg tgggtggatc acatggtcag aggttcgaga ccagcctgac caacatggtg  100497
aaaccctgtc tgtactaaaa atacaaaaat tagctgggca tggtggcagg cacctgtaat  100557
ccaagctact caggaggctg aggcaggaga attgcttgaa cctgggaggc ggaggttgca  100617
gtgagccgag atcgcgccac tgcactccag cctgggtgac agagcgagac tctgtctcaa  100677
gaaaaaaaaa tttgaagcta ttatggctga gaattttcca gaagcaatgt atgacattga  100737
tccacagata cagatggaaa atgaatacca aggaaaacaa atagaaagaa atctacactt  100797
aaacatattt ctgtgaaata caaaacacca atgcccctcc ctaccactcc cctcacacac  100857
acagaatgca actactgaga taaaatagat taccaataat ggaatgacaa ttagagtgat  100917
aacagacttt ttcataatgt gggaaggcag gagatagtgg aataatatct tcaaagtgtt  100977
gagaaaaaat tctgtcaatc ttaaattgta tacccagaaa aactatctaa ttttaggaaa  101037
tgcattgtga agtatttaga ggtaaagtac ttaagagtac tataaatctg taacttaact  101097
tcaaacattt aagaaaaaaa atacataaat aaatatatgt gtacacacat atatatttaa  101157
agagagagag aagcaaataa gataaaatgt taacatttgg agaatcttag tgaagggat  101217
atttgggaat tctttatgct attttacac ctttaggagt ataaaatgat ttcaaaattt  101277
caaaagataa aacttacaat agcagtaata aatataagta cctagaaata aaagatatga  101337
agaagactac aaaggagaaa cacactgcat tgatgagaga acacttagta ttatacaatg  101397
tatataatta tacaattaca cactacactt cacaacatcc cccacattta cctacagact  101457
caatgctttt cctataaaaa tcccaaaagg agtatttgag taacttaagc tgactctaaa  101517
atttatgtaa cagataaaag accccaaaat aattaaaata gccctgaaga acaacaacaa  101577
caaaaaacat gagtgaggac atgccctgtc agatagcaag acttatcata gatgacatag  101637
tacttaacac agcttagtat cagttcagat agacaaagta atcatctgaa caaaattgaa  101697
agcctgaaaa aaaaggccca cacttacgtg gacacttgat ttatgacaaa aatggtgaac  101757
tattcagtaa atggtgttgg gacaataggt tatgaaaaaa aacaaagaaa atcatatact  101817
tatatatcat acacagaagc agtctctgct gtattatata caaaacttga attctcttag  101877
agaacgttat aggataatat ttttataacc ttaaggtagg gaagtatttc ttaaacaaga  101937
ttgaaaggca cagataaatt cagctacatt aaaattaaga acttttagcc aggcacggtg  101997
gctcacgcct gtaatcccag cacttgtgag gcggagacgg gcggatcact tgaggccagg  102057
agtttgagat cagcctggcc aacatggtga aaccccatct ctactaaaaa atacaaaaac  102117
tgagtatggt ggtgcacgcc tgtaatccca gctactcagg aggctgaggc acaagaatca  102177
cttgaaccca ggaggtggag gttgcagtga gccaagatca cgccactgca ctgcaccctg  102237
```

```
ggtgacagag tgagactctg tctcaaaaaa agaaaaaaaa aaagaacttt tgttctttaa   102297
aaggcaccat agagaaataa agaagctatt tgctacactt ataatcattg aagggttagt   102357
atccagaata tccaaagtcc aaaaaattag taatccataa aacagtaaat cagtaaaaca   102417
cacatgatgc aatatagttc tggacaggaa gtatgagcag gcatctcaca aaagagaaaa   102477
tatgaatggt gaaagagat atgaaagttc ctcaaactca ctagtaatta gcaaaataag    102537
accataagga attatatttt acacccactg gattgccaaa agttaagaag cctgagtcta   102597
cagagttggt gaaattttag atcaactgta actcatatat acaattgttg gggctgggca   102657
tggtggctca cacctgtaat cccagcactc tgggaggctg aggcaggagg attgcttgag   102717
cctagacatt caagaccagc ttgggcaaca tagcaagacc ctgtctctac aaaacaaaat   102777
aataataatt taaaaagtaa ctgggcatgg tggtgcttgc ctgcattccc agctacttag   102837
gaggctgagg tggaagaatt gcttgagcct gggagattga ggctgcagtg agctgtgata   102897
atgcctctat acctcagcct gggtgacaga gtgagacctc atctcaaaaa caataaatta   102957
attaattaaa taaataaaac ctcatcttgg taagcttctt ctcaatacac aggtgactat   103017
atttccagat ttttaaaaaa atgtggtttc ttggccaggt gtggtagctc acacctgtaa   103077
tctcagcacc ttgggaggct gaggcaggtg gattgcttgg gctcagcagt tcaagaccag   103137
catgggcaac atggtaaaat gccgtcccta caaaaaatac aaaaaacaaa acaaaacaaa   103197
acaaaaaaat tacccgatca tgttggcacg tgcctgtagt cccagctact cagaagactg   103257
aggtagaaga atcgcttgag cccaggagct taaggctgaa gtgagccatg atcatgccac   103317
tgcactccag cctgggggac acagtgagat cctgtctcaa aagaaaataa tatatatatg   103377 tttcttttaaa gatatctttg gattctttga ggttttttaca aatactaaca taatcttcat  103437
ctctttagca aggctatcca cattgactct ggatatatat ccaggagtaa tttttttaaag  103497 tttacttaca atcataaaac tgtgtttgca ttgctcagta gccctgcata gtttactaaa   103557
acagttcaaa tcatttcgac atagtaacac cagctaatta tcacaaacta atcacacttg   103617
gaagaattgt ttccttgact aacaattgcc atatctcaga accgttactt ctcaataata   103677
taagctcttg gtcattagga ttgaaaaaag aggagatgag ctcatcatca tctttggaga   103737
gacaagcagg gggcaaaagc aacaagactg catgtcctgg ctattttccc cagaatagat   103797
tccagtttgc ctttctccta atatgctcag aatataaacc aacacttcac atttggtcta   103857
tttcttgctt cagtcattac gctttcatta gtggactttt tagttccttt aattctttat   103917
ctctcactag cactactttt taatatttca ttttatagtc tttattagct tattggttgt   103977
atctcttttt atttgttctc ttttgtctgg gtttgtggct ttggggtcta cagtgtacat   104037
tcctcacttg ttcttttttc tctttctttt ttacagacat gatctcactt ccatcaccca   104097
gactgcagtg cagtggtgca atcgcagctc actgcagcct ggaattccag agctcaagcg   104157
atcttcccac ctcagcctct caagtagctg ggactatggg tacacacaac tacaccctgc   104217
aaagtctaca gtgtaccttc ttaacttatc agtctctttt caaataatat tagactacct   104277
ttttattgat ttattttta atcgagacgg agtcttgctc tcttgcccag gctggagtgc   104337
agtggtgcaa tcttggctca ctgcaacctc tgcctccgg gttcaagtga ttctcctgcc    104397
tcagctccca agtagctggg attacaggtc tgtgccacca cgcccagcta ttttttgtat   104457
ttttagtaga gacagggttt caccatgttg gccaggctga tctcgagctc ctgatctcaa   104517
atgatccacc caactcagcc tcccaaagtg ctgggattac aagcgtgagc caccacacct   104577
ggcctagacc ccctttttgta gaagaatttg gcctattata taaaagcctt acaacagtgt   104637
```

```
gcttccattt ttctctccca gtttctgtgc tattgttgcc ttttacttta cttctgtata 104697 cactttattc tcattattta cagattctat atttgtaaag tcacctactt gctacaattt 104757 atttgtaact ccaaaatcta tatggtaatt ctgtaattat ttgtgaacat gctcagagca 104817 gcaaaatctt tgagtccctt gaggttcaca atccaatcag aagaaataag gcaatgcctg 104877 tcttctttgt ttcagctctt ctaatgtaaa taagtgtcct attttggtc tagttattgc 104937 cacattgttt atatgttgtg ctttccatgt agatgatttc actgtttaaa gtggccccc 104997 aaaagacttg tatactgaaa actatgaaat gttgttgaaa gaaataagta aatggaaaga 105057 catctggtgt tcatggaaga cttggtattg ttaggatgtc aatattaccc aaagtgatct 105117 acagatgcaa tgcaattcct atcaaaatcc aatgacatt tttttttgca aaaatagaaa 105177 agtccatctt aaaattcatg tagaatctca aggaaccacc aaatagccaa acaatcttg 105237 aaaaagaaga aagttagaag tctcatattt tctgatttaa aaattttctg caaaggtatg 105297 gtaatcaaaa tagactggta ctggcataaa gacagatata gagactagtg aagaaaata 105357 gagaactcag aaataaaccc tctcatatgg tcaaatgatt ttcaacaagg cttccagcca 105417 tactcaatag ggaaaggaca gactccttaa caaatagtgt caagaaaact ggatgtcagg 105477 ccaggcgcgg tggctcacgc ttgtaatccc agcaccttgg gaggccaaga caggcggatc 105537 acctgaggtc aggagtttga ccagcctg gccaacatgg tgaaacccg tctctaataa 105597 aaatacaaaa gttagccggg cgtggtggca catgcctgta atcccagcta cataggaggc 105657 tgaggcagga gaatcacttg aacccaggag gtggaggttg cagtgaacct agatcatgcc 105717 actgcactcc agcctgggcg acagagcgag actctgtcaa aaaaaaaaa cagaaaaaaa 105777 gaaagaaaga gaaaactaga tgtccacatg caaaagaata aagttggacc tttatcttat 105837 accatataca aaaatggact caaggccggg cgcggtggct cacgcctgtt atcccagcac 105897 tttgggaggc cgaggcgggt ggatcacgag gtcaggagat cgagaccatc ctggctaaca 105957 cagtgaaacc ccgtctctac taaaaataca aaaattagc cgggcgtggt agcgggcgcc 106017 tgtagtccca gctactcggg aggctgaggc aggagaatgg cgtgaacccc gggggcgga 106077 gccctgcagt gagccgagat cgcgccactg cactccagcc tgggtgacag agcaagactc 106137 cgtctcaaaa aaaaaaaaa aaaaaaaaa atggactcaa aatggattaa agatctaaac 106197 atgaggccta gacctataaa actcctagaa gaaaacatag gggaaaagct tcatgatgtt 106257 ggatttggca atgatttagt ggatatcact ggataatgat aaatattaga taatgatttc 106317 ttcctttgga tatgacacca aaagcacgag caacaaaaga aaaaaagac aaatggaact 106377 acatcaaact caaaaacttt tgctcatcaa aggacacagt ccacagagtg aaagggaac 106437 ctatggaatg ggagaaaata ttttgaaatc ctatatctga taagggatcc agaatatata 106497 aacaactaca actcaacaac aataaaaaaa tcaaataacc catttttaaaa gtgggtaaag 106557 gcatggaata ctgtgtggct ataaaatga gtgagatcgc cgggtgcggt ggctcatgcc 106617 tgtaatcgca gcactttggc aggcagataa tgaggtcagg aattcaagac cagcctggcc 106677 aacatggtaa aaccctgtct ctactaaaaa tacaaaacag ctggctgtgg tggcaggtgc 106737 ctgtaatccc agctactcag gaggctgagg aaggagaatg acttggagcc gggaggtgga 106797 ggttgcagtg agccaagatc atgccactgc actccaccct gggtgacaca gcgagactct 106857 gtctcaaaaa aataaaaat aaataagatc atgtcctttg cagcaacatg gatggagcta 106917 gaggccatta tcctaagcaa atacagaaac agaaagccaa atactgcatg ttctcactta 106977
```

```
taagtgggag ctaaacaatg agtgcacatg aacacaaata agggaacaac agacaccagg   107037
acctacctga gggtagaggg tgggaggagg gtgaggatgc ccaaactacc tatctggtac   107097
tatgctgatt atatgagtga caaaataatc cgtacaccaa actcctgtga gacacagctt   107157
acctatatca caaacctgca catgtagccc tgaccctaaa ataaaagtga aaaaatgga    107217
taaaggatct gcttgagtag acatttctcc aatgataata cacaaatgac catcaagcat   107277
atgcaaagat gctcaacatg actaatcatc agagaaaagc aaatcaaaac cacaatgaga   107337
tatcactttta cacctcttag aatatcaaaa acaacaaaca agcaaaaccc cagaaaacag   107397
caagtattgg caggaatatg gagaggcctg gacccttgaa cactgttggt atgactataa   107457
aatggtacaa ccacggtgga aaacagtatg gtggttcttc aaaaagttaa aacagaacta   107517
ccgtatggtc tagcaatccc acttctgaat atatctccaa aagaactgaa atcagggttt   107577
tgaagagaga tttgcaaacc cctatatcta gcagcactat taacaatagc gaagagttgg   107637
gaacaaacta aatgtccatc catggatgaa tcaatagaca aaatgcaata tgtatgcaca   107697
atggaatact atgcagcctt aagaaggaaa gaaatcctgt cacatgcaac agcatagatt   107757
acccttgagg acattatgct aagtgaaaca agccagttac aaaagaacaa acaccgtgtg   107817
attcttccta tataaggtat ccaaaatagt cgaattcatt gatatagaaa gtagaatggc   107877
tgttaccagg ggatgaggga aagggaaaat ggggagatgt tgtttaatgg atatagaatt   107937
tcagttctgc aagatgaaaa agtactggtg atctatttca taacaatgta aatatgctta   107997
acactactga accgtatact taaaaaaggt taattatggg ctaggcgtgg tggttcatgc   108057
ctgtaatcct agcactttgg gaggccgagg tgggtggatc acctgaggtc aggagttgga   108117
gaggagcctg gccaacatgg tgaaacccca tctctaccaa aaatacaaaa attagctggg   108177
caaggtggtg cgcacctgta atgccagcta ctcgggaggc tgaagcagga gaattgcttg   108237
aacacggaag gtggaggttg cagtgagcca ggattacgcc actgtactct agcctgggcg   108297
acagagctgg actcaatctc caaaaaaaaa aaatattgtt aacatggtaa cttttatgat   108357
ttgttttta accacaattt ttaaaatctt attttagtgc atatgtataa ctaagatata   108417
cagaaattcc tggctcagtg acccttccag atgctttgcc tttggggag aaatcaagta   108477
gaagttcgga ggggctaata cagttacaca gatcataaaa tatgctgtga gagaaaagag   108537
gcagagttgt ttgtctattt tgtgttttgg gctcacattt gctcaagagc tttatgttta   108597
tcaatcagat aattaaagaa tatttgctta aatatcactt tggtttgctg aaatcaacac   108657
agcctaagga taaaaaccta gttttttcctc aaattttgtc atgactggtt gaattaagtg   108717
atcccctcag attcacacat tgaagtcata cccccccagt cccttaaaat tgatacattt   108777
tatgttgtgt ttttccccc caaatgaaaa ttttttaaaac tatttttaaa aaataaataa   108837
actcaaaagg gatcaaagcc ccaactataa aactataaat ttttttaaa agaaaacata   108897
aaactgggcg tggtggttca tgcctgtaat ctcagcactt tgggaggcca agaagagtgg   108957
attgcttgag tccaggagtt tgagaccagc ccaggcaaca tggggagacc cccatctcta   109017
taaaaataca aaaattagcc aggcgtagtg gcggacgcct gtagtccctc ctgttcagga   109077
ggctagggtg gaggatcact tgagcctggg aggtagaggc tgcagtgagc tgtggtcaca   109137
ccactgcact ccagcctggg tgacagagta aaaccttgtc tcaaaaaaaa aattagggaa   109197
gaagctttat gacattgggt ttgacaatga tttattggat atgacatcaa aagcataggc   109257
aacaaaagaa aaaattgata agatggactt cttcaagatt gaaaacttt gtgcatcaaa   109317
gggcactatc aacagggtga aagggaatcc acgaaatggg agaaagtatt tgtaaatcat   109377
```

-continued

```
atatctgata agagattgat attcaagata tatagagaac tctcttaaaa tgcaacaacc   109437
aaaaaaacca acctgatttt aaaatgagca aaagattcaa ataaatgatt ttcaaaaaaa   109497
atacaaatgg ccaataagta catttaaaaa tggtcaaaat gaggccaggt gcagtggctc   109557
acctgtaatc ccagcacttt aggaggctga ggtgggaaga tcacttgagg ccaaagttca   109617
agatcagcct ggtcaacatg gtgaaatccc atctctacta gaaatacaaa aaaaaaaaaa   109677
aaaaaaatt atctgggcat ggcagtacat gcctgtggtc ccagctactc atgaggctga    109737
ggtaggagga tggcctgagg ccaggaggtg gaggttgcaa tgagtcaaga ccatgccact   109797
gcaatccagc ctgggcgaca gagcaagacc ctgtctcaaa aaataaata aataaaaat     109857
aacatcagta agcattaggg aaatgaataa caaaacacag taaaatacca cttcacatac   109917
acccattaga atggctatta cttattattt taaaaatga caacaacaaa taatgtgttg    109977
gtgaaaatgt ggagaaacag gaaccettgt gcattgctga ggaaaatgt aaatggagc     110037
agctgctgtg aaaacagta tggcaatttc tcaaaacatt agacatagaa ttaccataag    110097
atccagcaat tccacttctg ggtgtatacc caaagaacta aaatcaaggt cttaaagaga   110157
catttgtaca cctgcgttca tatcacactg tgattatagc attattcata ataaccaaaa   110217
gatagaagca accccagcgt tcatcaatga atgaatgaat aaacaaaatg tggcgtatac   110277
atacaaggga atattattca accttgtcac aaaaggacaa atattgtatg attccactta   110337
tatgagtgtg ggaacaagag tgacttctga ctaaccctga gtccaaaaat gcctccaaa    110397
tgtctaggtg tcagtacttt ttgtgtagaa acagctagtc actgtaagtt tcctccaaaa   110457
caacacttaa tgctgttaca aacatcatag gctaggattc ctgtagcacc tatacattcc   110517
ttccagcaca catattttta tacttttccc caagacatca gcctccctaa ggatctggga   110577
ggttgtggtg ctaagatcta cctgtcttgc agccccaag accatgcttc tgtccataaa    110637
ttccctgat aaataatctc ataccaacaa actggatttg tctgcttcct tctttgattt    110697
cttcacttct ttggtatttg gggatctctt tgcatataca gcccctttcac agaacaatga  110757
ggtacctaga gtactcaaat tcatagagac aaaaagtaga atggtggttg tcagggcaga   110817
aggcacagga caggggagtt attgtttaat gggtatggag gtttcatttg agaagatgaa   110877
aacgttctag agatgggtaa tggtggtggt ggtggttgca gaataatata aaaatgctta   110937
atggcactga attgtacact gaaaaataat taaaatagta aattttatgc catatatatt   110997
tttcaccata aaaaaatggc tcccagggc aattgtaaaa ttatatctgg tattcctagt    111057
acgagaagac atggatgtgc cttatgtgtg tgttagatga gctttgttca gacatgttgg   111117
ctgtgagctc catgttaata aatcaatgat ttgtattaca taagctgact ttaagtagag   111177
acacacataa aacaaggtta tgtgttgatt gcttgacaaa agtgttgcaa ccagaggttt   111237
acagaatcta actctgtatt tccccctgtga acaatgttca gtgttcacta attcatcatt  111297
ttcaacaact ttacagagca taactatcat gactaaaaag aatcagctga gacagacaca   111357
gtggctcaca cctgtaatcc cagcatttg ggaggatgag gtgggatgac tgcctgagtc    111417
caggagttca aaatcagcct gggcaacata gtgaaacccc atctctaatt ttttttttaaa  111477
aagtaaaaaa aaaaaaacca acaaaaaaac tgtatgttat aaactccaca atatattact   111537
attttttgctt taaaatattc aattatcttt aaaagagatc ttttaaaaac atctttata   111597
tttacccaca tattttttat ttgcaggcat gttcccatct acgtctttgc acttgttct    111657
acctctgtct ggaattctct tgctccagca agccatgtga tcagttctcc acattctctt   111717
```

```
taggtctcta ttcaaaagtt acttttttcag ttagaccttc catggctact ttatctaaat   111777
agctatatat cttcacatct atttccttat ttaactatca atgtccttat ttaattctca   111837
actattaatt atccttattt tacaaatgag gcaagtggaa gtcagaggga tgaagtgaat   111897
tgcccgaggt cacactgcta gtaaatggta aagcacgtag attgtctcca gaaacttctc   111957
aatatattta ccttatgtac atgatattta gcctatataa acatttacat atatttatca   112017
tgtgtataca cacacctata gatatatccc atcttcaagc tatatttcat catagctgtt   112077
tctaagtcct ccatgattga tgcaactggt agagacttgg aagtaagatg atgcactgac   112137
ccagctagca tttactgggc atctgctagt aggtgctagg cattgtgatg aatgctaagg   112197
atatagagat gaaagatgca gttgctgtca tcaatgtcct cacagttggg aatagggaga   112257
agacagacac ttagaagttc catggagaaa gaactaggta ggacccaatg gataaaaaat   112317
actgaatgaa gattctaatc caacacaaga aagtttctaa tggtcaaagc tgtctgaaaa   112377
tgaaatgggt tagagggtgg agttcctctc acaggagttg tcccagcaaa agtatggtga   112437
cagttgagct ggctgttata gaagggattg acttaaacat aacatggctg atcaggagcc   112497
aggtaaccaa tgtgagctag ggttttttaaa gacactttttc aacaaagcga ctatttgcag   112557
agatgtgtgt agggctaatg gaactaacaa gaattttgat gcacccaggg gactagcaga   112617
aactagaagg catttccact tcatgcctga aggcacaggg ggagtctgat taaaagccag   112677
agcctaggaa aataggctct caaagagaaa aagaatttct agagaagcag caactgccag   112737
aactggaaca atataacatt cccagaaaca atatacctgc agttctctat ccttaggttg   112797
ttcggttatt tgcagtgcca cttattcacc aaatgcaaat ggaagccaga ggcaagcgcc   112857
tgccagtgac gcagttgata aaggaactaa tactgtccac aaaggtcagt gtccgagggc   112917
acccagcagg gcagaagagg gcgaaatgga tccagatgga aaacgcagga taatcagcag   112977
agttgttttt aagggccctt tatttattca gaggcaaaat tttctttccc tttagactct   113037
acaaatgaac aatcgggaag cgaacctcaa ctgtgggtg agtggcgctt ggagaaaatt   113097
ggagctgagt ggataatccg gctatgccct tcccacgtct cttcccacg cagcgtcacc   113157
gtcgtgctct ccagtgcaca ccaccagcca tccctgccct ggcgcccgga cgaagctcac   113217
gggctgggga gcctctttcc tgcgccggtg atcaagggcg tcccagccca ctgagggcca   113277
ggaggcgagg cttgggcaca cgtcccttcc cgcccggacg ctggtgcccg cgaggtcctc   113337
ttggccctgc tggagcgca ggggtcgcgg caaccattca gaaccccggc tgccagacaa   113397
gcgaggcttt ccacgtgggc agaggcgacg ttgttcaggt ggcaaggatc caaggctgag   113457
ccttcctccc tctgcgtcca cccaccgccc ctccccaccc ccgacctaga aaaggacacg   113517
cacacaaaaa actttcgcca cactattaat atattcgcgt ttcctcccac tttcccaatg   113577
ggctaccagc tgcagaactc ctgaatagaa agcttaattg tgctttgtca tgcagagtac   113637
ctcgattttc tatagaaggt tacaaagggc catttgaagt atttctttct cgcctaatag   113697
tgaaccattt gcatacggca cctctgcgcc tgccagaccc aggtagctgt gccgaagctc   113757
cggggggccc ggagtaacaa aacccagggc ggtttccaaa gggcgcccta ccccgcctct   113817
cgcccagcgt ttggactttt ctctccaatt ccctcgggtc acggcccgcc ctaggcagct   113877
gatttggagg acgcgaaata tggcctgcag gccgcgggtg cccagccggt ccgtctgata   113937
tcttggaggc ctcgggccat ccaggccctt ctagcctgga cccgagcctt ttttaggccg   113997
ggtctaccga acccaggtgg tgttttttcat ctactatctg caggtccaga gaccaggcct   114057
ttgcccacgc ggggtcctcc acccacttgc ttctcacgta aggcccaagt gaggcgctga   114117
```

```
agaactggaa ggtgattatg atttcgatac cacgctgttc gtttctcctg gttgattgac  114177
agggctgcgt tcagaatatc ttttcttgtt gcttgttttg acagttcaaa tccaggtctg  114237
tgtgacatat aaagctaata aaattctaat ttcattgtta atcttatttc attgcagtat  114297
aggtttttac cctcacacct gcatggcagg gtgtaattcc attaataaaa aaaatcaaca  114357
tattcattgc atgtcttttc cctgatgata tattgtgagc agtgtgagtt gagaaagagc  114417
catttattcc caccgtgaat gagcctgcat ggggcgggag cttcacctgc ccctcagtca  114477
attaggaatg tatcgaaaag tctagcagaa aacgagttaa attaaccgtt ggctaatttc  114537
cttatgtccc tcctacataa tccccccttt tcagcttgcc ccagaaatta ccacatgttg  114597
caaggttcaa atagtgccta atgaaacagt gactaaacgc ttctccctcc ggcgccaccg  114657
acggggagc cctttcgccg gccttcaaag cttgcaggat ttcgtggttc tggttcccgt  114717
atccaagaaa aaaaaaaga aaaaagaga agaaagaaa gagaaagaaa tttttgacaa  114777
gcagaaaaaa gaaaatctaa gctgtcaata actctcgatc cagcgagtga aactacatta  114837
atgcccaccc acttcctgcc accgatgatg cagtgggatt ccgagatgcc tgtgcccgca  114897
gtagataccc aagtaggaat ggcagcttta gcatcctcct ctttccccgg agagctagga  114957
ggattgagcc atggccaggg gagactggat ggggaaaacg gccaggagaa caaagggtgg  115017
gggtggggc ggatatcaag gcagaaggag atggagacaa gacagagaaa tgcagacaga  115077
gaaagatcac tggggaagca gatgcaaagg caaaaaaaaa aaaaaaaaaa aaaaagaca  115137
gagtgacagc aaacacacct ctaaagtctc aactcccta tcccaagtta aaactacatg  115197
tatggcttaa gcaactcatc agcctctagc caaaggcatt ttgaagcctt gacattcaaa  115257
atcctaataa ttaatcattc ttattaatta attaaggagg aaaggaggaa ggtggctggc  115317
tgctgcttga ccccaaacaa tctaaattag ggtttgtgaa ggaagtctcc aaaagcatgc  115377
actccctctc cttcgtattc tttctttttc acactctcaa aaatttccat tataatcctt  115437
caaggtctgg ggcaggcaga gcttctcacc ctgctccatc ccttcgcagc aaactgagac  115497
caagctggct tctgctcctt ggagccggct gccactcata ggcagggagc tctttcccat  115557
cgggagcaac tcccacctgc cttttttct ctgcacctgc tgtgggtggt ttctccttga  115617
acttcagaaa ccaagtagtt gcctagaatt actttcgcca cagtgctcac aggctaaata  115677
ttactacatt ctctctctct ctctctctct ctctctctct ctctcttgtc  115737
ttctctctcc tctctccct tgcctccctc tcactagaga cttgagtccc ctatttgaaa  115797
tggtgcagct aatacaaagt catcaaagca ctatggttct tgtcttaaag tgacagcctg  115857
ctttatgaga ctgtttgaaa tactccccctt gcttttcaat gtctctctat ccatctttgt  115917
ctgctcttca gaaaagggga caatataaag cccagcctgg cgagctcccc acgctcaggc  115977
ctgggcagtg ccaacctccg cctttaagca gattgaaatt gtcactgctt cattaatctg  116037
aaactagtta ctttcctaag cacacagcat acacttccga tctgttagga ttcactcagg  116097
ggagcccctg gggccttcct gggtttggga tttagaaggc tcaacaaaga tacagcaagg  116157
gttcaggaaa catagggct cagcttgaag aaaagcagtg tccagtaccg aagggcggca  116217
ttgacatcag tatattaaga gagcacaaaa cactattttc agagacaatg ggatgccag  116277
gattttggag ggtacacttg agaataagta gtctggctat ggcaacagac aaggttatct  116337
attgccacat ggagcagcac tagaggtctc acaggcctca gaattttttt ccccaaacag  116397
aagaaactgg aatccaaatt tctttgcaag ttggagtttt gctgacttc tttttttta  116457
```

```
gttttttttt tttttttaatc tgagttctga ttcaagtctg attctaagag atgtcttaag    116517
ttctgtgctt ctttggcccc tcccttagtt ccagcctgtg ttgcccactc caagtgccag    116577
atgttggatg tagaagcctc gggtccttat agaatttcta tgagacaagt tgccccttt     116637
cttcatacc ccaccattaa caaaagacaa tacaaaggat tctattactt ttaatatttc    116697
tagctggctt agaatagcaa gttttttgggt tctattctat gtagtttagg gaagagatgt   116757
gggcattttt taagagaagc tcaattttca gtaatgtgag cctaaagatt tataaaatag   116817
attatatta aattatgtta atagacgcct agtaaatgca ccatttaatt gcatggaaaa    116877
aaatgttccc tttaaaagg tctgtcacct taacaggtac attcaaagat ttcctgtgaa    116937
taatgaaaat aggaacaatt gctttgatgc actgaactgc attcatcgtc taggacagct   116997
ttgggctgtg tttggagaag atgggaggag ctcttttgaa aggagtgatt gctccttaa    117057
acttgatttc ctctagcaaa taggttctat tggagtgtca ttctcctccc ctctctcaca   117117
cccgtaaggc tgggcttgag atcatgcccc agagctcttc tccatgtctc ccctccatgt   117177
tcagactgtt tttcctcccc acaacccaac actgagcacc tccccatctc cctcaaagaa   117237
atctctcaag gagtgccatt aaaagcgagt ggaacctgca ggaaaggtat aagtgggaaa   117297
caaaagaaa aagaaaacct ggttaaaaat tactcttttc cacctacatc accaccatca    117357
aaggaccctc tctgtctctt tcacacacac atgtgcctca tgcatgcaca cactacacac   117417
atgtacatac aaagcccctg ttgccctctg tgactgcttt tagttagaac caccacctt    117477
ctggcaattg tctgaccaca gttagagtgt gccaagcaaa ctgcatttct aatcctgacc   117537
agatataact ggacagaact ggtggggcgt tgtgggttag cggggtggtg gttggcaatg   117597
aggagacgga ggcggaggtc agaaatcaaa gacttcacat ccccaagtgt tttgtctctc   117657
ctaaaattat tagatattct ttaggggagt ggggaaggga ctgagctatg atgaccactt   117717
cagaataagg accctagagg aaaagaggtc tatgggcacc agtgtctcca tcatgcaggc   117777
ccactgacac cctaaggatg ggctactggg tcacttttgc ttttggccta gtttgctatc   117837
agtatcaggc ccttggcctt aggcatttgt tggtggctga gtgggagagt gaaggggaaa   117897
agtctctgtt cctcctctat gctctgaatg tctgggctgg gccagggcac atgggtgaga   117957
ggtcatcctt cctgctctcc actctgcctt ccacccccag ctcttttcct gtttaaaact   118017
aacatgagac ttgttctcaa aaagatggac tcaaccacac tcacagcggg tgctacccac   118077
tgattttctc ttggtggagc aagttcctgt tttctaattc tcattctcat tttcattctc   118137
tttcttcca ttctttcttt ctttccatga cctctctaag aggtcatgct ctgggggaac    118197
atagttctgt ttctgttttt caattggggc ataatggaaa ctagtatcta gtgcttccca   118257
ggtagagaaa ttgtcaaggg tgaccccata catcttaaac tttcctctta aatgggtgtt   118317
tgatatcaag attatttagc tgagaatgtg agtttctgag ggttggctta aatgctctta   118377
aactaaagtg aaactgttgg tctttagaat cagaccgact ccaaaatacc aaagcattat   118437
tccgatttga aaacttcaaa aacatcaact gatatttttt gaggagtggg gatagggaaa   118497
catgtaaaac ttattctagc atagtaggag acctcatact ccattttgaa agtgaccaaa   118557
ggagtccact ttgcatcgga tgtcctagaa ggaagacctc cctgggaacc ctggagaacc   118617
tttttttta tggagagtgt cccaacattt aaataggtat cgctacgctt ttttttttt    118677
tttttttttt ttttttttgc ctctgggcag aaatactttg tttattctcc tttccctagg   118737
gaacttcccc aaagatcgaa gcaagagggg ctggggccat ccaagcagat ccaaaccatc   118797
taaacagggt tggcactgcg gctatctgcg gcatggcaga gctgggtcca ccgcgcgcgg   118857
```

```
tacctggtgt tccaagtgct tggctccgca gggcctggga gccggggggcc gggagaggct   118917
taagagactg tgatcggggc tagtcatgga catagggggag ggctaaaccc aagcgctgag   118977
ccccagaggg gccgggctgg gtagatgaaa cggggaccag aggagtctcc ccacagccca   119037
aaggaagctt aactttgggc aaaaacgcaa agagctgcag caggcgctct ttgtgcttct   119097
tatttcccct ggtggaaata gactgcttaa actcctgttc tttgcgcctg caaactcccg   119157
tcctcccacc tctgttctcg cgcgcggaga ggcctgcttc ttgggaagaa gggagacaga   119217
atcttttgga aaggcagccg gcctgcgcct cctcccttcc gtggcgggca gggcgaagag   119277
cccggagctc tgcgcgtgag agacaggagg aaagagatcc agaggcctga gcttcccagg   119337
ccaggcagta gtgagccggc tgtctgggac ctctgcgcag acagagctc agcacattgc    119397
acaaagcgcc ggcagctccc ttttcagcct cacacagtgc gggccctcct ccctatgtcc   119457
cttgacggaa cgaagaggga ttttccttct gagcctactg tgtgtgtgtg tgtgtgtgtg   119517
tgtgtgtgtg tgtgtgtgtg tgcgcgcgcg cgcgcgcgct aaagacaaca ctcagggaaa   119577
accgtgtcca gttttagaac cccagccgta cctggtgagg ttcagtccga ccggcctcta   119637
gtaactcaga cctaaagccc ttgtgtatgt gtgttgtcat taactcctgt ggcttgaacc   119697
tattgggtgg cgtctttata gaacctaatc agaaatcaca ccggttgagg attagtgggg   119757
ctcagcttgc agggaatgag atctcttcgt tttcctgttt ccagtttctt cacttctctc   119817
cctaagataa caagcccagg ccgcactgag gagagagcca gttgccctgc tgagggaaga   119877
gctagaaata agtcttctct gggaccaggc ttaaggaag tgattctgct aggctatggg    119937
aaggggggtg ggctggaagg gactagaagg gagccaaatt aactgaatat tagggtgacc   119997
gggaaaaaaa gccccaaaac tcaaagctct aaaggcatct ctgggctgct ttgaaaaagt   120057
gagattataa atctttgaac agaatacttc ctgtccctga cttttttgttt tcttaacatt   120117
gagggaaacc cgctaattct gcttgtagca tcgttattaa gtttccactg tttgcttctg   120177
acctgtttga tggattgttg ctcttcctaa aactattctg actctacaaa ttccttcaca   120237
taattcaagt tttcgtactg agagaaatga ggaagtagaa agaagaaaac aaaaactaga   120297
tgggggattt ttaccccttcc ttgctaaata aaggtttacc tgtcgttaat ggtcagtgtc   120357
attccaaatg gagtgatttg tcctatcaac tgtgaggagg ttgcctattt taaggatgga   120417
gaggcactgc ctggtagatg ccatcatgac taaaggtgtc tccttggcga aagttctgtt   120477
acatagaaaa cccattgagc cacaaactcc ctcagtcaag agaccacat taccaagttc     120537
ttactcaaca ttttcctcga attcctcaga cagcttttc ctgcatatgc ctttctctag    120597
acattggagg agggggcagg agaagatagg gagagcaaac accacagatt taaaattctg   120657
gttttttgttt catttatttta aataaatata aatataaatt ttatataaac ctattcacat  120717
acaaagggac ttccagcgac ttagatttta aattctcccc aggcgaaatt tcagaaagca   120777
agacctacaa ggtctaattt tctaaattat tttcaacttg ggtgtttttg tttgaaaacg   120837
acaacagaaa ataatcaata aatcctgtgt tcttatcgag ttctgaaaga gagtagggat   120897
gggggaactga catgtgcttt caaaaacccc atacagtgtt aaacttaaac caaccctgtt   120957
tttcctctgt tatacgacaa gaatgagttg aattataggt tatttacatt ttttaaaaaa   121017
atctgtaact tcaagttgga gtcctagata aacaggtcaa gaaggagacg cgaagggtca   121077
ggtcccggct tgtccattcc agaacttcca ggttcgtttc ttctccagat gggaccactg   121137
caatgagcaa ggattctggc ccctgggtgc cccacgcctt ggcgttgcct ggtctgccag   121197
```

```
gagcggggga tgtgagggag gaggccctcc ctcataaggg ggaaatctcc ttgtcatcgt   121257
tggctgaggc cggcgacagg gagtcctcat cctcggagcg cgcgtagtgc acctggctcc   121317
cgacgcactt gcagcccgcg tgactgttcc tctgcgtgcc cttcccctcc ttcttgtgct   121377
tcactcggcg gttctgaaac cagattttca cctgcttctc cgacaggttc aggtaagtgg   121437
cgatttcaat cctccggagt cgagacaggt acatgttgga agagaattct ctctccagct   121497
ccaggagttg cgtgctagtg aacgccgtcc tcatcctctt gccattgggt acctggctgg   121557
cgtcagagcc tcctgcggac cggcgaagag agggtagaga ggtaaggctc gggcaaggtg   121617
ctcccacccc atgtgctaac caggacgcat ttcaggacc cacccgggga agcccagccg   121677
aacatctgta tccctttccc atttcaaggc acgtggttgc ttagcgggga agaaaagaga   121737
cgtgcaaagc aaataaaggt cttcgatgcg caggatgcga agtcacagga ttaaagaggg   121797
atgggggctt gcactatctg atcgcctccc tttgagccaa gcggagaagc gcgcaggctt   121857
agccaaaaac gtcaagacgc tttagccgcc ccgacgcggg gatgccacac aggttcaaac   121917
acacccaccc caaatcccaa gcagttaacc tctggtttat ccgccgtgac gttcgaggtc   121977
cctaaggccc cagtattaat aaggcaatac tcgagcacct actactagga gtaaaacgca   122037
ccaggctgag tggagaagct ggcaaactaa cttccacttt cgtggaactt ctgtggctga   122097
ctctacggtt acactaaaag cccgtcctct ctcttcaccc tgtccccggg ctcccacttc   122157
ctccactgga ggtggaaagt ttgctccagg agcgcgaaag gcgcggagcg caggtgcccc   122217
aagacccgc cctacccatg gtgaggcagt ggaatctccg cgggtccgcc acgttgtagg   122277
tggtggcggt gcagacaggt gcgtggtgct gcgggtgccc caaggccgcc gcggccgccg   122337
ccgccgctgc tgctgctgcc gccgccgcgg ccgagccagg ctgctgggc tgatgatggt   122397
gatggtggtg ctgcggcggg tggtggtgat gatgcgcatg gttcacccgc gggcaaaact   122457
gcgcgtcccc aggagccgaa gagaactggc ccttaagcag aggcagtgcc cctgcggccc   122517
ctgccacccc actgcctccg gccccggtaa ccccggcccc tgcgccccg ctgccggcgc   122577
ccacagaccc ccgagaggag tgcaggtgcg aagtgacgca gagagggcac acgcagaacg   122637
cgccgctctt gcgggacggg cagccggggc cggacacgga catcaccaat gggggcggca   122697
tgccaagcgg gatgaagaaa tccggcccgg ggtgcggttc aggcagcgag ggcgcaggcc   122757
gtgaggtgtc cttgatgatg agcgagtcga catagaagga gcgcgacatg tcgagagggg   122817
tgggtggctg gaagcccggg cagttcgcgg cgacccctct cctctagtgt tctaagctct   122877
gccctgggag ccgcgcagac acgggcagtc aagcccttgg ggacgcagag gtgttggcgt   122937
ctgggctggg aacaaagggg tccccggaga gggctggtcc tcacgtcccc cgccggcgc   122997
cccggctcgg gtatttttata gccccccacc ctggcacgtg atgctgcgga gtaccgctcg   123057
gctcaggctc ctcggcagct ccgcacccte gggataggct gcccgagtca aacagaagc   123117
cgcgaggagg ggcgggcgcg cggcggggaa gaactcgggg gaggggatg ggggagactt   123177
tgcaaagtgt aggttttgtt aatttcccgg ggaggccggc ctcctccccc tctttctcca   123237
cgctttactg agaaatcaca gcgctgcatc ctccatccca ccccctctcg ctaccctggc   123297
cgcagcccaa ctcttcccca cgcccaccg caaagcgtac caggtgggga cttggaggct   123357
tatttaatag gaatgctcag tgtttccagc tcctctgtgg taggggtggc tgcggcgcgg   123417
tgaagtgtga ggcctgcggt ttggagcagg attgtgcggg cgacggactg gcagtcgtcc   123477
agtccctgag cgcagctctg gccacggtta cacctacccc tgtccacagc ttttggactt   123537
ggcagaggtc attcaggtgg ttagttcagg actgtccggc gcagaactgt gaggcctccc   123597
```

```
agctaagaaa ccgtcaagct tttcatgctg atgttcgaca aggtctgaag tgtctttgta   123657
cttggggccc tcctggggcc actcagacca acgacccttc cttgtttccc tttctgatcg   123717
gcacctccca cttccgcaga gagagagaga tgttgaagag tcaccctttt ctttctccaa   123777
gtagtaacac catggcattc cagggcaatc ctacaaactc catcctgaag attttggagg   123837
gaggacctca acaccaagc cctcctaaag acgcagcagg gattagatag accttcgctc    123897
tgggtctgag gatttcctgt ccctcatttt taccaatcat gggcagctta gcaaggctaa   123957
ccaggaagca ctctttcctc tgcatcttaa gaacctaaaa aggatgaaga ggattcagcc   124017
atccagggaa tcttgcctct gattggcaga agtggctttg taagggaact ctctctggtc   124077
catggaagtc ttgcacaccc cttactgccc gagagagggt ggctgccaaa ctattgggac   124137
tatttatctt cggagaaggc aaggcagcag aggtggccat tttctctctt catttccccc   124197
tgcagaaaag cgggctgggg ccatgtggtt gggcaatagt tagaagtctg atccttttc    124257
cagagcagct aacttcaatc ctgagttcat gatggtgcta agaaacttag agacaggact   124317
ccctccacct gagagaacaa ggtgcccaaa tccaggagag cactagctag aggcacggct   124377
ctatctttcc atcctctgtc ttcccctctc catctctgtg acagtctctc ttgcctgcta   124437
gagaagtgta attgggttgt agggatgccc ggctctgggg agcccaggat ttatggatgg   124497
caattaaagt tttatgaatt gcagctgagg ctggttattg agctatttga atgtgattag   124557
aattcaatta gaaagcggtt agtggacggt gggtctctgg agtgtaaaca gacagctatt   124617
ccagaaatgt gctaatccaa catcttgtga caacaattaa ggagtctcag ggcttaacat   124677
ggggcagctc agctgtaact acttttgtac cacaaggtct gcagacgctc aggctcaccc   124737
cagcccgccc ttgttcatga ctggaggatc taggcaatcc ccgaaatcat ttcagcccca   124797
agaagaaggc ttggagccac tgatggagaa tggcaataaa aaacataccc tgctgaatgg   124857
caggatattt tttacagtcc taaactgtcc aaatagatga ctcgattccc cccattcact   124917
ttgcaactat acaagcatat atagatatag atacagatac tctttaagaa taatagcttt   124977
ctctcttttc ctcctctggg ttaggtccca ggttatccac agtctgtttt gggctgatgg   125037
tttgagtcac aatgttccca gcagtttggg atgtgttcag aggaagagct cctatgctaa   125097
agtcctagaa atcgcaccca tgtgcagacc attttacctt agagaatctt aactatgcaa   125157
gaggcttgtg catcttattc aatttgtgtc tgactgtgga aactttcatt tttcagtgcc   125217
aaggagtttt gagaaatgtg aggggctcat ggggtttcct aaagacttca aggggagcag   125277
tggtttcaga ccaggctgag gctgaaagca agaccatgtc tgaaaaactt gacccttagg   125337
gtacttggtt aattccttca gcccaccaag agcaagtata ctggaatccc atttcttgca   125397
cagtttctgt ccactctgac tcacttctct agttctcttt ggatctctca gtgtctgcca   125457
gtctctctcc ctccttctct tctgagtcca gcccctatct ggcctacct gcctatcccc    125517
tcctcaaagg aagcctaccc tccatgcccc cggggcagca ctgcccaccc cccacccag    125577
ccctgcccag ccctactgtt ccccagagtg cagtgccctg aaccagcagg agaccccaag   125637
ttcagctttc ttttcctgag agggaacaga cagaccattg gcgtgtgccc atggtgtctg   125697
agccgccaca caatttttatt tctcagtgat tctgtccgat aaaatttcat cgtccattaa   125757
gtaatcccca aaatgagagc tcttatgagc ctataatgag ctctaattgc cacaactcca   125817
ggagccacgt ggaaggattt attctgtatt aagcagtcgg gtacagagta caggctgtta   125877
cctaagccat tactttcata attcaaggag aaaattagtt cttttaaagg aaaggggaaa   125937
```

```
tcttttttatt atctccctct tgcttgggac aatagagtat ggttttgtct tccttgagtg  125997
caagacagtg tcacatatgt gatggtaaca aaattgttct ttgtacctcc tcctggccaa  126057
ggcactccac ccttaccctc aacttacaaa aaaaaaatca aagcttttct agaaagaaca  126117
gcagaggcat ggccttcttg tctctcgatt ctccaagttg agcctgggtg agcagtttcc  126177
tttcagccca accctgagat ttggattctc agttctagct tccaaaaggt ctccagtact  126237
tcttcccagc tctggaatgg cacctgacct gaacccaca ttcctgtctc acttctcttt  126297
cttcctgttt gctttcatgg gcaaagtcag gacaagtaaa gggcagggac ttagcattgc  126357
ttattcaaca ggccccagag ttctgacccg ttcctgtgct tagctgtttt tttcaggctg  126417
taactcccac tttgcccctc cctctgtgtc ctccaaacct ccccacctcc cccaccacca  126477
ctttcatccc cagtccttt ttctcttagt ttcagcattt gcccacatgg ttctccagct  126537
ccaaatggag gctgcaggca gggcgggaca gccggggagt tggcggggcc gcctcggatt  126597
tatttgctcc tcttacattg atttcatatt agtttccaaa gcgatgaatg atctcaaagc  126657
tgggttttgt tagccgaaca caaacaggag acaggactta cttgcccca gctccctta  126717
atgaggtcat tatcaaagcg tgaacaagtc tatgaatgtt ttattgaaag tgcatcgtta  126777
acttgtatcc atccttttct ccgagtggca ttgtgatatt gctgtctgtg gcacatctta  126837
cccgatatag cccgagattt ccccattctc tgtaaccagg caacccttc tgaatacca  126897
aaaattgaaa agaaccgctt agtcttcaag aaagtcctca ataatagtgg aaaagaacaa  126957
agatccagga gacaacaaaa tgccacaggg gtgacttttc atgagcaatt atctctcatt  127017
aatcagaaga acagctgcaa tattaatttt ctctcttct tcctctcttt tcacagtccc  127077
caacatttga ataatcataa attttgattt tatgaaggag tcacattttc agggctgga  127137
ggaaagcagc tacctaggtg aagacaagaa gaaaatgctc tcattttatt ttattttttg  127197
tttgggtaaa gctgccaaca aagcaaaatg gaaaaaataa aataagaaa tgccagaaa  127257
aatgcccccc cccctttctt cttctagatg gctgttgaga ataaggactc tcttctcccc  127317
caccctctgc tcacaactac ccctccttc tttcctcccc ccgcccagac ccattcccca  127377
gttttgctct gagcagggcg gagggaaacg tccctggcgt ctggcgtggg agtttcagcc  127437
gggtttctgc ccgtttaact tgcaaacgtg aagccaagcg ttgtcgatct gaccaaagag  127497
acactctttg ggcgtaactt gcattgtggc catcaaaagc ccgccagcct tggatgaact  127557
gagaagtgta ttcagcagaa atggggcgct cgctctcctt tcaggctctg gagaggcaat  127617
tgttcacagg atgtgtagcc agggtggaaa acgtgggtcc ccagataagg ctataacctg  127677
caaacgagct tgggggagtt aaaagaatct cattaaagcc ccggctgcaa ttagcaaata  127737
cacactcata gagaactcaa gctcctcttg aaaagctgtg ggtcaagatg aaagagggca  127797
gttgggagct agtccccaca ttcttgtact gcttgagtga tgggggggctc aggagccagg  127857
ctattccttc agctgcccca atattgttag ttttaatgca aggccaggga aggcctttct  127917
agagggaggg caggctgtgg gccctgtgtt catgcaccac caaaaataat cttgcttctc  127977
cctggtgttt attcagaacg gatgggcttt tgagaaacct gaattcgcct ttgtgctcac  128037
cacagttgca agagttcaat tcggccctct gagaagaagc agcggggaga gggggtggg  128097
gggtggtagt ggaggtcttc tgagaaataa gtgaggggtt tggcttagaa tttcaggaac  128157
ggcccagttg gaaaaaagtt gtgatggcac tgaatgcctg ccacacagcc cctctgctcc  128217
ccacttcact ttaattaata ttcgcccacc cccaaatcct caagccgaac aaggcatccc  128277
tctcccaccc tcagagctct cctctgtcat cagaataaaa tttatcgagc gcctactctg  128337
```

```
tgcccagcgt gtgctaggca ctgcagggag caggcctgaa aaggccaaga cagtatccaa 128397 tagaatattg tttcatttca gtaacaatgg cctgaggtgg ggaacaatta tccggataat 128457 tgaagcaaat gcttcacctc cctccctccc tctccagttc tcctggcact tactattttt 128517 tactacccta ttcagagatg tggttttttgt attggagggc gggcggggga ggcaggagtg 128577 tgtaagagga gggttgaatt attcacatgc ataccaattc cccacttccc ttggcctaaa 128637 ttttctgaaa gcttggagcc aaaatagctg cttagttatg ggagcaaaga cttaaaaaaa 128697 aaaaagtcac taaaataaga gcaattcttt ataattttta gcagcccagc ccttctggtt 128757 tttgatcttg gtcatctaca aaaatcacct ggagagcttt ataaaaatac tgattaccta 128817 agggatttcg atttaatgat gtgaggctgg aacacggcgg ggtgtagatg gaggggggaga 128877 cagaagtcaa ccagaattct gcatgcggtt ctgatgtagt tgagaaataa ctgataaatc 128937 ctgcccccta cgccctccta ccatggaatc tgaagagagc aacgtaactt ttttgagcct 128997 tatctggtca tttgatagtt ggaaagtgtg tattgagcgc ctattatacc ccaggctgcg 129057 cgcaagggaa ttcagtagca caagacccgc ccccggggag tttccaggtt aagcgaatca 129117 acaaattaac tcggagctgg tgagttaaaa aggtcgtgtg aatatgaaag aaaagctcaa 129177 ggggctctgg gtgatgataa aaccgaagct tgaagtgaca tttaaacgga gacctgcaag 129237 atgtgcgggt gttggcctgg gaaagaggga tggggaatgc gttcccggcc acctaagggt 129297 gctcacggga gcctccgaga gtttctcttg gttaattgca aaaactgaaa ggaggcctag 129357 gaaagtggag aaagaatttc agtttctgca tctgtaaaat agagaaaatg ccatcgtctt 129417 cgagttttg tgaggaattc aggactgcct aacaccgggc ctggtgcctg gtaaggctcg 129477 tggcttctct tgttggtttt attattatct gagacctgca gctccatagg ctcttgaagc 129537 ttgtaaatta ggtatcagag tccctgggct tggcaactag gagccaggaa gccgctgcac 129597 aatcatctct ccgtcccccc gcgccttttc ccggccgagt gttgccctct aaggctcctc 129657 cacagcctgg cgctcgcacc ctgaaggcgc ccagtgtggg gcctttctat ccctcggttt 129717 ccgggcatat gtttgttcag cagttacatt aacctcgcca ctccccaccc ccgtcaaagg 129777 ctctggcgtc ctggccgtcc ctacttggga ctgcgcccta aatttcaaaa cgttcctatg 129837 atattagaaa cctcccagct ttgctgcaca cccacctgct ttgcatagga ggaaaacagt 129897 cgcctttcga gtatatgaca atactcgtag gtacattttc tgagctctca ctgtgtggca 129957 gttcttgaac caagagcctt gcctgcatga cctcattaat ccgcacaaca gccctcccag 130017 ataaaatgcc attattttct cctcattatg tttgcggaga accctatttg aactactgaa 130077 gttcaaagac tgaaccaagg tcacacagct agtgatggca gagcctttta ggcactaagc 130137 aatactaacc acctgataac acctagcatt tattgaacac ctactatatg cctggcagtg 130197 gctgaagact ttaatgcctc ctttatttct cacagcaacc ctgtgaggta ggtgctttta 130257 ttacttcctt atttgttggc tgtccatttg ttggttagtg tggttggttt tcctacatat 130317 taaaggttct gagggccagt ccaatgtacg gactgaaatt agaatgagga cagggaacat 130377 gattgttttt attcacctgt gcccagaaca cagtaagcgc tgaaaaacat ttggagtgga 130437 tgaaagcaat attttattat ttaattcaaa agccctcttc ataatcaatc cgtatgcttg 130497 ttgactgcaa actgctcctg gcagaaaact gggtctgttt tatgtattca ccagtgtatg 130557 ccaaatgtcc agaccagagg tgacatatat taggatggca attaatattt gttgaatgaa 130617 tgattcctta tttcagatag gaaacggagg ctccgagaca acgtaaaact ggccaaggcc 130677
```

```
acatagcaag tggcagggg agaattccaa ccatagtttc taacgctgag tcccttttc  130737
agcctcctgc cctgtgtccc cggggcatag ggacagggcg cgggaaccct gtgctgcgcg  130797
gccgaggacg gttgtaagtc tgtcctcact cgcccgcgtc ccacacctgg gcgagggcaa  130857
gggaggcaga agaaatgaga cgctggagaa gccgctccga ggaagagggt aaacaaacag  130917
gctctgggc tgcgcgaggt gctctctgcg cgacagctcc tacccggcgc tcttgctccc  130977
acggctctaa aacctcaacc tactccctc ctccagtctc ggtctccctg ggtctccgcc  131037
tctctctctt cctggctaac ttatttctca ctgggaaacc aaggaaatct aaacgatcgc  131097
actgaccca cagcctcaaa acaagcccat ccgcaaaggc caccaaacac ccgctcccac  131157
accaggcaca aagtcctctc cgcgacggat gcgcatgcac gagcgcgagt gaggaggcag  131217
agttagcgtg tgcgcctgtg cgcatgcgtg agtgtaagtg ggtagggagt ccttgagtgt  131277
gtctgcgcgc aagctcgtgt aaagagcgaa ggcgaggtgg gggcgagtgt gcatgagcgc  131337
gagcataagt gtactgtcaa cagtgagatt aaggtacgtg ggcgtgatgg tgtgtgaaga  131397
ggtgaaaagt gaattagaat gagggtaggg aatgagattg cttttccttt tttattttta  131457
aattatttca atagttttt gaggaacagg tggtgttagg ttacatggat aggttcttta  131517
gtggtgattt ctgagatttt ggtgcaccca tcacccaagc agtgtacact gtacccaatg  131577
tggtctttga tccctgtgcg cggagctgtg tgagtgaagc gtgtttggga gcatgggtgt  131637
gtgtgaatat atgagtgtat gaatgtgtga atgtgaggaa tacgagaaac tggggatgtg  131697
cacagggtga gtgcggtgtg aatgagagtg tgagaacgtg cgtagagaga gcaggagtgt  131757
gtctgcgtgt gcccggcccc tggagcccg cctccccact aggcacgcct tcctcttggt  131817
ggggtgcgct acgggcgcag cccagtgcct cgtccgcgc agacccgctc tgctggtcct  131877
ggagcctggc gtgggctgag gcttgaaact ggcgtcactc agcgagccag aaaggagtgg  131937
gcgggagtgt ctgggggtg cgctgtctcc ccatgtagaa gcctggacac tctaagcagg  131997
aggggctctg gcagtattgc ctcgaggtcc tcccttcac ctgcccccag tattgttcac  132057
ccacctgtgg atcatcttta tgttcatgta ctcagggagc acccatggtg tgcctatagt  132117
atgccaggct ctacttgggc ttgggaaacc gtgagaacaa gatagcttag atctcatttg  132177
ttttggaact tccactgggc ctttttattaa tgtgtaacca gcttgcaaaa tgccagtcat  132237
acacaagttt tgtcgcctct gtcctcaagc agagggcat ggagattatg agacaaacac  132297
tgatcgtaat aagacgatgc attgaaatca gtgcaaatcc atttcatctc caacccaacc  132357
tcacccttc actgcaccac tgagtttggg attgggttta ggaggtcctg gatgtgaatc  132417
caccttctct ctgaccatgg aaataataat gaccctcttc tcacaggatg gttgtgagca  132477
ttaagtgagt taagcctgac atcccttggc acaacgcctt gcacatactt agcactcagt  132537
atacaaacta tgacgacgtt gatgtgtgat gacgttccct gagtctgatg gaatgttgtg  132597
gggaaagagg aggatgcgt ttgtgagcta caaaatttaa gggattattt ctggatttag  132657
gttaaattag gccggttgtg gtggctcatg tcaataatcc tagcactttg gcaggccgag  132717
gcaggcagat tacttgaggc tagaagttcg agaccagcct ggccaatata gtgaaacccc  132777
atctctacta aaaatacaaa aattagccag cgtggtggta cacgcctgta gccgcagcta  132837
cttgggaggc tgacagga gaattcttga acctgagagg tggaggttgc agtgagccga  132897
gattgcacca ctgcacttca gcctgggcca tagagcaaaa cttcatctaa aaaatatata  132957
tatataaaat aaaataatta aattgtgtat aatttataca gattgagtat ccttcattag  133017
aaatgcttgg gaccagatgt gtctgaagat tttggatttt ttatggtttt ggaacatttg  133077
```

```
catgtatata atgagatatc ttggaagagg accctagtct aaacacaaaa ttcatttata    133137
tttcacatac agcttattca gtgtacatag cctaaaagtt ttttatacaa tattttaaat    133197
gattttttgc atgaagcaat atgttttaag tacttctgtg tggaattttc cacttgtgat    133257
gtcatgttgg tgctcaataa gttgcaaatt ttcaatattc agcctgtatt acattctcct    133317
ctagcatcag gctagtgtta tagtatcaga tactccatct tcatccttta ctatgacttc    133377
ttttcttcca ccaatgttat caaaagtact gttaccaagg gaaataaaaa tgcagcaaga    133437
acctatagga gctgaatatt cttttaggca gctttggaag cattttttagt cctgttaaaa   133497
tggaagggaa tattttcaca gtggcacaaa atgaatgctg taatttaacc ttgtgagcaa    133557
aatttctgat taaatacaac ataggaaata tgtttcctga ttagccatgt acctccctgg    133617
aacaaggtat tgtataaaca attgcaagac atacttattt ttattttaga gaagctgact    133677
tattaaaaac attttttgat attttgatca aatattttga tcactatata tgtgtgtgta    133737
tatatatata tatatatata tggaatgtgg tggtgggatc atagctcact gtagccttga    133797
actcctaggc tcaagctgat cacaatataa ttttgtttaa aaccaaaatt tttaaagatt    133857
ggatttcatt attgagatgt tttcccaagg aaaaaaaatc aaaagaaagg cttgaaagat    133917
tggagaaccg attgcagatc taggttcttg aatttaacag caagaaagga attctgtcct   133977
tatgtaactg acctatctca tgttataagt agggagactg aggtctcaag ggatgaaatg    134037
gtcttagtgg tcagtctctc ctacagtcac caaataggac catatcagct ttgttcctct    134097
acctacagtt ttatacactt gcaggaagat gccctggaaa ctaggagaag agaaggtaca    134157
ggagttccag gttcctgcat taccctcagg tctctgttgc tggcacctcc atcttctggt    134217
ggctcttgcc caaatccttt gaatcttctg tgactcctct cttgctcttt ctctaatcct    134277
gtacatttaa cccatcatga agtcctgaag gctttaactt caaatgtaac tggaaactga    134337
ccacttctta acactccaac tactatcgca cgggtccaag ccatcaccac tgcatagggg    134397
tgactgggtt cattcttcct atacttgcct ctacaatctg ttctcaacag agcagccaga    134457
aggatcgttt tgaaatagaa gtctgatcag gtcagaccaa gaacaaaagg ccctccatga    134517
tgccaccatg gctgtctctg accactccaa ccactggcct acttgctccc tctgttttcc    134577
ttgctggtct ggccctctct agccttcccc tctgttgaga actcttcccc tacaagctca    134637
cacgtcttac ttcctcacct ttaggtcttt cctccaaaga cactttctta ctgtctttt    134697
tcttttttgc tttgaaattt agaaacaaat tttatttaag atctgaaatg taattcctaa    134757
aatatcaact ttttcagaaa actgtggctt acacaataat gcattgcctc tatcacgtta    134817
caacatgcat tagactcaaa tgcaaaaacc atgaaacaaa cgaccaccct tcaacaattt    134877
gcgcaaagac agaatgccta aggaacaaca tagacggatt tgcagaggat gggctgtttt    134937
acttcaagca tcattaaaaa aaagagaaca aatgcatggg ttttttgggta tatatatcaa   134997
attgaatgtt tggcactagg agtcagggca ttttgtcatg tagcattaac acatattaga    135057
aaattgtgta gtgtcaaagg ggtagaacca ccagcattca agcaatgttg tcaactaggc    135117
aataaaatgt tccactgaat atttcttctt tgttctaatt actgcatacc ctggtagcaa    135177
ctttgaaatg agaaaaggag cttacactcc ttttattttc tgtttaaaac agaacagaaa    135237
acaaactgaa acataagccc tgttttacat taacaatgtt aagaatatc cattttacaa     135297
gaaaaagact aagaacaaaa agtgtttcca gatctcaggg aaataacagt gaatggtctg    135357
tagaccagca cagggctttg tggtggtact tagcagaagc tactttgtaa tcaccgccag    135417
```

```
taaaaagaga tgcagaattc tttgccagat attttaggaa atcatgcaaa tggcccaaca    135477
ataacgcaag gctcttctca tcaagggata tataggccaa catttctcct attcttacaa    135537
ataacctcag taggtgtgtg ccccttaaac ctgggacaca ggagcatcag ggtgagccaa    135597
gaggatttct gcatacaggg gcctctcaaa tttgtagagc agctgagtgc ctaacatcac    135657
gtcgaaatat tcttttattc ttgtcacaat ttcattaact gcctatgcct tattatcgac    135717
gtttccctgc gatgttttac aatttgcata ctcctttaga attgcatcta cattttgctt    135777
agcagggagt taaaacagct gcttctgctt ggtaactaag ttccagtccc cagcaagcca    135837
tggtttcgat tcttcaggca tcttcacttt aacttccatt ctgttcttaa atgcgtcctc    135897
gctttcaaca gtgaggtctg cccaggctct ttccttccct ggggtctgag gtgctttgct    135957
ggtactgccc ccatatctgt ttccaggagt cctctgtttg ttctttctgg tcttcctcac    136017
ggatcctgaa gctaagaagt tctctgcaga gcgaccccac atcttcctga gagaggtggt    136077
tcaagatttt tctgctgtgg accagctgcc ttctttcctg aggaggcccc tctcatctct    136137
gcatgttgct tctagttggt tttttgaagt tgtcttcttc tgcagattgt tgtccatgag    136197
attgagaacc cggctttctg gaactcattc aacccttttt attccaacca acaatctttc    136257
ttctttccaa gaactcctag ggatttccca aaaggactct tatagatctt gcaggatggt    136317
ctaggaggat acagtgggag atacaatcca agattctgta atcagaggtt tctacaatca    136377
ggatcagatc tcctgagcct tactgtacag caaacttagc ttttctgaat ggtgacctga    136437
aatgagaatc cagatctttc tagctgccgc tttctcactc tttttaaaat atcaaagctg    136497
ctactgtgcc ttctgcactc ccaatccctt ttccatgctc tatttttttc tcccatagca    136557
gtcatcactt tccaactata tgctacataa tatcttctgt ttatgtttat cgtctgaatc    136617
tccctgctag aatggaagct cctgcaggat atttatgtct actgggttca ttgagaacaa    136677
ccacccctatg agaagagggc cattattatt tcaaagagag ggtgaattta catccaggac    136737
ctcctaaacc aaaccccaaa ctcaatggtg cagtaaaagg gtgaggttgg gatggagatg    136797
aaatggattt gcactgattt caatgcatca tcttattact atcatcatct gtctcataat    136857
cttctccatg cccctctgct tgagggcaga gcccaaaact tgtgtatgac cagcattttg    136917
caagctggtt gcacatgaat caaaggccta gtggaagctt caaaatgaat gagatctaag    136977
ctatcttgtt tacatgcttt cctaagcata taaagcagaa cctggcagag gagatgctca    137037
ataatttatg aaggattgaa agaagaatgt cagtgttcta ggtggatgct tcctcaccat    137097
tctattttac ctgtatacag gactgcagtt tataaagact ctaaccagtt atgtccttgg    137157
gttagcacaa ttatttaagc tagataggac ttttgttttt ttttttaact gttatttcca    137217
caataagata ttgagaggtt aaacgacttg ccaaaatcag atcctggatt tagacttgca    137277
atcaaagtat cattttgttt ttggtgggag acaagttccc tttccagacc tcctggctaa    137337
atgaggaaaa ctaataagtt actggattta ctgtggatgc ttctaaatcc agtggccctg    137397
agattagggc taaggttctc cctccactgt cggcctgtgg aattctttag ctgctcacat    137457
cacagctaca tgaacagttt ttgggaaaca caccataatg ccacatcct cttgttttta     137517
taatttacac agggttgaaa acaagagata ttgtcttgtt gttagctaga gctcatttgg    137577
agtctgccct gagtctctgg acttggctcg atgcccttcc tcatctgact gctctgggca    137637
aaccaactac tgtcttagtc attgtattac tctgtttgga ttctctgtca gtccatcaga    137697
tttagctgat gagctcattg actgaaaatt gattgagcaa gacagtgtcc ctaattctgt    137757
atgcatacac agcaccattg tcttccacag atacttcgta ataattggca tccccctacg    137817
```

```
agatcattgg tatctcaata attaaaatca atagctgttg ttaaggcaag aatttatcat    137877
agtaacctac aaaagtggta aaaaggtaat ataattcaga agatagatgt aaatataaaa    137937
ttaccaattc tgaacaggtt tttaaagata atacttgttc cttaaggaca ttcatattta    137997
ataaaataaa tgagttattt ctttatcatt tgaatgacat aaattgttac ttttttatgt    138057
gagtggggaa aatatagcac tttaacattt tgagataagg agtagaacac tttatttata    138117
tcaattcagt gtttagcttt tcacagattt tgtctctatg ctacctgttt gattttttttt   138177
tttttttttt tttttgagac agagcaaggc tgtgtctccc aggctggagt ttagtggtga    138237
aaccttggct cattgcaacc ttcgcctcct gagttcaagt ggttctcatg tgtcagcctc    138297
ccgagtagct gagattgcag gtatacacca ccacgcctga ctaattttttt atacttttttt  138357
gagtatactc taatttttttg ctttctgggg ttttaccatg ttggccaggt tggtctcaaa   138417
ctcctggcct caagtgacct gtctgccctg gcctcccaac gtactgggat tacaggtgta    138477
agccactgtg cttagcctgt tagaatttaa taggtctcag ttatacacta tttcactatt    138537
ctgggtgctc taaagcatca gtgacaataa ttatgaatgt agaaggtgca ttggtagcca    138597
aagttaacta tgtcattgct gtccttgaga ggggttttta cctgtgtttt cttttttttt    138657
tgtaattttt ctgagatcag acaagttagt tagattccaa acaatatggg cctaatataa    138717
tcacaattcc atttaaattg gccaaagaat gaccccttatc cagacaggac tcttagtgta   138777
cttagctgtc aacaaaatat aaaacttatc agaataatgg ctactttttaa atataaggcc   138837
tgcatcatat tgttagagga acttctggaa ataggagaca gttgctatta aaattcaatt    138897
tagtttaatt caccattatt tactgagtgc ctacatatgt taggtactag ggctacaaag    138957
atgactagac cccgggctgg gcacagtggc tcacctaacc atagccatca atgaattcaa    139017
gtaagtgtgt gatagtggca tgcaacaact gtggaaccat ggaggagaga tctgttctttt   139077
cttcctgctg gcatcatgga ctctgagact gaggcttgaa ctatttctag gagatgctca    139137
gagtaaaaac aacagcagga gaagagactt ctaggccaaa gtttcaagag tgagcacagg    139197
cccagaggat ggatatgcat taagctgcat gcaggagaca gaagcaggaa gggctgctta    139257
gtggcagaaa gcaaagagtg tgagtggcag gtgaagaagt atgaaggcct ctgtagtaag    139317
atgaatggtc tttgaaggat gctaagcaga aaattgaaat gattatattg taatcattgt    139377
aaaggatggg attggaagag agagaaacca gagacagtta gtgtccagta ccaaagtcca    139437
gacttgaaat gataagtgtc acattaatca gtagtggtgg gaatggagag gagagaataa    139497
attcaagagt aatttggaag gtagcaccaa tgagccttgg ttactaatta gataggacag    139557
gggtacagaa agacaaatgg gtcagtgggg acttgggttt ctagctcagg tgtctgtatt    139617
gaatatgatt gtgttaacaa atatagtggt tacagatgaa agataagcag ttttttgttg    139677
tttcagatga gactgtagat agagtgaatg gaacagaaaa aagataaatt ggttgtaaac    139737
atttgagtt ttaagtgcta taagaatagc caagaggaaa tttttgatgt agagtagcag    139797
ttggaaatat ggatctgaat ttaacagaaa ttgagattgg agttgggcgt ggtggctcat    139857
gcctgtaatc ccagcacttt gggaggctga ggtgggtgga tcacctgagg tcaggagttc    139917
gagaccagcc tgaccaacat agtgaaaccc cgtctctact aaaaatacaa aattagctgg    139977
gtgaggtggc acatccctgt aatcccagct acttggctgg ctgaggcagg agaatcgctt    140037
aaacccggga ggcagaggtt gcagtgagcc gagatcactc cagcctgggc aatagagcaa    140097
gactcagtct caaaaaaaaa aaaaaaaaaa aaaaagaaaa gaaagaaaaa agaaagtgag    140157
```

```
agtagaaata aaaatggcat cagcctatat tatttaaagc atatataata tttgaagcaa    140217
tatgatgaga tgaaattacc cagggttggt gtcatggtta ggatggtggt caggaaagtc    140277
attgttttgg tgtagtactt agagtagttt gaatatatta tgtgatatat ttgttggatg    140337
ctgagtctct tctacagtct cacttccctc ctctaaggac ttgtataatc ttttggtgag    140397
tctatctagg gataatccag tacttactat ttgacagtgg aactggaata cacctgggaa    140457
accaaattaa ggttgtaaga caggttggtg taaatatggg attggattta gaacgactg     140517
gtatgaatat gagattagag ttacaaatag ccctgaccac cagatgactt gaaaaggtgg    140577
ctgagtactc tttcctcatc cctctcatct aatagaaata gagtggagta gggaaatcct    140637
gatggagggt tcagacaccc tgccttcttt tctttccaaa agactttctt ttccatgtag    140697
accgtagatg ttttctgact gagtcaactt tatatccaca aggtctgttg acatttaaca    140757
tgccaaagat ccatacagtg gagcagccag atgtttaggg cctggtcctg gcttattgcc    140817
atgagcattg ctcagattcc cagtctgagt cagaatcctg agtgacagat cacaggatgt    140877
ttgtgtttcc tgaaggactt aaagggcttg caaaatgttc tgtcttatcc acctccagag    140937
agaagattgc tcattttga gatccatgta gatggaaaaa gaaggaaaa atggtatatc       140997
aatgcacaaa atcatataca gtatcaccat tcatcatcag ctatcactct tgattttcca    141057
tcagtcactt ccttacctat ctaatgccct catcccatta tgttcgggat caaccttttt    141117
gcttcgacca ggctagcctg tttgtggtcc atggcacaca tagttatctt accatatgtg    141177
gggtttccca ttgacacctt tctccacctc tatcatctat ttttcatctt taaattgcta    141237
ttcaaaacta tggcttctcc acaaaacatt tgcttcccaa tggtaaaaac ttaggctggg    141297
tgctatggct cacacctata atcccagcac tttgggaggg caaggcagga ggctcactta    141357
agaccaggag ttcgagacca tcttgggcaa catagtgaga cctcatctct aaaaacaaca    141417
acaacaacaa caacagcaac aagcaaccca aaacaagcac atcaaatcat cccaaattca    141477
ccagtggttt cctatatggc aattaaagtt ttatctcccc atagaaatta taccagaggt    141537
aaaatttata ctcatttggg cataaagtac ttatttatac atgtctaggg cagattcctg    141597
atctttccat agcagtatgt tacagagtag ccctcactta gagaggtaga taagtagaat    141657
agaatatttg actacatcaa attgaagtat cttagatgat gagaataata gcgataataa    141717
gtatcattca tcaagtgtct gccatgccag acactctact aagcatttg taatgttatt     141777
acatttaact atcacaataa agattaagaa gggtatcatg cccatcttat agactagaaa    141837
acaaagattc aaagaagtaa tttgaagcca ggcacagtgg tgtgtgcctg tagtcctagc    141897
tacttgggag gctaaggcag gaggatccct tcagctcagg agttcaaggc cagcctgggt    141957
aacatagtga gaccctgtct ctgaaaaaag aaaagaaaca aataaaggac taatttgccc    142017
aaggtcttaa tttataggca gtggaatctg gattcagacc taagtctttt ttttccccag    142077
cttttgaga tattaatcaa ataaaatttg tatatattta attgacaaat aaaaattgta      142137
tatatttaag gtatatgtgt gatgattta tatatatata tatatata tatatatata        142197
tatatatata tacacacaca cattgtgaaa tgattaccac aatcaagcta attagcacat    142257
ccattatctg acatagttac catgtgtggt gagaatactt aagatctact ctcacagtaa    142317
atttcaagta tacaatgcag tattaaccat tgtcaccatg ctgtacatta gagacccag      142377
tactttttt tttttttttg agacagagtc tcactctgta gcccaagctg gagtccagtg     142437
gtgcgatctc ggcctccacc tcctgggttc aagcaattct catacctcag cttcccaagt    142497
agctgagact acaggtgtgt gccaccacgc ccagctaatt ttttgtattt tagtagagat    142557
```

```
ggggtttcac catgttgctc aggttggtct tgaactcttg atttcagatg atccacctgc    142617
ctcagccttc caaagtgctg ggattatagg catgagccac tgcacccagc cgagacccca    142677
gtgctcttta atctttcaac agaaagtttg tacccttaac caacatcttc ccatctcttc    142737
cccttaccct gcaccccaaa cccctgcctc agctcctgga aaccactatt ctactttctg    142797
cctctgtgag ttcaattttt ttagattcca cctataagtg agattatata gcatttgtct    142857
ttctttgtct gtcttatttc acttagcata atgtcctcat tgtcacaaat ggtagaattt    142917
tcttttttt aatggctgaa tatatatata tatacacata tatacacaca tatatataca    142977
catatatata tacacataca tatacacata tatacacata tatatgtaa tatatatata    143037
ccaaattttc tttatccatt aactgtggat gaatacttaa gttgatatca taacatgcaa    143097
taaacatgag aatgcagata tctctttgag ataccgattt cattttgttt gactacatac    143157
ccagaagtgg gattgctgga tcatatagga gttctatttt taattttttg aggaactgcc    143217
gtactgtttt tcataatggc tataccaagt tacatttcct ccaacagtgt ataagggttc    143277
cctttctcca tacccttgca gacactcatc ttttatcttt tggataatag ccattctatt    143337
ttaaaaaatt tttattttt aatttgtttt tttttatttc tgagacctct cagggatgaa    143397
aatattaata attgccattc taacaggtgt gaagtgatat cccattgtgg ttttgatttg    143457
cacttacctg atgattagta atgctgagga ccttttatat acctgctgga cattggtaca    143517
tcttctttga aaaatgtct attctggtcc tttgcctatc tttaaatcag gttttttgtc    143577
tttcactatt gagttgtatg acttcttttt ctatattaaa tactaccccc ttctctgata    143637
cgtggtttct aaatattttc ttctattctg tgggttttct tttcatttgt tgcttgtttt    143697
ctttgctgtg cagaagcttt ttgatttgat gcagtgtact acttcttat ttttgttct    143757
attgcctgta ctttggtat cacatccaaa aaaatcatt gccaataaca acgtcaagga    143817
aattttcccc tattttttgt tctaggagtt ttgtggtttc agactttagc ttaagtctga    143877
aaggataaaa gttttctgga aggggaagtt ttgttgttgt tgttgtttct ttgtttgctt    143937
taaatggagt ctctgtcacc taggctcgag tgtgcagtgg cgcaatctca gctcactgca    143997
acctctgcct tccaggttca agcaattctc ctgcctcagc ctcctgagta gctgggatta    144057
caggcaccca ccaccatgcc tgcctaattt ttatatttt agtagaggcg gggtttcacc    144117
atgttggcta ggctggtctc gaactcctga cctcaagtga tctgcctgcc tcagcctccc    144177
aaaattgctag gattacagcc atgagccacc gcacccggct ctgtaagggg aagttttaac    144237
actaacatgg aaaagaaagt atatagtaaa atttcaaaga ttgtataatt taatgtcatg    144297
taggaaaaca taaagataat agttaacaaa tcataagaga ggccgggaac ggtggctcac    144357
ttatgtaatc ccagcacttt ggaggccaa ggtgggcaga tcacttgagg tcaggagatc     144417
gagaccagtc gtgaccaaca tggcgaaacc ccatctctac taaaaataca aaattaacgg    144477
ggtgtggtag tgcatgcctg taatcccagc tacttgggag gctgaggcca gataatcgct    144537
tgaacccagg aggcggaggt tgcagtaagc caagatcgtg tcactgcact ccagccctgg    144597
ggacagagac agactctgtc tcaaaacaat aaataaataa ataaatcatg agagatcttt    144657
taaggttgta tgcagaaaaa atgaaaggcc agctcaatac agacaaacta attcaagctt    144717
tattaataag gttgttccta tattatttta attatgatcc agaaacaaaa gaggaattag    144777
aaaagattgt ggaactgttc tctaatggca tgatcctaat atgactggat taaatctgac    144837
tggactgctc tgttcaacac aaccatcaaa atgttgattt tgaccatcct agcaacgaga    144897
```

```
ataaaaagca acatctgacc ctttgacagt ggcatttata aaaatgaaat ctcacatata   144957
catgagggta gggtcctgag ctacctaaag tttgtaaact catttcagta acttgaagaa   145017
acctctatta gtaagcacta attatagaat cccacatgtg agacacatta cattcatggg   145077
ttgattggca tcattctcag ttgatctgag attatcatca aaaaaatttt gacttaggat   145137
ttctttgcca agttacatca ttcctaaagc atctaaaatc aggcagggca gaatagaacc   145197
acatgctgat gtcacagggt gtaggtgggt ttgaatggtc tctgatttag tcaacattca   145257
tgctgtaatt gtgaatgata gctgctctgt gatactaata agaatgctca cctgctcaag   145317
tgatacgccc ttgaacaaca ggtcctcaca gttggcagcc gggtggcagg agggctgcta   145377
tagaaatgaa gttatagaga cctaacagaa ccactggcag agtgggatct ttgagccaaa   145437
gtgggatcat gtctaaggtg agtagtagcc tcaacagcct tgcaagtaca ttttgaggaa   145497
gcatattctt gtggagaaac ctcttacagg ctagtgacta tgctcatcct cagcaaaata   145557
acctgtctgt tccttagatg ataggtgcat agatagtgtg aactattcat ttgattctca   145617
gaaaacaata aaatcatgct ggctgttctt tccagttcag ccattgaact cttaaattgc   145677
cagacagcca tgtaagtctg aatgaatgac cattcatata ccctttccac tgcactgcaa   145737
tatggctctg ctcagaatgg caaggagaaa gactggaaga gaaaaatggt tgcaggatct   145797
tcttgtgttt ctacaaggct tgacggtgc tgagaacata atccattctg gtgaattttt   145857
tctgtgaagg aggcaactag aaaggaatat tgtcttcatt ctctagaaaa aaagaactga   145917
aggaagagaa tttatagttg gctgattata acagcatgaa aacgcatatc ttctactctt   145977
tatctagaat tttgtccatc ctgattaaaa taacaacacc ctcaataaca actaacgttg   146037
agtacttgtc atatattgta tcatttaat cctcccaaca actttatgaa tgagtactat   146097
aattagctgc attacacaga tgataacaag gatgacaatt gttgagttaa cccagtttcc   146157
tcagtttctt ttttaaatt tttaattgtt tatttatcag tacaaatgat tccttagccc   146217
acatattcat gtttcatagt tcaggaacat aggtcagtga caaacttctg aggaactcaa   146277
tcccaaaaca ttcttaacat tccaaaatca ctttgcactc tgaaaggtac cagccctctt   146337
cacctcctca aaatctttca tggaatcata gtttctgtag aaatctacat atatctgctt   146397
tcttggttca gcaatgtaaa ctttaagaga gctgcaaccc ccagcattac aagaaatgct   146457
ctgacaatat gaaatcacag acacctggcc aaaaggctat gcatctgaaa tttcttcaaa   146517
acactggaag ccgtggtagt tattgtcctc aacaccaatg tccttcctgg ctgatggaga   146577
aatgcccagt ttcttaaata tcatcatggg attgtaaaat ctttggggaa gcatatagac   146637
ttttaaaata accactcaac aattgctaat tatactgagt aaaaccagtt agctttattt   146697
tctcattgct tatattttt ccttcttatt tatcttttct cccttgcagt agaaacattt   146757
acctacagca gaagtcttag accttagttg tatttcagct tttagggcc atctgagctg   146817 agtaagtcat ttttaaaaat taatttaatt aattaattaa ttttttttt gagacagatt   146877 ttcactctat tgcccaggct ggactacagt ggcatgatca tggctcactg tagtcttggc   146937
tttcctggct caagcaattc tgcctgagcc ccccaaataa ctgggactac agctgtgcct   146997
taccacgcct acctaattta tttgaatttt tagtagagac aagatctcgc tatgttgcat   147057
aggctgttct tgaactcctg agctcaagca aacctcctgc ctcagctgcc caaagtgcta   147117
ggattacagg tgtgagccac catgcccagc ctgagtaagt catttaactt aagttttctc   147177
tgaagtttat agaatgggat gaatatctct ctgtttacag cactgggta tggtgagggt   147237 cagatgtgac attgcaaatg aacatgtttt ataaaatatt aagcagtatg taaatactga   147297
```

```
tataaatatg gccggcacag tggctcacat ctgtaatccc agcatttggg gaggccgagg  147357
cgggccttga ggtcaggagt tcaagaacag cctatgcaac atagcgagat cttgtctcta  147417
ctaaaaatac aaataaatta gggcggtggg ggtaagtcca tgaaatggcg gctagtcagg  147477
agctgatgca agagaattct tgaacccaaa aggacacggt gcaatgaact gaaaagaacc  147537
cactgcattc catttgcgca ctagatgaca ctcagccccc aacaacaata aactcacaaa  147597
aatcctcccc cccattacaa acccaaaaca tccccactac tctctgcaca aaaactgcac  147657
ctcctcacca cacaaatnnn nnnnnnnnnn nnnnnnnnnn nnnnnnnnnn nnnnnnnnnn  147717
nnnnnnnnnn nnnnnnnnnn nnnnnnnnnn nnnnnnnnnn nnnnnnnnnn nnnnnntgc  147777
tcagacaagg ttgattttca gggttttttta gcaaaagtga tctaattttt tgatgggctg  147837
ccttgccaac cccaacataa ttcattgata ataaagtccc atattcctgt gataattgaa  147897
atagttaagg ttatatttgt tttacattgg ggcataattt tttttttaata aaagtaaagt  147957
tttttttttag aaagctattt tttttgaaaa gggaggttct tttgtaggta ataccctatgt 148017
tgagaatgtg atatgatgat atttatagac tcaacgttca gccaagattg acatttcctg  148077
cttctgatat ttttttttttt ggatatatga tgaatatttt tttttttttt ttagaaaacc  148137
ccgagttttg gtgaaatatt gttttttttt tatatgctac cagacgccaa aatttacgga  148197
tttaaaagtt gatttacttt ttattaattt ttcccgaggg ggaccttaat tgtaagggga  148257
atttttttttt tttttttttt tttttttttt tttttttttt tttttttttt ttttagttta  148317
gggtctcttt gttttttcca acataatgtt tctgcattca tctattctta aaatgaaaac  148377
cacataattt acttcttata aagtcttaaa tgggaaacca agaaatttaa tcgagcagta  148437
aaaacattct caaaatgtag accatgatct cagtttcttc cattttttctc ccgagtagaa  148497
aatagacttc tgcataagaa agctaaaatg tgttaatatt tttaagttaa aggtttaata  148557
ttatcagaat acaatccaaa gagtaaatca aattacataa ttcattttt atttattaaa  148617
tatggaatca tctactgaat tgcaatacat taaatatact gtttcctctt aaataaaact  148677
gcttgacagt taaaaaatta tgggcttgcc atacttgcag gtctcttatg ttttttagatc 148737
ttatttactt atttatattt ttacagtgaa atagtaattt aaaagagga tgggaaaatt  148797
ctgtagtcac ttgagttttcc tctagccaca ttttattgca aaccagttcc tcctttgaac  148857
atctttataa tttaagtctt taaaaatgct ttcatttcaa acactaaata tttctatatt  148917
agaaaagttt ttacagtata ttaaattatt ttttccacat gccccacccc tttacagtat  148977
attttaaata ctatctttgg atttcatttc tttctgtttt gtaagatgga tactataatt  149037
caccctggta aactcagttt ttcttttcagt attatgtgta caatatacat tgtactgtac  149097
aatgtacatt aatgaaaaac acataataca cattcagtgt acattttctt tcagtactat  149157
gtgttttca ttaatgtaca cttcataatg tatattgaaa ctgaacatgt tgaagctcaa  149217
caagagtttt cgattaattc tgtttatatt ctgaacgatt agaatgtcta agtgtaaggc  149277
agagtacgag ctttggagtt gggcatctgg cttggtcact tacttggcaa actcttttg  149337
tcttgatgaa cttccatatc tctgtgcaca aaatgggaaa aacaaaatc tcataaattt  149397
tggattaatt taattctcac aaaatgtcta tgaagcaaat tctaatgtta tcttcagaga  149457
aaaaatggc caagctgaat agcaccatgt gtaagcacgt tctgcagaac tggcagagct  149517
tccagcataa aagaagggga gagaggaaat gttctagagt caaagagact taagagacct  149577
cacttggatc ctcacttgaa aaaacaactg taaaaaggta ttttggagac aattggggaa  149637
```

```
atgtgaataa aattcattaa atgtcaagga gctattattt ttgtttggta tgataatggt   149697
tattatggtt agattttctt aatccccata atttacagat atatgtataa gtgaaatcac   149757
ataagggata agatttacct tgacatactt tagaagaaaa ccccacaact gattaaatga   149817
agcaagtgca gcttaattgt tgcagacttt tggatagttg tggaatctgg gtgatggtta   149877
tgtttgaaat gtttcagaat taaaaaaaga gaaaaattat gcagtggact cagatatgaa   149937
ataactggga tactagtgac acagatacag agactatgca aacatatgtt cccaggtgcc   149997
tggagaactc tcttgcatgc cagtgtatga caaaaatact ttcatccaag cactttcata   150057
ttcactttgt aattattgtg aatgtgtaga tatgctagtt tgccctaata tggtttatta   150117
agttggcctc cccatctaaa ctgtaatttt ctctgagact gagaagatcg gtttgatatc   150177
tttatccttt tcccattgcc cttgcatgat tactattcaa tcattgctga attaaacaac   150237
actttccttt gtttaggaag atgctggatg ctaaacacct gtcttactca ggcttcttat   150297
tgacatagca aattctaaac gtgttacata tacatgtgtt cctttctgc tttaaataaa    150357 actgatgggt attttatttct cccattgtgt aatgtagtct gtggaaatag tagccagtgt   150417
aggatgcctc agatatatcc agctctgcag gccaaagctc agcttttaaa gtggcgattc   150477
ccagttattt tgttaaatgg atgttaaagt catccctggg ttggagttta gacttttatt   150537
gaaaagcttt tctactaatc accagttaat ggatgaataa aattcacact tttggtctct   150597
tcattgtttt attgtcaaca cattctttct caagggagag aattaatttg gaagttggag   150657
gtcttcaaat taggaaagtc tgacaaatag gccaactcta atattcatat ttacagtgga   150717
gattttcaaa gaagtttgac ataatacacc tcacaaaggg atgccaataa gtcagtttta   150777
ggcattattt ttgaatacaa ggagactgtt catttcttct tttctagtat aaacacacca   150837
tatgtttaag tgtttgtaag gcatgttgtc atcttaaata atatttaaaa aaatcaaagt   150897
ggtacagaca caagctcctg gaaatgtgct ggtatctttt tttttttttt tgattgttga   150957
gtaatcctga aatgaatttc ttccaaataa agggatgtag ctttgtatta aattttgtaa   151017
taaaagttct caaatgatag attcaaaatt ctaaacattt ttaaggatta taaaaagata   151077
tgcctgaaat cttgcatgtt ttaaaacgta gtacaaagta agcttttat atgtaggcat    151137 ttgtaattta aaaaaaagtt ttatttgtgt tttcagaata aacgagctaa cataaattgt   151197
acatatttac agcaataaac tacatttcag aagctgcaca acaacttta taagtacagc    151257 tgatgatttt tgacaccagc tttcaaatgt gttttcattc tttcatttgc tgcaacattt   151317
aaaatcttgt agtaccaaag caaaggaaac accaagttat tttatagcaa agccacatta   151377
ttaacaaaaa atactgagtg aactacagtc ccgtgactgt tatggtatct gtgagtcctg   151437
aaatcgagag cacaagcatt tcttgtgtcc atacctgatt gcatgtaaat tgattttgca   151497
ttttacaaga acacacaatt actcaaggaa taattaagaa tagaaaaaag gccatgaagg   151557
gtaaaagggt caggaatcag aggccactga acagtttctt attcactgat tcactgctta   151617
ggaggaaatt ggtttttttc tttcacgtgt ataaatcaca gtcaacaggc ttcatggatt   151677
ttgtccacag atagcttttg agataacaaa gccataaatg tcacatacat taagcacata   151737
aaaaggaatt aatgaaacgg ttagagtatt ttaatcaaat ccctaacaga aggggtacag   151797
ttaagcacac acagtatgaa agtttgcttt caaatgtaaa aagcaactac agaaaatcac   151857
aagtttcatt agacagaaca gcaatttcaa tcagaaaatg cagcatatat tgatacaaaa   151917
tagaaaactt gaaatataaa agtaaggagt ccaccttttc ctttcttggc attttttaa    151977 acctgtccca tttcattaaa atttctacag gttttactga aatactcact cttgacattt   152037
```

```
agcttcttta gtgtctggta ggtatacaaa agtattacct gcttaggtaa gaaagcaaat    152097
gcttatgtca aagagcctta aaatattgta atttatgttt atttgcaatg aaagaagtct    152157
acttggtaaa aataaagagg gagaaaagga ttcttttatt tacaagaatt gtaataccaa    152217
tcaggatatg agttggttaa ataatgtttg gtaggaggat agatagcaaa ttggtaactg    152277
gagatctaaa aacacaagga atgaaacatt taacatgtaa cgtatttggt gagtttagca    152337
taacggattt tgagaggcaa cagaaggtat gtatttcttt ctgtatatac gtagcacctg    152397
cttttgaaag ccccagctat ttagtacagg atgctatgaa ttaaaattgc aggagactga    152457
tgtggaaagt tcagctaatt ttctgattca atgaagtttt aggtgaggtg gtagccaaag    152517
aggtgtccca ttgctggcag gatagtagtt tcctaatttt tagtctcatg agtcctgctt    152577
tctcaaacct cctgaatcac tgtaggatta ggccccttga gtaaagtcaa gaggagcaaa    152637
ataatgttca gagatgatag acaggagaag ttttcaagca agccacgctc aacacagatg    152697
cctttctttc aaaaacaatt ttatttgtat taaacaatat taaacttccc aattttcatg    152757
tctgttaacc ttttaaatga catgccaaca ttatttcaca ttagccatca ggcttccatc    152817
atgatggcac agcatgctgc atggtggtta aaaaggataa agcttatttt aaaatatcaa    152877 aaagttttg gtccttgtaa acatgtaagt catttggaat tttcaaaaat gttgtgaaat     152937
cttggctttg tataatgcca cgtggtagtt tttttttttt tttttttttt cctttattta    152997
ggcagtgtct cactctgtca cccaggctgg agtacagtgg cacgatctca gctcactgca    153057
gcctcagcca cccgggctca agtgatcctc ccacctcagc cctccagta gctgagacta     153117 caggcacgcg ccaccatgcc tggctaattt ttgtatttta agtagaaacg ggcttcacc     153177 acgttgtcct ggctggtctt gagctcatgg gctcaagaaa tcagcccacc tcagcctccc    153237
aaagtgctgg gattacaggt gtgaaccacc gtgcttggct gacatggtag tttttatcaa    153297
gaaaaagagt tactgactct ccttgagata agaagctgag caacacagtc aataaatata    153357
tgtgtatata atcatgaaca ttcccttctt ggaagagtac tggatgttct gaatatgaaa    153417
gaacacttgg atatataatt ctgttttcca tgacactgaa gttaagttag aataatcaaa    153477
ggacttccct aaaattgtct caggggcatt gttgtaaaat ttcaagcttt atccagtgag    153537
tattttaaaa agatctaaca aacagatcaa caatgaatta attagcttaa aaaagaaaa    153597 agcagataca ctgcaattca atttatttga ggagtatcag gtagaaaaat acgttatcta    153657
gtaaactggg atggctggtt gccactctga ggtaaggctt gcaaattata tatttctttt    153717
atgcaaatta gtaaattatt taacaggaca actggaaagt taataattga aaaaaggggg    153777
tggaggcaga aaatgcattt ccttgtacat ctattatatt ttatgcactc ttgagaagca    153837
gtggtgaatg tcaagaactg tccatccctc ttatatagtt ctaaatcttc tatttatatc    153897
ttggcagaaa taggatttgt tgtgcagtac cttctgggag tattagaatt cacatggaa    153957 tgttccatca ataatacagt gtagccccag cttcaagaat aaatacccta gaacctag     154017 atttaaaagg ccattaataa ggcaaacaat gataaacagg ggaaaaaact ataaagaaa    154077 actttccttt ttccataaag gaaaagcagc ggtaattagc aaggaatatt caattcttct    154137
agaactggta gaatctagat tggtggtatt atcaggattc agtctgcttg gaaaatccca    154197
gtagaaaaaa atcttaatga ccactttgca agacacaaac ctggattcaa ctgtaccttt    154257
gactgcattt tttattcttt gagaggttgt agatagaggc tctatgggac taaaataatt    154317
tgagagagga ggtcatctgt cccacaaggt attatctata atcctgaaat attgcctgtt    154377
```

```
atgaaaaagt gtttgtcttt tgctgccttt cccactgtag gtgatctaat cagcatttat  154437
agaccctgcc atgggcagaa caatagttgc tttggacaat acaaaagaat tagaaaatgg  154497
ggtgtttgct tttaaggacc tcacaaaggg aggcagaata tctctttgca aaactagaaa  154557
tgtgcaaata aactgtctat tattattgaa taaagtgacc acaagaattg agggagtgtt  154617
aacaggagag tgaacagaat gaggcagggt gctcatggac agcatttttg aggatgttgg  154677
cctgattcat aaaccacgat tgagatgggg ctaggaagaa aaatatctaa tcagtggaaa  154737
taaaatgtaa aacttcaagc acagcagtga ggacattttg ggatgatgtg tggatgttgg  154797
agtggaagga taaggaagac ctgaggatga gcttgcttgc agctaattaa ggaactcatg  154857
gagaaataag gtgagtatga acgagtggtg gagaagactg ggccagactt aaatgatttg  154917
tagggagcca agacatgttt tctgtagtgt gttaatgtta catttattaa tatttcccca  154977
cccttcaggt ggctgagatc ccataattat ggtggtcgta tcatttatta ttcacatgga  155037
caattttgag agtgaaaagg agttttatta ataattacac actgagactg tctgaggcaa  155097
attgggtcat atggtctaaa caataatgtt aaccaaaaag aactggagca catttcaggc  155157
tattttgctg ctgtgcaaac tttccttcta tatattttct caagagacta aggaaaggct  155217
tttatgtatg ggtaagcaag tgggtggaac agatggaaaa agcagaaaac aaaactggac  155277
acagagtgtc tactgagcat gatatttatc tgttgggagt gggaatagtt ctcttccccc  155337
ttactctcta ctcattttg aactgcccaa aatctggatc atcaaggtaa aatggataaa  155397
atctagacag cttagtagag tggaaaaagc ttgaatggcc aggaaatact caggaaaatc  155457
atgaaagttt agagttggaa ggtatctttc aacaaagaag aaaaagttaa gaacatctgt  155517
ttacagaagt tgtattgagg acaatgttca gagaccggaa ttcttcatgc atgcttgaag  155577
aacatgaata gctagaatgc taatcacaaa ttaataaact gtcagttttg tcatggctgt  155637
gcctaacacc agtggattta actaggtaag tagttaacta ggtaagtagt taactaggta  155697
agccggggtg gaaggacttg agcaaggaga gtggataaca gatgttctaa agaccttgga  155757
tctttccaac tattatagat ggaaagctgc ttcttgcctg agagctcaaa aatatctgct  155817
actctacttt caggaaacaa gacagtgtgg ggtccaagac tgaggagggc actgcaacaa  155877
catttgggct tagatgctgc ctagagattg gcttttctac ccatgatggg gtgttgcatg  155937
gctgttcctt aattgaatta cagagaatgg tttaagaaca tctttatctt ccagggatct  155997
aaaaataaag gatttgtatt atctgagact ctctcttaaa gggaaatatt gtagttatag  156057
aaaattacaa aaatagtaac attttttccac ttggcttgca aatgtaactg tatgtcctat  156117
atatttttaa aggaacatga ataggtattg aattcaattc acttgatacc agatggctta  156177
ctctcaaaga catgatatca agaattatta ccaaattagt tgggttatgt tagcagaggc  156237
catggtcctc ctgtatcttt ctgctaacct cccatacaaa tgaacttctc taaaattacc  156297
tttgaaattt agttttggaa gagaacttgg aggtcatctg gtggcatgtt caagtcatg  156357 ctcctaggca gtggcagaga cagcaccaag accaggtccc caatcatatt aataattcca  156417
aggtgtcttc catccactgt gaattccctc tctccatcat gatgctcact tattgttaac  156477
ttttcgaggt taggctgcat actctttggt atatgtttag agaactctct tccaaatcta  156537
tataaatgct gtctagagga aacagatgtt ctacatattt ttatgggaga aatttagaca  156597
gtttgcaggc tgtctgcaag gctgagggga agtgggtagg gtgttatata gaagtagaaa  156657
tttgtaatgg gggtaatata caaaaaagat gaaatggatc aaggatagtc tgtaactagt  156717
ggtgtgctat ttgaatgata agcccttcta ggaggaataa taataaattg taaaatgggc  156777
```

```
ctactggaga ctgaaaaagc taatgaataa acaagtttga taaaggattg atacactttta  156837
agttcactat attacaatta tagtgtaagg agatggcctt atcttcaaac tctggggtag  156897
ataatataaa tttctgtaag attgagctaa agattttttat ttccactttta ttttgaaata  156957
ggccgggaca gagaaggttt atgtaaatac atgtactctt tacataagtg acagaaaagc  157017
agaaaagaaa aacaactcaa ggcagttcag aggaggctat tatgattata caacctgcct  157077
ctaaaggact tttaaaggca atgggaataa gaatttggaa aaaaattatt aaaattcatt  157137
gttttagtga attcnnnnnn nnnnnnnnnn nnnnnnnnnn nnnnnnnnnn nnnnnnnnnn  157197
nnnnnnnnnn nnnnnnnnnn nnnnnnnnnn nnnnnnnnnn nnnnnnnnnn nnnnctaatc  157257
acttcccagg aggtcccagc tcttctcagg ccatcctcct accttggcct cccaaagcac  157317
tgggattaca gatatgaacc accacgcctg gccactggta gttaatttct ttttttaaaa  157377
aaattattat gttaaaactt tgtgggtac atagtaactg tatatattta tgggtacat  157437
gacataggca tgcgataagc aataatcaca tcatggaaaa tgaggtatcc atcccctcaa  157497
gcatttatcc tttgtattac agacaatcca attcactct tagatatttt taaatgtaca  157557
gttaaatatc attgactata atcactcttt tgtgctatca aatactaggt cttactcatt  157617
ctttctaact gtatacactt tttgttccca ctaaccatcc gcaggctggg cggagtggct  157677
cactcctgta atcccagcac tttgggaggc ccaggcaggc agatcacttg aggccaagaa  157737
ttcaagacca gcctggccaa catggcgaaa tcttatctct gctaaaaata caaaaattag  157797
caggtgtagt ggtgggtgcc tgtaacccca gctacttggg acactgaggc atgagaactg  157857
ctcgaagctg ggaggtggag gctgcagtga gccaagatca tgccactgca ctccagcctg  157917
tgacagtgtg tgactctgtc tcaaaacaaa acaaaaacc atctccgctt accccccaacc  157977
cctcactacc cttcccagcc tctggtaact atccttctac tctctatctc cacaagttca  158037
attgtactga ttttttaccac ccacaaataa gtaagaacat gtgaagtttg tctttctgtg  158097
tctgacttat ttcacttaag ataatgaccc ccagttccac acatgttgtt acaaatgaca  158157
gaatctcatt cttttcatgg ctgcatagta ctccattgta catatgtatc atatttttctt  158217
tatccagtga tatgttgatg aacatttagg ttccttccaa atcttggcta tgtgaacaa  158277
tgctgcaaca acatggagg tgatagctga catactgatt tcctttcttt tgggtatata  158337
cccagcagtg ggattgctgg atcgcatgat agctctattt ttaggttttt tttgaggaac  158397
ctccaaactg ttgtctataa tggctatact aatttatatt ctcaccaaca gtgtatgagg  158457
gttccctttc ctccacatcc tcaccagcat ttgttattgc ctgtcttttg gagataagcc  158517
attttaactg gagtgaaatg atatctcact gtagttttga tttgcatttc tctgatgatc  158577
aatgatgttg agcacatttt tatatgcctg tttgccattt gcatggcttc tttggagaaa  158637
tgactattca aatcttttgc ccattttaaa atcagattat taaatttttc ctacagagag  158697
gtttgagctc cttatatatt ctcgttatta atctcttgtc agatgagtag tttgcaaata  158757
tttttttccc attctgtggg ttgtctcttg attttgttga ttgtttcctt ggctgtgcag  158817
aagcttttta acttgatgtg atcccatttg tccattttttg tttggttgcc tatgcttgtg  158877
gggtattact caagaatttt ttgcccagac caatgtcctg gagagtttcc tcagtgtttt  158937
cctgtagtaa tttcatagtt tgaggtctta agatcaagtc tttaatccat tttaatttga  158997
tttttgtata tgatgagtcg tagggtctaa gttttatttt tctgtatatg gatatccagt  159057
tttcccagca ccatttattt aagagactgt ccttgctcca atgtatattc ttggcacctt  159117
```

```
tgtcaaaaat gagttaactg taggtgtata gatttgtttc tggcttcttt attctgttca    159177
attggtctat gtgtctgttt ttatgccagt accatgctgt tttgattact atagctttgt    159237
aatataattt gaagtcaggt aatgtgattt ttccagtttc attcttttttg ctcaggatag   159297
ctttggtgag tctgggtctt tgtggttcca tataaatttt agcgttgttt tttctattcc    159357
tgtgaagaat gtcattggta ttttgatagg gattgtattt aatctgtaga ccgccttggg    159417
tagaatggac attttaacaa taatgattct tccaatacat gaatatgaa tatatttcta     159477
tttttaagtg tcctcttcca ttcctttcat cagtgttttta tagttttttat tgtagagatc  159537
tttcacatct ttggttaact cctgggcatt taattttatt tgtggctatt gtaaatggga    159597
ttccattttt gattcttttt cagattgttc actgttggca tatagaaatg ctacaaattt    159657
ttctatgtta attttgtaac ctgtaacttt actgaatttg tttattagtt ctaatagttt    159717
tttggtggag tctttaggtt ttttttttaaa tataagatca tatcatctac atacaaggat   159777
aatttgactt ctttctttcc aatttggagg ccctttatct ttctcttgtt taattttttcc   159837
atttaggact tccagtactt tccattgttg aaagtggaca tacttgtgct ccagatctta    159897
gagaaaggct tccagttttt ccccatgcag tatgatacta gctgtgagtc tgtcatatat    159957
ggcttttatt atgttgaggt atgttccttc tatttccagt ttttggaggg tttttatcat    160017
gaagagatgt tgaattctat ctaatgcttt ctcagcatcg attgaaatga tcacatggtt    160077
tttgtctttc attctgttga tatgatgtgt tatatcacat tgattggttt gcgtatgttt    160137
gaccattctt gcatccctgg gataaatctt acttcatcat gatgaatgaa taatctttttt  160197
agtgtattgc tgaattagct tgctcatatt ttgttgagga ttttttgcaaa aatattctttt 160257
agaggtattg gcctgtagtt ttcttttttt gatgtgtctt tgtctggttt tggtatcagg    160317
atgatactgg ccttgtagaa tgagtttgga agtatttccc tctcctctat ttttttcagtt  160377
catttttgagc aggattggta ttatttcttc tttaaatgtt tgctagaatt cagcagagaa   160437
gctattaggt tctgggcttc tctttgctgg gagacctttt aattacggct ttgatctcat    160497
tatttgttat tggtctgttc aggttttgga tttcctcatg gttcaatctt ggtaggtagg    160557
ttgtatgtgt ctaggaattt atccatttcc tctagacttt ccaatgtgtt ggcatacagt    160617
tgctcatagt agccactaat gatccgttga atttctgtga tatcagttgt aatgcctcct    160677
ttttcatctc tgatttttatt tatttttgtct tctttctttt tatctttttag tctggataat 160737
gatttgccga ttttatattt tcaaaaaacc aactttttgt tctgtcaatt ttttgtattt    160797
ttcgttcatt ttaaattcat tcattctgc tctgattttt tttttttttt tttttttttt     160857
tttttttttt taaaaaaaaa tctggctggg tcactcagga ggcacaaagg ggtgattttg    160917
gctcaaggca accccacct ccggggttaa acctttctc ctgcctaacc cttttgggta      160977
gctgggatta caagggcccg tcaccatacc cagttaattt ttgtttttttt agaaaaaacg   161037
gggtttcacc atgttggcca ggctggtctt gaactcctac ctgggattac agggggggagc  161097
caccaagccc ggcccataca ttacatttta aaaaacggc atctgaattt ctgctctata    161157
ctctacattt tattgaaagg ccctctgatc aaaaagttcc caaatttatt aaaaatccct    161217
taaaaattat attttttttac actatcttcc tcaaaattgg gcaaattaaa acaaaccttc   161277
acaaattttt gaaagtaaac tgtttctcaa caattgaaat gggtagcctc tgtagctaca    161337
cattttgact atgccttca tatgataaaa attcccttgg cacaatttct taaaggttgg    161397
aaatttctc attaaaataa aaaaaaacca caagtcctct acccattgaa aaaatttttt    161457
gaaaaatgct atcaggtnnn nnnnnnnnn nnnnnnnnnn nnnnnnnnnn nnnnnnnnnn    161517
```

```
nnnnnnnnnn nnnnnnnnnn nnnnnnnnnn nnnnnnnnnn nnnnnnnnnn nnnnnncctt    161577 ggaactttc  tcttttttct tgattagtct agcttttgtt aaggtttgtc agttttgcta    161637
atctttaaaa aaaacaactc ttagtttcat tgttctttta tattgtttta tgagtccctg    161697
tttcatttat ttctgctctg attttatta tttatttctt tttgctaaca ttaggcttac     161757
tttgtacttc cttttctatt tccttgaggc atagcactaa gttgtttatc tgcaatcttt    161817
cttctctttt gacgtaggca tttattgctt taaatttttt tcttagaact gcttttgcta    161877
aacccataag ttttggtatg ttgtgtttct attttcattt gtctcaagat aattttaaat    161937
ttccatttta atttctttat tgacctattg gttattcagg agcatgttgt ttaatttcca    161997
tgtatttgtg aattttctaa aatttcttct gctattgatt tctagtttca taccattgtg    162057
gtcaaaaaag tacttgatat gacttcagtc ttcttaagtt tactaagact tgtcttgtgg    162117
cctaacatat gatctattct ggagaatgtt ttatgtactt gagaagaatg tgtattctgt    162177
tgatgttaga tggaatgctc tatatatgtc tgttagatcc atttgttctt gaatgctgtt    162237
taagtccgat gtttacttgt ttatttctc  tctgcatgat ttgtccatta ccaaaagtgg    162297
tatattgaag tccctacac  tattattcta ttgcagtcta tatctccttc agattttaa    162357 atatttgctt tatatattta ggtgtgccat tattgcatgc atatatat   atatatat     162417 atatatattt tttttttttt ttttgagatg ggggctcact ctgtcaccga aatggagtg    162477 cagtggcttg atcttggctc actgcaacct ctgcctcttg ggctcaagtg aatctctgag    162537
tatctgggac cacacatgcg ccaccataca cgtgtttgta ttttttggtag aggtgggggt   162597 ttgccatgtt gccaggctgg tctcaaactc ctgacctcag cttaagcgat ttgcctacct   162657
cggcctccca aagtgctggg attacaggca tgagccactg cacccagcca tcatgcatat   162717
atatttgcaa tcattttatc ctgttgatga attgacccct ttaccattat aaaatgtcct   162777
tcttggtctc gtttttacag tttttgactt aaaatctatt ttgtttaatt taactattgc   162837
tatccctgct cttttttggt ttcatttata taaaacattt ttctattcct ttactttcag   162897
acaatgtgtg tccttaaaat tgaagtgagt ctcctatagg cagcatagag ttgggttttg   162957
tttttaaatc ccattcattc actctatgtc tttttttaaa aaaaaattaa gacaacattc   163017
atggcacatt taatcaggaa ttccaaatta gtgctacaaa cactaaaagt ataatgtttt   163077
attaatataa atatcacccc tcactgacat aagcaaaaaa aagctcaatt atgtggaaag   163137
aaatgtttac ccaaagaggt gccttccgct tataaacaca gactatatca catagcatat   163197
cagttctcaa aaggaagtaa ttctagatct aaagcttctt ctgtaagtaa catcaggttt   163257
atggacctgt atggaagaaa agtggctaca aaaaaggac  atgactattt ttctaatatc   163317
gttgtcgcgt gcaaacatta gcataagttt tacacattct tcaaaataca catacatgca   163377
tagaaaagtc acatttgcct taggcttct  aagattgtgc tacactaagt tatggataaa   163437
agactatgtg ttgcttcacc tttaaaataa aaagattttc agtacaaaga agaaaatgac   163497
acactgactc tgcatctgga ttcagtgtaa taagtagtaa ttgtatctca ttacaggcag   163557
atttcctcca accatttaaa aagttacttc ctatcataat tcaattttt  aattccaaac   163617 tttagaacta catataacct caggatttag ctgaaattgt actatctgat tattttgtaa   163677
attagcaaag ctaaaaattc tagcttgaat aatttcttca tagtataagg gatagtattt   163737
tatagtaata aaattattct taaagtcaat agttatcatt tattgaacac ttttatgtg    163797 tgctctacaa actcatttac acccacctca atcctcagaa atagatacta ttgtcatttt   163857
```

```
aggaaaaaca gattcgaaat ttaaataact tgcttaaggt cagagacagc agacgtagga    163917
ttcaaacctt agcctttccc actccaaagt caaggctcct aattctcctt gaggacacta    163977
agatttgtaa aagaaatctt cagggtcaaa gtggtaaaag ggtgtcctgt tggtaaatgc    164037
agtgctgaga tctgttttag agaagtgacc agtaccaaaa ataaaaaaat ggttagtaac    164097
atcaaagaaa tcctgccaga gagtttatgt gcagcacata tgttgggttc tgtaaacttg    164157
aatgaaattt gaagtataat gttactagag gccttccaaa cttcatttct ttttattgaa    164217
taacttaacc catttacaat caaggtaatt attgacaggt aaggacttgc tactgccatt    164277
ttgttaatta ttttctgatt gttttgtaga gactgtttct ttcttcatct tttgctgtct    164337
ttttttgtgg tttgatagtt ttcttttagtg atgtcttatg aatcttttttc attttgtatt    164397
gtgtttctta taaatgttga ttttggttac catgaggctt acatagaata tcttatactt    164457
aacattgtat ttcaagctga taacaactta actttgattg tataaaataa cgctacatttt    164517
tactatcccc tccaacattt tatgttttttg atgtctgaat ttacattatg ttataatatg    164577
tatcccttga ccatttatct taggtaacat tgttattaat aattttgtcc ttatactaga    164637
gataaaatta cactagagat aaacacttat actagagata aaattacttt acacactact    164697
atgataatcc tagagtattc tgactatttc tctatactac ttataccatt aagttttgta    164757
ctttcataag ttttatgtta ttaattagca gattttcgtt tccattaata aaaatttag    164817
caatacctat aaagaaggcc tagtggtgat gaactctctt agcttctgtt tgtgtgggaa    164877
agttttatt tctcatttct gaaagacagt tttgctgggg aaagtactct tggttggcag    164937
tttttttctt tcaacatttt gaatgtacca tcccactctc tcctggcctg tagggtttct    164997
gctgaaaagt atactgataa ttatattggg actcctttgt atgtggtaca tttattgtct    165057
ctaacttctc tcagaatttt ttctttgttt ttgatgcttg ataggttgat tattatgtgt    165117
cttggtgaac tcttctttgg gatgaatttg atgggagact tctgcactct ctgtacttgg    165177
attttggctt ctttcctcag attaagaaaa tttgcatcaa ttattccttt aaatatgctt    165237
tcnnnnnnnn nnnnnnnnnn nnnnnnnnnn nnnnnnnnnn nnnnnnnnnn nnnnnnnnnn    165297
nnnnnnnnnn nnnnnnnnnn nnnnnnnnnn nnnnnnnnnn nnaaggacaa tcaaatgggc    165357
acatactata tttatgcaca tacatacaca cacacacaca cacacacaca cacacaacca    165417
gatgtcattt ataatccatg taaaatattt ttggggaagt ttctctttaa taaagtttga    165477
agagacatat attttttttt tttgaagagg catatttttt ctaacttttt tttttttttt    165537
tgagatggag tcttgctctg tcacccaggc tggagtgcag cggtacgatc acggctcact    165597
gcaacctccg cctcctgggt tcaagcgatt cttcagcttc agcctcctga gtagctggga    165657
ttacaggcat gtgccaccat gcctggctaa ttttttttttt tttgtatttt tagtagagat    165717
gggggtttca ccatgtttgt gaggctggtc tcgaactcct gacctcaagt gattcaccta    165777
ccttggcctc ccaaagtgct gggattacag gtgtgagtca tcacccag cctataactt    165837
tttttttaata ggtgatagaa tcccgtgctt gaaaataat caaacaaaaa gagaatgcat    165897
tgtaagaagc ctcactgtac tcctgtcccc agctgcccag ttctcccctc ctccccacag    165957
ggaaacatct tcattagttt cattaggttc ttatgaaacc ttccagagtt tctttaagca    166017
aaatacaagc aagtaggact gtcatatcct gcagaccgct acatacaaat acatagaaag    166077
tgtcctcatt ctatcctcca gtgatattcc attttttggc tgaaccacct aaatgatgga    166137
tatttagggg aagcaagtat ttttttaaaaa aggtaaaaat caaaggtttt tatttttat    166197
tttttttaaag aaaagttggt aggctgtgtt tattcattca gaagtcaggc cgtggctgaa    166257
```

```
ctgatagctc ttggagatgg ccattgctca tctctgaatg tctggttttc tcttgtaaga   166317
attgtgtgta tgatccagac cttcagtgtg tgcactatat attgagaatt ccagaagaga   166377
tgatatggaa agaaaaaaaa gatgacttta cttttacag  taaaaataaa acttaaattg   166437
aagagtacaa ttgtttaaac aattggaact tacttagcta ctgcttgttg aaacaaaatc   166497 cttttttaa aag g tat cga agc aaa tta aag ctg atc cgt gct aag gaa     166547
            Tyr Arg Ser Lys Leu Lys Leu Ile Arg Ala Lys Glu
            375             380             385 gaa gac agt ggc cat tat act att gta gct caa aat gaa gat gct gtg    166595
Glu Asp Ser Gly His Tyr Thr Ile Val Ala Gln Asn Glu Asp Ala Val
390             395             400 aag agc tat act ttt gaa ctg tta act caa g gtatgtaaag ggagtataaa    166646
Lys Ser Tyr Thr Phe Glu Leu Leu Thr Gln
    405             410 gataatgcta gctctgtaga tgagtgtctt ccaaggaaag cctggcactt ttctccccgg   166706
tcatggaaga aaagcagcac ttaggggaga agcagtgtct gcatatgtca catatcggga   166766
atacctctgc tggactcatg aattcaggta tttctgggag gttctgggtt actctagagt   166826
aggcgaggaa tccctaggct ccaccagcta gctttatttt tgtagagatg gagtcttgcc   166886
atgttgctca ggctggtctc ctgggttcaa gctatcttcc cccttggcc tctcaaagta    166946 ctgggattac aggtgtgagc cactgcacct ggcctccacc agcttactta gcacctgctt   167006
ctcaatctga aagagagaa gcagatgacc ttagattgtt ctggagagtt ttgctacaag    167066
ttttccttat agacattgta cagtggtcct taccagaagg gagtgcccaa gtctgtttac   167126
attcaggctc agcacctatc cagagtccca gccatgagcc aggtgctgtc tgaggtgcgc   167186
tcatgtgatc ctcacagtaa aacctgtgat acaagcaaca ccgtatatct aatttatttg   167246
accacagatt tagaaaagaa tctttaaaac ctaataacat accacagatg cattttggta   167306
aatgctgctt tagattatac tttagctgaa tccattagtt gaatcctaag ctataatata   167366
attttaagaa cctccttgcc tttcaagcca ataaccaag ggactttctc tctctctttc    167426
cctccctccc ttccttcctt ccttccttct tctctccctc ccttgttatc tcttttcctt   167486
tcctttctct ccttccttcc ctcttccctt tttccttcct ctccttcctt ccttccttgc   167546
ttccttcttc cctccctcct ttgttctctc ttttcctttc ctttctcttt ttctttcctt   167606
ccttccttcc tcactcactc ttttcttttc ctttctctcc ttccttcctt ccttcctccc   167666
tccctcactc tctcttttct ttgcctttct ctccttcctt ccttccttt ccctccctccc   167726 tccctcccctt gttctccctt ttccttcctt ccttctttcc tttcttcctt ccttccctct   167786
tccctcactc tctcttttcc tttctctcct tccttccttc cttcattctc ccctcccctc    167846 cccctcccc tcccctcccc ctcccccctc ccccctccc ctccccttcc cttccttcc      167906 cattttctt ctcaccatgt tgcccaggct tgcctcaaac tcctgggctc aagtgtttct    167966
cttccacctc agcctcccaa gtagctgggg ctacatgtgt gaggcatcac aaccatggac   168026
ttttcacttt cttcactcca ggttaaaaac atcacaggga taaatctcaa aacaccaaaa   168086
ctgtgaaaat gctgctaacc atgtgggtct gtctaaactg gagtgttact tgtacaactg   168146
gtttcagccc ctccggagtg ttttgaatgc catgtgatg  agttgtgaac tcatattcca   168206
ctttgtagtc tcatatgttc tgggacacga gctattccat tctgacttct ttctgcctct   168266 tgcag tt  cct tca tcc att ctg gac ttg gtc gat gat cac cat ggc tca   168315
     Val Pro Ser Ser Ile Leu Asp Leu Val Asp Asp His His Gly Ser
         415             420             425
```

```
act ggg gga cag acg gtg agg tgc aca gct gaa ggc acg ccg ctt cct    168363
Thr Gly Gly Gln Thr Val Arg Cys Thr Ala Glu Gly Thr Pro Leu Pro
        430                 435                 440 gat att gag tgg atg ata tgc aaa gat att aag aa  gtatggaaaa         168408
Asp Ile Glu Trp Met Ile Cys Lys Asp Ile Lys Lys
        445                 450                 455 cagatgtgtc ttcttctttc gtggtcagaa tatttctccc ttgacacaaa tgatgtcaaa  168468 tacatttac ttattgacta aagataggg ttttgggtgt gatagcttca gggtgtgtat    168528
cttttgtcat gaatagctgt gagaagaagg tccagggctc tcattagacc ttcaaaatgt  168588
ctccaatcta aaaacaagag tgaattttaa gaaccactgt tctaagaaga tttttactac  168648
cctggctcac atatcttatt tggtgaactt tgtttggtag tcggactgca tgtaaacata  168708
aatgtgactg cttagtccct tatctgccca cctgctgttt ggtgggttaa ttcgccattc  168768
cctcctccct cccccgagtc ctcagccttc ttaaatgggc acatgagcaa tgtgtttaca  168828
cttcatccat ggtaactggt tgtgttcaga agcctcagtt gtttcttcct ctagacagag  168888
actcctcatc ttaacttcta gggctaagaa cagacttgga tgttgactgg ggtttctagt  168948
agattccagt gtggagcagg attctaggtc ttataactca atctgaggat catcgcaacc  169008
ctagtgacac cctaggggct cttcccagtg tgagtgttga aagggaggg ctccaggcct   169068 ttttgaaggg gtgggagatt gagatcatta aatatggttg aagttgaact gttcagtttg  169128
ctcataggtt caagattggg gaatggtagt catattttat taaacttgat tatctctgcc  169188
tgctatgtaa acacttagct ttcagttgtt catgtgtgag ttattccctc ttcagcacat  169248
gcagacaagt tttaatgttc atctgcatgt aaaataaatc agtgtgtatt gccccgaaat  169308
gcagacaagg tcccaactcc ttgccatctt agagtgttcc cgtggctcca ctcattgcca  169368
tgactctcag gaattggccc tatacttagg ccctttttct ctctag a tgt aat aat   169424
                                                    Cys Asn Asn gaa act tcc tgg act att ttg gcc aac aat gtc tca aac atc atc acg    169472
Glu Thr Ser Trp Thr Ile Leu Ala Asn Asn Val Ser Asn Ile Ile Thr
        460                 465                 470 gag atc cac tcc cga gac agg agt acc gtg gag ggc cgt gtg act ttc    169520
Glu Ile His Ser Arg Asp Arg Ser Thr Val Glu Gly Arg Val Thr Phe
475                 480                 485                 490 gcc aaa gtg gag gag acc atc gcc gtg cga tgc ctg gct aag aat ctc    169568
Ala Lys Val Glu Glu Thr Ile Ala Val Arg Cys Leu Ala Lys Asn Leu
            495                 500                 505 ctt gga gct gag aac cga gag ctg aag ctg gtg gct ccc a gtgagttcct   169618
Leu Gly Ala Glu Asn Arg Glu Leu Lys Leu Val Ala Pro
        510                 515 caacagtcag dacaactcat cagctgagcc gcatctgccc caggcggaac tttgaatccc  169678 agatagggt tatatagaaa tgaaggtccc aaggcagaaa ttcagttatg aatgctctta   169738
aagtcatgtg ggactttgtt ttattttgtt ttgttttttg agacagagtt ttgctctgtg  169798
gcccaggctg gagtgcaatg gcacaatatt ggctcactgc aacctctacc taggacgttg  169858
ttttagattc agatccaaaa ctgcattttt gcagaggccc ctcaacattt tgcttgtcta  169918
ataatatagc tacagtctct actttgaatg tctgtgtatg tggatggagt gtggggaagg  169978
atcttctgtc tcattgctcc ttaaaagata gatgaagcca aaagcaatat aagcaaaatg  170038
caacttacaa aataagcttt ataataaagc atatgaagta gaggtgtctg cccatatagt  170098
agctgtcaat tgcatttatc ctattcaaat tctgtccaca aggttactgt tggagcaact  170158
ttggagaaaa tactgagttc tcctgattga atttgtcccc cttcttgtat aaggaaagag  170218
```

```
ttgatgtagt ttcctgggtg tagatggttt gagagatggt actgcctatc cctaaaatga  170278
accaggcagc cctcacactt ccccaccagc agtgagagat tcctggctca gacacagcca  170338
cactaccttg ctgccctgt  gcatgtctgc caggaaactt ttcattgtgc ctctctctct  170398
tgtcacgtag cc  ctg cgt tct gaa ctc acg gtg gct gct gca gtc ctg      170446
               Thr Leu Arg Ser Glu Leu Thr Val Ala Ala Ala Val Leu
                       520                 525                 530 gtg ctg ttg gtg att gtg atc atc tca ctt att gtc ctg gtt gtc att      170494
Val Leu Leu Val Ile Val Ile Ile Ser Leu Ile Val Leu Val Val Ile
             535                 540                 545 tgg aaa cag gtagatattt tctcataaaa ctaaagatct ttgaagccaa              170543
Trp Lys Gln
        550 tgagaacaag catagcaacc tagttcagtg cttggcacag agaaggagct cagcaattac    170603 atgtggagtg aacgttgttg gactctactg tgtccagtca ctgtgctgct tcagtgaagc    170663 tctggtgcac tgggactttg gtaattcacc agttacctgt cctggtcatt tatag aaa     170721
                                                            Lys ccg agg tat gaa att cgc tgg agg gtc att gaa tca atc agc cca gat      170769
Pro Arg Tyr Glu Ile Arg Trp Arg Val Ile Glu Ser Ile Ser Pro Asp
            555                 560                 565 gga cat gaa tat att tat gtg gac ccg atg cag ctg cct tat gac tca      170817
Gly His Glu Tyr Ile Tyr Val Asp Pro Met Gln Leu Pro Tyr Asp Ser
            570                 575                 580 aga tgg gag ttt cca aga gat gga cta gtg ctt g gtaagttcca             170861
Arg Trp Glu Phe Pro Arg Asp Gly Leu Val Leu
585                 590                 595 tggggtaacc tcccaagact cccttttccc ttgcacacaa ctttacaatt tataggcctt    170921 ggcagaaatag agatctgagc ttgtgcttag taagaactag gcaatggaaa tttgctttca   170981
gaaatacatt tctgtcttga cagtaagtta attggatcat tgcaatgatt tttttaaatc    171041
tctttccata acaaattata gttaaggaaa attttacaaa gggagaagag aatatgaaga    171101
gggctggcaa agatacccac caaaattgct tttctttaga aatgacacaa attgaaaatg    171161
aatttctgtg actaaaaatg agcagatgag aaatgaatga ggacaaccac aaaatgtatt    171221
ttgattcagt acattctgaa gatgcattag atactccttt ttacatattt ggaatatgga    171281
atataaaaat ataggtacat tttgaggcaa aatatgtaaa aataagcaag ccaacttatc    171341
acaagcattt caagtatttc aatcctgggc tgagaccaag tatatgaagc tttagtccaa    171401
gggagtattt cttttttaaa tcacattcct aatgaatgaa agcaagacaa aggcaaatga    171461
aagtagaggt agaggttgtg ttatgatgaa tgatctaaca gtatatatgt taaagaatgc    171521
caaatgcagg ttttaattat ccaccggtct cattgcaaaa tacagaagag tttaagtctt    171581
cttagagagt taggtaaact gaaatcaagc aaggcaccag agtgaaatca cctttgcaaa    171641
aattgtaact gaggaaatta tgacagtgaa tgagatatga cctaaccaac tccattttgc    171701
tttagcctcc aagttgtcct tgttccttcc tgggcatagg ccgaactaac tttgagagga    171761
acttagttta tagtttgact ttgaaaaaaa gacaataata gcccttttgcc aaaacaaacc   171821 ctcttttttcc ctgggaacta gactgccttt gcgggactaa cgaattagct acaagattag   171881
aaagtatggt ttaggggtca ctgttgtaaa acctgaggtc agtgcttgag atattttgga    171941
gaccctgtat ttcgatgcac cagctgacac cacccaggtc aataaactgg ctcatctgat    172001 cttgggccc ctacctagga actgactcag tgcaagagga cagcatcagc tccctataat     172061
ttcatctttg acccaaccaa tcagcactcc cctttttcacc ccctacccac caaatcatcc   172121
```

```
ttaaaaaccc cattccccca gtttcagaga cactgatttg agtaatagca gaatagtaga   172181
aattccccca gtttcagaga cactgattcg agtaatagta gtaatagtag aataggtctc   172241
ccgtacagct ggctctgtgt gaattaaacc cttttttctat tgcaattccc ctgtcttggt   172301
aaatcggctc tgtctaggca gcggacaagg agaatccatg gggcggttat aagagctgcc   172361
ccccaatttc aaatatttat atctaagctt tctttatttt cctgcctatt tcccaacaag   172421
ggatgaggag cttagggagt taaaaagtag taaaatatgg ggaaaagggc ataattccca   172481
ttataccaag aggcattgct ggtgaagcaa tacctttcca ggtacgattt tcagtaacac   172541
agacgtgcag taagaggcag tgttggctgt tagtgtcttt tatgagccaa gtctttcct   172601
ggcttggcta tccgtggtga gactgacacc ccgggaaatg tttctctcag ggtgagctct   172661
ttcagggtgg gacaacagct tcagtgtctt tacgtatgtc tcctcccaac atgaagctaa   172721
ttgctgtgct ctcgggcatg tttagctctt ggtagagtgg cttttcctaac aaatagggag   172781
cagtgagccc agcctgaagt ttttatttag tcactcctta gaatcagtga tattttgaat   172841
actgaagtat ttccagtggc tagtaattta ctaagacaaa agatgcccct gtttgcatat   172901
ggaaaacaga aggggagaga gccaggaggt gtgggtgaga gccccgaagg caagaggatc   172961
ccaggggctg gcccagcacg gagctggtag acagcgcgct cacaccaggg agggctgcac   173021
cctcctttct cccgtctgtg ttttctttcc cttgcaagtg ttattcgaca aaagcaatta   173081
tgctaatttc cttccctgtg ggctcaattc ctttttttgac acgatgactt ggaggagtca   173141
ttatgattac tccaaacagg aaagacactc gcccagctgt ccgcccgcag agagctggct   173201
acggtgcaga aagctgagga ggcgtctgga gttttttgggt gttaatgatt ctgcctgccc   173261
acag gt  cgg gtc ttg ggg tct gga gcg ttt ggg aag gtg gtt gaa gga   173309
     Gly Arg Val Leu Gly Ser Gly Ala Phe Gly Lys Val Val Glu Gly
              600                 605                 610
aca gcc tat gga tta agc cgg tcc caa cct gtc atg aaa gtt gca gtg   173357
Thr Ala Tyr Gly Leu Ser Arg Ser Gln Pro Val Met Lys Val Ala Val
        615                 620                 625
aag atg cta aaa c gtaagtgctc cttcctgggg attttttgag cacggggatt     173410
Lys Met Leu Lys
        630
ttttgagcat ggggatatta agggaatttc tcaaaatcat gcagctagta aataagacat   173470
ttaggactag gtcctgatta ttttgactcc aggttttatg tgtatttaga ttaggtttat   173530
ttagattgct cttgctgcct gtatgttgga aaattaagag cttgttattt ccagtgactt   173590
cttttttacta gaaagaccag gaattagtta ttagcactga ggccaagtag ctatctgctt   173650
cttttagact tctggtaaat agaatgatat ccaatcacag gattagtcat attcttggtt   173710
tttttctgag aacaggaagt tggtagctca gctggactga tatgtgattt attctttcaa   173770
cag cc  acg gcc aga tcc agt gaa aaa caa gct ctc atg tct gaa ctg   173817
    Pro Thr Ala Arg Ser Ser Glu Lys Gln Ala Leu Met Ser Glu Leu
            635                 640                 645
aag ata atg act cac ctg ggg cca cat ttg aac att gta aac ttg ctg   173865
Lys Ile Met Thr His Leu Gly Pro His Leu Asn Ile Val Asn Leu Leu
        650                 655                 660
gga gcc tgc acc aag tca g gtgggctcac tgacctggag tgaggatttt        173914
Gly Ala Cys Thr Lys Ser
        665
cactggacac atgtggttgt gaaaactgtt caatcaggct taaatcctcc actctccatc   173974
cccacacatg gcagggaata gaagtccctt gaatggagct gactggtccc ttgaattgat   174034
ggaagctcat tggttttttga gcaaaatctg ttgccagtcc agtcatagcc attcatggct   174094
```

```
ctttattaaa aaaaaaaaaa aaaaaaaaaa aaaaaaactt ttttggtatc ttatttttt   174154 ctgtgccata tggtctgcag gacaattcat ggcttttctg ttcttcattt tcatacccat   174214
ctcctaacgg cttttgtccc catag gc ccc att tac atc atc aca gag tat       174265
                             Gly Pro Ile Tyr Ile Ile Thr Glu Tyr
                                 670                 675 tgc ttc tat gga gat ttg gtc aac tat ttg cat aag aat agg gat agc       174313
Cys Phe Tyr Gly Asp Leu Val Asn Tyr Leu His Lys Asn Arg Asp Ser
            680                 685                 690 ttc ctg agc cac cac cca gag aag cca aag aaa gag ctg gat atc ttt       174361
Phe Leu Ser His His Pro Glu Lys Pro Lys Lys Glu Leu Asp Ile Phe
        695                 700                 705 gga ttg aac cct gct gat gaa agc aca cgg ag gtgggtgcaa agagagatgt      174413
Gly Leu Asn Pro Ala Asp Glu Ser Thr Arg Ser
    710                 715 tgctgtctat cattatctta caggcatcac aaatggaaag acccatgtcc tgatagatat   174473
catgtctgca gattcagtgc ccaaggtagc aagacttaga gtcaaaccac cctgtccagt   174533
ctttccatgg tcatgcagag agatgcatga tgtctaaagg tgttttggac tggggtgtca   174593
catgggaagg ccttgctgat aggtttgaat gagagtgagt tagaatgact ctgggagctc   174653
ttctgctatt tacatgtgat ccacttagac ctataaaatg cagctctggc cagggatgct   174713
tgagttctgg aaccttgcaa gaactgtctg tggatctcca agctcgaggt ccttgctgaa   174773
cctggaccta taaatgacgt caatgatagt gatccctact gcagaaatct acaagtggct   174833
ataaagaact ctgtaggtaa gaaattctgt aagatcagaa agtacaatga attcacttca   174893
taataaatta cttggtggac accaaatggg tgctaaattg attgggtaga aggaattgta   174953
tgcccaagcc acatggccac acggctcaag ttccaaccaa ggcttgtgag ttgaaaaact   175013
gagaaagaat aatgacagac ttaacgtagt gaattcttca aactttaagt gtaatggact   175073
tacaggtcca tgggagcaca gccccactgt cttagatgtg gctcttcagg atgtgcgggc   175133
tcctgctaag gatgtgcagg gaactggctc tgaaaacaag tgaacagtag tcatcatggc   175193
agctgacatt tgtggagtcc tttgtatgtg ccaggtgcca tgacaaatat tccgctagtc   175253
tttcccatct tgtcagtgg gatccattct acgtcttctg aaaagtgctt ccttgacccc   175313
cagatcaagt cattttcctt acaagctatt gaaacctttc ttccttcaca acacagctga   175373
gtttgagttg atctgtgtat ttattttgtt ttttacattt cttttttttcc ctatttaaaa   175433 aatttttta tttccatagg ttttgggga acaagtggta tttggttaca tgagtaaatt   175493
cttcagtggt gatttgtgag attttggtgc acccatcact ggagcagtat acactgaacc   175553
cagtttgtag tcttttatcc ctcacctgcc tctcaatttt tccccgagtc ccaagtcca   175613 ttgtgtcatt cttatgcctt tgcatcctca tagcttagct ctcacttatg agtgagaacg   175673
tacgatgttt ggtttccatt tctgagttac ttcacttaga ataatagtct ctaatcccat   175733
ccaggttgct gcaaaagcca ttaattcatt ccttttata gctgagttac atatatatat   175793
atatatatgc acacctacac atacatatgt atagatacac tgcagtttct ttatccactc   175853
cttgattgat gggcatttgg ggttggttcc acatttttc aatatgtgaa ttgtgctgct   175913
ataaacatgt gtgtgcaagt atcttttag tatgacttcc tttcctctgg tagatacca   175973 gtagtggaat tgctgtgatg catgtatttg tgcgactatt tgattaatgc tcatttcctt   176033
gactagatca cctcatgtga aaggtatgga ttggttttgc ttttacccag ttagctccca   176093
tgcctacctc agtacctggc acataatcat catctactga aagtggaatg accacttcag   176153
```

```
aagggcaccc tgggtaagat ttctctttct gtttttacag c tat gtt att tta tct  176209
                                              Tyr Val Ile Leu Ser
                                              720 ttt gaa aac aat ggt gac tac atg gac atg aag cag gct gat act aca    176257
Phe Glu Asn Asn Gly Asp Tyr Met Asp Met Lys Gln Ala Asp Thr Thr
725                 730                 735                 740 cag tat gtc ccc atg cta gaa agg aaa gag gtt tct aaa tat tcc gac    176305
Gln Tyr Val Pro Met Leu Glu Arg Lys Glu Val Ser Lys Tyr Ser Asp
                745                 750                 755 atc cag aga tca ctc tat gat cgt cca gcc tca tat aag aag aaa tct    176353
Ile Gln Arg Ser Leu Tyr Asp Arg Pro Ala Ser Tyr Lys Lys Lys Ser
                760                 765                 770 atg tta g gtaaaagtgt ctatactcac tctgggtgtt gggactttcc agtggtttaa   176410
Met Leu tatgatactt aaagtattta gagggaagtg tatagggatg gtaagtgaac ctggcagccc  176470
acgtggtctc taaatgcagg tctgcacaac cagttctgtg acatgtttcc aggtttgtgg  176530
cctgtaaatt gaaagaata aaagctgaca atgtaacaaa ttttttaaac tttaaattta   176590
atagttttaa agaattttct tggtgtgttc ctgcagtaaa cattttttaa aaaaaataat  176650
tatttattct gatataatga acttcctttt ttattgctgt cttttcttt tttaatgaaa   176710
atatggtgat tgatttttt taatgcccct acttggcaga attacaagtt ggctgtctta   176770
tgttggttcc tcaccttgct ttttttccct taagttttag aagtctctga tgtctatgag  176830
ttcagtaacc cttgctttta cttttcctaa cattcaattt gtataggaa ctctagagta   176890
gataatttgc agttatattt tctggaccag tgttctgtt gaatgtattt tgaaggtggg   176950
tctatctgtt tttcaagtac atgaatatgt ggcagggtta aattgattta taaactccag  177010
ggagtccagc tgatgcccag accagatgga tcacttcaca tctgctcagg gtggttcctc  177070
cagagccctg aactggtcac agacatgaag ctggaagtct gacattggct tgtcctgtga  177130
gcttgccttt ttgggtctga gccttcccat tagtcaatgc aaaaaagtgt tgagctgccc  177190
tggacattgt tttggaaatt attgatgtgc tctgaatgtt ttcaggttct taagtgaaag  177250
gtacaatcca tttaaaaaag aatgtgtttg ttttgcaaag ctcagtacac aatatttcc   177310
atttctgcgg ttccaagttc cattcacttc tcattgccaa atgggtgaac ttccaagcgc  177370
ttttaaaaga ttagccagtg agagttatcg gaaccagtac ttcctctccc ctcccatatt  177430
gttaaaaata gtttacattg cttcccaggc tgggctggtg gagttggcac gagatgtcag  177490
aggaacctga gtcatgctca ggcccaagcc ctgttggcag gcagaccact gctttctggc  177550
cttccgtgac tatctgaaaa aaatcgtgaa tggctagagc tactcttcac ttgctgaaca  177610
ttttcaaaaa gaattgagaa cttctggatt aaattgcctt cttcctcgaa acccctggga  177670
cccttccaga tgggactaac tggggaaagt ggacaagtta caaacaaaga aactcaaagg  177730
aaagtcattg gcactgatct ctaagatgct atcacatgtg attggtggtt gattttatta  177790
acaaattata agcaaagtac tacaaaggtg gctttaaaaa gaaataaag caattcacag   177850
aaactacttt ttcatgtagc ttgtatgtgt gctccatgta tttcatcatg gaagattta   177910
gtgtgtgttt atgtgtatgt gtgttttaaa ggtagctgag atgatttgct aattatggtt  177970
gaaaaaaaga aatttaggag gtaaacaaaa taattatgtg taagattggt ccttgtggct  178030
gtgtgtgtgt tttgtgtgtg cgtgtatgtc tctgtgtgtt ttaggctgtt cttttattgc  178090
tataaataaa tacttgagac tgggtaaattt ataagggaaa gaggtttaat tagttcatga  178150
ttctgcaggc tttacaggaa tcaagatact ggtagatctg ctcagttttt ggagaggcct  178210
```

```
catgaagcca tgaagtcatg gcagaaggca aagcagtgca ggcacatcac atggccagag    178270
caagagcaag cgagagagag aaagagagag gtgccacaca cttctaaaca gtcagatctt    178330
acaagaagtc acttactatt gcgaggacag caccagaagg atggtgctaa attgttcgta    178390
agaaatctgt ccccatgatc cattcatctg ccaccagtcc ccacctccaa tactggagat    178450
tacaattcaa catgagattt gggtggggac acatattcaa actatatcat actgaccctg    178510
gaccctccca aatctcatgt ccttctcaca tttcaaaata caatcatccc tccacaatag    178570
tccccctcaag ccttaactca ttccagcatc aactcaaagt ccaaagtctt atctgacaca    178630
aggcaggtcc cttccaccta tgagcctgta aaataaagaa caagttattt actttcaaga    178690
tacaatgggg ttataggcat tgggtcaaca ttcccattcc caagggaga aatcggccaa    178750
aagaaagggg ctacaagccc cacagaagtt cagaacccag cagggctgaa aactccaaat    178810
aaactccatt gactccatat cccatgtcca gagcacactg atgcaagggg tggagctctt    178870
gggagggatg gaacaccctg tggctttgca gggtttagcc cctgcagctg ctctcagggg    178930
ctgttgtcga gtgcctgtgg ttttcctgg tgcagagtgc aggctgttgg tggatatatt    178990
attcatggag gatggtggcc ctcccctcgt agcttcacga ggcagtgccc cagtggagac    179050
tctgtgtggg gacttcaacc ccacatttcc cctctgcagt gccctagtag aggttctctg    179110
tgagggctcc aatcctgcag catgcttctg tctggacacc ctggtttttt aatatatcct    179170
ccgaaatcta ggcagaggct cccaagcctc aactcttaac actctgtgca cccacaggct    179230
aacaccacat ggaagcggcc aaggtttatg gctgtcacaa gctgaagcag cagcccaagc    179290
tgcacctgaa ctcctttgag ccacagctgg agctggagtc atagggatgc agggagcagt    179350
gtctcgaggc tgcacagggc agtggaccct ggggctggcc catgagacca ttcttccctc    179410
ctaggcctct gggcctgtga tgggaggggc tgccatgaag gtgtctgaaa tgccttaaag    179470
gccttttttcc cattgttttg gcaatcagcc tttgcctcct ttttagttat gcaaatttct    179530
ctagcaagtg gttgcccagc agccctcttt aattctctcc caaaaaagct tttactttct    179590
ctgtcacatg gccaagctac aaattttcca accttttatg ctctgcttcc cttttacttt    179650
tttttttattt taaagagatg gggtctcact atgttgtcca ggctagtttg aactcttgga    179710
ctcaagcaat cctctcactc atcctcccaa agtgttggga ttataggtgt gagccactgc    179770
gcccagcctc tgcttctctt ttaaatataa gtttcaactt caagtcattt ctttgcttct    179830
gcatctgact gtaggctatt ggaagcagcc aggccatatc gtgaacactt tgctgcttag    179890
aaatttcttc caccagatat cctaggtcat cactctcaag ttcaaacttc cacatattcc    179950
tagggcatgg acataatgtg gccaagttct ttgctgaagc ttaacaaggg tgaccttttac    180010
tccagttccc aataagttct tcattttcat ccgagacctt ggcagcctgg atttcattgt    180070
ccatatcatt atcagcattt tggtcacaag catttaacca gtctctaaga agttccaaac    180130
tttccttcat cttcctgtct tcttctgagc cctccaaact cttcttatct ctgcctgtta    180190
cccagttatc tttacagcaa ttccccattc cttgatacca atttctctta ttaggctgtt    180250
tttgcattgc tataaagaaa tacctgagac tgagtaattt ataaagaaaa gaggtttcat    180310
tggcacatgg attctgcagg ctatacaggc atttgcttct ggagaggcct caggaagctt    180370
ccaatcatgt tggaaggtaa aggggagca ggcatatcac atggccagag caggagcaag    180430
tgagagagag acagagagag agagagagag agagagagag agagaggtgc catacagttt    180490
taaacaggca gatcttgtaa gaagtcactc acttttgcaa ggatagcacc aaggggatgg    180550
tgctaaacca tttgtgagaa attcacccccc atgatccagt cacctcccac caggccccac    180610
```

-continued

```
ctccaatact gggqattaca cttcaacatg agatttgggt ggggacacat atccaaacta    180670
tatcattgcg tgtgtgtgtg tgtgtataat ttttaaacca gatatatgtt tctgcatatc    180730
tctttccttt ctttcattct ttctatcttt tttttttttt ttttttttttg agacagagtc   180790 tcactctgtc acccaggctg cagtgcagtg tgtgatctt ggctcactgc aactcattgc     180850
aacctcctcc tccctgattc aagcaattcc cctgcctcag cctcctgagt agctgggatt    180910
acaggcacat gccaccatgc ctggctaatt ttttgtatt attagtagag atagggtttt     180970
accatgttgg ccagactggt ctcaaacttc tgacctcagg caatccaccc acctcggcct    181030
cccaaagtgc tgggattata ggcataagcc accatgcctg gcctatatat ctattttcta    181090
agatagaatc tttgcatagt gatattcatc tgtgagatct aaacattcta caaaaaaatt    181150
aagaaaatat ttttggatgt gttctttggg catgcctctg caacctgatg atttcctgct    181210
gcctgccagc accaatacat ttaatttctt ttctgcag ac  tca gaa gtc aaa aac    181265
                                             Asp Ser Glu Val Lys Asn
                                                 775             780 ctc ctt tca gat gat aac tca gaa ggc ctt act tta ttg gat ttg ttg      181313
Leu Leu Ser Asp Asp Asn Ser Glu Gly Leu Thr Leu Leu Asp Leu Leu
        785                 790                 795 agc ttc acc tat caa gtt gcc cga gga atg gag ttt ttg gct tca aaa      181361
Ser Phe Thr Tyr Gln Val Ala Arg Gly Met Glu Phe Leu Ala Ser Lys
    800                 805                 810 aat gtaagttcaa ggaacacaga ccttttaga cccagatttc agtgagtgga            181414
Asn gtgtggacgg agatgctagg agatagatgt tggaaaggcc attaataaca ggggcctctt    181474
acttacctgt ctctctcctt catccctac gcaggtcagg gagtctgaaa tcatcaggca     181534
tctactcttc tctagagctt tctctctgtt gggagtgggt ggagtgagaa cctggagaa     181594 ggccagccct ttatatccag gcagacagct ccaagtgcca ccatggatca gccagtcttg    181654
caggggtgat gctattcagc tacagatggc ttgatcctga gtcatttctt ccttttccat    181714 gcag tgt gtc cac cgt gat ctg gct gct cgc aac gtc ctc ctg gca caa     181763
     Cys Val His Arg Asp Leu Ala Ala Arg Asn Val Leu Leu Ala Gln
         815                 820                 825 gga aaa att gtg aag atc tgt gac ttt ggc ctg gcc aga gac atc atg      181811
Gly Lys Ile Val Lys Ile Cys Asp Phe Gly Leu Ala Arg Asp Ile Met
    830                 835                 840 cat gat tcg aac tat gtg tcg aaa ggc agt gtacgtcctc acttccctca        181861
His Asp Ser Asn Tyr Val Ser Lys Gly Ser
845                 850 ctggtcaggc tcatcctcct tcactttaat ctctaaagtc aggtgttgct tctagagatt    181921
cggtgcctgt ttttaaaac atcaatagat ttcaaggggt cagtacactg ccttggcagc     181981
agattgccca ggtttgagtg ccagctccac cacttactta atttggattt ggggctagat    182041
acttgactgt tctgccctc tgtctccctg attgtagtgg gaggtgataa tagtacctat     182101
ttgctgagtt gctatgggga ttaaatcaat gaattcatgt aaagtgctta ggacagtgcc    182161
tggcatatag aaacagcact caataatgtt agctattta tttatttatt tatttatta     182221 tttatttatt tatttatttt cttttttttt gagacagagt ctcactctgt cacccaggct    182281
ggagtgcagt ggcgcaatct tggctcactg caaacttctg cctcccaggt tgaagcaatt    182341
ctcctgcctt agcctcccga gtaggtggga ttacaggcat gcaccaccat gttcagctaa    182401
tttttgtatt tttagtagag acaggggttc accatgttgc ccagactggt ctcgaactcc    182461
tggcctcaag tgatctacct gcctcagcct cccaaagtgc tgggatgaca ggtgtgagcc    182521
```

```
actgcatctg gcaagtgtta gctattaata tgtcaattgc gtgtatgcat ggacaagcat   182581
gcattcccaa ggatggtgtc tttacatttt aagcttttat cagattttca aaagccatct   182641
gtgaccccta aaatagattg gaaccatttg ggtttatgta tcttggaggc acagtttcct   182701
taaagatact cattttgttg tctacttgaa ccattcttcc catcccttcc acttctcagc   182761
agatgacata gctccctgtg gggatatatc tgctccctgt aggtacaatt ccaaatcacc   182821
tcactgcact ggatgtgaga cagcttatgg cagctgctgc ttccacctag agaaagacat   182881
gggcctgcat ccatgctgtg tgtgattcat gtactcatgt ggccgtgata gctgtaatcg   182941
gctcatagat cattggatct gttcttagtt ttgttcccag gaatatctaa aaataggaaa   183001
ctggtccatt cagggcttac acctttgggg tgaaaattca ggattaatgt ttttggatat   183061
tattcctttg gaggacataa aaggcaatat tgaccattca tcattcatct agtatttatt   183121
gagcacctac tatgtgccag ggactgagag ttcagtaatg aacaaaacac atgtaaaaga   183181
cactcaaatg ggacaagata attagcacaa gttattaaga gcccaagggg aacccttttc   183241
tatttccact gctgtggatc atcagtgagt agacatgggt ttaactgtct ccctccttcc   183301 ttgcag acc ttt ctg ccc gtg aag tgg atg gct cct gag agc atc ttt      183349
       Thr Phe Leu Pro Val Lys Trp Met Ala Pro Glu Ser Ile Phe
           855                 860                 865 gac aac ctc tac acc aca ctg agt gat gtc tgg tct tat ggc att ctg     183397
Asp Asn Leu Tyr Thr Thr Leu Ser Asp Val Trp Ser Tyr Gly Ile Leu
        870                 875                 880 ctc tgg gag atc ttt tcc ctt g gtatgggcct gacattgctg cttatttggg      183449
Leu Trp Glu Ile Phe Ser Leu
885                 890 ctgttctgaa acaccactgg aaggaaaatg tgttctttca gccccagga tgtagacagt    183509 gttaagataa cctggtgtga ggccagtatg ctgcagccac ctcaaaccac atgttgtgcc   183569
ttattgtgtc tgagataggc ccatgcaggt ggagatgggg gttttgttg ggggttgcgt    183629 cttactcctg gcctctgccc ctcctctcct ttgggctatg ccagagtgac ttcctcccac   183689
tggaagtggt cccaatgaca ttcgcatccc agctgctttt tcattttggg ctttgggtca   183749
catgggttca cccatggaga gtgggccctc cctcacctgg tggcgattga tgctcaggtg   183809
aaaaggggta cgtggcggga agggcagggc tctcattcct ggttgtcatt ggccagtctt   183869
gacaacccag gtgctgaaca acccaggtgc cctgggctat ccggtgaggt ccctaagaga   183929
aggatgagcc ataaccctga catctggatg gttcatctgg ggagatgaga cttacacact   183989
tagggataaa cagtgtgctg ctgatttaaa attgtaattt gagtcttgag taaagagaaa   184049
ggagtcctgg aatagtgtgg gaaggcttca gagagggaac ttaacttgac ctggccttgg   184109
ctttgaaagt gtgaaatgtt tcatgaattt atctgtgatc aggatgtaat agtaaagtgt   184169
gtcttcctgc cccgtctcct tttcatcct agttctccct ccatggatga tcacaatgga   184229
tcatccccca gtggcttaat ggagtcctgt actcccttaa aagcagagag gccacaactt   184289 tgattttgc tttagctatt tgaacatacc tggtgaaaaa gactctctgg ttttaatga    184349 ttcagaattt ctccttgctt ttctagttca ttttgtctgt gttgatccag tagtcataca   184409
cattgaaaaa cacttgaacg cttatttcta aagatgtaga attttgtga tggtacttgg    184469 acttgaccaa cctggagtcc taattaaact taaggtttga gctggtctct gaagtcaagg   184529
agatgatgac actgaatttt cttgaaaaaa ccagtgcttc aaggctatag gatctgaaag   184589
gttttctaac agtgttctat catgccaagt gtttcagcaa tgcactgagc gtttgttagt   184649
```

```
cctggtgttt tattgtttgg cttttag gt  ggc acc cct tac ccc ggc atg atg    184702
                                 Gly Gly Thr Pro Tyr Pro Gly Met Met
                                             895                 900 gtg gat tct act ttc tac aat aag atc aag agt ggg tac cgg atg gcc      184750
Val Asp Ser Thr Phe Tyr Asn Lys Ile Lys Ser Gly Tyr Arg Met Ala
                905                 910                 915 aag cct gac cac gct acc agt gaa gt  gtgagctcct tccccatccc             184796
Lys Pro Asp His Ala Thr Ser Glu Val
                920             925 gggggcctgt gttcacagtc tgtgggtcta gggggaggga ggggccctga gacttccccc    184856
tgtgcccact cttgagttct gtccccacag c tac gag atc atg gtg aaa tgc       184908
                                   Tyr Glu Ile Met Val Lys Cys
                                                           930 tgg aac agt gag ccg gag aag aga ccc tcc ttt tac cac ctg agt gag      184956
Trp Asn Ser Glu Pro Glu Lys Arg Pro Ser Phe Tyr His Leu Ser Glu
            935                 940                 945 att gtg gag aat ctg ctg cct gga caa tat aaa aag gtgtgtttgg           185002
Ile Val Glu Asn Leu Leu Pro Gly Gln Tyr Lys Lys
        950                 955                 960 atctgtgggt ggaaaggtct ggataaagct ggaagttata ccagtgagct gtgctgttcc    185062
gcagttctag aggagcattt tcaaaagagg caaaagactg tgtgatccag tggctgggct    185122
tcatggcggt gctccacgag accctagtag caatgatgaa tgaaaaccct cccctteccg    185182 tggggctttc ctttcatctt atatgtacag tacctgtaag cactattctc cagatgtttg    185242
agtatcagaa gttagtgtgc agttagaaga ctcagggcat ccatggccat tacatcacta    185302
atttgagtgc acttaaatcc atgcgaaatt ggcttttacc agcggactgg aaggaacaac    185362
ctcagctgtt atctgtggca ccagctggtt ttttgtggaa tgggaagcat tgttcaaagg    185422
aacaaatgta atttcttgga accaggcagg atatgtaaat gaatgaaaca actttctgct    185482
gaggtgttga gaggaaaact cagacataac ctcagtttct tagattgaga ttagtccctg    185542
tgtagacttt ttatacttat cattttctt ccttcttctc aaggaggaat agtgttagga    185602
gattgtgtgc cgaactggaa gttaaatgct tctgtctgtt aattatctca ctgcccacta    185662
caactttcac aggtgaggca gtgaggaggc agaaggaaat taaccctcag ttggtcaaag    185722
atgctctgac tggtggaaat gtgttggtgg gaagagattg aagttattgt tgaaaatagg    185782
gtcttttcac atccaatgtt agacctctcc aatgtttaag gatcatgaag gctttgggta    185842
ttatccaccc aatagaaggc ctcactgcct ctctatggga cccatccaag ccctggaaag    185902
gcaacgtgat ggggaccaga aggattctca gttgtagcta ctgacttgga gaaggggcta    185962
ctggtatctt agcacctaat ggcagaagct ctttaccatt ggtggcccct tcttcatgtt    186022
ctatgtctct ggggatagtt gacatgactc tccttcaact aagtcccaca tcttccaggt    186082
agtttggaga tatgtacagt taaataatag taagttctga gtgtctctat tcattttga    186142 ggtttggttt ttaacacttg attaaatatg ttcaatgaat gtttatag agt tat gaa    186199
                                                       Ser Tyr Glu aaa att cac ctg gac ttc ctg aag agt gac cat cct gct gtg gca cgc      186247
Lys Ile His Leu Asp Phe Leu Lys Ser Asp His Pro Ala Val Ala Arg
        965                 970                 975 atg cgt gtg gac tca gac aat gca tac att ggt gtc acc tac aaa aac      186295
Met Arg Val Asp Ser Asp Asn Ala Tyr Ile Gly Val Thr Tyr Lys Asn
980                 985                 990                 995 gag gaa gac aag ctg  aag gac tgg gag ggt  ggt ctg gat gag cag        186340
Glu Glu Asp Lys Leu  Lys Asp Trp Glu Gly  Gly Leu Asp Glu Gln
                1000                 1005                 1010
```

| | | | | | | | | | | | | | |
|---|---|---|---|---|---|---|---|---|---|---|---|---|---|
| aga | ctg | agc | gct | gac | agt | ggc | tac | atc | att | cct | ctg | cct | gac | att | 186385
| Arg | Leu | Ser | Ala | Asp | Ser | Gly | Tyr | Ile | Ile | Pro | Leu | Pro | Asp | Ile |
| | | | 1015 | | | | 1020 | | | | 1025 |

```
aga ctg agc gct gac agt ggc tac atc att cct ctg cct gac att      186385
Arg Leu Ser Ala Asp Ser Gly Tyr Ile Ile Pro Leu Pro Asp Ile
            1015            1020            1025 gac cct gtc cct gag gag gag gac ctg ggc aag agg aac aga cac      186430
Asp Pro Val Pro Glu Glu Glu Asp Leu Gly Lys Arg Asn Arg His
            1030            1035            1040 ag  gtagctgtgg gggcagcctc ggtgtctcac ctttcccctc ccctataggc       186482
Ser cctgaaggag aggacccatt ttcccgataa tggtgcactc ccggttggta aatatgtact 186542
cagggacaag ttgcagaatc ctcaggaggt ccacgtggtt ttgaaaatgc ttcccagatg 186602
attctaatat gttcccctg gggctgggag agggatgtgc atgttgtggg gagagggaca  186662
tgcttccctg gtgagaatc tttgagctaa attctcaggt aatttgatca aattgataca  186722
gaactgtgat tactgagatc atataagcct ctcctgccat tgtcttaaat agtcattgaa 186782
ctggggaaaa agtgaagaga ggcgggactg ggtcctttga cgctataccc tacctgtgaa 186842
ttggaatcac ctgcagagat ttaaaaactg ctgatctaca agcctcaccc aaaacaacaa 186902
attagaatcc ctggggggtgg tggccaactg ctccctggct gatttgtttc ttctttcttt 186962
taaattttgt attatggaag atttctaacg tgtgcacaat tcacatagta tagtgagctg 187022
ttcagtattc gtcacccagc ttcaatgact atgccctctg ccagcctgga tgcacacatg 187082
gccatgtctg tctctcctca gcctcctctg gattgtttgg aagcaaatcc tagacacctt 187142
atcatttcac ccataaatat tccagtgtgt gtctcttaaa gataagggct ctattttaaa 187202
gaagaacaac agttattaaa aataactaca atgccgttat ctcacccaaa acagggacaa 187262
taaatcgtta aggcatcagg cagccagtta aagttcaaat tatctcacaa atattatcat 187322
actccattaa aaagtgggca gaggacataa gcagacactt ttcaaaagaa gacatacctg 187382
cagccaacaa gcatatgaaa aaatgctcaa catcactgat cactagagaa atgcaaatca 187442
gaaccgtgat gagataccat ctcacaccag acagaatggt tattattaaa aagtcaaaaa 187502
ataacagatg ctggtgaggt tgtggagaaa aggggaagcg tatacactgc ttgttgaagt 187562
gcaaattagt tcagctattg tggaaagcag tgtggtgatt tctcaaagaa cttttaacag 187622
aattaccatt ggatccagca atcccattac tgggtatata accaaaggaa tataaatcat 187682
tctaccataa agacatgcat acgtatgttc actgcagcac tattcacgat agcaaagaca 187742
tggaatcatc ctaaatgccc attgacagta gactggataa agaacatctg gcacatatac 187802
accatggaat actatgtgtt gataaaaaag aacaagatct gagataccat ctcccaccag 187862
tcagaatggc tattatttaa aagtcaaaaa gcaacagatt gtggcgaggt tgtggagaaa 187922
aagaaacact tttacaatgt tggttggagt gtaaattagt tcaaccattg tggaagacag 187982
tgtggcgatt ccccaaagac ctagaggcag aaatactgtt tgacccatca atcccattac 188042
tgagtatata cccagagtga tgtaaatcat tctattataa aggcacatga atgtgtatgt 188102
tcactgctgc actgttcaca atagcaaaat catggaatca acctaaatgc ccatcaatga 188162
tagactggat aaagaaaatg tgatacatat acaccatgga atacgatgca gccgtaaaaa 188222
ggaatgagat catgtccttt gcagggacat ggatggagct ggaagccgtt accgtcagca 188282
aactaacaca ggaacagaaa accaaacacc acatgttctc acttataagt gggagctgaa 188342
cgatgaggac acatggacac atggagggaa acaacacaca ctggagcctt tcaggggttg 188402
gggattgggt ggaacatcag gaagaatagc taatggatac tggcataat  acctgggtga 188462
tgggatgatc tgtgcggcaa accaccatga cgcatgttta cccatgtaac aaacctgcac 188522
```

```
atcctgcata tgtaccectg aacttaaaaa gtggaaaata caaaaatgaa attaaaaaaa  188582
gaacaagatc atgtcctttg cagcaacgtg gatggagccg gaggtcacta tccttagcaa  188642
actaatacgg gaacagaaga ccagataccg catgttctca cttataagtg ggagctaaaa  188702
ctacgagaac acatggacac aaagagggga acaacagaca ccagggcata gttgagggtg  188762
cagggtggga aaggaagag gatcagaaaa aataccatc ggatactgtg cttattattt  188822
gggtgatgaa ataatctgta catcaaaccg ccatgacatg tgatttatcc atgtaacctg  188882
cacacgtgcc cttgaacata aaataaaagt taaaaaaaaa ttatcataca cttgttttgt  188942
tctgtctgag atccagataa gagtcacaca ttgcacttgg ttgctatgtc tctgtaagtt  189002
cactatgtct ctattttttg ccctcttaca tattatttgt gaagaaacca tagtgtttgc  189062
ctgtggagtt cccacaatcg gcattttgct gattacatcc ttgaagtgtc cttctcaggt  189122
gcttctgtct tctctatgtg ttgtaaactg gtagttagtc taggaactta acctgactca  189182
ggttagatct ttggcaaaca tgcttcatag atggttctgt gtgcttctgt caagaggtat  189242
gcactgtcca gttgtctgcc ttttgtaaca ttatcagtca ttgggtgatc attacctaga  189302
atttcttttt tttttttttt ttttgagatg gagtctcgct ctgtcaccca ggctggagtg  189362
cagtggtgtg atctcagctt actgtaacct ccacctcctg agttcaagcc attctcatac  189422
ctccgcctcc tgagtagctg ggattacagg cacatgccac catgcccagc taattttgt  189482
atttttagta gaaatggggt ttcagcatgt tggccaggct ggttttgaac tcctgacctc  189542
aagtgatctg ccggtctcgg cctcccaaga tgctgggatt ataggcatga accacctcac  189602
ccggcctaga ttctttaact cagcaccaag gtggagctaa tgcccaggca ggactgagaa  189662
tcactggctg acgtggtcag atggaggaga ccatgcccca gttctccgct gtctttgcat  189722
ggcccttgga cagaggtagg agaaggtgat gatagtggcc cctagttcaa ggtccaagtt  189782
gcttgtgtgt gtgtgtgtgt gtgtgtgtgt gtgtgtgttt tcctcttctt tcccatcaga  189842
acattatttt ggaggcttat gactgtgacc tttgttaacc aatttaggta taatatgtag  189902
acagcccttg tttatttgta tggactgggt aattttgaaa gtatggcttt tctattttgt  189962
tttagaatat gttatgtgat ttgaagatgg gacacagtgg cccatcagtc ttcggttttt  190022
tattatgctt tgctcaggcc agtttttata acgtgtttat atctcttgag catacggtgt  190082
tcctccaagt tttgggggtc tgcgatggaa cttcacgggg gtcggggaag gctgggcagt  190142
gaatctaggg ctctctgtct cagatccttt ctcaatttgg ttactttgtg tttgtgggct  190202
ctgaataata tttgagttgt aagagggttc tgcttttata taaagttaga aagtcacatt  190262
ggaataaata acatgagaaa ggtgcccaga agttttctag gctacaaca ggctgagctg  190322
cagaatttga cacgccagga attgaacttt ctcagttgaa gttcacgttc aagttaagta  190382
acttgtgtgg catcacacag ctagtaagtg gggggaccat tccagaccta aggctttctg  190442
actccagaac tcccctttca gccacttctc tagtacgtaa ggagccgtca cctgggccct  190502
caagttgggg gttggtgggg gggcatttga tgtcaagaga gagggaaga gggcattcca  190562
ggcaagtggc aggagatcct gagaacacag tttggatgct caggaggctt ccgggagagc  190622
acctgatggg cctggctgca gcttgcaccc tgatgggcct gacttcaccc cctgctctgc  190682
cttcccaggc ctttggatca ggcattgctt atgttctctt ccactaggat tgagtaggga  190742
aagtagaaat tcttgcagct tgtcagtaac tttgatgaaa gacccagcag aaaagcagga  190802
aagctgaaga gtaaaaatga tgggtggacc ttggttttcc acgtggccta ccacagcatg  190862
tcaggcctgg gggcagaatc ttgccatact gtgcagccca aatttgaatg ccaaaggctt  190922
```

```
tcgtttgtct ctgggggggcc acagtctagg tctagttctg tgcaggagtt gtaatatttg    190982
ctcttctctc cctcctccag c tcg cag acc tct gaa gag agt gcc att gag        191033
                        Ser Gln Thr Ser Glu Glu Ser Ala Ile Glu
                                1045                1050 acg ggt tcc agc agt tcc acc ttc atc aag aga gag gac gag acc            191078
Thr Gly Ser Ser Ser Ser Thr Phe Ile Lys Arg Glu Asp Glu Thr
        1055            1060                1065 att gaa gac atc gac atg atg gat gac atc ggc ata gac tct tca            191123
Ile Glu Asp Ile Asp Met Met Asp Asp Ile Gly Ile Asp Ser Ser
1070            1075                1080 gac ctg gtg gaa gac agc ttc ctg taa                                    191150
Asp Leu Val Glu Asp Ser Phe Leu
            1085
```

<210> SEQ ID NO 20
<211> LENGTH: 6633
<212> TYPE: DNA
<213> ORGANISM: Homo sapiens
<220> FEATURE:
<221> NAME/KEY: CDS
<222> LOCATION: (395)..(3664)

<400> SEQUENCE: 20

```
ttctccccgc cccccagttg ttgtcgaagt ctgggggttg ggactggacc ccctgattgc        60
gtaagagcaa aaagcgaagg cgcaatctgg acactgggag attcggagcg cagggagttt      120
gagagaaact tttattttga agagaccaag gttgaggggg ggcttatttc ctgacagcta      180
tttacttaga gcaaatgatt agttttagaa ggatggacta acattgaa tcaattacaa        240 aacgcggttt ttgagcccat tactgttgga gctacaggga gagaaacagg aggagactgc      300
aagagatcat ttgggaaggc cgtgggcacg ctctttactc catgtgtggg acattcattg      360
cggaataaca tcggaggaga agtttcccag agct atg ggg act tcc cat ccg gcg      415
                                    Met Gly Thr Ser His Pro Ala
                                     1               5 ttc ctg gtc tta ggc tgt ctt ctc aca ggg ctg agc cta atc ctc tgc        463
Phe Leu Val Leu Gly Cys Leu Leu Thr Gly Leu Ser Leu Ile Leu Cys
        10                  15                  20 cag ctt tca tta ccc tct atc ctt cca aat gaa aat gaa aag gtt gtg        511
Gln Leu Ser Leu Pro Ser Ile Leu Pro Asn Glu Asn Glu Lys Val Val
    25                  30                  35 cag ctg aat tca tcc ttt tct ctg aga tgc ttt ggg gag agt gaa gtg        559
Gln Leu Asn Ser Ser Phe Ser Leu Arg Cys Phe Gly Glu Ser Glu Val
40                  45                  50                  55 agc tgg cag tac ccc atg tct gaa gaa gag agc tcc gat gtg gaa atc        607
Ser Trp Gln Tyr Pro Met Ser Glu Glu Glu Ser Ser Asp Val Glu Ile
                60                  65                  70 aga aat gaa gaa aac aac agc ggc ctt ttt gtg acg gtc ttg gaa gtg        655
Arg Asn Glu Glu Asn Asn Ser Gly Leu Phe Val Thr Val Leu Glu Val
            75                  80                  85 agc agt gcc tcg gcg gcc cac aca ggg ttg tac act tgc tat tac aac        703
Ser Ser Ala Ser Ala Ala His Thr Gly Leu Tyr Thr Cys Tyr Tyr Asn
        90                  95                 100 cac act cag aca gaa gag aat gag ctt gaa ggc agg cac att tac atc        751
His Thr Gln Thr Glu Glu Asn Glu Leu Glu Gly Arg His Ile Tyr Ile
    105                 110                 115 tat gtg cca gac cca gat gta gcc ttt gta cct cta gga atg acg gat        799
Tyr Val Pro Asp Pro Asp Val Ala Phe Val Pro Leu Gly Met Thr Asp
120                 125                 130                 135 tat tta gtc atc gtg gag gat gat gat tct gcc att ata cct tgt cgc        847
```

-continued

```
Tyr Leu Val Ile Val Glu Asp Asp Ser Ala Ile Ile Pro Cys Arg
                140             145             150 aca act gat ccc gag act cct gta acc tta cac aac agt gag ggg gtg    895
Thr Thr Asp Pro Glu Thr Pro Val Thr Leu His Asn Ser Glu Gly Val
                155             160             165 gta cct gcc tcc tac gac agc aga cag ggc ttt aat ggg acc ttc act    943
Val Pro Ala Ser Tyr Asp Ser Arg Gln Gly Phe Asn Gly Thr Phe Thr
                170             175             180 gta ggg ccc tat atc tgt gag gcc acc gtc aaa gga aag aag ttc cag    991
Val Gly Pro Tyr Ile Cys Glu Ala Thr Val Lys Gly Lys Lys Phe Gln
                185             190             195 acc atc cca ttt aat gtt tat gct tta aaa gca aca tca gag ctg gat   1039
Thr Ile Pro Phe Asn Val Tyr Ala Leu Lys Ala Thr Ser Glu Leu Asp
200             205             210             215 cta gaa atg gaa gct ctt aaa acc gtg tat aag tca ggg gaa acg att   1087
Leu Glu Met Glu Ala Leu Lys Thr Val Tyr Lys Ser Gly Glu Thr Ile
                220             225             230 gtg gtc acc tgt gct gtt ttt aac aat gag gtg gtt gac ctt caa tgg   1135
Val Val Thr Cys Ala Val Phe Asn Asn Glu Val Val Asp Leu Gln Trp
                235             240             245 act tac cct gga gaa gtg aaa ggc aaa ggc atc aca atg ctg gaa gaa   1183
Thr Tyr Pro Gly Glu Val Lys Gly Lys Gly Ile Thr Met Leu Glu Glu
            250             255             260 atc aaa gtc cca tcc atc aaa ttg gtg tac act ttg acg gtc ccc gag   1231
Ile Lys Val Pro Ser Ile Lys Leu Val Tyr Thr Leu Thr Val Pro Glu
265             270             275 gcc acg gtg aaa gac agt gga gat tac gaa tgt gct gcc cgc cag gct   1279
Ala Thr Val Lys Asp Ser Gly Asp Tyr Glu Cys Ala Ala Arg Gln Ala
280             285             290             295 acc agg gag gtc aaa gaa atg aag aaa gtc act att tct gtc cat gag   1327
Thr Arg Glu Val Lys Glu Met Lys Lys Val Thr Ile Ser Val His Glu
                300             305             310 aaa ggt ttc att gaa atc aaa ccc acc ttc agc cag ttg gaa gct gtc   1375
Lys Gly Phe Ile Glu Ile Lys Pro Thr Phe Ser Gln Leu Glu Ala Val
            315             320             325 aac ctg cat gaa gtc aaa cat ttt gtt gta gag gtg cgg gcc tac cca   1423
Asn Leu His Glu Val Lys His Phe Val Val Glu Val Arg Ala Tyr Pro
            330             335             340 cct ccc agg ata tcc tgg ctg aaa aac aat ctg act ctg att gaa aat   1471
Pro Pro Arg Ile Ser Trp Leu Lys Asn Asn Leu Thr Leu Ile Glu Asn
345             350             355 ctc act gag atc acc act gat gtg gaa aag att cag gaa ata agg tat   1519
Leu Thr Glu Ile Thr Thr Asp Val Glu Lys Ile Gln Glu Ile Arg Tyr
360             365             370             375 cga agc aaa tta aag ctg atc cgt gct aag gaa gaa gac agt ggc cat   1567
Arg Ser Lys Leu Lys Leu Ile Arg Ala Lys Glu Glu Asp Ser Gly His
            380             385             390 tat act att gta gct caa aat gaa gat gct gtg aag agc tat act ttt   1615
Tyr Thr Ile Val Ala Gln Asn Glu Asp Ala Val Lys Ser Tyr Thr Phe
            395             400             405 gaa ctg tta act caa gtt cct tca tcc att ctg gac ttg gtc gat gat   1663
Glu Leu Leu Thr Gln Val Pro Ser Ser Ile Leu Asp Leu Val Asp Asp
            410             415             420 cac cat ggc tca act ggg gga cag acg gtg agg tgc aca gct gaa ggc   1711
His His Gly Ser Thr Gly Gly Gln Thr Val Arg Cys Thr Ala Glu Gly
425             430             435 acg ccg ctt cct gat att gag tgg atg ata tgc aaa gat att aag aaa   1759
Thr Pro Leu Pro Asp Ile Glu Trp Met Ile Cys Lys Asp Ile Lys Lys
440             445             450             455
```

```
tgt aat aat gaa act tcc tgg act att ttg gcc aac aat gtc tca aac     1807
Cys Asn Asn Glu Thr Ser Trp Thr Ile Leu Ala Asn Asn Val Ser Asn
            460                 465                 470 atc atc acg gag atc cac tcc cga gac agg agt acc gtg gag ggc cgt     1855
Ile Ile Thr Glu Ile His Ser Arg Asp Arg Ser Thr Val Glu Gly Arg
        475                 480                 485 gtg act ttc gcc aaa gtg gag gag acc atc gcc gtg cga tgc ctg gct     1903
Val Thr Phe Ala Lys Val Glu Glu Thr Ile Ala Val Arg Cys Leu Ala
        490                 495                 500 aag aat ctc ctt gga gct gag aac cga gag ctg aag ctg gtg gct ccc     1951
Lys Asn Leu Leu Gly Ala Glu Asn Arg Glu Leu Lys Leu Val Ala Pro
        505                 510                 515 acc ctg cgt tct gaa ctc acg gtg gct gct gca gtc ctg gtg ctg ttg     1999
Thr Leu Arg Ser Glu Leu Thr Val Ala Ala Ala Val Leu Val Leu Leu
520                 525                 530                 535 gtg att gtg atc atc tca ctt att gtc ctg gtt gtc att tgg aaa cag     2047
Val Ile Val Ile Ile Ser Leu Ile Val Leu Val Val Ile Trp Lys Gln
            540                 545                 550 aaa ccg agg tat gaa att cgc tgg agg gac att gaa tca atc agc ccg     2095
Lys Pro Arg Tyr Glu Ile Arg Trp Arg Asp Ile Glu Ser Ile Ser Pro
        555                 560                 565 gat gga cat gaa tat att tat gtg gac ccg atg cag ctg cct tat gac     2143
Asp Gly His Glu Tyr Ile Tyr Val Asp Pro Met Gln Leu Pro Tyr Asp
        570                 575                 580 tca aga tgg gag ttt cca aga gat gga cta gtg ctt ggt cgg gtc ttg     2191
Ser Arg Trp Glu Phe Pro Arg Asp Gly Leu Val Leu Gly Arg Val Leu
585                 590                 595 ggg tct gga gcg ttt ggg aag gtg gtt gaa gga aca gcc tat gga tta     2239
Gly Ser Gly Ala Phe Gly Lys Val Val Glu Gly Thr Ala Tyr Gly Leu
600                 605                 610                 615 agc cgg tcc caa cct gtc atg aaa gtt gca gtg aag atg cta aaa ccc     2287
Ser Arg Ser Gln Pro Val Met Lys Val Ala Val Lys Met Leu Lys Pro
            620                 625                 630 acg gcc aga tcc agt gaa aaa caa gct ctc atg tct gaa ctg aag ata     2335
Thr Ala Arg Ser Ser Glu Lys Gln Ala Leu Met Ser Glu Leu Lys Ile
        635                 640                 645 atg act cac ctg ggg cca cat ttg aac att gta aac ttg ctg gga gcc     2383
Met Thr His Leu Gly Pro His Leu Asn Ile Val Asn Leu Leu Gly Ala
        650                 655                 660 tgc acc aag tca ggc ccc att tac atc atc aca gag tat tgc ttc tat     2431
Cys Thr Lys Ser Gly Pro Ile Tyr Ile Ile Thr Glu Tyr Cys Phe Tyr
        665                 670                 675 gga gat ttg gtc aac tat ttg cat aag aat agg gat agc ttc ctg agc     2479
Gly Asp Leu Val Asn Tyr Leu His Lys Asn Arg Asp Ser Phe Leu Ser
680                 685                 690                 695 cac cac cca gag aag cca aag aaa gag ctg gat atc ttt gga ttg aac     2527
His His Pro Glu Lys Pro Lys Lys Glu Leu Asp Ile Phe Gly Leu Asn
            700                 705                 710 cct gct gat gaa agc aca cgg agc tat gtt att tta tct ttt gaa aac     2575
Pro Ala Asp Glu Ser Thr Arg Ser Tyr Val Ile Leu Ser Phe Glu Asn
        715                 720                 725 aat ggt gac tac atg gac atg aag cag gct gat act aca cag tat gtc     2623
Asn Gly Asp Tyr Met Asp Met Lys Gln Ala Asp Thr Thr Gln Tyr Val
        730                 735                 740 ccc atg cta gaa agg aaa gag gtt tct aaa tat tcc gac atc cag aga     2671
Pro Met Leu Glu Arg Lys Glu Val Ser Lys Tyr Ser Asp Ile Gln Arg
        745                 750                 755 tca ctc tat gat cgt cca gcc tca tat aag aag aaa tct atg tta gac     2719
Ser Leu Tyr Asp Arg Pro Ala Ser Tyr Lys Lys Lys Ser Met Leu Asp
760                 765                 770                 775
```

```
tca gaa gtc aaa aac ctc ctt tca gat gat aac tca gaa ggc ctt act    2767
Ser Glu Val Lys Asn Leu Leu Ser Asp Asp Asn Ser Glu Gly Leu Thr
            780                 785                 790 tta ttg gat ttg ttg agc ttc acc tat caa gtt gcc cga gga atg gag    2815
Leu Leu Asp Leu Leu Ser Phe Thr Tyr Gln Val Ala Arg Gly Met Glu
        795                 800                 805 ttt ttg gct tca aaa aat tgt gtc cac cgt gat ctg gct gct cgc aac    2863
Phe Leu Ala Ser Lys Asn Cys Val His Arg Asp Leu Ala Ala Arg Asn
    810                 815                 820 gtc ctc ctg gca caa gga aaa att gtg aag atc tgt gac ttt ggc ctg    2911
Val Leu Leu Ala Gln Gly Lys Ile Val Lys Ile Cys Asp Phe Gly Leu
825                 830                 835 gcc aga gac atc atg cat gat tcg aac tat gtg tcg aaa ggc agt acc    2959
Ala Arg Asp Ile Met His Asp Ser Asn Tyr Val Ser Lys Gly Ser Thr
840                 845                 850                 855 ttt ctg ccc gtg aag tgg atg gct cct gag agc atc ttt gac aac ctc    3007
Phe Leu Pro Val Lys Trp Met Ala Pro Glu Ser Ile Phe Asp Asn Leu
            860                 865                 870 tac acc aca ctg agt gat gtc tgg tct tat ggc att ctg ctc tgg gag    3055
Tyr Thr Thr Leu Ser Asp Val Trp Ser Tyr Gly Ile Leu Leu Trp Glu
        875                 880                 885 atc ttt tcc ctt ggt ggc acc cct tac ccc ggc atg atg gtg gat tct    3103
Ile Phe Ser Leu Gly Gly Thr Pro Tyr Pro Gly Met Met Val Asp Ser
    890                 895                 900 act ttc tac aat aag atc aag agt ggg tac cgg atg gcc aag cct gac    3151
Thr Phe Tyr Asn Lys Ile Lys Ser Gly Tyr Arg Met Ala Lys Pro Asp
905                 910                 915 cac gct acc agt gaa gtc tac gag atc atg gtg aaa tgc tgg aac agt    3199
His Ala Thr Ser Glu Val Tyr Glu Ile Met Val Lys Cys Trp Asn Ser
920                 925                 930                 935 gag ccg gag aag aga ccc tcc ttt tac cac ctg agt gag att gtg gag    3247
Glu Pro Glu Lys Arg Pro Ser Phe Tyr His Leu Ser Glu Ile Val Glu
            940                 945                 950 aat ctg ctg cct gga caa tat aaa aag agt tat gaa aaa att cac ctg    3295
Asn Leu Leu Pro Gly Gln Tyr Lys Lys Ser Tyr Glu Lys Ile His Leu
        955                 960                 965 gac ttc ctg aag agt gac cat cct gct gtg gca cgc atg cgt gtg gac    3343
Asp Phe Leu Lys Ser Asp His Pro Ala Val Ala Arg Met Arg Val Asp
    970                 975                 980 tca gac aat gca tac att ggt gtc acc tac aaa aac gag gaa gac aag    3391
Ser Asp Asn Ala Tyr Ile Gly Val Thr Tyr Lys Asn Glu Glu Asp Lys
985                 990                 995 ctg aag gac tgg gag ggt  ggt ctg gat gag cag  aga ctg agc gct     3436
Leu Lys Asp Trp Glu Gly  Gly Leu Asp Glu Gln  Arg Leu Ser Ala
1000                 1005                 1010 gac agt ggc tac atc att  cct ctg cct gac att  gac cct gtc cct     3481
Asp Ser Gly Tyr Ile Ile  Pro Leu Pro Asp Ile  Asp Pro Val Pro
1015                 1020                 1025 gag gag gag gac ctg ggc  aag agg aac aga cac  agc tcg cag acc     3526
Glu Glu Glu Asp Leu Gly  Lys Arg Asn Arg His  Ser Ser Gln Thr
1030                 1035                 1040 tct gaa gag agt gcc att  gag acg ggt tcc agc  agt tcc acc ttc     3571
Ser Glu Glu Ser Ala Ile  Glu Thr Gly Ser Ser  Ser Ser Thr Phe
1045                 1050                 1055 atc aag aga gag gac gag  acc att gaa gac atc  gac atg atg gac     3616
Ile Lys Arg Glu Asp Glu  Thr Ile Glu Asp Ile  Asp Met Met Asp
1060                 1065                 1070 gac atc ggc ata gac tct  tca gac ctg gtg gaa  gac agc ttc ctg     3661
Asp Ile Gly Ile Asp Ser  Ser Asp Leu Val Glu  Asp Ser Phe Leu
```

-continued

| | |
|---|---|
| taa ctggcggatt cgaggggttc cttccacttc tggggccacc tctggatccc | 3714 |
| gttcagaaaa ccactttatt gcaatgcgga ggttgagagg aggacttggt tgatgtttaa | 3774 |
| agagaagttc ccagccaagg gcctcgggga gcgttctaaa tatgaatgaa tgggatattt | 3834 |
| tgaaatgaac tttgtcagtg ttgcctctcg caatgcctca gtagcatctc agtggtgtgt | 3894 |
| gaagtttgga gatagatgga taagggaata ataggccaca gaaggtgaac tttgtgcttc | 3954 |
| aaggacattg gtgagagtcc aacagacaca atttatactg cgacagaact tcagcattgt | 4014 |
| aattatgtaa ataactctaa ccaaggctgt gtttagattg tattaactat cttctttgga | 4074 |
| cttctgaaga gaccactcaa tccatccatg tacttccctc ttgaaacctg atgtcagctg | 4134 |
| ctgttgaact ttttaaagaa gtgcatgaaa aaccattttt gaaccttaaa aggtactggt | 4194 |
| actatagcat tttgctatct tttttagtgt taagagataa agaataataa ttaaccaacc | 4254 |
| ttgtttaata gatttgggtc atttagaagc ctgacaactc attttcatat tgtaatctat | 4314 |
| gtttataata ctactactgt tatcagtaat gctaaatgtg taataatgta acatgatttc | 4374 |
| cctccagaga aagcacaatt taaacaatc cttactaagt aggtgatgag tttgacagtt | 4434 |
| tttgacattt atattaaata acatgtttct ctataaagta tggtaatagc tttagtgaat | 4494 |
| taaatttagt tgagcataga gaacaaagta aaagtagtgt tgtccaggaa gtcagaattt | 4554 |
| ttaactgtac tgaataggtt ccccaatcca tcgtattaaa aaacaattaa ctgccctctg | 4614 |
| aaataatggg attagaaaca aacaaaactc ttaagtccta aaagttctca atgtagaggc | 4674 |
| ataaacctgt gctgaacata acttctcatg tatattaccc aatggaaaat ataatgatca | 4734 |
| gcaaaaagac tggatttgca gaagtttttt ttttttttct tcatgcctga tgaaagcttt | 4794 |
| ggcaaccccca atatatgtat ttttgaatc tatgaacctg aaaagggtca gaaggatgcc | 4854 |
| cagacatcag cctccttctt tcaccccctta ccccaaagag aaagagtttg aaactcgaga | 4914 |
| ccataaagat attctttagt ggaggctgga tgtgcattag cctggatcct cagttctcaa | 4974 |
| atgtgtgtgg cagccaggat gactagatcc tgggtttcca tccttgagat tctgaagtat | 5034 |
| gaagtctgag ggaaaccaga gtctgtattt ttctaaactc cctggctgtt ctgatcggcc | 5094 |
| agttttcgga aacactgact taggtttcag gaagttgcca tgggaaacaa ataatttgaa | 5154 |
| cttttggaaca gggttggaat tcaaccacgc aggaagccta ctatttaaat ccttggcttc | 5214 |
| aggttagtga catttaatgc catctagcta gcaattgcga ccttaattta actttccagt | 5274 |
| cttagctgag gctgagaaag ctaaagtttg gttttgacag gttttccaaa agtaaagatg | 5334 |
| ctacttccca ctgtatgggg gagattgaac tttcccgtc tcccgtcttc tgcctcccac | 5394 |
| tccataccccc gccaaggaaa ggcatgtaca aaaattatgc aattcagtgt tccaagtctc | 5454 |
| tgtgtaacca gctcagtgtt ttggtggaaa aacatttta agttttactg ataatttgag | 5514 |
| gttagatggg aggatgaatt gtcacatcta tccacactgt caaacaggtt ggtgtgggtt | 5574 |
| cattggcatt ctttgcaata ctgcttaatt gctgatacca tatgaatgaa acatgggctg | 5634 |
| tgattactgc aatcactgtg ctatcggcag atgatgcttt ggaagatgca gaagcaataa | 5694 |
| taaagtactt gactacctac tggtgtaatc tcaatgcaag ccccaacttt cttatccaac | 5754 |
| ttttttcatag taagtgcgaa gactgagcca gattggccaa ttaaaaacga aaacctgact | 5814 |
| aggttctgta gagccaatta gacttgaaat acgtttgtgt ttctagaatc acagctcaag | 5874 |
| cattctgttt atcgctcact ctcccttgta cagcctatt ttgttggtgc tttgcatttt | 5934 |
| gatattgctg tgagccttgc atgacatcat gaggccggat gaaacttctc agtccagcag | 5994 |

```
tttccagtcc taacaaatgc tcccacctga atttgtatat gactgcattt gtgggtgtgt    6054
gtgtgttttc agcaaattcc agatttgttt ccttttggcc tcctgcaaag tctccagaag    6114
aaaatttgcc aatctttcct actttctatt tttatgatga caatcaaagc cggcctgaga    6174
aacactattt gtgactttt aaacgattag tgatgtcctt aaaatgtggt ctgccaatct    6234
gtacaaaatg gtcctatttt tgtgaagagg gacataagat aaaatgatgt tatacatcaa    6294
tatgtatata tgtatttcta tatagacttg gagaatactg ccaaaacatt tatgacaagc    6354
tgtatcactg ccttcgttta tattttttta actgtgataa tccccacagg cacattaact    6414
gttgcacttt tgaatgtcca aaatttatat tttagaaata ataaaaagaa agatacttac    6474
atgttcccaa acaatggtg tggtgaatgt gtgagaaaaa ctaacttgat agggtctacc    6534
aatacaaaat gtattacgaa tgcccctgtt catgttttg ttttaaaacg tgtaaatgaa    6594
gatctttata ttcaataaa tgatatataa tttaaagtt                            6633
```

<210> SEQ ID NO 21
<211> LENGTH: 1089
<212> TYPE: PRT
<213> ORGANISM: Homo sapiens

<400> SEQUENCE: 21

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255
```

-continued

```
Gly Ile Thr Met Leu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
            325                 330                 335

Val Glu Val Arg Ala Tyr Pro Pro Arg Ile Ser Trp Leu Lys Asn
        340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
            405                 410                 415

Ile Leu Asp Leu Val Asp Asp His His Gly Ser Thr Gly Gln Thr
        420                 425                 430

Val Arg Cys Thr Ala Glu Gly Thr Pro Leu Pro Asp Ile Glu Trp Met
    435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
            485                 490                 495

Ile Ala Val Arg Cys Leu Ala Lys Asn Leu Leu Gly Ala Glu Asn Arg
        500                 505                 510

Glu Leu Lys Leu Val Ala Pro Thr Leu Arg Ser Glu Leu Thr Val Ala
    515                 520                 525

Ala Ala Val Leu Val Leu Leu Val Ile Val Ile Ile Ser Leu Ile Val
            530                 535                 540

Leu Val Val Ile Trp Lys Gln Lys Pro Arg Tyr Glu Ile Arg Trp Arg
545                 550                 555                 560

Asp Ile Glu Ser Ile Ser Pro Asp Gly His Glu Tyr Ile Tyr Val Asp
            565                 570                 575

Pro Met Gln Leu Pro Tyr Asp Ser Arg Trp Glu Phe Pro Arg Asp Gly
        580                 585                 590

Leu Val Leu Gly Arg Val Leu Gly Ser Gly Ala Phe Gly Lys Val Val
    595                 600                 605

Glu Gly Thr Ala Tyr Gly Leu Ser Arg Ser Gln Pro Val Met Lys Val
610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
            645                 650                 655

Ile Val Asn Leu Leu Gly Ala Cys Thr Lys Ser Gly Pro Ile Tyr Ile
        660                 665                 670

Ile Thr Glu Tyr Cys Phe Tyr Gly Asp Leu Val Asn Tyr Leu His Lys
```

-continued

```
                    675                 680                 685
Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                 1005

Glu Gln  Arg Leu Ser Ala Asp  Ser Gly Tyr Ile Ile   Pro Leu Pro
    1010                1015                 1020

Asp Ile  Asp Pro Val Pro Glu  Glu Asp Leu Gly  Lys Arg Asn
    1025                1030                1035

Arg His  Ser Ser Gln Thr Ser  Glu Glu Ser Ala Ile  Glu Thr Gly
    1040                1045                1050

Ser Ser  Ser Ser Thr Phe Ile  Lys Arg Glu Asp Glu   Thr Ile Glu
    1055                1060                1065

Asp Ile  Asp Met Met Asp Asp  Ile Gly Ile Asp Ser   Ser Asp Leu
    1070                1075                1080

Val Glu  Asp Ser Phe Leu
    1085
```

<210> SEQ ID NO 22
<211> LENGTH: 6618
<212> TYPE: DNA
<213> ORGANISM: Homo sapiens
<220> FEATURE:
<221> NAME/KEY: CDS
<222> LOCATION: (395)..(3649)

<400> SEQUENCE: 22

```
ttctccccgc cccccagttg ttgtcgaagt ctgggggttg ggactggacc ccctgattgc        60
gtaagagcaa aaagcgaagg cgcaatctgg acactgggag attcggagcg cagggagttt      120
gagagaaact tttattttga agagaccaag gttgagggg ggcttatttc ctgacagcta       180
tttacttaga gcaaatgatt agttttagaa ggatggacta taacattgaa tcaattacaa      240
aacgcggttt ttgagcccat tactgttgga gctacaggga gagaaacagg aggagactgc      300
aagagatcat ttgggaaggc cgtgggcacg ctctttactc catgtgtggg acattcattg      360
cggaataaca tcggaggaga agtttcccag agct atg ggg act tcc cat ccg gcg      415
                                    Met Gly Thr Ser His Pro Ala
                                      1               5 ttc ctg gtc tta ggc tgt ctt ctc aca ggg ctg agc cta atc ctc tgc        463
Phe Leu Val Leu Gly Cys Leu Leu Thr Gly Leu Ser Leu Ile Leu Cys
             10                  15                  20 cag ctt tca tta ccc tct atc ctt cca aat gaa aat gaa aag gtt gtg        511
Gln Leu Ser Leu Pro Ser Ile Leu Pro Asn Glu Asn Glu Lys Val Val
         25                  30                  35 cag ctg aat tca tcc ttt tct ctg aga tgc ttt ggg gag agt gaa gtg        559
Gln Leu Asn Ser Ser Phe Ser Leu Arg Cys Phe Gly Glu Ser Glu Val
 40                  45                  50                  55 agc tgg cag tac ccc atg tct gaa gaa gag agc tcc gat gtg gaa atc        607
Ser Trp Gln Tyr Pro Met Ser Glu Glu Glu Ser Ser Asp Val Glu Ile
                 60                  65                  70 aga aat gaa gaa aac aac agc ggc ctt ttt gtg acg gtc ttg gaa gtg        655
Arg Asn Glu Glu Asn Asn Ser Gly Leu Phe Val Thr Val Leu Glu Val
             75                  80                  85 agc agt gcc tcg gcg gcc cac aca ggg ttg tac act tgc tat tac aac        703
Ser Ser Ala Ser Ala Ala His Thr Gly Leu Tyr Thr Cys Tyr Tyr Asn
         90                  95                 100 cac act cag aca gaa gag aat gag ctt gaa ggc agg cac att tac atc        751
His Thr Gln Thr Glu Glu Asn Glu Leu Glu Gly Arg His Ile Tyr Ile
        105                 110                 115 tat gtg cca gac cca gat gta gcc ttt gta cct cta gga atg acg gat        799
Tyr Val Pro Asp Pro Asp Val Ala Phe Val Pro Leu Gly Met Thr Asp
120                 125                 130                 135 tat tta gtc atc gtg gag gat gat gat tct gcc att ata cct tgt cgc        847
Tyr Leu Val Ile Val Glu Asp Asp Asp Ser Ala Ile Ile Pro Cys Arg
                140                 145                 150 aca act gat ccc gag act cct gta acc tta cac aac agt gag ggg gtg        895
Thr Thr Asp Pro Glu Thr Pro Val Thr Leu His Asn Ser Glu Gly Val
            155                 160                 165 gta cct gcc tcc tac gac agc aga cag ggc ttt aat ggg acc ttc act        943
Val Pro Ala Ser Tyr Asp Ser Arg Gln Gly Phe Asn Gly Thr Phe Thr
        170                 175                 180 gta ggg ccc tat atc tgt gag gcc acc gtc aaa gga aag aag ttc cag        991
Val Gly Pro Tyr Ile Cys Glu Ala Thr Val Lys Gly Lys Lys Phe Gln
    185                 190                 195 acc atc cca ttt aat gtt tat gct tta aaa gca aca tca gag ctg gat       1039
Thr Ile Pro Phe Asn Val Tyr Ala Leu Lys Ala Thr Ser Glu Leu Asp
200                 205                 210                 215
```

```
cta gaa atg gaa gct ctt aaa acc gtg tat aag tca ggg gaa acg att    1087
Leu Glu Met Glu Ala Leu Lys Thr Val Tyr Lys Ser Gly Glu Thr Ile
            220                 225                 230 gtg gtc acc tgt gct gtt ttt aac aat gag gtg gtt gac ctt caa tgg    1135
Val Val Thr Cys Ala Val Phe Asn Asn Glu Val Val Asp Leu Gln Trp
                235                 240                 245 act tac cct gga gaa gtg aaa ggc aaa ggc atc aca atg ctg gaa gaa    1183
Thr Tyr Pro Gly Glu Val Lys Gly Lys Gly Ile Thr Met Leu Glu Glu
            250                 255                 260 atc aaa gtc cca tcc atc aaa ttg gtg tac act ttg acg gtc ccc gag    1231
Ile Lys Val Pro Ser Ile Lys Leu Val Tyr Thr Leu Thr Val Pro Glu
    265                 270                 275 gcc acg gtg aaa gac agt gga gat tac gaa tgt gct gcc cgc cag gct    1279
Ala Thr Val Lys Asp Ser Gly Asp Tyr Glu Cys Ala Ala Arg Gln Ala
280                 285                 290                 295 acc agg gag gtc aaa gaa atg aag aaa gtc act att tct gtc cat gag    1327
Thr Arg Glu Val Lys Glu Met Lys Lys Val Thr Ile Ser Val His Glu
                300                 305                 310 aaa ggt ttc att gaa atc aaa ccc acc ttc agc cag ttg gaa gct gtc    1375
Lys Gly Phe Ile Glu Ile Lys Pro Thr Phe Ser Gln Leu Glu Ala Val
            315                 320                 325 aac ctg cat gaa gtc aaa cat ttt gtt gta gag gtg cgg gcc tac cca    1423
Asn Leu His Glu Val Lys His Phe Val Val Glu Val Arg Ala Tyr Pro
        330                 335                 340 cct ccc agg ata tcc tgg ctg aaa aac aat ctg act ctg att gaa aat    1471
Pro Pro Arg Ile Ser Trp Leu Lys Asn Asn Leu Thr Leu Ile Glu Asn
    345                 350                 355 ctc act gag atc acc act gat gtg gaa aag att cag gaa ata agg tat    1519
Leu Thr Glu Ile Thr Thr Asp Val Glu Lys Ile Gln Glu Ile Arg Tyr
360                 365                 370                 375 cga agc aaa tta aag ctg atc cgt gct aag gaa gaa gac agt ggc cat    1567
Arg Ser Lys Leu Lys Leu Ile Arg Ala Lys Glu Glu Asp Ser Gly His
            380                 385                 390 tat act att gta gct caa aat gaa gat gct gtg aag agc tat act ttt    1615
Tyr Thr Ile Val Ala Gln Asn Glu Asp Ala Val Lys Ser Tyr Thr Phe
                395                 400                 405 gaa ctg tta act caa gtt cct tca tcc att ctg gac ttg gtc gat gat    1663
Glu Leu Leu Thr Gln Val Pro Ser Ser Ile Leu Asp Leu Val Asp Asp
            410                 415                 420 cac cat ggc tca act ggg gga cag acg gtg agg tgc aca gct gaa ggc    1711
His His Gly Ser Thr Gly Gly Gln Thr Val Arg Cys Thr Ala Glu Gly
        425                 430                 435 acg ccg ctt cct gat att gag tgg atg ata tgc aaa gat att aag aaa    1759
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac    1807
Cys Asn Asn Glu Thr Ser Trp Thr Ile Leu Ala Asn Asn Val Ser Asn
            460                 465                 470 atc atc acg gag atc cac tcc cga gac agg agt acc gtg gag ggc cgt    1855
Ile Ile Thr Glu Ile His Ser Arg Asp Arg Ser Thr Val Glu Gly Arg
                475                 480                 485 gtg act ttc gcc aaa gtg gag gag acc atc gcc gtg cga tgc ctg gct    1903
Val Thr Phe Ala Lys Val Glu Glu Thr Ile Ala Val Arg Cys Leu Ala
            490                 495                 500 aag aat ctc ctt gga gct gag aac cga gag ctg aag ctg gtg gct ccc    1951
Lys Asn Leu Leu Gly Ala Glu Asn Arg Glu Leu Lys Leu Val Ala Pro
505                 510                 515 acc ctg cgt tct gaa ctc acg gtg gct gct gca gtc ctg gtg ctg ttg    1999
Thr Leu Arg Ser Glu Leu Thr Val Ala Ala Ala Val Leu Val Leu Leu
```

-continued

| | |
|---|---|
| gtg att gtg atc atc tca ctt att gtc ctg gtt gtc att tgg aaa cag<br>Val Ile Val Ile Ile Ser Leu Ile Val Leu Val Val Ile Trp Lys Gln<br>520             525             530             535<br>                540                 545                550 | 2047 |
| aaa ccg agg tat gaa att cgc tgg atc agc ccg gat gga cat gaa tat<br>Lys Pro Arg Tyr Glu Ile Arg Trp Ile Ser Pro Asp Gly His Glu Tyr<br>               555                 560                 565 | 2095 |
| att tat gtg gac ccg atg cag ctg cct tat gac tca aga tgg gag ttt<br>Ile Tyr Val Asp Pro Met Gln Leu Pro Tyr Asp Ser Arg Trp Glu Phe<br>          570                 575                 580 | 2143 |
| cca aga gat gga cta gtg ctt ggt cgg gtc ttg ggg tct gga gcg ttt<br>Pro Arg Asp Gly Leu Val Leu Gly Arg Val Leu Gly Ser Gly Ala Phe<br>585                   590                 595 | 2191 |
| ggg aag gtg gtt gaa gga aca gcc tat gga tta agc cgg tcc caa cct<br>Gly Lys Val Val Glu Gly Thr Ala Tyr Gly Leu Ser Arg Ser Gln Pro<br>600             605             610             615 | 2239 |
| gtc atg aaa gtt gca gtg aag atg cta aaa ccc acg gcc aga tcc agt<br>Val Met Lys Val Ala Val Lys Met Leu Lys Pro Thr Ala Arg Ser Ser<br>               620                 625                 630 | 2287 |
| gaa aaa caa gct ctc atg tct gaa ctg aag ata atg act cac ctg ggg<br>Glu Lys Gln Ala Leu Met Ser Glu Leu Lys Ile Met Thr His Leu Gly<br>          635                 640                 645 | 2335 |
| cca cat ttg aac att gta aac ttg ctg gga gcc tgc acc aag tca ggc<br>Pro His Leu Asn Ile Val Asn Leu Leu Gly Ala Cys Thr Lys Ser Gly<br>650                   655                 660 | 2383 |
| ccc att tac atc atc aca gag tat tgc ttc tat gga gat ttg gtc aac<br>Pro Ile Tyr Ile Ile Thr Glu Tyr Cys Phe Tyr Gly Asp Leu Val Asn<br>               665                 670                 675 | 2431 |
| tat ttg cat aag aat agg gat agc ttc ctg agc cac cac cca gag aag<br>Tyr Leu His Lys Asn Arg Asp Ser Phe Leu Ser His His Pro Glu Lys<br>680                   685                 690                 695 | 2479 |
| cca aag aaa gag ctg gat atc ttt gga ttg aac cct gct gat gaa agc<br>Pro Lys Lys Glu Leu Asp Ile Phe Gly Leu Asn Pro Ala Asp Glu Ser<br>               700                 705                 710 | 2527 |
| aca cgg agc tat gtt att tta tct ttt gaa aac aat ggt gac tac atg<br>Thr Arg Ser Tyr Val Ile Leu Ser Phe Glu Asn Asn Gly Asp Tyr Met<br>          715                 720                 725 | 2575 |
| gac atg aag cag gct gat act aca cag tat gtc ccc atg cta gaa agg<br>Asp Met Lys Gln Ala Asp Thr Thr Gln Tyr Val Pro Met Leu Glu Arg<br>730                   735                 740 | 2623 |
| aaa gag gtt tct aaa tat tcc gac atc cag aga tca ctc tat gat cgt<br>Lys Glu Val Ser Lys Tyr Ser Asp Ile Gln Arg Ser Leu Tyr Asp Arg<br>               745                 750                 755 | 2671 |
| cca gcc tca tat aag aag aaa tct atg tta gac tca gaa gtc aaa aac<br>Pro Ala Ser Tyr Lys Lys Lys Ser Met Leu Asp Ser Glu Val Lys Asn<br>760                   765                 770                 775 | 2719 |
| ctc ctt tca gat gat aac tca gaa ggc ctt act tta ttg gat ttg ttg<br>Leu Leu Ser Asp Asp Asn Ser Glu Gly Leu Thr Leu Leu Asp Leu Leu<br>               780                 785                 790 | 2767 |
| agc ttc acc tat caa gtt gcc cga gga atg gag ttt ttg gct tca aaa<br>Ser Phe Thr Tyr Gln Val Ala Arg Gly Met Glu Phe Leu Ala Ser Lys<br>          795                 800                 805 | 2815 |
| aat tgt gtc cac cgt gat ctg gct gct cgc aac gtc ctc ctg gca caa<br>Asn Cys Val His Arg Asp Leu Ala Ala Arg Asn Val Leu Leu Ala Gln<br>810                   815                 820 | 2863 |
| gga aaa att gtg aag atc tgt gac ttt ggc ctg gcc aga gac atc atg<br>Gly Lys Ile Val Lys Ile Cys Asp Phe Gly Leu Ala Arg Asp Ile Met<br>               825                 830                 835 | 2911 |
| cat gat tcg aac tat gtg tcg aaa ggc agt acc ttt ctg ccc gtg aag | 2959 |

```
His Asp Ser Asn Tyr Val Ser Lys Gly Ser Thr Phe Leu Pro Val Lys
840                 845                 850                 855 tgg atg gct cct gag agc atc ttt gac aac ctc tac acc aca ctg agt    3007
Trp Met Ala Pro Glu Ser Ile Phe Asp Asn Leu Tyr Thr Thr Leu Ser
                860                 865                 870 gat gtc tgg tct tat ggc att ctg ctc tgg gag atc ttt tcc ctt ggt    3055
Asp Val Trp Ser Tyr Gly Ile Leu Leu Trp Glu Ile Phe Ser Leu Gly
            875                 880                 885 ggc acc cct tac ccc ggc atg atg gtg gat tct act ttc tac aat aag    3103
Gly Thr Pro Tyr Pro Gly Met Met Val Asp Ser Thr Phe Tyr Asn Lys
        890                 895                 900 atc aag agt ggg tac cgg atg gcc aag cct gac cac gct acc agt gaa    3151
Ile Lys Ser Gly Tyr Arg Met Ala Lys Pro Asp His Ala Thr Ser Glu
    905                 910                 915 gtc tac gag atc atg gtg aaa tgc tgg aac agt gag ccg gag aag aga    3199
Val Tyr Glu Ile Met Val Lys Cys Trp Asn Ser Glu Pro Glu Lys Arg
920                 925                 930                 935 ccc tcc ttt tac cac ctg agt gag att gtg gag aat ctg ctg cct gga    3247
Pro Ser Phe Tyr His Leu Ser Glu Ile Val Glu Asn Leu Leu Pro Gly
                940                 945                 950 caa tat aaa aag agt tat gaa aaa att cac ctg gac ttc ctg aag agt    3295
Gln Tyr Lys Lys Ser Tyr Glu Lys Ile His Leu Asp Phe Leu Lys Ser
            955                 960                 965 gac cat cct gct gtg gca cgc atg cgt gtg gac tca gac aat gca tac    3343
Asp His Pro Ala Val Ala Arg Met Arg Val Asp Ser Asp Asn Ala Tyr
        970                 975                 980 att ggt gtc acc tac aaa aac gag gaa gac aag ctg aag gac tgg gag    3391
Ile Gly Val Thr Tyr Lys Asn Glu Glu Asp Lys Leu Lys Asp Trp Glu
    985                 990                 995 ggt ggt ctg gat gag cag aga ctg agc gct gac agt ggc tac atc        3436
Gly Gly Leu Asp Glu Gln Arg Leu Ser Ala Asp Ser Gly Tyr Ile
1000                1005                1010 att cct ctg cct gac att gac cct gtc cct gag gag gag gac ctg        3481
Ile Pro Leu Pro Asp Ile Asp Pro Val Pro Glu Glu Glu Asp Leu
1015                1020                1025 ggc aag agg aac aga cac agc tcg cag acc tct gaa gag agt gcc        3526
Gly Lys Arg Asn Arg His Ser Ser Gln Thr Ser Glu Glu Ser Ala
1030                1035                1040 att gag acg ggt tcc agc agt ccc acc ttc atc aag aga gag gac        3571
Ile Glu Thr Gly Ser Ser Ser Pro Thr Phe Ile Lys Arg Glu Asp
1045                1050                1055 gag acc att gaa gac atc gac atg atg gac gac atc ggc ata gac        3616
Glu Thr Ile Glu Asp Ile Asp Met Met Asp Asp Ile Gly Ile Asp
1060                1065                1070 tct tca gac ctg gtg gaa gac agc ttc ctg taa ctggcggatt             3659
Ser Ser Asp Leu Val Glu Asp Ser Phe Leu
1075                1080 cgagggggttc cttccacttc tggggccacc tctggatccc gttcagaaaa ccactttatt    3719
gcaatgcgga ggttgagagg aggacttggt tgatgtttaa agagaagttc ccagccaagg    3779
gcctcgggga gcgttctaaa tatgaatgaa tgggatattt tgaaatgaac tttgtcagtg    3839
ttgcctctcg caatgcctca gtagcatctc agtggtgtgt gaagtttgga gatagatgga    3899
taagggaata ataggccaca gaaggtgaac tttgtgcttc aaggacattg gtgagagtcc    3959
aacagacaca atttatactg cgacagaact tcagcattgt aattatgtaa ataactctaa    4019
ccaaggctgt gtttagattg tattaactat cttctttgga cttctgaaga gaccactcaa    4079
tccatccatg tacttccctc ttgaaacctg atgtcagctg ctgttgaact ttttaaagaa    4139
```

```
gtgcatgaaa aaccattttt gaaccttaaa aggtactggt actatagcat tttgctatct    4199
tttttagtgt taagagataa agaataataa ttaaccaacc ttgtttaata gatttgggtc    4259
atttagaagc ctgacaactc attttcatat tgtaatctat gtttataata ctactactgt    4319
tatcagtaat gctaaatgtg taataatgta acatgatttc cctccagaga aagcacaatt    4379
taaaacaatc cttactaagt aggtgatgag tttgacagtt tttgacattt atattaaata    4439
acatgtttct ctataaagta tggtaatagc tttagtgaat taaatttagt tgagcataga    4499
gaacaaagta aaagtagtgt tgtccaggaa gtcagaattt ttaactgtac tgaataggtt    4559
ccccaatcca tcgtattaaa aaacaattaa ctgccctctg aaataatggg attagaaaca    4619
aacaaaactc ttaagtccta aaagttctca atgtagaggc ataaacctgt gctgaacata    4679
acttctcatg tatattaccc aatggaaaat ataatgatca gcaaaagac tggatttgca    4739
gaagttttt ttttttttct tcatgcctga tgaaagcttt ggcaaccca atatatgtat    4799
tttttgaatc tatgaacctg aaaagggtca gaaggatgcc cagacatcag cctccttctt    4859
tcacccctta ccccaaagag aaagagtttg aaactcgaga ccataaagat attctttagt    4919
ggaggctgga tgtgcattag cctggatcct cagttctcaa atgtgtgtgg cagccaggat    4979
gactagatcc tgggtttcca tccttgagat tctgaagtat gaagtctgag ggaaaccaga    5039
gtctgtattt ttctaaactc cctggctgtt ctgatcggcc agttttcgga aacactgact    5099
taggtttcag gaagttgcca tgggaaacaa ataatttgaa ctttggaaca gggttggaat    5159
tcaaccacgc aggaagccta ctatttaaat ccttggcttc aggttagtga catttaatgc    5219
catctagcta gcaattgcga ccttaattta actttccagt cttagctgag gctgagaaag    5279
ctaaagtttg gttttgacag gttttccaaa agtaaagatg ctacttccca ctgtatgggg    5339
gagattgaac tttccccgtc tcccgtcttc tgcctcccac tccatacccc gccaaggaaa    5399
ggcatgtaca aaaattatgc aattcagtgt tccaagtctc tgtgtaacca gctcagtgtt    5459
ttggtggaaa aaacatttta agttttactg ataatttgag gttagatggg aggatgaatt    5519
gtcacatcta tccacactgt caaacaggtt ggtgtgggtt cattggcatt ctttgcaata    5579
ctgcttaatt gctgatacca tatgaatgaa acatgggctg tgattactgc aatcactgtg    5639
ctatcggcag atgatgcttt ggaagatgca gaagcaataa taaagtactt gactacctac    5699
tggtgtaatc tcaatgcaag ccccaacttt cttatccaac tttttcatag taagtgcgaa    5759
gactgagcca gattggccaa ttaaaaacga aaacctgact aggttctgta gagccaatta    5819
gacttgaaat acgtttgtgt ttctagaatc acagctcaag cattctgttt atcgctcact    5879
ctcccttgta cagccttatt ttgttggtgc tttgcatttt gatattgctg tgagccttgc    5939
atgacatcat gaggccggat gaaacttctc agtccagcag tttccagtcc taacaaatgc    5999
tcccacctga atttgtatat gactgcattt gtgggtgtgt gtgtgttttc agcaaattcc    6059
agatttgttt cctttttggcc tcctgcaaag tctccagaag aaaatttgcc aatctttcct    6119
actttctatt tttatgatga caatcaaagc cggcctgaga acactatttt gtgactttt    6179
aaacgattag tgatgtcctt aaaatgtggt ctgccaatct gtacaaaatg gtcctatttt    6239
tgtgaagagg gacataagat aaaatgatgt tatacatcaa tatgtatata tgtatttcta    6299
tatagacttg gagaatactg ccaaaacatt tatgacaagc tgtatcactg ccttcgttta    6359
tatttttta actgtgataa tccccacagg cacattaact gttgcacttt tgaatgtcca    6419
aaatttatat tttagaaata ataaaagaa agatacttac atgttcccaa acaatggtg     6479
tggtgaatgt gtgagaaaaa ctaacttgat agggtctacc aatacaaaat gtattacgaa    6539
```

```
tgcccctgtt catgttttg ttttaaaacg tgtaaatgaa gatctttata tttcaataaa      6599
tgatatataa tttaaagtt                                                  6618

<210> SEQ ID NO 23
<211> LENGTH: 1084
<212> TYPE: PRT
<213> ORGANISM: Homo sapiens

<400> SEQUENCE: 23

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350
```

```
Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
        370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
        450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
            530                 535                 540

Leu Val Val Ile Trp Lys Gln Lys Pro Arg Tyr Glu Ile Arg Trp Ile
545                 550                 555                 560

Ser Pro Asp Gly His Glu Tyr Ile Tyr Val Asp Pro Met Gln Leu Pro
                565                 570                 575

Tyr Asp Ser Arg Trp Glu Phe Pro Arg Asp Gly Leu Val Leu Gly Arg
            580                 585                 590

Val Leu Gly Ser Gly Ala Phe Gly Lys Val Val Glu Gly Thr Ala Tyr
        595                 600                 605

Gly Leu Ser Arg Ser Gln Pro Val Met Lys Val Ala Val Lys Met Leu
        610                 615                 620

Lys Pro Thr Ala Arg Ser Ser Glu Lys Gln Ala Leu Met Ser Glu Leu
625                 630                 635                 640

Lys Ile Met Thr His Leu Gly Pro His Leu Asn Ile Val Asn Leu Leu
                645                 650                 655

Gly Ala Cys Thr Lys Ser Gly Pro Ile Tyr Ile Ile Thr Glu Tyr Cys
            660                 665                 670

Phe Tyr Gly Asp Leu Val Asn Tyr Leu His Lys Asn Arg Asp Ser Phe
        675                 680                 685

Leu Ser His His Pro Glu Lys Pro Lys Lys Glu Leu Asp Ile Phe Gly
        690                 695                 700

Leu Asn Pro Ala Asp Glu Ser Thr Arg Ser Tyr Val Ile Leu Ser Phe
705                 710                 715                 720

Glu Asn Asn Gly Asp Tyr Met Asp Met Lys Gln Ala Asp Thr Thr Gln
                725                 730                 735

Tyr Val Pro Met Leu Glu Arg Lys Glu Val Ser Lys Tyr Ser Asp Ile
            740                 745                 750

Gln Arg Ser Leu Tyr Asp Arg Pro Ala Ser Tyr Lys Lys Lys Ser Met
        755                 760                 765

Leu Asp Ser Glu Val Lys Asn Leu Leu Ser Asp Asp Asn Ser Glu Gly
```

```
                    770            775            780
Leu Thr Leu Leu Asp Leu Leu Ser Phe Thr Tyr Gln Val Ala Arg Gly
785                 790                 795                 800

Met Glu Phe Leu Ala Ser Lys Asn Cys Val His Arg Asp Leu Ala Ala
                    805                 810                 815

Arg Asn Val Leu Leu Ala Gln Gly Lys Ile Val Lys Ile Cys Asp Phe
                    820                 825                 830

Gly Leu Ala Arg Asp Ile Met His Asp Ser Asn Tyr Val Ser Lys Gly
                    835                 840                 845

Ser Thr Phe Leu Pro Val Lys Trp Met Ala Pro Glu Ser Ile Phe Asp
850                 855                 860

Asn Leu Tyr Thr Thr Leu Ser Asp Val Trp Ser Tyr Gly Ile Leu Leu
865                 870                 875                 880

Trp Glu Ile Phe Ser Leu Gly Gly Thr Pro Tyr Pro Gly Met Met Val
                    885                 890                 895

Asp Ser Thr Phe Tyr Asn Lys Ile Lys Ser Gly Tyr Arg Met Ala Lys
                    900                 905                 910

Pro Asp His Ala Thr Ser Glu Val Tyr Glu Ile Met Val Lys Cys Trp
                    915                 920                 925

Asn Ser Glu Pro Glu Lys Arg Pro Ser Phe Tyr His Leu Ser Glu Ile
930                 935                 940

Val Glu Asn Leu Leu Pro Gly Gln Tyr Lys Lys Ser Tyr Glu Lys Ile
945                 950                 955                 960

His Leu Asp Phe Leu Lys Ser Asp His Pro Ala Val Ala Arg Met Arg
                    965                 970                 975

Val Asp Ser Asp Asn Ala Tyr Ile Gly Val Thr Tyr Lys Asn Glu Glu
                    980                 985                 990

Asp Lys Leu Lys Asp Trp Glu Gly  Gly Leu Asp Glu Gln  Arg Leu Ser
                995              1000              1005

Ala Asp  Ser Gly Tyr Ile Ile  Pro Leu Pro Asp Ile  Asp Pro Val
    1010              1015              1020

Pro Glu  Glu Glu Asp Leu Gly  Lys Arg Asn Arg His  Ser Ser Gln
    1025              1030              1035

Thr Ser  Glu Glu Ser Ala Ile  Glu Thr Gly Ser Ser  Ser Ser Thr
    1040              1045              1050

Phe Ile  Lys Arg Glu Asp Glu  Thr Ile Glu Asp Ile  Asp Met Met
    1055              1060              1065

Asp Asp  Ile Gly Ile Asp Ser  Ser Asp Leu Val Glu  Asp Ser Phe
    1070              1075              1080

Leu

<210> SEQ ID NO 24
<211> LENGTH: 6633
<212> TYPE: DNA
<213> ORGANISM: Homo sapiens
<220> FEATURE:
<221> NAME/KEY: CDS
<222> LOCATION: (395)..(3664)

<400> SEQUENCE: 24
ttctccccgc cccccagttg ttgtcgaagt ctgggggttg ggactggacc ccctgattgc      60
gtaagagcaa aaagcgaagg cgcaatctgg acactgggag attcggagcg cagggagttt     120
gagagaaact tttattttga agagaccaag gttgaggggg ggcttatttc ctgacagcta     180
tttacttaga gcaaatgatt agttttagaa ggatggacta taacattgaa tcaattacaa     240
```

-continued

```
aacgcggttt ttgagcccat tactgttgga gctacaggga gagaaacagg aggagactgc      300
aagagatcat ttgggaaggc cgtgggcacg ctctttactc catgtgtggg acattcattg      360
cggaataaca tcggaggaga agtttcccag agct atg ggg act tcc cat ccg gcg      415
                                     Met Gly Thr Ser His Pro Ala
                                     1               5 ttc ctg gtc tta ggc tgt ctt ctc aca ggg ctg agc cta atc ctc tgc        463
Phe Leu Val Leu Gly Cys Leu Leu Thr Gly Leu Ser Leu Ile Leu Cys
        10                  15                  20 cag ctt tca tta ccc tct atc ctt cca aat gaa aat gaa aag gtt gtg        511
Gln Leu Ser Leu Pro Ser Ile Leu Pro Asn Glu Asn Glu Lys Val Val
 25                  30                  35 cag ctg aat tca tcc ttt tct ctg aga tgc ttt ggg gag agt gaa gtg        559
Gln Leu Asn Ser Ser Phe Ser Leu Arg Cys Phe Gly Glu Ser Glu Val
 40                  45                  50                  55 agc tgg cag tac ccc atg tct gaa gaa gag agc tcc gat gtg gaa atc        607
Ser Trp Gln Tyr Pro Met Ser Glu Glu Glu Ser Ser Asp Val Glu Ile
                 60                  65                  70 aga aat gaa gaa aac aac agc ggc ctt ttt gtg acg gtc ttg gaa gtg        655
Arg Asn Glu Glu Asn Asn Ser Gly Leu Phe Val Thr Val Leu Glu Val
             75                  80                  85 agc agt gcc tcg gcg gcc cac aca ggg ttg tac act tgc tat tac aac        703
Ser Ser Ala Ser Ala Ala His Thr Gly Leu Tyr Thr Cys Tyr Tyr Asn
         90                  95                 100 cac act cag aca gaa gag aat gag ctt gaa ggc agg cac att tac atc        751
His Thr Gln Thr Glu Glu Asn Glu Leu Glu Gly Arg His Ile Tyr Ile
     105                 110                 115 tat gtg cca gac cca gat gta gcc ttt gta cct cta gga atg acg gat        799
Tyr Val Pro Asp Pro Asp Val Ala Phe Val Pro Leu Gly Met Thr Asp
120                 125                 130                 135 tat tta gtc atc gtg gag gat gat gat tct gcc att ata cct tgt cgc        847
Tyr Leu Val Ile Val Glu Asp Asp Asp Ser Ala Ile Ile Pro Cys Arg
                140                 145                 150 aca act gat ccc gag act cct gta acc tta cac aac agt gag ggg gtg        895
Thr Thr Asp Pro Glu Thr Pro Val Thr Leu His Asn Ser Glu Gly Val
            155                 160                 165 gta cct gcc tcc tac gac agc aga cag ggc ttt aat ggg acc ttc act        943
Val Pro Ala Ser Tyr Asp Ser Arg Gln Gly Phe Asn Gly Thr Phe Thr
        170                 175                 180 gta ggg ccc tat atc tgt gag gcc acc gtc aaa gga aag aag ttc cag        991
Val Gly Pro Tyr Ile Cys Glu Ala Thr Val Lys Gly Lys Lys Phe Gln
185                 190                 195 acc atc cca ttt aat gtt tat gct tta aaa gca aca tca gag ctg gat       1039
Thr Ile Pro Phe Asn Val Tyr Ala Leu Lys Ala Thr Ser Glu Leu Asp
200                 205                 210                 215 cta gaa atg gaa gct ctt aaa acc gtg tat aag tca ggg gaa acg att       1087
Leu Glu Met Glu Ala Leu Lys Thr Val Tyr Lys Ser Gly Glu Thr Ile
                220                 225                 230 gtg gtc acc tgt gct gtt ttt aac aat gag gtg gtt gac ctt caa tgg       1135
Val Val Thr Cys Ala Val Phe Asn Asn Glu Val Val Asp Leu Gln Trp
            235                 240                 245 act tac cct gga gaa gtg aaa ggc aaa ggc atc aca atg ctg gaa gaa       1183
Thr Tyr Pro Gly Glu Val Lys Gly Lys Gly Ile Thr Met Leu Glu Glu
        250                 255                 260 atc aaa gtc cca tcc atc aaa ttg gtg tac act ttg acg gtc ccc gag       1231
Ile Lys Val Pro Ser Ile Lys Leu Val Tyr Thr Leu Thr Val Pro Glu
265                 270                 275 gcc acg gtg aaa gac agt gga gat tac gaa tgt gct gcc cgc cag gct       1279
Ala Thr Val Lys Asp Ser Gly Asp Tyr Glu Cys Ala Ala Arg Gln Ala
```

```
                280                 285                 290                 295
acc agg gag gtc aaa gaa atg aag aaa gtc act att tct gtc cat gag         1327
Thr Arg Glu Val Lys Glu Met Lys Lys Val Thr Ile Ser Val His Glu
                    300                 305                 310 aaa ggt ttc att gaa atc aaa ccc acc ttc agc cag ttg gaa gct gtc         1375
Lys Gly Phe Ile Glu Ile Lys Pro Thr Phe Ser Gln Leu Glu Ala Val
            315                 320                 325 aac ctg cat gaa gtc aaa cat ttt gtt gta gag gtg cgg gcc tac cca         1423
Asn Leu His Glu Val Lys His Phe Val Val Glu Val Arg Ala Tyr Pro
        330                 335                 340 cct ccc agg ata tcc tgg ctg aaa aac aat ctg act ctg att gaa aat         1471
Pro Pro Arg Ile Ser Trp Leu Lys Asn Asn Leu Thr Leu Ile Glu Asn
    345                 350                 355 ctc act gag atc acc act gat gtg gaa aag att cag gaa ata agg tat         1519
Leu Thr Glu Ile Thr Thr Asp Val Glu Lys Ile Gln Glu Ile Arg Tyr
360                 365                 370                 375 cga agc aaa tta aag ctg atc cgt gct aag gaa gaa gac agt ggc cat         1567
Arg Ser Lys Leu Lys Leu Ile Arg Ala Lys Glu Glu Asp Ser Gly His
                380                 385                 390 tat act att gta gct caa aat gaa gat gct gtg aag agc tat act ttt         1615
Tyr Thr Ile Val Ala Gln Asn Glu Asp Ala Val Lys Ser Tyr Thr Phe
            395                 400                 405 gaa ctg tta act caa gtt cct tca tcc att ctg gac ttg gtc gat gat         1663
Glu Leu Leu Thr Gln Val Pro Ser Ser Ile Leu Asp Leu Val Asp Asp
        410                 415                 420 cac cat ggc tca act ggg gga cag acg gtg agg tgc aca gct gaa ggc         1711
His His Gly Ser Thr Gly Gly Gln Thr Val Arg Cys Thr Ala Glu Gly
    425                 430                 435 acg ccg ctt cct gat att gag tgg atg ata tgc aaa gat att aag aaa         1759
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac         1807
Cys Asn Asn Glu Thr Ser Trp Thr Ile Leu Ala Asn Asn Val Ser Asn
                460                 465                 470 atc atc acg gag atc cac tcc cga gac agg agt acc gtg gag ggc cgt         1855
Ile Ile Thr Glu Ile His Ser Arg Asp Arg Ser Thr Val Glu Gly Arg
            475                 480                 485 gtg act ttc gcc aaa gtg gag gag acc atc gcc gtg cga tgc ctg gct         1903
Val Thr Phe Ala Lys Val Glu Glu Thr Ile Ala Val Arg Cys Leu Ala
        490                 495                 500 aag aat ctc ctt gga gct gag aac cga gag ctg aag ctg gtg gct ccc         1951
Lys Asn Leu Leu Gly Ala Glu Asn Arg Glu Leu Lys Leu Val Ala Pro
    505                 510                 515 acc ctg cgt tct gaa ctc acg gtg gct gct gca gtc ctg gtg ctg ttg         1999
Thr Leu Arg Ser Glu Leu Thr Val Ala Ala Ala Val Leu Val Leu Leu
520                 525                 530                 535 gtg att gtg atc atc tca ctt att gtc ctg gtt gtc att tgg aaa cag         2047
Val Ile Val Ile Ile Ser Leu Ile Val Leu Val Val Ile Trp Lys Gln
                540                 545                 550 aaa ccg agg tat gaa att cgc tgg agg gtc att gaa tca atc agc ccg         2095
Lys Pro Arg Tyr Glu Ile Arg Trp Arg Val Ile Glu Ser Ile Ser Pro
            555                 560                 565 gat gga cat gaa tat att tat gtg gac ccg atg cag ctg cct tat gac         2143
Asp Gly His Glu Tyr Ile Tyr Val Asp Pro Met Gln Leu Pro Tyr Asp
        570                 575                 580 tca aga tgg gag ttt cca aga gat gga cta gtg ctt ggt cgg gtc ttg         2191
Ser Arg Trp Glu Phe Pro Arg Asp Gly Leu Val Leu Gly Arg Val Leu
    585                 590                 595 ggg tct gga gcg ttt ggg aag gtg gtt gaa gga aca gcc tat gga tta         2239
```

```
                                                            -continued

Gly Ser Gly Ala Phe Gly Lys Val Val Glu Gly Thr Ala Tyr Gly Leu
600             605                 610                 615 agc cgg tcc caa cct gtc atg aaa gtt gca gtg aag atg cta aaa ccc        2287
Ser Arg Ser Gln Pro Val Met Lys Val Ala Val Lys Met Leu Lys Pro
                620                 625                 630 acg gcc aga tcc agt gaa aaa caa gct ctc atg tct gaa ctg aag ata        2335
Thr Ala Arg Ser Ser Glu Lys Gln Ala Leu Met Ser Glu Leu Lys Ile
            635                 640                 645 atg act cac ctg ggg cca cat ttg aac att gta aac ttg ctg gga gcc        2383
Met Thr His Leu Gly Pro His Leu Asn Ile Val Asn Leu Leu Gly Ala
        650                 655                 660 tgc acc aag tca ggc ccc att tac atc atc aca gag tat tgc ttc tat        2431
Cys Thr Lys Ser Gly Pro Ile Tyr Ile Ile Thr Glu Tyr Cys Phe Tyr
    665                 670                 675 gga gat ttg gtc aac tat ttg cat aag aat agg gat agc ttc ctg agc        2479
Gly Asp Leu Val Asn Tyr Leu His Lys Asn Arg Asp Ser Phe Leu Ser
680                 685                 690                 695 cac cac cca gag aag cca aag aaa gag ctg gat atc ttt gga ttg aac        2527
His His Pro Glu Lys Pro Lys Lys Glu Leu Asp Ile Phe Gly Leu Asn
                700                 705                 710 cct gct gat gaa agc aca cgg agc tat gtt att tta tct ttt gaa aac        2575
Pro Ala Asp Glu Ser Thr Arg Ser Tyr Val Ile Leu Ser Phe Glu Asn
            715                 720                 725 aat ggt gac tac atg gac atg aag cag gct gat act aca cag tat gtc        2623
Asn Gly Asp Tyr Met Asp Met Lys Gln Ala Asp Thr Thr Gln Tyr Val
        730                 735                 740 ccc atg cta gaa agg aaa gag gtt tct aaa tat tcc gac atc cag aga        2671
Pro Met Leu Glu Arg Lys Glu Val Ser Lys Tyr Ser Asp Ile Gln Arg
    745                 750                 755 tca ctc tat gat cgt cca gcc tca tat aag aag aaa tct atg tta gac        2719
Ser Leu Tyr Asp Arg Pro Ala Ser Tyr Lys Lys Lys Ser Met Leu Asp
760                 765                 770                 775 tca gaa gtc aaa aac ctc ctt tca gat gat aac tca gaa ggc ctt act        2767
Ser Glu Val Lys Asn Leu Leu Ser Asp Asp Asn Ser Glu Gly Leu Thr
                780                 785                 790 tta ttg gat ttg ttg agc ttc acc tat caa gtt gcc cga gga atg gag        2815
Leu Leu Asp Leu Leu Ser Phe Thr Tyr Gln Val Ala Arg Gly Met Glu
            795                 800                 805 ttt ttg gct tca aaa aat tgt gtc cac cgt gat ctg gct gct cgc aac        2863
Phe Leu Ala Ser Lys Asn Cys Val His Arg Asp Leu Ala Ala Arg Asn
        810                 815                 820 gtc ctc ctg gca caa gga aaa att gtg aag atc tgt gac ttt ggc ctg        2911
Val Leu Leu Ala Gln Gly Lys Ile Val Lys Ile Cys Asp Phe Gly Leu
    825                 830                 835 gcc aaa atc atc atg cat gat tcg aac tat gtg tcg aaa ggc agt acc        2959
Ala Lys Ile Ile Met His Asp Ser Asn Tyr Val Ser Lys Gly Ser Thr
840                 845                 850                 855 ttt ctg ccc gtg aag tgg atg gct cct gag agc atc ttt gac aac ctc        3007
Phe Leu Pro Val Lys Trp Met Ala Pro Glu Ser Ile Phe Asp Asn Leu
                860                 865                 870 tac acc aca ctg agt gat gtc tgg tct tat ggc att ctg ctc tgg gag        3055
Tyr Thr Thr Leu Ser Asp Val Trp Ser Tyr Gly Ile Leu Leu Trp Glu
            875                 880                 885 atc ttt tcc ctt ggt ggc acc cct tac ccc ggc atg atg gtg gat tct        3103
Ile Phe Ser Leu Gly Gly Thr Pro Tyr Pro Gly Met Met Val Asp Ser
        890                 895                 900 act ttc tac aat aag atc aag agt ggg tac cgg atg gcc aag cct gac        3151
Thr Phe Tyr Asn Lys Ile Lys Ser Gly Tyr Arg Met Ala Lys Pro Asp
    905                 910                 915
```

-continued

| | | |
|---|---|---|
| cac gct acc agt gaa gtc tac gag atc atg gtg aaa tgc tgg aac agt<br>His Ala Thr Ser Glu Val Tyr Glu Ile Met Val Lys Cys Trp Asn Ser<br>920                    925                    930                    935 | 3199 |
| gag ccg gag aag aga ccc tcc ttt tac cac ctg agt gag att gtg gag<br>Glu Pro Glu Lys Arg Pro Ser Phe Tyr His Leu Ser Glu Ile Val Glu<br>                    940                    945                    950 | 3247 |
| aat ctg ctg cct gga caa tat aaa aag agt tat gaa aaa att cac ctg<br>Asn Leu Leu Pro Gly Gln Tyr Lys Lys Ser Tyr Glu Lys Ile His Leu<br>955                    960                    965 | 3295 |
| gac ttc ctg aag agt gac cat cct gct gtg gca cgc atg cgt gtg gac<br>Asp Phe Leu Lys Ser Asp His Pro Ala Val Ala Arg Met Arg Val Asp<br>          970                    975                    980 | 3343 |
| tca gac aat gca tac att ggt gtc acc tac aaa aac gag gaa gac aag<br>Ser Asp Asn Ala Tyr Ile Gly Val Thr Tyr Lys Asn Glu Glu Asp Lys<br>985                    990                    995 | 3391 |
| ctg aag gac tgg gag ggt ggt ctg gat gag cag aga ctg agc gct<br>Leu Lys Asp Trp Glu Gly Gly Leu Asp Glu Gln Arg Leu Ser Ala<br>1000                   1005                   1010 | 3436 |
| gac agt ggc tac atc att cct ctg cct gac att gac cct gtc cct<br>Asp Ser Gly Tyr Ile Ile Pro Leu Pro Asp Ile Asp Pro Val Pro<br>1015                   1020                   1025 | 3481 |
| gag gag gag gac ctg ggc aag agg aac aga cac agc tcg cag acc<br>Glu Glu Glu Asp Leu Gly Lys Arg Asn Arg His Ser Ser Gln Thr<br>1030                   1035                   1040 | 3526 |
| tct gaa gag agt gcc att gag acg ggt tcc agc agt tcc acc ttc<br>Ser Glu Glu Ser Ala Ile Glu Thr Gly Ser Ser Ser Thr Phe<br>1045                   1050                   1055 | 3571 |
| atc aag aga gag gac gag acc att gaa gac atc gac atg atg gac<br>Ile Lys Arg Glu Asp Glu Thr Ile Glu Asp Ile Asp Met Met Asp<br>1060                   1065                   1070 | 3616 |
| gac atc ggc ata gac tct tca gac ctg gtg gaa gac agc ttc ctg<br>Asp Ile Gly Ile Asp Ser Ser Asp Leu Val Glu Asp Ser Phe Leu<br>1075                   1080                   1085 | 3661 |
| taa ctggcggatt cgaggggttc cttccacttc tggggccacc tctggatccc | 3714 |
| gttcagaaaa ccactttatt gcaatgcgga ggttgagagg aggacttggt tgatgtttaa | 3774 |
| agagaagttc ccagccaagg gcctcgggga gcgttctaaa tatgaatgaa tgggatattt | 3834 |
| tgaaatgaac tttgtcagtg ttgcctctcg caatgcctca gtagcatctc agtggtgtgt | 3894 |
| gaagtttgga gatagatgga taagggaata ataggccaca gaaggtgaac tttgtgcttc | 3954 |
| aaggacattg gtgagagtcc aacagacaca atttatactg cgacagaact tcagcattgt | 4014 |
| aattatgtaa ataactctaa ccaaggctgt gtttagattg tattaactat cttctttgga | 4074 |
| cttctgaaga gaccactcaa tccatccatg tacttccctc ttgaaacctg atgtcagctg | 4134 |
| ctgttgaact ttttaaagaa gtgcatgaaa aaccatttttt gaaccttaaa aggtactggt | 4194 |
| actatagcat tttgctatct tttttagtgt taagagataa agaataataa ttaaccaacc | 4254 |
| ttgtttaata gatttgggtc atttagaagc ctgacaactc attttcatat tgtaatctat | 4314 |
| gtttataata ctactactgt tatcagtaat gctaaatgtg taataatgta acatgatttc | 4374 |
| cctccagaga aagcacaatt taaaacaatc cttactaagt aggtgatgag tttgacagtt | 4434 |
| tttgacattt atattaaata acatgtttct ctataaagta tggtaatagc tttagtgaat | 4494 |
| taaatttagt tgagcataga gaacaaagta aaagtagtgt tgtccaggaa gtcagaattt | 4554 |
| ttaactgtac tgaataggtt ccccaatcca tcgtattaaa aaacaattaa ctgccctctg | 4614 |
| aaataatggg attagaaaca aacaaaactc ttaagtccta aaagttctca atgtagaggc | 4674 |
| ataaacctgt gctgaacata acttctcatg tatattaccc aatggaaaat ataatgatca | 4734 |

-continued

```
gcaaaaagac tggatttgca gaagtttttt ttttttttct tcatgcctga tgaaagcttt    4794
ggcaacccca atatatgtat tttttgaatc tatgaacctg aaaagggtca gaaggatgcc    4854
cagacatcag cctccttctt tcacccctta ccccaaagag aaagagtttg aaactcgaga    4914
ccataaagat attctttagt ggaggctgga tgtgcattag cctggatcct cagttctcaa    4974
atgtgtgtgg cagccaggat gactagatcc tgggtttcca tccttgagat tctgaagtat    5034
gaagtctgag ggaaaccaga gtctgtattt ttctaaactc cctggctgtt ctgatcggcc    5094
agttttcgga acactgact taggtttcag gaagttgcca tgggaaacaa ataatttgaa    5154
ctttggaaca gggttggaat tcaaccacgc aggaagccta ctatttaaat ccttggcttc    5214
aggttagtga catttaatgc catctagcta gcaattgcga ccttaattta actttccagt    5274
cttagctgag gctgagaaag ctaaagtttg gttttgacag gttttccaaa agtaaagatg    5334
ctacttccca ctgtatgggg gagattgaac tttccccgtc tcccgtcttc tgcctcccac    5394
tccatacccc gccaaggaaa ggcatgtaca aaaattatgc aattcagtgt tccaagtctc    5454
tgtgtaacca gctcagtgtt ttggtggaaa aaacatttta agttttactg ataatttgag    5514
gttagatggg aggatgaatt gtcacatcta tccacactgt caaacaggtt ggtgtgggtt    5574
cattggcatt ctttgcaata ctgcttaatt gctgatacca tatgaatgaa acatgggctg    5634
tgattactgc aatcactgtg ctatcggcag atgatgcttt ggaagatgca gaagcaataa    5694
taaagtactt gactacctac tggtgtaatc tcaatgcaag ccccaacttt cttatccaac    5754
tttttcatag taagtgcgaa gactgagcca gattggccaa ttaaaaacga aaacctgact    5814
aggttctgta gagccaatta gacttgaaat acgtttgtgt ttctagaatc acagctcaag    5874
cattctgttt atcgctcact ctcccttgta cagccttatt ttgttggtgc tttgcatttt    5934
gatattgctg tgagccttgc atgacatcat gaggccggat gaaacttctc agtccagcag    5994
tttccagtcc taacaaatgc tcccacctga atttgtatat gactgcattt gtgggtgtgt    6054
gtgtgttttc agcaaattcc agatttgttt ccttttggcc tcctgcaaag tctccagaag    6114
aaaatttgcc aatctttcct actttctatt tttatgatga caatcaaagc cggcctgaga    6174
aacactattt gtgacttttt aaacgattag tgatgtcctt aaaatgtggt ctgccaatct    6234
gtacaaaatg gtcctatttt tgtgaagagg gacataagat aaaatgatgt tatacatcaa    6294
tatgtatata tgtatttcta tatagacttg gagaatactg ccaaaacatt tatgacaagc    6354
tgtatcactg ccttcgttta tattttttta actgtgataa tccccacagg cacattaact    6414
gttgcacttt tgaatgtcca aaatttatat tttagaaata ataaaagaa agatacttac     6474
atgttcccaa aacaatggtg tggtgaatgt gtgagaaaaa ctaacttgat agggtctacc    6534
aatacaaaat gtattacgaa tgcccctgtt catgtttttg tttaaaacg tgtaaatgaa     6594
gatctttata tttcaataaa tgatatataa tttaaagtt                           6633
```

<210> SEQ ID NO 25
<211> LENGTH: 1089
<212> TYPE: PRT
<213> ORGANISM: Homo sapiens

<400> SEQUENCE: 25

```
Met Gly Thr Ser His Pro Ala Phe Leu Val Leu Gly Cys Leu Leu Thr
 1               5                   10                  15
Gly Leu Ser Leu Ile Leu Cys Gln Leu Ser Leu Pro Ser Ile Leu Pro
            20                  25                  30
```

-continued

```
Asn Glu Asn Glu Lys Val Val Gln Leu Asn Ser Ser Phe Ser Leu Arg
        35                  40                  45
Cys Phe Gly Glu Ser Glu Val Ser Trp Gln Tyr Pro Met Ser Glu Glu
 50                  55                  60
Glu Ser Ser Asp Val Glu Ile Arg Asn Glu Glu Asn Asn Ser Gly Leu
 65                  70                  75                  80
Phe Val Thr Val Leu Glu Val Ser Ser Ala Ser Ala Ala His Thr Gly
                 85                  90                  95
Leu Tyr Thr Cys Tyr Tyr Asn His Thr Gln Thr Glu Glu Asn Glu Leu
                100                 105                 110
Glu Gly Arg His Ile Tyr Ile Tyr Val Pro Asp Pro Asp Val Ala Phe
            115                 120                 125
Val Pro Leu Gly Met Thr Asp Tyr Leu Val Ile Val Glu Asp Asp Asp
130                 135                 140
Ser Ala Ile Ile Pro Cys Arg Thr Thr Asp Pro Glu Thr Pro Val Thr
145                 150                 155                 160
Leu His Asn Ser Glu Gly Val Val Pro Ala Ser Tyr Asp Ser Arg Gln
                165                 170                 175
Gly Phe Asn Gly Thr Phe Thr Val Gly Pro Tyr Ile Cys Glu Ala Thr
            180                 185                 190
Val Lys Gly Lys Lys Phe Gln Thr Ile Pro Phe Asn Val Tyr Ala Leu
        195                 200                 205
Lys Ala Thr Ser Glu Leu Asp Leu Glu Met Glu Ala Leu Lys Thr Val
210                 215                 220
Tyr Lys Ser Gly Glu Thr Ile Val Val Thr Cys Ala Val Phe Asn Asn
225                 230                 235                 240
Glu Val Val Asp Leu Gln Trp Thr Tyr Pro Gly Glu Val Lys Gly Lys
                245                 250                 255
Gly Ile Thr Met Leu Glu Glu Ile Lys Val Pro Ser Ile Lys Leu Val
            260                 265                 270
Tyr Thr Leu Thr Val Pro Glu Ala Thr Val Lys Asp Ser Gly Asp Tyr
        275                 280                 285
Glu Cys Ala Ala Arg Gln Ala Thr Arg Glu Val Lys Glu Met Lys Lys
290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
                325                 330                 335
Val Glu Val Arg Ala Tyr Pro Pro Arg Ile Ser Trp Leu Lys Asn
            340                 345                 350
Asn Leu Thr Leu Ile Glu Asn Leu Thr Glu Ile Thr Thr Asp Val Glu
        355                 360                 365
Lys Ile Gln Glu Ile Arg Tyr Arg Ser Lys Leu Lys Leu Ile Arg Ala
370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp Asp His His Gly Ser Thr Gly Gly Gln Thr
            420                 425                 430
Val Arg Cys Thr Ala Glu Gly Thr Pro Leu Pro Asp Ile Glu Trp Met
        435                 440                 445
Ile Cys Lys Asp Ile Lys Lys Cys Asn Asn Glu Thr Ser Trp Thr Ile
```

-continued

```
            450                 455                 460
Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Thr
                485                 490                 495

Ile Ala Val Arg Cys Leu Ala Lys Asn Leu Leu Gly Ala Glu Asn Arg
                500                 505                 510

Glu Leu Lys Leu Val Ala Pro Thr Leu Arg Ser Glu Leu Thr Val Ala
                515                 520                 525

Ala Ala Val Leu Val Leu Leu Val Ile Val Ile Ser Leu Ile Val
530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
                595                 600                 605

Glu Gly Thr Ala Tyr Gly Leu Ser Arg Ser Gln Pro Val Met Lys Val
                610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
                675                 680                 685

Asn Arg Asp Ser Phe Leu Ser His His Pro Glu Lys Pro Lys Lys Glu
                690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
                740                 745                 750

Lys Tyr Ser Asp Ile Gln Arg Ser Leu Tyr Asp Arg Pro Ala Ser Tyr
                755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
                820                 825                 830

Lys Ile Cys Asp Phe Gly Leu Ala Lys Ile Ile Met His Asp Ser Asn
                835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880
```

-continued

```
Tyr Gly Ile Leu Leu Trp Glu Ile Phe Ser Leu Gly Gly Thr Pro Tyr
                885                 890                 895
Pro Gly Met Met Val Asp Ser Thr Phe Tyr Asn Lys Ile Lys Ser Gly
            900                 905                 910
Tyr Arg Met Ala Lys Pro Asp His Ala Thr Ser Glu Val Tyr Glu Ile
        915                 920                 925
Met Val Lys Cys Trp Asn Ser Glu Pro Glu Lys Arg Pro Ser Phe Tyr
    930                 935                 940
His Leu Ser Glu Ile Val Glu Asn Leu Leu Pro Gly Gln Tyr Lys Lys
945                 950                 955                 960
Ser Tyr Glu Lys Ile His Leu Asp Phe Leu Lys Ser Asp His Pro Ala
                965                 970                 975
Val Ala Arg Met Arg Val Asp Ser Asp Asn Ala Tyr Ile Gly Val Thr
            980                 985                 990
Tyr Lys Asn Glu Glu Asp Lys Leu  Lys Asp Trp Glu Gly  Gly Leu Asp
        995                 1000                1005
Glu Gln  Arg Leu Ser Ala Asp  Ser Gly Tyr Ile Ile  Pro Leu Pro
    1010                1015                1020
Asp Ile  Asp Pro Val Pro Glu  Glu Asp Leu Gly  Lys Arg Asn
    1025                1030                1035
Arg His  Ser Ser Gln Thr Ser  Glu Glu Ser Ala Ile  Glu Thr Gly
    1040                1045                1050
Ser Ser  Ser Ser Thr Phe Ile  Lys Arg Glu Asp Glu  Thr Ile Glu
    1055                1060                1065
Asp Ile  Asp Met Met Asp Asp  Ile Gly Ile Asp Ser  Ser Asp Leu
    1070                1075                1080
Val Glu  Asp Ser Phe Leu
    1085

<210> SEQ ID NO 26
<211> LENGTH: 6633
<212> TYPE: DNA
<213> ORGANISM: Homo sapiens
<220> FEATURE:
<221> NAME/KEY: CDS
<222> LOCATION: (395)..(3664)
<223> OTHER INFORMATION: Insertion of the sequence "GAGAGG" in PDGFRA
      insertion ER561-562
<220> FEATURE:
<221> NAME/KEY: misc_feature
<222> LOCATION: (2072)..(2086)
<223> OTHER INFORMATION: Any N may equal either no nucleotide (i.e.,
      a deletion) or any nucleotide (i.e., a, t, g, or c)
<220> FEATURE:
<221> NAME/KEY: misc_feature
<222> LOCATION: (2074)..(2075)
<223> OTHER INFORMATION: Insertion of the sequence "GAGAGG" in PDGFRA
      insertion ER561-562
<220> FEATURE:
<221> NAME/KEY: misc_feature
<222> LOCATION: (2090)..(2107)
<223> OTHER INFORMATION: Any N may equal either no nucleotide (i.e., a
      deletion) or any nucleotide (i.e., a, t, g, or c)
<220> FEATURE:
<221> NAME/KEY: misc_feature
<222> LOCATION: (2916)..(2937)
<223> OTHER INFORMATION: Any N may equal either no nucleotide (i.e., a
      deletion) or any nucleotide (i.e., a, t, g, or c)

<400> SEQUENCE: 26
ttctccccgc cccccagttg ttgtcgaagt ctgggggttg ggactggacc ccctgattgc      60
gtaagagcaa aaagcgaagg cgcaatctgg acactgggag attcggagcg cagggagttt    120
```

-continued

```
gagagaaact tttattttga agagaccaag gttgagggg ggcttatttc ctgacagcta      180
tttacttaga gcaaatgatt agttttagaa ggatggacta taacattgaa tcaattacaa    240
aacgcggttt ttgagcccat tactgttgga gctacaggga gagaaacagg aggagactgc    300
aagagatcat ttgggaaggc cgtgggcacg ctctttactc catgtgtggg acattcattg    360
cggaataaca tcggaggaga agtttcccag agct atg ggg act tcc cat ccg gcg    415
                                      Met Gly Thr Ser His Pro Ala
                                       1               5 ttc ctg gtc tta ggc tgt ctt ctc aca ggg ctg agc cta atc ctc tgc      463
Phe Leu Val Leu Gly Cys Leu Leu Thr Gly Leu Ser Leu Ile Leu Cys
         10                  15                  20 cag ctt tca tta ccc tct atc ctt cca aat gaa aat gaa aag gtt gtg      511
Gln Leu Ser Leu Pro Ser Ile Leu Pro Asn Glu Asn Glu Lys Val Val
 25                  30                  35 cag ctg aat tca tcc ttt tct ctg aga tgc ttt ggg gag agt gaa gtg      559
Gln Leu Asn Ser Ser Phe Ser Leu Arg Cys Phe Gly Glu Ser Glu Val
 40                  45                  50                  55 agc tgg cag tac ccc atg tct gaa gaa gag agc tcc gat gtg gaa atc      607
Ser Trp Gln Tyr Pro Met Ser Glu Glu Glu Ser Ser Asp Val Glu Ile
                 60                  65                  70 aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
         75                  80                  85 agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
         90                  95                 100 cac act cag aca gaa gag aat gag ctt gaa ggc agg cac att tac atc      751
His Thr Gln Thr Glu Glu Asn Glu Leu Glu Gly Arg His Ile Tyr Ile
105                 110                 115 tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135 tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150 aca act gat ccc gag act cct gta acc tta cac aac agt gag ggg gtg      895
Thr Thr Asp Pro Glu Thr Pro Val Thr Leu His Asn Ser Glu Gly Val
            155                 160                 165 gta cct gcc tcc tac gac agc aga cag ggc ttt aat ggg acc ttc act      943
Val Pro Ala Ser Tyr Asp Ser Arg Gln Gly Phe Asn Gly Thr Phe Thr
            170                 175                 180 gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
            185                 190                 195 acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215 cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230 gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245 act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
            250                 255                 260 atc aaa gtc cca tcc atc aaa ttg gtg tac act ttg acg gtc ccc gag     1231
```

```
Ile Lys Val Pro Ser Ile Lys Leu Val Tyr Thr Leu Thr Val Pro Glu
    265                 270                 275 gcc acg gtg aaa gac agt gga gat tac gaa tgt gct gcc cgc cag gct      1279
Ala Thr Val Lys Asp Ser Gly Asp Tyr Glu Cys Ala Ala Arg Gln Ala
280                 285                 290                 295 acc agg gag gtc aaa gaa atg aag aaa gtc act att tct gtc cat gag      1327
Thr Arg Glu Val Lys Glu Met Lys Lys Val Thr Ile Ser Val His Glu
                    300                 305                 310 aaa ggt ttc att gaa atc aaa ccc acc ttc agc cag ttg gaa gct gtc      1375
Lys Gly Phe Ile Glu Ile Lys Pro Thr Phe Ser Gln Leu Glu Ala Val
                315                 320                 325 aac ctg cat gaa gtc aaa cat ttt gtt gta gag gtg cgg gcc tac cca      1423
Asn Leu His Glu Val Lys His Phe Val Val Glu Val Arg Ala Tyr Pro
            330                 335                 340 cct ccc agg ata tcc tgg ctg aaa aac aat ctg act ctg att gaa aat      1471
Pro Pro Arg Ile Ser Trp Leu Lys Asn Asn Leu Thr Leu Ile Glu Asn
        345                 350                 355 ctc act gag atc acc act gat gtg gaa aag att cag gaa ata agg tat      1519
Leu Thr Glu Ile Thr Thr Asp Val Glu Lys Ile Gln Glu Ile Arg Tyr
360                 365                 370                 375 cga agc aaa tta aag ctg atc cgt gct aag gaa gaa gac agt ggc cat      1567
Arg Ser Lys Leu Lys Leu Ile Arg Ala Lys Glu Glu Asp Ser Gly His
                380                 385                 390 tat act att gta gct caa aat gaa gat gct gtg aag agc tat act ttt      1615
Tyr Thr Ile Val Ala Gln Asn Glu Asp Ala Val Lys Ser Tyr Thr Phe
                395                 400                 405 gaa ctg tta act caa gtt cct tca tcc att ctg gac ttg gtc gat gat      1663
Glu Leu Leu Thr Gln Val Pro Ser Ser Ile Leu Asp Leu Val Asp Asp
            410                 415                 420 cac cat ggc tca act ggg gga cag acg gtg agg tgc aca gct gaa ggc      1711
His His Gly Ser Thr Gly Gly Gln Thr Val Arg Cys Thr Ala Glu Gly
        425                 430                 435 acg ccg ctt cct gat att gag tgg atg ata tgc aaa gat att aag aaa      1759
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac      1807
Cys Asn Asn Glu Thr Ser Trp Thr Ile Leu Ala Asn Asn Val Ser Asn
                460                 465                 470 atc atc acg gag atc cac tcc cga gac agg agt acc gtg gag ggc cgt      1855
Ile Ile Thr Glu Ile His Ser Arg Asp Arg Ser Thr Val Glu Gly Arg
                475                 480                 485 gtg act ttc gcc aaa gtg gag gag acc atc gcc gtg cga tgc ctg gct      1903
Val Thr Phe Ala Lys Val Glu Glu Thr Ile Ala Val Arg Cys Leu Ala
            490                 495                 500 aag aat ctc ctt gga gct gag aac cga gag ctg aag ctg gtg gct ccc      1951
Lys Asn Leu Leu Gly Ala Glu Asn Arg Glu Leu Lys Leu Val Ala Pro
        505                 510                 515 acc ctg cgt tct gaa ctc acg gtg gct gct gca gtc ctg gtg ctg ttg      1999
Thr Leu Arg Ser Glu Leu Thr Val Ala Ala Ala Val Leu Val Leu Leu
520                 525                 530                 535 gtg att gtg atc atc tca ctt att gtc ctg gtt gtc att tgg aaa cag      2047
Val Ile Val Ile Ile Ser Leu Ile Val Leu Val Val Ile Trp Lys Gln
                540                 545                 550 aaa ccg agg tat gaa att cgc tgg nnn nnn nnn nnn atc nnn nnn          2095
Lys Pro Arg Tyr Glu Ile Arg Trp Xaa Xaa Xaa Xaa Ile Xaa Xaa
                555                 560                 565 nnn nnn nnn nnn tat att tat gtg gac ccg atg cag ctg cct tat gac      2143
Xaa Xaa Xaa Xaa Tyr Ile Tyr Val Asp Pro Met Gln Leu Pro Tyr Asp
            570                 575                 580
```

-continued

| | | |
|---|---|---|
| tca aga tgg gag ttt cca aga gat gga cta gtg ctt ggt cgg gtc ttg<br>Ser Arg Trp Glu Phe Pro Arg Asp Gly Leu Val Leu Gly Arg Val Leu<br>585                     590                    595 | 2191 |
| ggg tct gga gcg ttt ggg aag gtg gtt gaa gga aca gcc tat gga tta<br>Gly Ser Gly Ala Phe Gly Lys Val Val Glu Gly Thr Ala Tyr Gly Leu<br>600                     605                    610                   615 | 2239 |
| agc cgg tcc caa cct gtc atg aaa gtt gca gtg aag atg cta aaa ccc<br>Ser Arg Ser Gln Pro Val Met Lys Val Ala Val Lys Met Leu Lys Pro<br>              620                    625                    630 | 2287 |
| acg gcc aga tcc agt gaa aaa caa gct ctc atg tct gaa ctg aag ata<br>Thr Ala Arg Ser Ser Glu Lys Gln Ala Leu Met Ser Glu Leu Lys Ile<br>           635                    640                   645 | 2335 |
| atg act cac ctg ggg cca cat ttg aac att gta aac ttg ctg gga gcc<br>Met Thr His Leu Gly Pro His Leu Asn Ile Val Asn Leu Leu Gly Ala<br>650                     655                    660 | 2383 |
| tgc acc aag tca ggc ccc att tac atc atc aca gag tat tgc ttc tat<br>Cys Thr Lys Ser Gly Pro Ile Tyr Ile Ile Thr Glu Tyr Cys Phe Tyr<br>665                     670                    675 | 2431 |
| gga gat ttg gtc aac tat ttg cat aag aat agg gat agc ttc ctg agc<br>Gly Asp Leu Val Asn Tyr Leu His Lys Asn Arg Asp Ser Phe Leu Ser<br>680                     685                    690                   695 | 2479 |
| cac cac cca gag aag cca aag aaa gag ctg gat atc ttt gga ttg aac<br>His His Pro Glu Lys Pro Lys Lys Glu Leu Asp Ile Phe Gly Leu Asn<br>              700                    705                   710 | 2527 |
| cct gct gat gaa agc aca cgg agc tat gtt att tta tct ttt gaa aac<br>Pro Ala Asp Glu Ser Thr Arg Ser Tyr Val Ile Leu Ser Phe Glu Asn<br>           715                    720                    725 | 2575 |
| aat ggt gac tac atg gac atg aag cag gct gat act aca cag tat gtc<br>Asn Gly Asp Tyr Met Asp Met Lys Gln Ala Asp Thr Thr Gln Tyr Val<br>              730                    735                   740 | 2623 |
| ccc atg cta gaa agg aaa gag gtt tct aaa tat tcc gac atc cag aga<br>Pro Met Leu Glu Arg Lys Glu Val Ser Lys Tyr Ser Asp Ile Gln Arg<br>745                     750                    755 | 2671 |
| tca ctc tat gat cgt cca gcc tca tat aag aag aaa tct atg tta gac<br>Ser Leu Tyr Asp Arg Pro Ala Ser Tyr Lys Lys Lys Ser Met Leu Asp<br>760                     765                    770                   775 | 2719 |
| tca gaa gtc aaa aac ctc ctt tca gat gat aac tca gaa ggc ctt act<br>Ser Glu Val Lys Asn Leu Leu Ser Asp Asp Asn Ser Glu Gly Leu Thr<br>              780                    785                   790 | 2767 |
| tta ttg gat ttg ttg agc ttc acc tat caa gtt gcc cga gga atg gag<br>Leu Leu Asp Leu Leu Ser Phe Thr Tyr Gln Val Ala Arg Gly Met Glu<br>           795                    800                   805 | 2815 |
| ttt ttg gct tca aaa aat tgt gtc cac cgt gat ctg gct gct cgc aac<br>Phe Leu Ala Ser Lys Asn Cys Val His Arg Asp Leu Ala Ala Arg Asn<br>810                     815                    820 | 2863 |
| gtc ctc ctg gca caa gga aaa att gtg aag atc tgt gac ttt ggc ctg<br>Val Leu Leu Ala Gln Gly Lys Ile Val Lys Ile Cys Asp Phe Gly Leu<br>825                     830                    835 | 2911 |
| gcc ana nnn nnn nnn nnn nnn nnc tat gtg tcg aaa ggc agt acc<br>Ala Xaa Xaa Xaa Xaa Xaa Xaa Xaa Tyr Val Ser Lys Gly Ser Thr<br>840                     845                    850                   855 | 2959 |
| ttt ctg ccc gtg aag tgg atg gct cct gag agc atc ttt gac aac ctc<br>Phe Leu Pro Val Lys Trp Met Ala Pro Glu Ser Ile Phe Asp Asn Leu<br>              860                    865                   870 | 3007 |
| tac acc aca ctg agt gat gtc tgg tct tat ggc att ctg ctc tgg gag<br>Tyr Thr Thr Leu Ser Asp Val Trp Ser Tyr Gly Ile Leu Leu Trp Glu<br>875                     880                    885 | 3055 |
| atc ttt tcc ctt ggt ggc acc cct tac ccc ggc atg atg gtg gat tct<br>Ile Phe Ser Leu Gly Gly Thr Pro Tyr Pro Gly Met Met Val Asp Ser<br>           890                    895                   900 | 3103 |

-continued

```
act ttc tac aat aag atc aag agt ggg tac cgg atg gcc aag cct gac    3151
Thr Phe Tyr Asn Lys Ile Lys Ser Gly Tyr Arg Met Ala Lys Pro Asp
        905                 910                 915 cac gct acc agt gaa gtc tac gag atc atg gtg aaa tgc tgg aac agt    3199
His Ala Thr Ser Glu Val Tyr Glu Ile Met Val Lys Cys Trp Asn Ser
920                 925                 930                 935 gag ccg gag aag aga ccc tcc ttt tac cac ctg agt gag att gtg gag    3247
Glu Pro Glu Lys Arg Pro Ser Phe Tyr His Leu Ser Glu Ile Val Glu
                940                 945                 950 aat ctg ctg cct gga caa tat aaa aag agt tat gaa aaa att cac ctg    3295
Asn Leu Leu Pro Gly Gln Tyr Lys Lys Ser Tyr Glu Lys Ile His Leu
            955                 960                 965 gac ttc ctg aag agt gac cat cct gct gtg gca cgc atg cgt gtg gac    3343
Asp Phe Leu Lys Ser Asp His Pro Ala Val Ala Arg Met Arg Val Asp
        970                 975                 980 tca gac aat gca tac att ggt gtc acc tac aaa aac gag gaa gac aag    3391
Ser Asp Asn Ala Tyr Ile Gly Val Thr Tyr Lys Asn Glu Glu Asp Lys
        985                 990                 995 ctg aag gac tgg gag ggt ggt ctg gat gag cag aga ctg agc gct        3436
Leu Lys Asp Trp Glu Gly Gly Leu Asp Glu Gln Arg Leu Ser Ala
1000                1005                1010 gac agt ggc tac atc att cct ctg cct gac att gac cct gtc cct        3481
Asp Ser Gly Tyr Ile Ile Pro Leu Pro Asp Ile Asp Pro Val Pro
1015                1020                1025 gag gag gag gac ctg ggc aag agg aac aga cac agc tcg cag acc        3526
Glu Glu Glu Asp Leu Gly Lys Arg Asn Arg His Ser Ser Gln Thr
1030                1035                1040 tct gaa gag agt gcc att gag acg ggt tcc agc agt tcc acc ttc        3571
Ser Glu Glu Ser Ala Ile Glu Thr Gly Ser Ser Ser Thr Phe
1045                1050                1055 atc aag aga gag gac gag acc att gaa gac atc gac atg atg gac        3616
Ile Lys Arg Glu Asp Glu Thr Ile Glu Asp Ile Asp Met Met Asp
1060                1065                1070 gac atc ggc ata gac tct tca gac ctg gtg gaa gac agc ttc ctg        3661
Asp Ile Gly Ile Asp Ser Ser Asp Leu Val Glu Asp Ser Phe Leu
1075                1080                1085 taa ctggcggatt cgagggggttc cttccacttc tggggccacc tctggatccc        3714
gttcagaaaa ccactttatt gcaatgcgga ggttgagagg aggacttggt tgatgtttaa  3774
agagaagttc ccagccaagg gcctcgggga gcgttctaaa tatgaatgaa tgggatattt  3834
tgaaatgaac tttgtcagtg ttgcctctcg caatgcctca gtagcatctc agtggtgtgt  3894
gaagtttgga gatagatgga taagggaata ataggccaca gaaggtgaac tttgtgcttc  3954
aaggacattg gtgagagtcc aacagacaca atttatactg cgacagaact tcagcattgt  4014
aattatgtaa ataactctaa ccaaggctgt gtttagattg tattaactat cttctttgga  4074
cttctgaaga gaccactcaa tccatccatg tacttccctc ttgaaacctg atgtcagctg  4134
ctgttgaact ttttaaagaa gtgcatgaaa aaccattttt gaaccttaaa aggtactggt  4194
actatagcat tttgctatct ttttagtgt taagagataa agaataataa ttaaccaacc   4254
ttgtttaata gatttgggtc atttagaagc ctgacaactc attttcatat tgtaatctat  4314
gtttataata ctactactgt tatcagtaat gctaaatgtg taataatgta acatgatttc  4374
cctccagaga aagcacaatt taaaacaatc cttactaagt aggtgatgag tttgacagtt  4434
tttgacattt atattaaata acatgtttct ctataaagta tggtaatagc tttagtgaat  4494
taaatttagt tgagcataga gaacaaagta aaagtagtgt tgtccaggaa gtcagaattt  4554
```

```
ttaactgtac tgaataggtt ccccaatcca tcgtattaaa aaacaattaa ctgccctctg    4614
aaataatggg attagaaaca aacaaaactc ttaagtccta aaagttctca atgtagaggc    4674
ataaacctgt gctgaacata acttctcatg tatattaccc aatggaaaat aaatgatca     4734 gcaaaaagac tggatttgca gaagtttttt tttttttct tcatgcctga tgaaagcttt    4794
ggcaacccca atatatgtat tttttgaatc tatgaacctg aaaagggtca gaaggatgcc    4854
cagacatcag cctccttctt tcaccccta ccccaaagag aaagagtttg aaactcgaga     4914
ccataaagat attctttagt ggaggctgga tgtgcattag cctggatcct cagttctcaa    4974
atgtgtgtgg cagccaggat gactagatcc tgggtttcca tccttgagat tctgaagtat    5034
gaagtctgag ggaaaccaga gtctgtattt ttctaaactc cctggctgtt ctgatcggcc    5094
agttttcgga aacactgact taggtttcag gaagttgcca tgggaaacaa ataatttgaa    5154
ctttggaaca gggttggaat tcaaccacgc aggaagccta ctatttaaat ccttggcttc    5214
aggttagtga catttaatgc catctagcta gcaattgcga ccttaattta actttccagt    5274
cttagctgag gctgagaaag ctaaagtttg gttttgacag gttttccaaa agtaaagatg    5334
ctacttccca ctgtatgggg gagattgaac tttccccgtc tcccgtcttc tgcctcccac    5394
tccatacccc gccaaggaaa ggcatgtaca aaaattatgc aattcagtgt tccaagtctc    5454
tgtgtaacca gctcagtgtt ttggtggaaa aaacatttta agttttactg ataatttgag    5514
gttagatggg aggatgaatt gtcacatcta tccacactgt caaacaggtt ggtgtgggtt    5574
cattggcatt ctttgcaata ctgcttaatt gctgatacca tatgaatgaa acatgggctg    5634
tgattactgc aatcactgtg ctatcggcag atgatgcttt ggaagatgca gaagcaataa    5694
taaagtactt gactacctac tggtgtaatc tcaatgcaag ccccaacttt cttatccaac    5754
tttttcatag taagtgcgaa gactgagcca gattggccaa ttaaaaacga aaacctgact    5814
aggttctgta gagccaatta gacttgaaat acgtttgtgt ttctagaatc acagctcaag    5874
cattctgttt atcgctcact ctcccttgta cagccttatt ttgttggtgc tttgcattt     5934 gatattgctg tgagccttgc atgacatcat gaggccggat gaaacttctc agtccagcag    5994
tttccagtcc taacaaatgc tcccacctga atttgtatat gactgcattt gtgggtgtgt    6054
gtgtgttttc agcaaattcc agatttgttt ccttttggcc tcctgcaaag tctccagaag    6114
aaaatttgcc aatctttcct actttctatt tttatgatga caatcaaagc cggcctgaga    6174
aacactattt gtgacttttt aaacgattag tgatgtcctt aaaatgtggt ctgccaatct    6234
gtacaaaatg gtcctatttt tgtgaagagg gacataagat aaaatgatgt tatacatcaa    6294
tatgtatata tgtatttcta tatagacttg gagaatactg ccaaaacatt tatgacaagc    6354
tgtatcactg ccttcgttta tatttttta actgtgataa tccccacagg cacattaact    6414
gttgcacttt tgaatgtcca aaatttatat tttagaaata ataaaagaa agatacttac     6474 atgttcccaa aacaatggtg tggtgaatgt gtgagaaaaa ctaacttgat agggtctacc    6534
aatacaaaat gtattacgaa tgcccctgtt catgttttg ttttaaaacg tgtaaatgaa     6594
gatctttata tttcaataaa tgatatataa tttaaagtt                           6633
```

<210> SEQ ID NO 27
<211> LENGTH: 1089
<212> TYPE: PRT
<213> ORGANISM: Homo sapiens
<220> FEATURE:
<221> NAME/KEY: misc_feature
<222> LOCATION: (560)..(560)
<223> OTHER INFORMATION: The 'Xaa' at location 560 stands for Lys, Asn, -continued

```
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (561)..(561)
<223> OTHER INFORMATION: The 'Xaa' at location 561 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (562)..(562)
<223> OTHER INFORMATION: The 'Xaa' at location 562 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (563)..(563)
<223> OTHER INFORMATION: The 'Xaa' at location 563 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (564)..(564)
<223> OTHER INFORMATION: The 'Xaa' at location 564 stands for Lys, Asn,
      Arg, Ser, Thr,
      Ile, Met, Glu, Asp, Gly, Ala, Val, Gln, His, Pro, Leu, Tyr, Trp,
      Cys, or Phe.
<220> FEATURE:
<221> NAME/KEY: misc_feature
<222> LOCATION: (566)..(566)
<223> OTHER INFORMATION: The 'Xaa' at location 566 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (567)..(567)
<223> OTHER INFORMATION: The 'Xaa' at location 567 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (568)..(568)
<223> OTHER INFORMATION: The 'Xaa' at location 568 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (569)..(569)
<223> OTHER INFORMATION: The 'Xaa' at location 569 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (570)..(570)
<223> OTHER INFORMATION: The 'Xaa' at location 570 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (571)..(571)
<223> OTHER INFORMATION: The 'Xaa' at location 571 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (841)..(841)
<223> OTHER INFORMATION: The 'Xaa' at location 841 stands for Lys, Arg,
      Thr, or Ile.
<220> FEATURE:
<221> NAME/KEY: misc_feature
<222> LOCATION: (842)..(842)
<223> OTHER INFORMATION: The 'Xaa' at location 842 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (843)..(843)
<223> OTHER INFORMATION: The 'Xaa' at location 843 stands for Lys, Asn,
      Arg, Ser, Thr, Ile, Met, Glu, Asp, Gly, Ala, Val, Gln, His, Pro,
```

```
        Leu, Tyr, Trp, Cys, or Phe.
<220> FEATURE:
<221> NAME/KEY: misc_feature
<222> LOCATION: (844)..(844)
<223> OTHER INFORMATION: The 'Xaa' at location 844 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (845)..(845)
<223> OTHER INFORMATION: The 'Xaa' at location 845 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (846)..(846)
<223> OTHER INFORMATION: The 'Xaa' at location 846 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (847)..(847)
<223> OTHER INFORMATION: The 'Xaa' at location 847 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (848)..(848)
<223> OTHER INFORMATION: The 'Xaa' at location 848 stands for Asn, Ser,
      Thr, Ile, Asp, Gly, Ala, Val, His, Arg, Pro, Leu, Tyr, Cys, or
      Phe.

<400> SEQUENCE: 27

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240
```

```
Glu Val Val Asp Leu Gln Trp Thr Tyr Pro Gly Val Lys Gly Lys
                245                 250                 255

Gly Ile Thr Met Leu Glu Ile Lys Val Pro Ser Ile Lys Leu Val
                260                 265                 270

Tyr Thr Leu Thr Val Pro Glu Ala Thr Val Lys Asp Ser Gly Asp Tyr
                275                 280                 285

Glu Cys Ala Ala Arg Gln Ala Thr Arg Glu Val Lys Glu Met Lys Lys
            290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
                340                 345                 350

Asn Leu Thr Leu Ile Glu Asn Leu Thr Glu Ile Thr Thr Asp Val Glu
                355                 360                 365

Lys Ile Gln Glu Ile Arg Tyr Arg Ser Lys Leu Lys Leu Ile Arg Ala
            370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
                420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
            450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
                500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
            530                 535                 540

Leu Val Val Ile Trp Lys Gln Lys Pro Arg Tyr Glu Ile Arg Trp Xaa
545                 550                 555                 560

Xaa Xaa Xaa Xaa Ile Xaa Xaa Xaa Xaa Xaa Tyr Ile Tyr Val Asp
                565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
            595                 600                 605

Glu Gly Thr Ala Tyr Gly Leu Ser Arg Ser Gln Pro Val Met Lys Val
            610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
```

-continued

```
            660                 665                 670
Ile Thr Glu Tyr Cys Phe Tyr Gly Asp Leu Val Asn Tyr Leu His Lys
        675                 680                 685
Asn Arg Asp Ser Phe Leu Ser His His Pro Glu Lys Pro Lys Lys Glu
        690                 695                 700
Leu Asp Ile Phe Gly Leu Asn Pro Ala Asp Glu Ser Thr Arg Ser Tyr
705                 710                 715                 720
Val Ile Leu Ser Phe Glu Asn Gly Asp Tyr Met Asp Met Lys Gln
                725                 730                 735
Ala Asp Thr Thr Gln Tyr Val Pro Met Leu Glu Arg Lys Glu Val Ser
        740                 745                 750
Lys Tyr Ser Asp Ile Gln Arg Ser Leu Tyr Asp Arg Pro Ala Ser Tyr
        755                 760                 765
Lys Lys Lys Ser Met Leu Asp Ser Glu Val Lys Asn Leu Leu Ser Asp
        770                 775                 780
Asp Asn Ser Glu Gly Leu Thr Leu Leu Asp Leu Ser Phe Thr Tyr
785                 790                 795                 800
Gln Val Ala Arg Gly Met Glu Phe Leu Ala Ser Lys Asn Cys Val His
                805                 810                 815
Arg Asp Leu Ala Ala Arg Asn Val Leu Leu Ala Gln Gly Lys Ile Val
        820                 825                 830
Lys Ile Cys Asp Phe Gly Leu Ala Xaa Xaa Xaa Xaa Xaa Xaa Xaa
        835                 840                 845
Tyr Val Ser Lys Gly Ser Thr Phe Leu Pro Val Lys Trp Met Ala Pro
850                 855                 860
Glu Ser Ile Phe Asp Asn Leu Tyr Thr Thr Leu Ser Asp Val Trp Ser
865                 870                 875                 880
Tyr Gly Ile Leu Leu Trp Glu Ile Phe Ser Leu Gly Gly Thr Pro Tyr
                885                 890                 895
Pro Gly Met Met Val Asp Ser Thr Phe Tyr Asn Lys Ile Lys Ser Gly
                900                 905                 910
Tyr Arg Met Ala Lys Pro Asp His Ala Thr Ser Glu Val Tyr Glu Ile
        915                 920                 925
Met Val Lys Cys Trp Asn Ser Glu Pro Glu Lys Arg Pro Ser Phe Tyr
        930                 935                 940
His Leu Ser Glu Ile Val Glu Asn Leu Leu Pro Gly Gln Tyr Lys Lys
945                 950                 955                 960
Ser Tyr Glu Lys Ile His Leu Asp Phe Leu Lys Ser Asp His Pro Ala
                965                 970                 975
Val Ala Arg Met Arg Val Asp Ser Asp Asn Ala Tyr Ile Gly Val Thr
                980                 985                 990
Tyr Lys Asn Glu Glu Asp Lys Leu  Lys Asp Trp Glu Gly  Gly Leu Asp
                995                 1000                1005
Glu Gln  Arg Leu Ser Ala Asp  Ser Gly Tyr Ile Ile  Pro Leu Pro
1010                1015                1020
Asp Ile Asp Pro Val Pro Glu  Glu Glu Asp Leu Gly  Lys Arg Asn
1025                1030                1035
Arg His Ser Ser Gln Thr Ser  Glu Glu Ser Ala Ile  Glu Thr Gly
        1040                1045                1050
Ser Ser Ser Ser Thr Phe Ile  Lys Arg Glu Asp Glu  Thr Ile Glu
        1055                1060                1065
```

```
Asp Ile  Asp Met Met Asp Asp  Ile Gly Ile Asp Ser  Ser Asp Leu
    1070                 1075                1080

Val Glu  Asp Ser Phe Leu
    1085
```